US008048992B2

(12) United States Patent
Kurosawa et al.

(10) Patent No.: US 8,048,992 B2
(45) Date of Patent: Nov. 1, 2011

(54) ANTI-IGSF4 ANTIBODY AND UTILIZATION OF THE SAME

(75) Inventors: Yoshikazu Kurosawa, Nagoya (JP); Yasushi Akahori, Nagoya (JP); Nobuhiro Takahashi, Tokyo (JP); Atsushi Sugioka, Nagoya (JP); Nobuhiro Hayashi, Toyoake (JP); Akihiko Takasaki, Nagoya (JP); Kazuhiro Suzuki, Toyota (JP); Miwa Morita, Toyoake (JP); Gene Kurosawa, Nagoya (JP); Sari Fujiyama, Tokyo (JP); Susumu Tsustumi, Nagoya (JP); Keiko Ogawa, Toyoake (JP); Kazuki Matsuda, Nagoya (JP); Chiho Muramatsu, Toyoake (JP); Yoshitaka Iba, Nagoya (JP); Mariko Sumitomo, Nagoya (JP); Masachika Azuma, Nagoya (JP); Yoshinori Ukai, Nagoya (JP); Kazuhiro Morishita, Miyazaki (JP)

(73) Assignees: Institute for Antibodies Co., Ltd., Nagoya (JP); Yoshikazu Kurosawa, Nagoya (JP)

(*) Notice: Subject to any disclaimer, the term of this patent is extended or adjusted under 35 U.S.C. 154(b) by 745 days.

(21) Appl. No.: 11/885,245

(22) PCT Filed: Feb. 22, 2006

(86) PCT No.: PCT/JP2006/303195
§ 371 (c)(1),
(2), (4) Date: Jun. 9, 2008

(87) PCT Pub. No.: WO2006/090750
PCT Pub. Date: Aug. 31, 2006

(65) Prior Publication Data
US 2009/0053243 A1 Feb. 26, 2009

(30) Foreign Application Priority Data
Feb. 28, 2005 (JP) ................................. 2005-054624

(51) Int. Cl.
*C07K 16/00* (2006.01)
(52) U.S. Cl. .................................................. 530/387.1
(58) Field of Classification Search ........................ None
See application file for complete search history.

(56) References Cited

FOREIGN PATENT DOCUMENTS

| WO | WO-01/062907 A1 | 8/2001 |
| WO | WO-01/096401 A1 | 12/2001 |
| WO | WO 02/14557 A1 * | 2/2002 |
| WO | WO-2005/012530 | 2/2005 |

OTHER PUBLICATIONS

Yageta et al (Cancer Research, 2002, 62(18): 5129-5133).*
Ito et al (Cancer Research, 2001, 63: 6320-6326).*
Mountain et al (Biotechnol. Genet Eng Rev, 1992, 10: Abstract).*
Gilbert Laurent et al., "Nectin-like Protein 2 Defines a Subset of T-cell Zone Dendritic Cells and Is a Ligand for Class-I-restricted T-cell-associated Molecule," The journal of biological chemistry, vol. 280, No. 23, 2005, pp. 21955-21964 (Epub. Mar. 21, 2005).
Tetsuo Ito et al., "Involvement of TSLC1 in Progression of Esophageal Squamous Cell Carcinoma," Cancer Research, vol. 63, No. 19, Oct. 1, 2003, pp. 6320-6326.
Hidenori Sasaki et al., "Overexpression of a cell adhesion molecule, TSLC1, as a possible molecular marker for acute-type adult T-cell leukemia," BLOOD, Cancer Research, vol. 105, No. 3, Feb. 1, 2005, pp. 1204-1213 (Epub. Oct. 7, 2004).
Suzanne A. Eccles, "Monoclonal antibodies targeting cancer: 'Magic bullets' or just the trigger?," Breast Cancer Research, 2001, vol. 3, No. 2, pp. 86-90 (Epub. Dec. 20, 2000).
L. G. Presta et al., "Engineering therapeutic antibodies for improved function," Biochemical Society Transactions, 2002, vol. 30, No. 4, pp. 487-490.
Raymond J. Owens et al., "The genetic engineering of monoclonal antibodies," Journal of Immunological Methods, 1994, vol. 168, No. 2, pp. 149-165.
Greg Winter et al., "Humanized antibodies," Immunology Today, 1993, vol. 14, No. 6, pp. 243-246.
Greg Winter et al., "Antibody-based therapy," Trends in pharmacologicalsciences, vol. 14, No. 5, May 1993, pp. 139-143.
Mass R et al., Proc Am Soci Clin Oncol , vol. 19, 2000, 75a (1 page).
N. L. Berinstein et al.. "Association of serum Rituximab (IDEC-C2B8) concentration and anti-tumor response in the treatment of recurrent low-grade or follicular non-Hodgkin's lymphoma," Annals of Oncology 9, 1998, pp. 995-1001.
Marianne Brüggemann et al., "Comparison of the effector functions of human immunoglobulins using a matched set of chimeric antibodies," Neuberger M. S., J.E. xp. Med., vol. 166, Nov. 1987, pp. 1351-1361.
Michael Loos, "The Classical Complement Pathway: Mechanism of Activation of the First Component by Antigen-Antibody Complexes," Prog. Allergy, vol. 30, 1982, pp. 135-192.
Jürg Tschopp, "Kinetics of Activation of the First Component of Complement (C1) by IgG Oligomers," Mol Immunol., vol. 19, No. 5, May 1982, pp. 651-657.
T. Wakayama et al., "Express on and Funct onal Character zat on of the Adhes on Molecule Spermatogen c Immunoglobul n Superfam ly n the Mouse Test s, "Biology of Reproduction, vol. 68, No. 5, XP-002517587, May 2003, pp. 1755-1763.
T. Ito et al., "Involvement of TSLC1 in Progression of Esophageal Squamous Cell Carcinoma," Cancer Research, XP003000773, Oct. 1, 2003, pp. 6320-6326.
Supplementary European Search Report dated Mar. 17, 2009, issued on the European application No. 06714335.4.

(Continued)

Primary Examiner — Sean Aeder
(74) Attorney, Agent, or Firm — Edwards Angell Palmer & Dodge LLP

(57) ABSTRACT

It is intended to clarify a molecule which is available as a target in treating or diagnosing cancer and utilize the molecule in the medical field or the research field. By treating IgSF4, which has been identified as a molecule specifically expressed in lung cancer cells, with an antibody, and ADCC activity is exerted. Based on this finding, an anti-IgSF4 antibody is provided as a means efficacious in treating cancer, etc.

6 Claims, 37 Drawing Sheets

OTHER PUBLICATIONS

Toyohide Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, vol. 278, No. 5, 2003, pp. 3466-3473.

* cited by examiner

Fig. 3-1

```
pscFvCA9-E8VHdVLd
                                        M  K  Y  L  L  P  T  A  A  A  G
AAGCTTGCATGCAAATTCTATTTCAAGGAGACAGTCATAATGAAATACCTATTGCCTACGGCAGCCGCTGGA
HindIII L  L  L  L  A  A  Q  P  A  M  A  Q  V  Q  L  Q  Q  S  G  A  E  L  V  K
TTGTTATTACTCGCTGCCCAACCAGCGATGGCCCAGGTGCAGCTGCAGCAGTCTGGGGCAGAGCTTGTGAAG
                                     PstI P  G  A  S  V  K  L  S  C  T  A  S  G  F  N  I  K  D  T  Y  M  H  W  V
CCAGGGGCCTCAGTCAAGTTGTCCTGCACAGCTTCTGGCTTCAACATTAAAGACACCTATATGCACTGGGTG K  Q  R  P  E  K  G ———————— L  T  S  E  D  T  A  V  Y  Y  C  A  G  Y
AAGCAGAGGCCTGAAAAGGGTCTAGAATTCCCTGACATCTGAGGACACTGCCGTCTATTACTGTGCTGGTTA
                   XbaI  EcoRI D  Y  G  N  F  D  Y  W  G  Q  G  T  T  V  T  V  S  R  G  G  G  G  S  G
TGATTACGGCAACTTTGACTACTGGGGCCAAGGCACCACGGTCACCGTCTCGAGAGGCGGTGGCGGATCAGG
                                   BstPI    XhoI G  G  G  S  G  G  G  G  S  M  A
TGGCGGTGGAAGTGGCGGTGGTGGGTCCATGGCC
                          NcoI D  I  E  L  T  Q  S  P  A  S  L  S  A  S  V  G  E  T  V  T  I  T
      GACATCGAGCTCACCCAGTCTCCAGCCTCCCTTTCTGCGTCTGTGGGAGAAACTGTCACCATCAC
            SacI C  R  A  S  G  N  I  H  N  Y  L  A ———————— K  L  E  I  K  R  A  D  A  A
ATGTCGAGCAAGTGGGAATATTCACAATTATTTAGCATGGTACCAAGCTCGAGATCAAACGGGCTGATGCTG
                                       KpnI   XhoI P  T  V  S  I  F  P  P  S  S  E  Q  L  T  S  G  G  A  S  V  V  C  F  L
   CACCAACTGTATCCATCTTCCCACCATCCAGTGAGCAGTTAACATCTGGAGGTGCCTCAGTCGTGTGCTTCT N  S  F  Y  P  K  D  I  N  V  K  W  K  I  D  G  S  E  R  Q  N  G  V  L
 TGAACAGCTTCTACCCCAAAGACATCAATGTCAAGTGGAAGATTGATGGCAGTGAACGACAAAATGGCGTCC N  S  W  T  D  Q  D  S  K  D  S  T  Y  S  M  S  S  T  L  T  L  T  K  D
 TGAACAGTTGGACTGATCAGGACAGCAAAGACAGCACCTACAGCATGAGCAGCACCCTCACGTTGACCAAGG E  Y  E  R  H  N  S  Y  T  C  E  A  T  H  K  T  S  T  S  P  I  V  K  S
  ACGAGTATGAACGACATAACAGCTATACCTGTGAGGCCACTCACAAGACATCAACTTCACCCATTGTCAAGA
```

Fig. 3-2

```
         F  N  R  N  E  C  S  A  R  Q  S  T  P  F  V  C  E  Y  Q  G  Q  S  S  D
GCTTCAACAGGAATGAGTGTTCGGCGCGCCAGTCGACTCCATTCGTTTGTGAATATCAAGGCCAATCGTCTG
                      AscI     SalI
    L  P  Q  P  P  V  N  A  G  G  G  S  G  G  G  S  G  G  G  S  E  G  G  G
ACCTGCCTCAACCTCCTGTCAATGCTGGCGGCGGCTCTGGTGGTGGTTCTGGTGGCGGCTCTGAGGGTGGTG

S  E  G  G  G  S  E  G  G  G  S  E  G  G  G  S  G  G  G  S  G  S  G  D
GCTCTGAGGGTGGCGGTTCTGAGGGTGGCGGCTCTGAGGGAGGCGGTTCCGGTGGTGGCTCTGGTTCCGGTG

F  D  Y  E  K  M  A  N  A  N  K  G  A  M  T  E  N  A  D  E  N  A  L  Q
ATTTTGATTATGAAAAGATGGCAAACGCTAATAAGGGGGCTATGACCGAAAATGCCGATGAAAACGCGCTAC

S  D  A  K  G  K  L  D  S  V  A  T  D  Y  G  A  A  I  D  G  F  I  G  D
AGTCAGACGCTAAAGGCAAACTTGATTCTGTCGCTACTGATTACGGTGCTGCTATCGATGGTTTCATTGGTG

V  S  G  L  A  N  G  N  G  A  T  G  D  F  A  G  S  N  S  Q  M  A  Q  V
ACGTTTCCGGCCTTGCTAATGGTAATGGTGCTACTGGTGATTTTGCTGGCTCTAATTCCCAAATGGCTCAAG

G  D  G  D  N  S  P  L  M  N  N  F  R  Q  Y  L  P  S  L  P  Q  S  V  E
TCGGTGACGGTGATAATTCACCTTTAATGAATAATTTCCGTCAATATTTACCTTCCCTCCCTCAATCGGTTG

C  R  P  F  V  F  G  A  G  K  P  Y  E  F  S  I  D  C  D  K  I  N  L  F
AATGTCGCCCTTTTGTCTTTGGCGCTGGTAAACCATATGAATTTTCTATTGATTGTGACAAAATAAACTTAT

R  G  V  F  A  F  L  L  Y  V  A  T  F  M  Y  V  F  S  T  F  A  N  I  L
TCCGTGGTGTCTTTGCGTTTCTTTTATATGTTGCCACCTTTATGTATGTATTTTCTACGTTTGCTAACATAC

R  N  K  E  S  *                                S  T  A  Q  H  D  E  A
TGCGTAATAAGGAGTCTTAATCATGCCAGTTCTTTTGGGTGCTAGCTGTCGACTGCGCAACACGATGAAGCC
                                                 NheI     SalI
 V  D  N  K  F  N  K  E  Q  Q  N  A  F  Y  E  I  L  H  L  P  N  L  N  E
GTAGACAACAAATTCAACAAAGAACAACAAAACGCGTTCTATGAGATCTTACATTTACCTAACTTAAACGAA

E  Q  R  N  A  F  I  Q  S  L  K  D  D  P  S  Q  S  A  N  L  L  A  E  A
GAACAACGAAACGCCTTCATCCAAAGTTTAAAAGATGACCCAAGCCAAAGCGCTAACCTTTTAGCAGAAGCT

K  K  L  N  D  A  Q  A  P  K  V  D  N  K  F  N  K  E  Q  Q  N  A  F  Y
AAAAAGCTAAATGATGCTCAGGCGCCGAAAGTAGACAACAAATTCAACAAAGAACAACAAAACGCGTTCTAT

E  I  L  H  L  P  N  L  N  E  E  Q  R  N  A  F  I  Q  S  L  K  D  D  P
GAGATCTTACATTTACCTAACTTAAACGAAGAACAACGAAACGCCTTCATCCAAAGTTTAAAAGATGACCCA

S  Q  S  A  N  L  L  A  E  A  K  K  L  N  D  A  Q  A  P  K  V  D  A  N
AGCCAAAGCGCTAACCTTTTAGCAGAAGCTAAAAAGCTAAATGATGCTCAGGCGCCGAAAGTAGACGCGAAT

*
TAGCTGGGAATTAATTC
```

Fig. 4-1

```
pscFvCA-E8VHd

M  K  Y  L  L  P  T  A  A  A  G
AAGCTTGCATGCAAATTCTATTTCAAGGAGACAGTCATAATGAAATACCTATTGCCTACGGCAGCCGCTGGA
HindIII L  L  L  L  A  A  Q  P  A  M  A  Q  V  Q  L  Q  Q  S  G  A  E  L  V  K
TTGTTATTACTCGCGGCCCAGCCGGCCATGGCCCAGGTGCAGCTGCAGCAGTCTGGGGCAGAGCTTGTGAAG
         SfiI          NcoI             PstI P  G  A  S  V  K  L  S  C  T  A  S  G  F  N  I  K  D  T  Y  M  H  W  V
CCAGGGGCCTCAGTCAAGTTGTCCTGCACAGCTTCTGGCTTCAACATTAAAGACACCTATATGCACTGGGTG K  Q  R  P  E  K  G ——————— L  T  S  E  D  T  A  V  Y  Y  C  A  G  Y
AAGCAGAGGCCTGAAAAGGGTCTAGAATTCCCTGACATCTGAGGACACTGCCGTCTATTACTGTGCTGGTTA
                       XbaI  EcoRI D  Y  G  N  F  D  Y  W  G  Q  G  T  T  V  T  V  S  S  G  G  G  G  S  G
TGATTACGGCAACTTTGACTACTGGGGCCAAGGCACCACGGTCACCGTCTCCTCAGGCGGTGGCGGATCAGG
                                     BstPI G  G  S  G  G  G  G  S  T  S  D  I  E  L  T  Q  S  P  A  S  L  S  A
TGGCGGTGGAAGTGGCGGTGGTGGGTCTACTAGTGACATCGAGCTCACCCAGTCTCCAGCCTCCCTTTCTGC
                          SpeI         SacI S  V  G  E  T  V  T  I  T  C  R  A  S  G  N  I  H  N  Y  L  A  W  Y  Q
GTCTGTGGGAGAAACTGTCACCATCACATGTCGAGCAAGTGGGAATATTCACAATTATTTAGCATGGTACCA
                                                               KpnI Q  K  P  G  K  S  P  Q  L  L  V  Y  N  A  K  T  L  A  D  G  V  P  S  R
GCAGAAACCAGGGAAATCTCCTCAGCTCCTGGTCTATAATGCAAAAACCTTAGCAGATGGTGTGCCATCAAG F  S  G  S  G  S  G  T  Q  Y  S  L  K  I  N  S  L  Q  P  E  D  F  G  S
GTTCAGTGGCAGTGGATCCGGAACACAATATTCTCTCAAGATCAACAGCCTGCAGCCTGAAGATTTTGGGAG
               BamHI Y  Y  C  Q  H  F  W  S  T  P  W  T  F  G  G  G  T  K  I  E  S  T  P  F
TTATTACTGTCAACATTTTTGGAGTACTCCGTGGACGTTCGGTGGAGGTACCAAGCTCGAGTCGACTCCATT
                                                   KpnI     XhoI  SalI V  C  E  Y  Q  G  Q  S  S  D  L  P  Q  P  P  V  N  A  G  G  G  S  G  G
CGTTTGTGAATATCAAGGCCAATCGTCTGACCTGCCTCAACCTCCTGTCAATGCTGGCGGCGGCTCTGGTGG
```

Fig. 4-2

```
  G  S  G  G  G  S  E  G  G  G  S  E  G  G  G  S  E  G  G  G  S  E  G  G
TGGTTCTGGTGGCGGCTCTGAGGGTGGTGGCTCTGAGGGTGGCGGTTCTGAGGGTGGCGGCTCTGAGGGAGG

G  S  G  G  G  S  G  S  G  D  F  D  Y  E  K  M  A  N  A  N  K  G  A  M
CGGTTCCGGTGGTGGCTCTGGTTCCGGTGATTTTGATTATGAAAAGATGGCAAACGCTAATAAGGGGGCTAT

T  E  N  A  D  E  N  A  L  Q  S  D  A  K  G  K  L  D  S  V  A  T  D  Y
GACCGAAAATGCCGATGAAAACGCGCTACAGTCAGACGCTAAAGGCAAACTTGATTCTGTCGCTACTGATTA

G  A  A  I  D  G  F  I  G  D  V  S  G  L  A  N  G  N  G  A  T  G  D  F
CGGTGCTGCTATCGATGGTTTCATTGGTGACGTTTCCGGCCTTGCTAATGGTAATGGTGCTACTGGTGATTT

A  G  S  N  S  Q  M  A  Q  V  G  D  G  D  N  S  P  L  M  N  N  F  R  Q
TGCTGGCTCTAATTCCCAAATGGCTCAAGTCGGTGACGGTGATAATTCACCTTTAATGAATAATTTCCGTCA

Y  L  P  S  L  P  Q  S  V  E  C  R  P  F  V  F  G  A  G  K  P  Y  E  F
ATATTTACCTTCCCTCCCTCAATCGGTTGAATGTCGCCCTTTTGTCTTTGGCGCTGGTAAACCATATGAATT

S  I  D  C  D  K  I  N  L  F  R  G  V  F  A  F  L  L  Y  V  A  T  F  M
TTCTATTGATTGTGACAAAATAAACTTATTCCGTGGTGTCTTTGCGTTTCTTTTATATGTTGCCACCTTTAT

Y  V  F  S  T  F  A  N  I  L  R  N  K  E  S  *
GTATGTATTTTCTACGTTTGCTAACATACTGCGTAATAAGGAGTCTTAATCATGCCAGTTCTTTTGGGTGCT
                                                                    Nhel
       S  T  A  Q  H  D  E  A  V  D  N  K  F  N  K  E  Q  Q  N  A  F  Y  E
AGCTGTCGACTGCGCAACACGATGAAGCCGTAGACAACAAATTCAACAAAGAACAACAAAACGCGTTCTATG
     Sa/l I  L  H  L  P  N  L  N  E  E  Q  R  N  A  F  I  Q  S  L  K  D  D  P  S
AGATCTTACATTTACCTAACTTAAACGAAGAACAACGAAACGCCTTCATCCAAAGTTTAAAAGATGACCCAA Q  S  A  N  L  L  A  E  A  K  K  L  N  D  A  Q  A  P  K  V  D  N  K  F
GCCAAAGCGCTAACCTTTTAGCAGAAGCTAAAAAGCTAAATGATGCTCAGGCGCCGAAAGTAGACAACAAAT N  K  E  Q  Q  N  A  F  Y  E  I  L  H  L  P  N  L  N  E  E  Q  R  N  A
TCAACAAAGAACAACAAAACGCGTTCTATGAGATCTTACATTTACCTAACTTAAACGAAGAACAACGAAACG F  I  Q  S  L  K  D  D  P  S  Q  S  A  N  L  L  A  E  A  K  K  L  N  D
CCTTCATCCAAAGTTTAAAAGATGACCCAAGCCAAAGCGCTAACCTTTTAGCAGAAGCTAAAAAGCTAAATG

A  Q  A  P  K  V  D  A  N  *
ATGCTCAGGCGCCGAAAGTAGACGCGAATTAGCTGGGAATTAATTC
```

Fig. 5

(A) HepG2 screening

| | input phage (cfu) | output phage (cfu) | recovering rate |
|---|---|---|---|
| 1st screening | $1 \times 10^{13}$ | $6.4 \times 10^6$ | $1/1.6 \times 10^6$ |
| 2nd screening | $1 \times 10^{10}$ | $3.9 \times 10^4$ | $1/2.6 \times 10^6$ |
| 3rd screening | $1 \times 10^9$ | $5.0 \times 10^6$ | $1/2.0 \times 10^2$ |

(B) Nuk-1 screening

| | input phage (cfu) | output phage (cfu) | recovering rate |
|---|---|---|---|
| 1st screening | $1 \times 10^{13}$ | $8.7 \times 10^7$ | $1/1.1 \times 10^5$ |
| 2nd screening | $2 \times 10^{10}$ | $2.1 \times 10^6$ | $1/9.5 \times 10^3$ |
| 3rd screening | $1 \times 10^9$ | $2.5 \times 10^6$ | $1/4.6 \times 10^2$ |

Fig. 6

| Screening | number of kinds of antibody clones | number of stained antibodies specific to cancer | number of stained antibodies specific to cancer membrane |
|---|---|---|---|
| HepG2 | 130 | 33 | 19 |
| Nuk-1 | 94 | 21 | 8 |

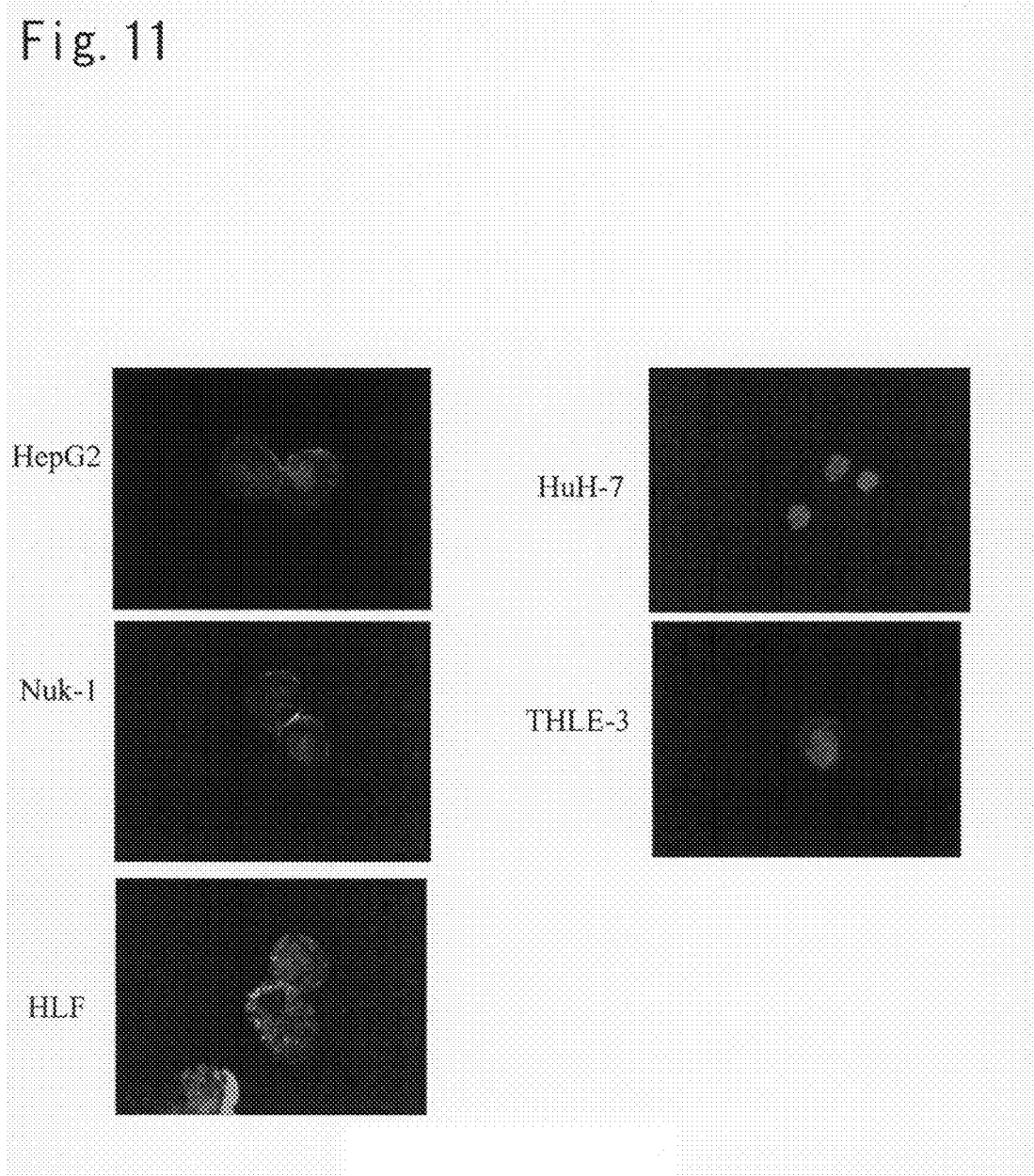

Fig. 12-1

```
                                                  M  K  Y  L  L  P  T  A  A  A  G
AAGCTTGCATGCAAATTCTATTTCAAGGAGACAGTCATAATGAAATACCTATTGCCTACGGCAGCCGCTGGA
HindIII L  L  L  L  A  A  Q  P  A  M  A
TTGTTATTACTCGCGGCCCAGCCGGCCATGGCC    (VH sequence)
            SfiI G  G  G  G  S  G  G  G  G  S  G  G  G  S  M  A
GGCGGTGGCGGATCAGGTGGCGGTGGAAGTGGCGGTGGTGGGTCCATGGCC    (VLCL sequence)
                                              NcoI S  A  R  Q  S  T  P  F  V  C  E  Y  Q  G  Q  S  S  D
                              TCGGCGCGCCAGTCGACTCCATTCGTTTGTGAATATCAAGGCCAATCGTCTG
                                 AscI    SalI
    L  P  Q  P  P  V  N  A  G  G  G  S  G  G  G  S  G  G  G  S  E  G  G  G
ACCTGCCTCAACCTCCTGTCAATGCTGGCGGCGGCTCTGGTGGTGGTTCTGGTGGCGGCTCTGAGGGTGGTG S  E  G  G  G  S  E  G  G  G  S  E  G  G  G  S  G  G  G  S  G  S  G  D
GCTCTGAGGGTGGCGGTTCTGAGGGTGGCGGCTCTGAGGGAGGCGGTTCCGGTGGTGGCTCTGGTTCCGGTG F  D  Y  E  K  M  A  N  A  N  K  G  A  M  T  E  N  A  D  E  N  A  L  Q
ATTTTGATTATGAAAAGATGGCAAACGCTAATAAGGGGGCTATGACCGAAAATGCCGATGAAAACGCGCTAC S  D  A  K  G  K  L  D  S  V  A  T  D  Y  G  A  A  I  D  G  F  I  G  D
AGTCAGACGCTAAAGGCAAACTTGATTCTGTCGCTACTGATTACGGTGCTGCTATCGATGGTTTCATTGGTG V  S  G  L  A  N  G  N  G  A  T  G  D  F  A  G  S  N  S  Q  M  A  Q  V
ACGTTTCCGGCCTTGCTAATGGTAATGGTGCTACTGGTGATTTTGCTGGCTCTAATTCCCAAATGGCTCAAG G  D  G  D  N  S  P  L  M  N  N  F  R  Q  Y  L  P  S  L  P  Q  S  V  E
TCGGTGACGGTGATAATTCACCTTTAATGAATAATTTCCGTCAATATTTACCTTCCCTCCCTCAATCGGTTG
```

Fig. 12-2

```
        C   R   P   F   V   F   G   A   G   K   P   Y   E   F   S   I   D   C   D   K   I   N   L   F
AATGTCGCCCTTTTGTCTTTGGCGCTGGTAAACCATATGAATTTTCTATTGATTGTGACAAAATAAACTTAT

R   G   V   F   A   F   L   L   Y   V   A   T   F   M   Y   V   F   S   T   F   A   N   I   L
TCCGTGGTGTCTTTGCGTTTCTTTTATATGTTGCCACCTTTATGTATGTATTTTCTACGTTTGCTAACATAC

R   N   K   E   S   *                           S   T   A   Q   H   D   E   A
TGCGTAATAAGGAGTCTTAATCATGCCAGTTCTTTTGGGTGCTAGCTGTCGACTGCGCAACACGATGAAGCC
                                                        Nhe I       Sal I
    V   D   N   K   F   N   K   E   Q   Q   N   A   F   Y   E   I   L   H   L   P   N   L   N   E
GTAGACAACAAATTCAACAAAGAACAACAAAACGCGTTCTATGAGATCTTACATTTACCTAACTTAAACGAA

E   Q   R   N   A   F   I   Q   S   L   K   D   D   P   S   Q   S   A   N   L   L   A   E   A
GAACAACGAAACGCCTTCATCCAAAGTTTAAAAGATGACCCAAGCCAAAGCGCTAACCTTTTAGCAGAAGCT

K   K   L   N   D   A   Q   A   P   K   V   D   N   K   F   N   K   E   Q   Q   N   A   F   Y
AAAAAGCTAAATGATGCTCAGGCGCCGAAAGTAGACAACAAATTCAACAAAGAACAACAAAACGCGTTCTAT

E   I   L   H   L   P   N   L   N   E   E   Q   R   N   A   F   I   Q   S   L   K   D   D   P
GAGATCTTACATTTACCTAACTTAAACGAAGAACAACGAAACGCCTTCATCCAAAGTTTAAAAGATGACCCA

S   Q   S   A   N   L   L   A   E   A   K   K   L   N   D   A   Q   A   P   K   V   D   A   N
AGCCAAAGCGCTAACCTTTTAGCAGAAGCTAAAAAGCTAAATGATGCTCAGGCGCCGAAAGTAGACGCGAAT

*
TAGCTGGGAATTAATTC
```

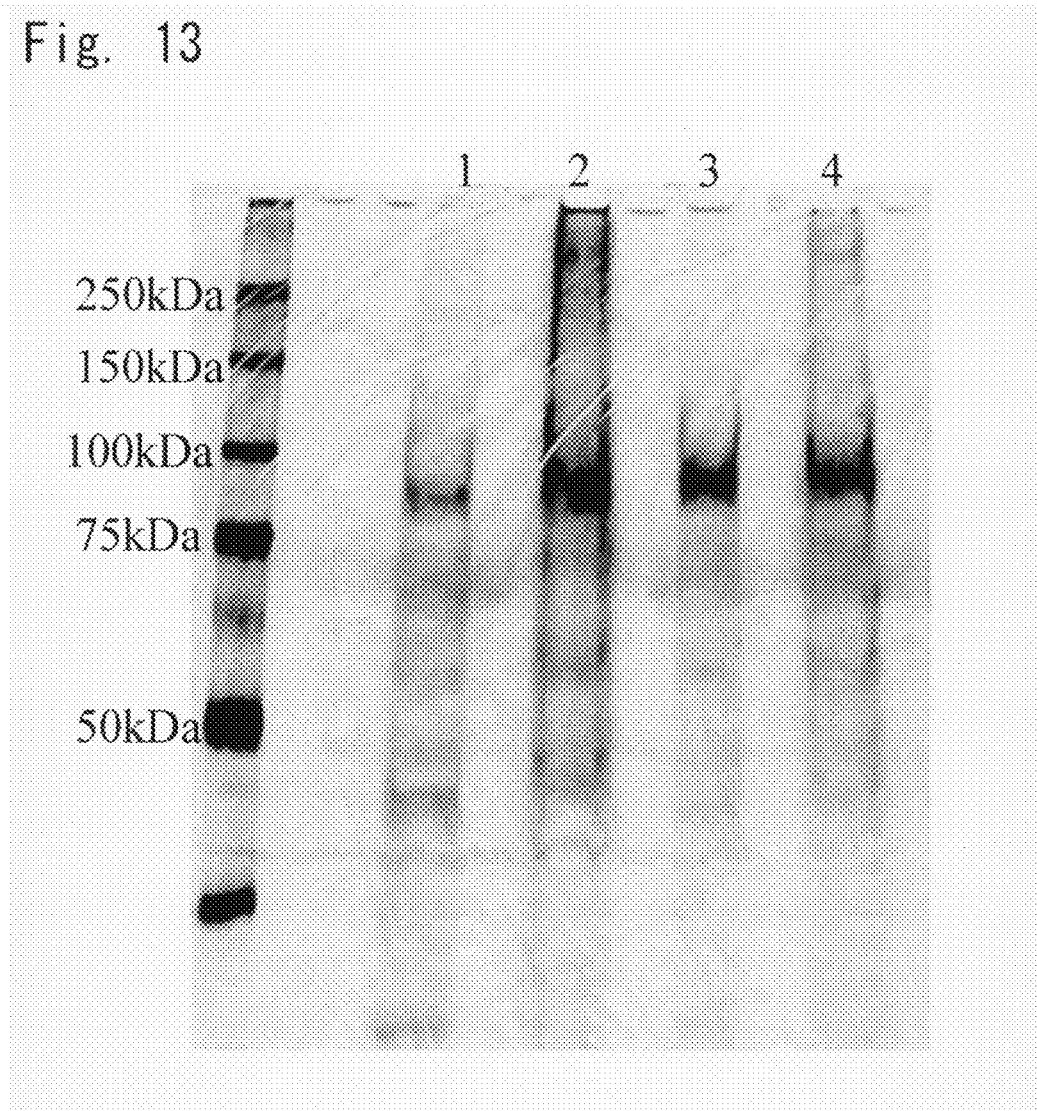

Fig. 14

MASVVLPSGSQCAAAAAAAPPGLRLRLLLLFSAAALIPTGDGQNLFTKDV
TVIEGEVATISCQVNK*SDDSVIQLLNPNRQTIYFRDFRPLKDSR*FQLLNFSSSEL
KVSLTNVSISDEGRYFCQLYTDPPQESYTTITVLVPPR*NLMDIQK*DTAVEGE
EIEVNCTAMASKPATTIRWFKGNTELKGKSEVEEWSDMYTVTSQLMLK*VHKE*
DDGVPVICQVEHPAVTGNLQTQRYLEVQYKPQVHIQMTYPLQGLTREGD
ALELTCEAIGKPQPVMVTWVR*VDDEMPQHAVLSGPNLFINNLNKTDNGTYR
CEASNIVGKAHSDYMLYVVYDPPTTIPPPTTTTTTTTTLTIITDSR*AGEEGS*
IR*AVDHAVIGGVVAVVFAMLCLLIILGR*YFARHK*GTYFTHEAK*GADDAAD
ADTAIINAEGGQNNSEEKKEYFI

Fig. 15-1 cDNA1 seq

```
M  A  S  V  V  L  P  S  G  S  Q  C  A  A  A  A  A  A  A  A
ATGGCGAGTGTAGTGCTGCCGAGCGGATCCCAGTGTGCGGCGGCAGCGGCGGCGGCGGCG

P  P  G  L  R  L  L  L  L  F  S  A  A  A  L  I  P  T  G
CCTCCCGGGCTCCGGCTTCTGCTGTTGCTCTTCTCCGCCGCGGCACTGATCCCCACAGGT

D  G  Q  N  L  F  T  K  D  V  T  V  I  E  G  E  V  A  T  I
GATGGGCAGAATCTGTTTACGAAAGACGTGACAGTGATCGAGGGAGAGGTTGCGACCATC

S  C  Q  V  N  K  S  D  D  S  V  I  Q  L  L  N  P  N  R  Q
AGTTGCCAAGTCAATAAGAGTGACGACTCTGTGATTCAGCTACTGAATCCCAACAGGCAG

T  I  Y  F  R  D  F  R  P  L  K  D  S  R  F  Q  L  L  N  F
ACCATTTATTTCAGGGACTTCAGGCCTTTGAAGGACAGCAGGTTTCAGTTGCTGAATTTT

S  S  S  E  L  K  V  S  L  T  N  V  S  I  S  D  E  G  R  Y
TCTAGCAGTGAACTCAAAGTATCATTGACAAACGTCTCAATTTCTGATGAAGGAAGATAC

F  C  Q  L  Y  T  D  P  P  Q  E  S  Y  T  T  I  T  V  L  V
TTTTGCCAGCTCTATACCGATCCCCCACAGGAAAGTTACACCACCATCACAGTCCTGGTC

P  P  R  N  L  M  I  D  I  Q  K  D  T  A  V  E  G  E  E  I
CCACCACGTAATCTGATGATCGATATCCAGAAAGACACTGCGGTGGAAGGTGAGGAGATT

E  V  N  C  T  A  M  A  S  K  P  A  T  T  I  R  W  F  K  G
GAAGTCAACTGCACTGCTATGGCCAGCAAGCCAGCCACGACTATCAGGTGGTTCAAAGGG

N  T  E  L  K  G  K  S  E  V  E  E  W  S  D  M  Y  T  V  T
AACACAGAGCTAAAAGGCAAATCGGAGGTGGAAGAGTGGTCAGACATGTACACTGTGACC

S  Q  L  M  L  K  V  H  K  E  D  D  G  V  P  V  I  C  Q  V
AGTCAGCTGATGCTGAAGGTGCACAAGGAGGACGATGGGGTCCCAGTGATCTGCCAGGTG
```

Fig. 15-2

```
E  H  P  A  V  T  G  N  L  Q  T  Q  R  Y  L  E  V  Q  Y  K
GAGCACCCTGCGGTCACTGGAAACCTGCAGACCCAGCGGTATCTAGAAGTACAGTATAAG

P  Q  V  H  I  Q  M  T  Y  P  L  Q  G  L  T  R  E  G  D  A
CCTCAAGTGCACATTCAGATGACTTATCCTCTACAAGGCTTAACCCGGGAAGGGGACGCG

L  E  L  T  C  E  A  I  G  K  P  Q  P  V  M  V  T  W  V  R
CTTGAGTTAACATGTGAAGCCATCGGGAAGCCCCAGCCTGTGATGGTAACTTGGGTGAGA

V  D  D  E  M  P  Q  H  A  V  L  S  G  P  N  L  F  I  N  N
GTCGATGATGAAATGCCTCAACACGCCGTACTGTCTGGGCCCAACCTGTTCATCAATAAC

L  N  K  T  D  N  G  T  Y  R  C  E  A  S  N  I  V  G  K  A
CTAAACAAAACAGATAATGGTACATACCGCTGTGAAGCTTCAAACATAGTGGGGAAAGCT

H  S  D  Y  M  L  Y  V  Y  D  P  P  T  T  I  P  P  P  T  T
CACTCGGATTATATGCTGTATGTATACGATCCCCCCACAACTATCCCTCCTCCCACAACA

T  T  T  T  T  T  T  T  T  T  T  I  L  T  I  I  T  D  S  R
ACCACCACCACCACCACCACCACCACCACCACCATCCTTACCATCATCACAGATTCCCGA

A  G  E  E  G  S  I  R  A  V  D  H  A  V  I  G  G  V  V  A
GCAGGTGAAGAAGGCTCGATCAGGGCAGTGGATCATGCCGTGATCGGTGGCGTCGTGGCG

V  V  V  F  A  M  L  C  L  L  I  I  L  G  R  Y  F  A  R  H
GTGGTGGTGTTCGCCATGCTGTGCTTGCTCATCATTCTGGGGCGCTATTTTGCCAGACAT

K  G  T  Y  F  T  H  E  A  K  G  A  D  D  A  A  D  A  D  T
AAAGGTACATACTTCACTCATGAAGCCAAAGGAGCCGATGACGCAGCAGACGCAGACACA

A  I  I  N  A  E  G  G  Q  N  N  S  E  E  K  K  E  Y  F  I
GCTATAATCAATGCAGAAGGAGGACAGAACAACTCCGAAGAAAAGAAAGAGTACTTCATC

*
TAG
```

Fig. 16-1 cDNA2 seq

```
          M  A  S  V  V  L  P  S  G  S  Q  C  A  A  A  A  A  A  A
         ATGGCGAGTGTAGTGCTGCCGAGCGGATCCCAGTGTGCGGCGGCAGCGGCGGCGGCGGCG

P  P  G  L  R  L  R  L  L  L  L  L  F  S  A  A  A  L  I  P
         CCTCCCGGGCTCCGGCTCCGGCTTCTGCTGTTGCTCTTCTCCGCCGCGGCACTGATCCCC

T  G  D  G  Q  N  L  F  T  K  D  V  T  V  I  E  G  E  V  A
         ACAGGTGATGGGCAGAATCTGTTTACGAAAGACGTGACAGTGATCGAGGGAGAGGTTGCG

T  I  S  C  Q  V  N  K  S  D  D  S  V  I  Q  L  L  N  P  N
         ACCATCAGTTGCCAAGTCAATAAGAGTGACGACTCTGTGATTCAGCTACTGAATCCCAAC

R  Q  T  I  Y  F  R  D  F  R  P  L  K  D  S  R  F  Q  L  L
         AGGCAGACCATTTATTTCAGGGACTTCAGGCCTTTGAAGGACAGCAGGTTTCAGTTGCTG

N  F  S  S  S  E  L  K  V  S  L  T  N  V  S  I  S  D  E  G
         AATTTTTCTAGCAGTGAACTCAAAGTATCATTGACAAACGTCTCAATTTCTGATGAAGGA

R  Y  F  C  Q  L  Y  T  D  P  P  Q  E  S  Y  T  T  I  T  V
         AGATACTTTTGCCAGCTCTATACCGATCCCCCACAGGAAAGTTACACCACCATCACAGTC

L  V  P  P  R  N  L  M  I  D  I  Q  K  D  T  A  V  E  G  E
         CTGGTCCCACCACGTAATCTGATGATCGATATCCAGAAAGACACTGCGGTGGAAGGTGAG

E  I  E  V  N  C  T  A  M  A  S  K  P  A  T  T  I  R  W  F
         GAGATTGAAGTCAACTGCACTGCTATGGCCAGCAAGCCAGCCACGACTATCAGGTGGTTC

K  G  N  T  E  L  K  G  K  S  E  V  E  E  W  S  D  M  Y  T
         AAAGGGAACACAGAGCTAAAAGGCAAATCGGAGGTGGAAGAGTGGTCAGACATGTACACT

V  T  S  Q  L  M  L  K  V  H  K  E  D  D  G  V  P  V  I  C
         GTGACCAGTCAGCTGATGCTGAAGGTGCACAAGGAGGACGATGGGGTCCCAGTGATCTGC
```

Fig. 16-2

```
Q  V  E  H  P  A  V  T  G  N  L  Q  T  Q  R  Y  L  E  V  Q
CAGGTGGAGCACCCTGCGGTCACTGGAAACCTGCAGACCCAGCGGTATCTAGAAGTACAG

Y  K  P  Q  V  H  I  Q  M  T  Y  P  L  Q  G  L  T  R  E  G
TATAAGCCTCAAGTGCACATTCAGATGACTTATCCTCTACAAGGCTTAACCCGGGAAGGG

D  A  L  E  L  T  C  E  A  I  G  K  P  Q  P  V  M  V  T  W
GACGCGCTTGAGTTAACATGTGAAGCCATCGGGAAGCCCCAGCCTGTGATGGTAACTTGG

V  R  V  D  D  E  M  P  Q  H  A  V  L  S  G  P  N  L  F  I
GTGAGAGTCGATGATGAAATGCCTCAACACGCCGTACTGTCTGGGCCCAACCTGTTCATC

N  N  L  N  K  T  D  N  G  T  Y  R  C  E  A  S  N  I  V  G
AATAACCTAAACAAAACAGATAATGGTACATACCGCTGTGAAGCTTCAAACATAGTGGGG

K  A  H  S  D  Y  M  L  Y  V  Y  D  P  P  T  T  I  P  P  P
AAAGCTCACTCGGATTATATGCTGTATGTATACGATCCCCCCACAACTATCCCTCCTCCC

T  T  T  T  T  T  T  T  T  T  T  T  T  I  L  T  I  I  T  D
ACAACAACCACCACCACCACCACCACCACCACCACCATCCTTACCATCATCACAGAC

T  T  A  T  T  E  P  A  V  H  D  S  R  A  G  E  E  G  S  I
ACAACGGCGACGACAGAACCAGCAGTTCACGATTCCCGAGCAGGTGAAGAAGGCTCGATC

R  A  V  D  H  A  V  I  G  G  V  V  A  V  V  V  F  A  M  L
AGGGCAGTGGATCATGCCCTGATCGGTGGCGTCGTGGCGGTGGTGGTGTTCGCCATGCTG

C  L  L  I  I  L  G  R  Y  F  A  R  H  K  G  T  Y  F  T  H
TGCTTGCTCATCATTCTGGGGCGCTATTTTGCCAGACATAAAGGTACATACTTCACTCAT

E  A  K  G  A  D  D  A  A  D  A  D  T  A  I  I  N  A  E  G
GAAGCCAAAGGAGCCGATGACGCAGCAGACGCAGACACAGCTATAATCAATGCAGAAGGA

G  Q  N  N  S  E  E  K  K  E  Y  F  I  *
GGACAGAACAACTCCGAAGAAAAGAAAGAGTACTTCATCTAG
```

Fig. 17
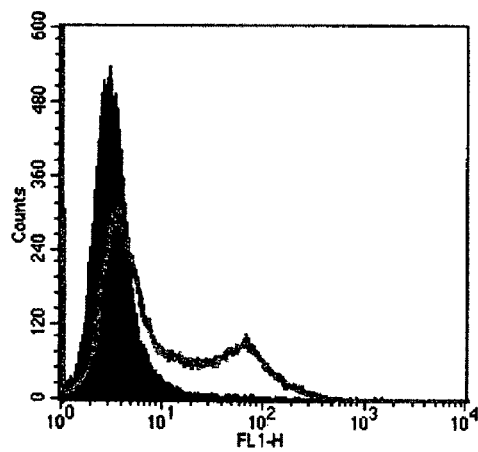
35-273
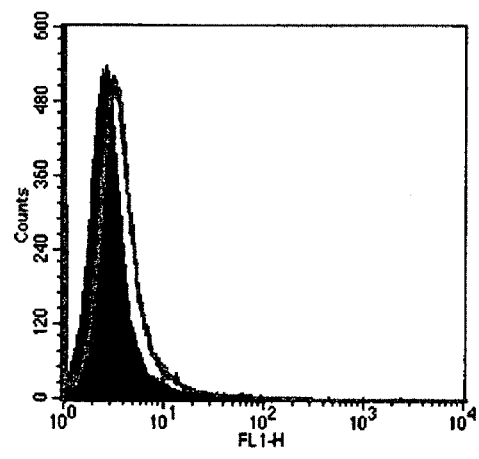
YA14

Fig. 18
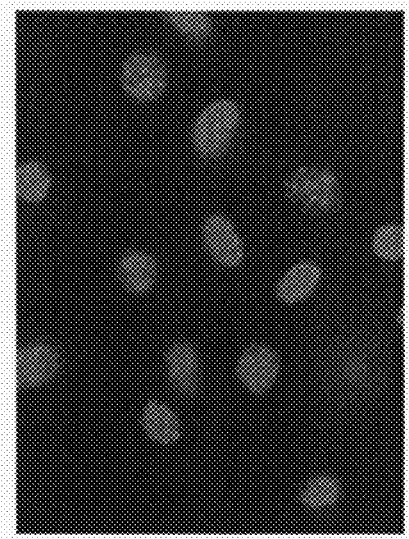
no DNA
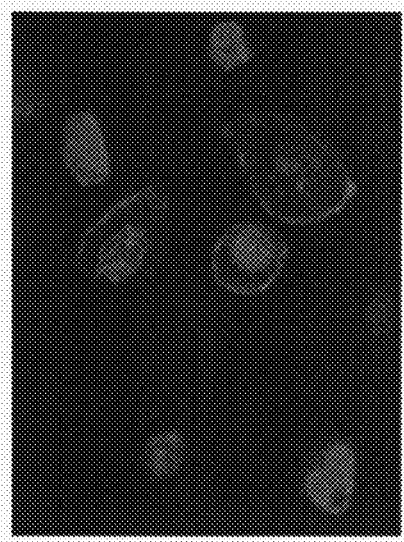
cDNA2
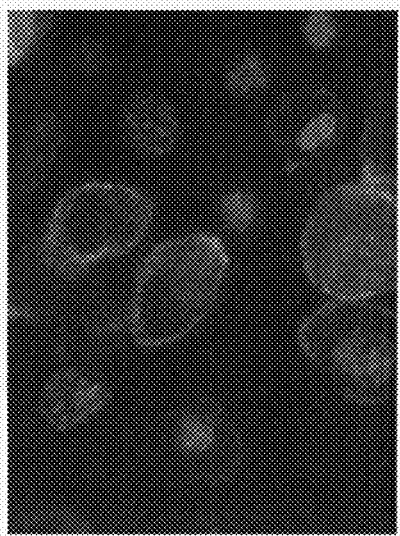
cDNA1

Fig. 21
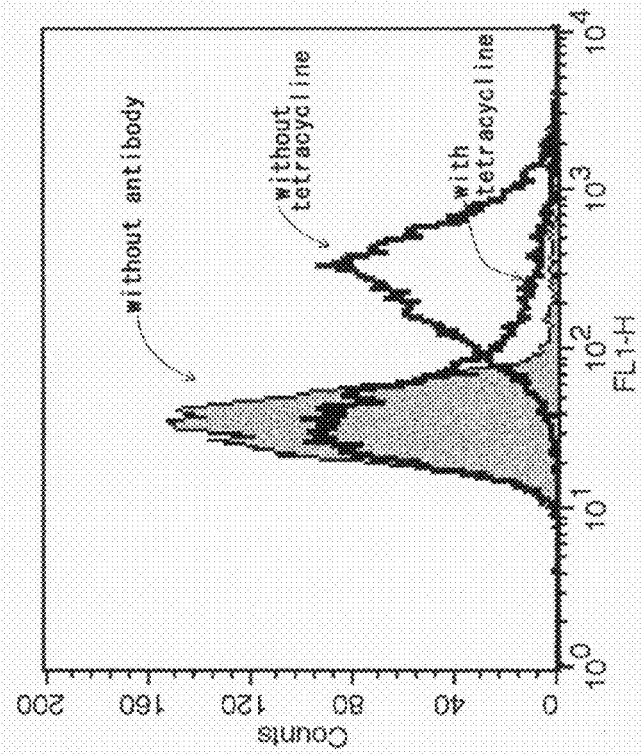
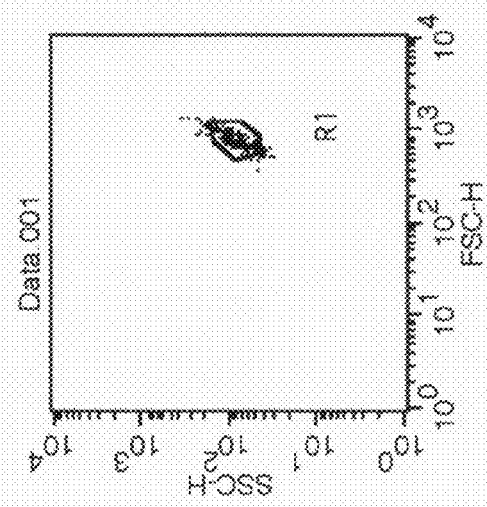

Fig. 25
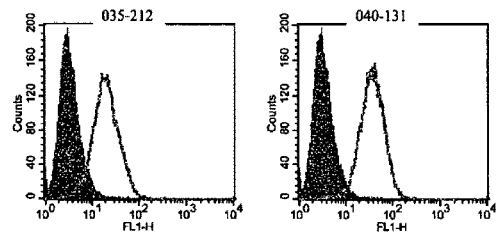
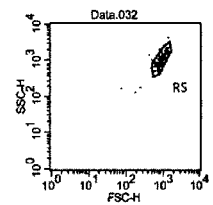
ACHN

Fig. 26
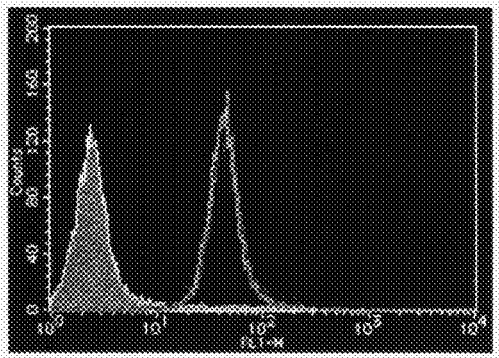
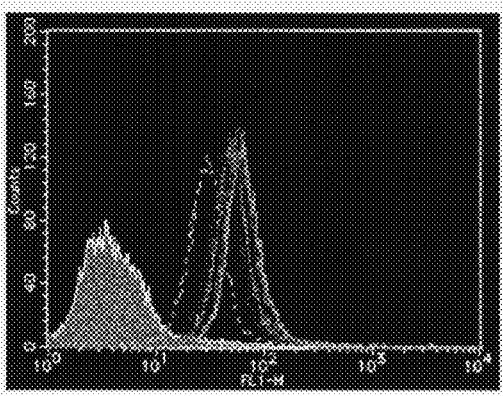

Fig. 28
ED (promoter methylation+)
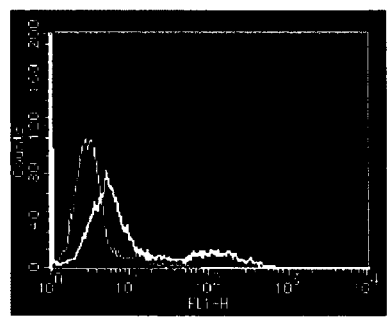
KOB
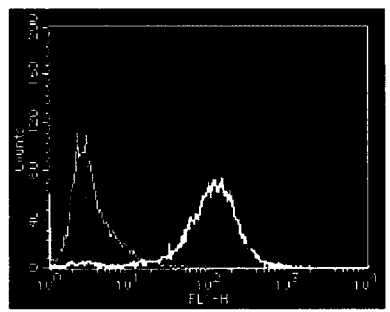
Su9T(promoter methylation+)
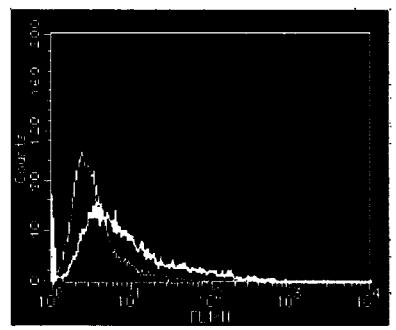
ST1
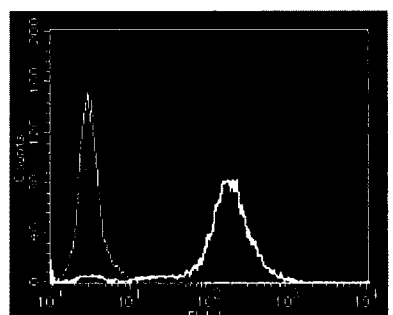
SO4(promoter methylation+)
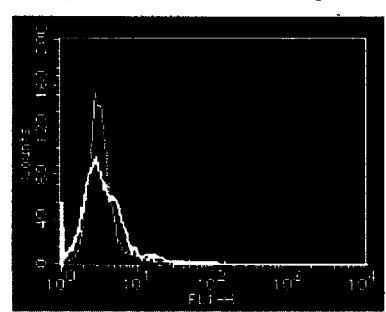
KK1
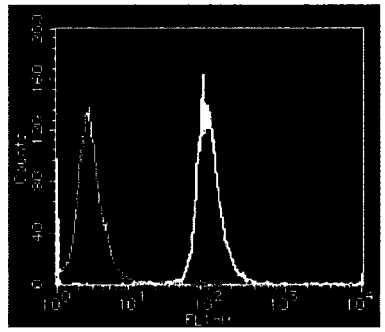

Fig. 29
T-ALL (Non-ATL)
MOLT4
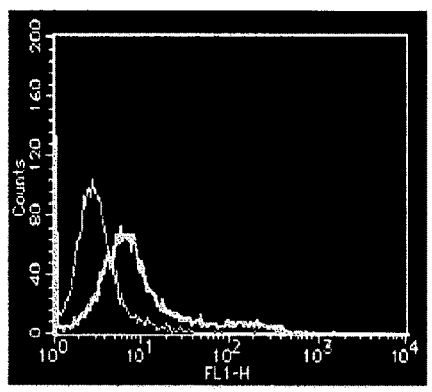
Jurkat
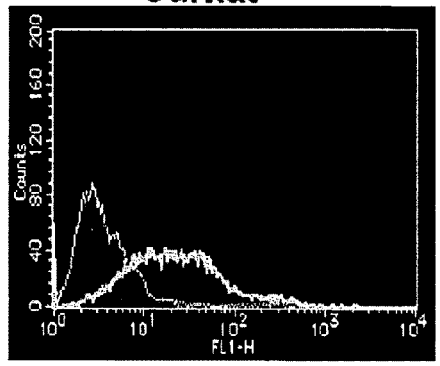
HTLV1 infected cell line
HUT102
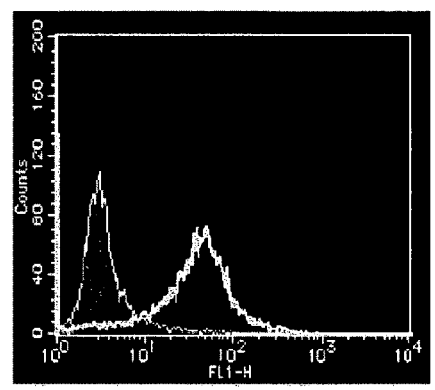
MT-2
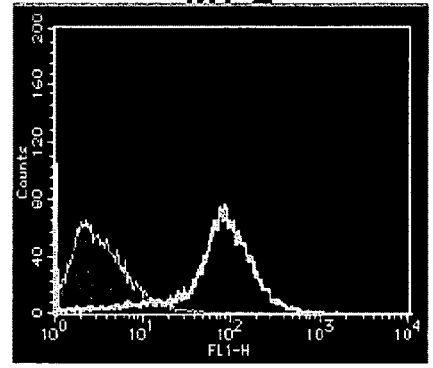

Fig. 31
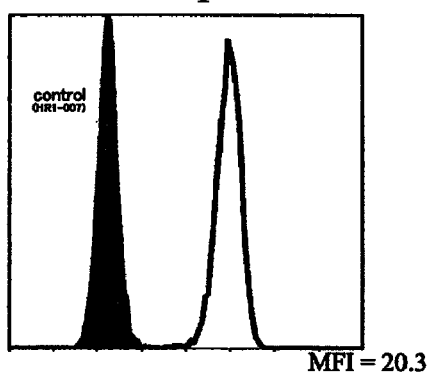
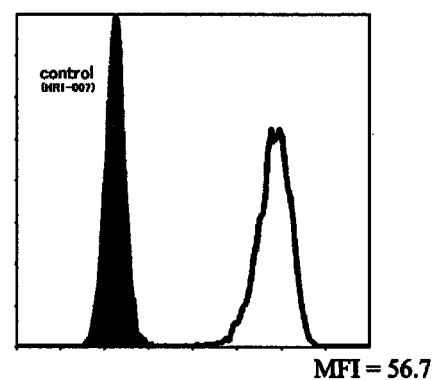
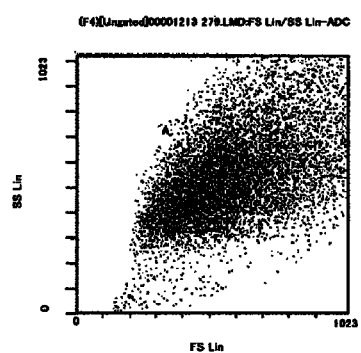

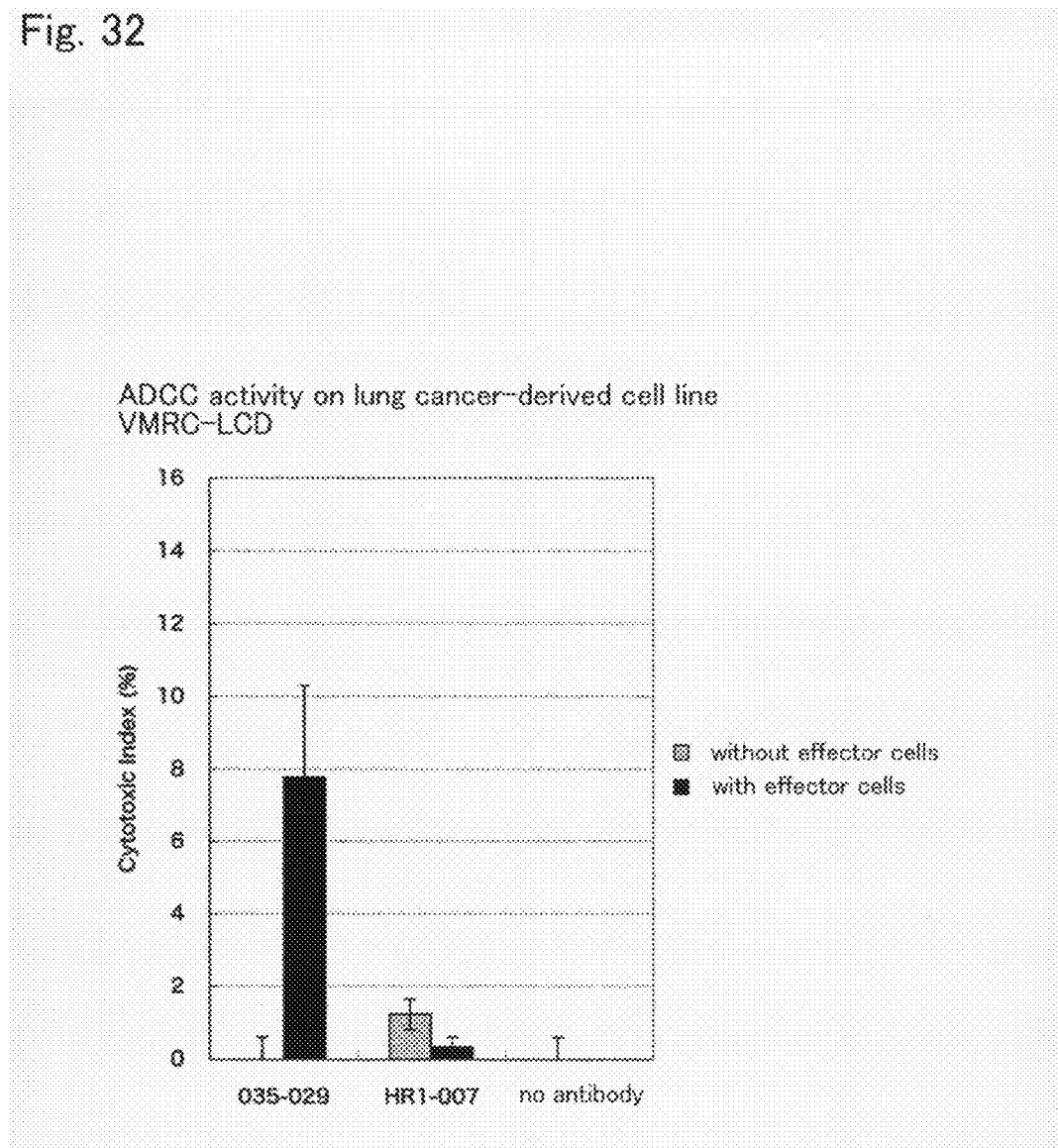

ANTI-IGSF4 ANTIBODY AND UTILIZATION OF THE SAME

TECHNICAL FIELD

The present invention relates to an antibody (anti-IgSF4 antibody) that specifically recognizes IgSF4 that is specifically expressed in cancer cells and the utilization of the same.

BACKGROUND ART

Success in treating breast cancer with Herceptin (non-patent document 1) and malignant B lymphoma with Rituxan (non-patent document 2) has shown that antibodies can be used as therapeutic drugs in treatment of cancers. Some kinds of antibodies form a complex with an antigen molecule existing cell membrane, triggering an ADCC activity (non-patent document 3) and a CDC activity (non-patent document 4) so as to kill the cell expressing antigen. The antigen-antibody complex formation may trigger apoptosis. A lethal action on cells by an antibody is a peculiar function found in cells regardless of whether they are cancer cells or normal cells. Success or failure of development of antibody therapeutic drugs for treating cancers depends upon the discovery of an antigen (a cancer antigen) as a target of an antibody capable of killing all the subjected cancer cells while minimizing the effect (adverse effect) to normal cells.

Because an entire base sequence of human genome has been determined, a primary sequence of amino acid of all proteins coded on the genome can be estimated. Abnormal expression of genes that are not used for normal cells causes canceration. If the gene product thereof is a membrane protein, it becomes a target of an antibody as shown in an example of HER2/Herceptin. Based on this idea, researches for analyzing the qualitative and quantitative difference of transcriptional products between cancer cells and normal cells by using DNA microarray have been carried out in many laboratories all over the world.

[Patent document 1] Translation Publication No. Saihyou 01/062907

[Patent document 2] Translation Publication No. Saihyou 01/096401

[Non-patent document 1] Mass R, et al.: The Concordance Between the Clinical Trials Assay (CTA) and Fluorescence in Situ Hybridization (FISH) in the Herceptin Pivotal Trials.: Proc Am Soci Clin Oncol 19, 75a, 2000

[Non-patent document 2] Berinstein N L, Grillo-López A J, White C A, Bence-Bruckler I, Maloney D, Czuczman M, et al. Association of serum Rituximab (IDEC-C2B8) concentration and anti-tumor response in the treatment of recurrent low-grade or follicular non-Hodgkin's lymphoma. Annals of Oncology 1998, 9:995-1001.

[Non-patent document 3] Bruggemann M., Williams G. T., Bindon C. I., Clark M. R., Walker M. R., Jefferis R., Waldmann H., Neuberger M. S. (1987). Comparison of the effector functions of human immunoglobulin using a matched set of chimeric antibodies. J. Exp. Med., 166, 1351-1361.

[Non-patent document 4] Loos M. (1982). The classical complement pathway: mechanism of activation of the first component by antigen-antibody complexes. Prog. Allergy, 30, 135-192. Mol. Immunol. 1982 May; 19(5): 651-7.

DISCLOSURE OF THE INVENTION

Problems to be Solved by the Invention

The analysis of the difference between cancer cells and normal cells in the order of proteins has been studied by various means including two-dimensional gel electrophoresis used in proteomics study. The remarkable improvement of analyzing instrument such as MS and the like and the expansion of database have significantly enhanced this value of this analysis method. However, for isolating an antibody for a cancer therapeutic drug, the above-mentioned two methods have to undergo a long process that requires much labor and cost in order to achieve an object. Because in the research for analyzing the qualitative and quantitative difference of transcriptional products between cancer cells and normal cells by using a DNA microarray, it is not possible to clearly distinguish the alternative splicing except for transcription products whose presence has been clearly known. Furthermore, when a three-dimensional structure after translation including post-translational modification is taken into consideration, there is left some critical defects as information for aiming the antibody drug development. On the other hand, the analysis of the difference between cancer cells and normal cells in the order of proteins has some serious problems as follows. In the two-dimensional gel electrophoresis used in proteomics study, clear two-dimensional unfolding cannot be achieved because the protein is a membrane protein. In the analysis using multidimensional LC, due to the nature of a solvent and the like to be used for LC, intact materials cannot be analyzed. Furthermore, as an experimental method, in the cases classified in the same cancer (for example, liver cancer), when gene expression patterns are compared in detail in individual cancers, there are many kinds of cases. Whether or not it can be judged that this individual difference in cancers is derived from the properties of cancers has never been clarified by both approaches of the microarray and the proteomics mentioned above. In order to dissolve these problems, the present inventors have prepared a large human antibody library including 100 billions independent clones and carried out various technological development using the library (Japanese Patent Application No. 2004-349783, Translation Publication No. Saihyou 01/062907 (Patent document 1), Translation Publication No. Saihyou 01/096401 (Patent document 2)).

Under the above-mentioned circumstances, it is an object of the present invention to clarify a molecule that is specifically expressed in cancer cells and that is available as a target in treating and diagnosing cancers and to utilize the molecule in medical field and the research field. In particular, the present invention aims to provide an efficacious means in treating cancer by utilizing this molecule.

Means to Solve the Problems

In order to achieve the above-mentioned objects, the present inventors attempt to obtain an antibody specific to liver cancer cells by using scFv-CL antibody phage library (Translation Publication No. Saihyou 01/096401) that is originally developed by the present inventors. As a result, they have succeeded in obtaining a plurality of antibodies specifically bonded to liver cancer cells with high specificity. They also have succeeded in identifying the sequences of the variable regions (VH and VL) of each antibody and succeeded in identifying the CDR thereof. Note here that the obtained antibodies precisely recognize a plurality of epitopese of intact protein on the cell membrane of liver cancer cells.

Then, the present inventors have investigated the efficacy of the obtained antibodies in the diagnosing field. Specifically, they have carried out immunostaining of liver cancer cells and liver cancer tissue by using the obtained antibodies. As a result, they have found that liver cancer cells and liver cancer tissues can be specifically stained. That is to say, the antibodies enable liver cancer cells or liver cancer tissues and normal tissues to be stained in a different colors. On the other hand, when the present inventors have examined the staining property with respect to liver cancer cells having different grades of differentiation (grades of malignancy), they have found a series of constant relation between differentiation and staining property of cells. From this result, it is thought that the use of the successfully obtained antibodies makes it possible to determine the grades of malignancy of liver cancer cells (tissues). As mentioned above, it has been clear that the successfully obtained antibodies are extremely useful in diagnosing liver cancer cells.

Next, the present inventors have attempted to identify protein of antigens of the obtained antibodies, that is, protein specifically expressed in liver cancer cells. After trial and error, they have succeeded in identifying objective protein. When they retrieved a public data base, they have found that the successfully identified protein is registered as IgSF4 (also referred to as BL2, ST17, NECL2, TSLC1, IGSF4A, SYN-CAM, and the like). IgSF4 is thought to be derived from the ORF (open reading frame) existing in 11q23.2 of human chromosome No. 11. IgSF4 is known to be a suppressor gene of, mainly, a lung cancer. It is also reported that IgSF4 is involved in the junction of the brain nerves. Furthermore, it is reported that IgSF4 is expressed in the brain, testis and thyroid gland in normal cells. Remarkable expression of IgSF4 in cells other than the above has never been known. According to the above-mentioned result of the study conducted by the present inventors, it has been newly clarified that IgSF4 can be also used as a liver cancer specific marker.

Furthermore, as to this IgSF4 molecule, it has been reported that the expression difference of IgSF4 is most significant in the microarray analysis of adult T cell leukemia (ATL). The present inventors have thought that the successfully obtained antibody capable of recognizing IgSF4 on the membrane surface can specifically recognize ATL and can be used for diagnosis and treatment of ATL.

The generation of adult T cell leukemia is concentrated in the Southwest area of Japan (carrier rate in each prefecture of Okinawa, Kagoshima, Miyazaki, and Nagasaki reaches about 5%) and Caribbean basin. Adult T cell leukemia is helper T cell leukemia having the worst treating performance and extremely bad prognosis among lymphotrophic diseases. In the present days, it has been clarified that the most important factor for the development of ATL is infection of HTLV-1 (Human T cell Leukemia Virus Type 1) that is a Human Retrovirus. Infants are infected from their mother via breast milk, develop HTLV-1 carrier at the frequency of 5 to 10%, and almost all of them die in two years. It is said that the number of carriers of HTLV-1 all over Japan is about one million and that the number of development of ATL is about 700 annually. Currently, no effective treatment for ATL has been established.

Rituxan (anti-CD20) is a cancer treatment antibody that is currently the most well known. It has already known to exert the treatment performance only to non-Hodgkin's lymphoma. It is thought as a result of the flow cytometry (FCM) that the antibody obtained by the present inventors has a highly specific binding property against IgSF4 expression type ATL, and that diagnosis using this antibody of IgSF4 expression type ATL, or this antibody conjugated with toxin or RI is useful for treatment of the IgSF4 expression type ATL.

On the other hand, when the present inventors have examined the function and effect of the successfully obtained antibody on cancer cells, surprisingly, it has been clarified that a part of the antibodies exerts an ADCC activity (Antibody-dependent Cell-mediated cytotoxicity). That is to say, it has been determined that the cytotoxic activity against cancer cells is high and effective antibody can be obtained as an antibody medicine. Furthermore, with an anti-IgSF antibody, cytotoxicity by ADCC is found. Therefore, it has been clarified that IgSF4 works as an efficacious target in cancer treatment. That is to say, by using an antibody whose target is IgSF4, it is possible to specifically damage cancer cells.

Based on the above-mentioned findings, the present invention provides an isolated antibody having a specific binding property against IgSF4.

The antibody of the present invention has a specific binding property against IgSF4. In one embodiment, the antibody of the present invention exerts cytotoxic activity against IgSF4. In a preferable embodiment, the antibody of the present invention has an ADCC activity via IgSF4. Furthermore, in another preferable embodiment, the antibody of the present invention has a cell-growth activity via IgSF4.

One embodiment of the antibody of the invention is characterized in that the antibody comprises a heavy chain variable region having CDR containing any one of the amino acid sequences of SEQ ID NOs.:2-4, 10-12, 18-20, 26-28, 34-36, 42-44, 50-52, 58-60, 222-224, 230-232, and 238-249, or an amino acid sequence substantially the same thereto, and a light chain variable region having CDR containing any one of the amino acid sequences of SEQ ID NOs.:6-8, 14-16, 22-24, 30-32, 38-40, 46-48, 54-56, 62-64, 226-228, 234-236, and 242-244, or an amino acid sequence substantially the same thereto.

One embodiment of the antibody of the invention is characterized in that the antibody comprises a combination of a heavy chain variable region and a light chain variable region selected from the group consisting of the following a to v.

(a) a combination of a heavy chain variable region having CDR consisting of CDR1 of SEQ ID NO. 2, CDR2 of SEQ ID NO.:3, and CDR3 of SEQ ID NO.:4, or a CDR substantially the same thereto and, a light chain variable region having CDR consisting of CDR1 of SEQ ID NO.:6, CDR2 of SEQ ID NO.:7, and CDR3 of SEQ ID NO.:8, or CDR substantially the same thereto, (b) a combination of a heavy chain variable region having CDR consisting of CDR1 of SEQ ID NO.:10, CDR2 of SEQ ID NO.:11, and CDR3 of SEQ ID NO.:12, or CDR substantially the same thereto and, a light chain variable region having CDR consisting of CDR1 of SEQ ID NO.:14, CDR2 of SEQ ID NO.:15, and CDR3 of SEQ ID NO.:16, or CDR substantially the same thereto, (c) a combination of a heavy chain variable region having CDR consisting of CDR1 of SEQ ID NO.:18, CDR2 of SEQ ID NO.:19, and CDR3 of SEQ ID NO.:20, or CDR substantially the same thereto and, a light chain variable region having CDR consisting of CDR1 of SEQ ID NO.:22, CDR2 of SEQ ID NO.:23, and CDR3 of SEQ ID NO.:24, or CDR substantially the same thereto, (d) a combination of a heavy chain variable region having CDR consisting of CDR1 of SEQ ID NO.:26, CDR2 of SEQ ID NO.:27, and CDR3 of SEQ ID NO.:28, or CDR substantially the same thereto and, a light chain variable region having CDR consisting of CDR1 of SEQ ID NO.:30, CDR2 of SEQ ID NO.:31, and CDR3 of SEQ ID NO.:32, or CDR substantially the same thereto, (e) a combination of a heavy chain variable region having CDR consisting of CDR1 of SEQ ID NO.:34, CDR2 of SEQ ID NO.:35, and CDR3 of SEQ ID NO.:36, or CDR substantially the same thereto and,
a light chain variable region having CDR consisting of CDR1 of SEQ ID NO.:38, CDR2 of SEQ ID NO.:39, and CDR3 of SEQ ID NO.:40, or CDR substantially the same thereto, (f) a combination of a heavy chain variable region having CDR consisting of CDR1 of SEQ ID NO.:42, CDR2 of SEQ ID NO.:43, and CDR3 of SEQ ID NO.:44, or CDR substantially the same thereto and,
a light chain variable region having CDR consisting of CDR1 of SEQ ID NO.:46, CDR2 of SEQ ID NO.:47, and CDR3 of SEQ ID NO.:48, or CDR substantially the same thereto, (g) a combination of a heavy chain variable region having CDR consisting of CDR1 of SEQ ID NO.:50, CDR2 of SEQ ID NO.:51, and CDR3 of SEQ ID NO.:52, or CDR substantially the same thereto and,
a light chain variable region having CDR consisting of CDR1 of SEQ ID NO.:54, CDR2 of SEQ ID NO.:55, and CDR3 of SEQ ID NO.:56, or CDR substantially the same thereto, (h) a combination of a heavy chain variable region having CDR consisting of CDR1 of SEQ ID NO.:58, CDR2 of SEQ ID NO.:59, and CDR3 of SEQ ID NO.:60, or CDR substantially the same thereto and,
a light chain variable region having CDR consisting of CDR1 of SEQ ID NO.:62, CDR2 of SEQ ID NO.:63, and CDR3 of SEQ ID NO.:64, or CDR substantially the same thereto, (i) a combination of a heavy chain variable region of the amino acid sequence of SEQ ID NO.:1 or a sequence substantially the same thereto and, a light chain variable region of the amino acid sequence of SEQ ID NO.:5 or a sequence substantially the same thereto, (j) a combination of a heavy chain variable region of the amino acid sequence of SEQ ID NO.:9 or a sequence substantially the same thereto and, a light chain variable region of the amino acid sequence of SEQ ID NO.:13 or a sequence substantially the same thereto, (k) a combination of a heavy chain variable region of the amino acid sequence of SEQ ID NO.:17 or a sequence substantially the same thereto and, a light chain variable region of the amino acid sequence of SEQ ID NO.:21 or a sequence substantially the same thereto, (l) a combination of a heavy chain variable region of the amino acid sequence of SEQ ID NO.:25 or a sequence substantially the same thereto and, a light chain variable region of the amino acid sequence of SEQ ID NO.:29 or a sequence substantially the same thereto, (m) a combination of a heavy chain variable region of the amino acid sequence of SEQ ID NO.:33 or a sequence substantially the same thereto and, a light chain variable region of the amino acid sequence of SEQ ID NO.:37 or that substantially the same thereto, (n) a combination of a heavy chain variable region of the amino acid sequence of SEQ ID NO.:41 or a sequence substantially the same thereto and, a light chain variable region of the amino acid sequence of SEQ ID NO.:45 or a sequence substantially the same thereto, (o) a combination of a heavy chain variable region of the amino acid sequence of SEQ ID NO.:49 or a sequence substantially the same thereto and, a light chain variable region of the amino acid sequence of SEQ ID NO.:53 or a sequence substantially the same thereto, (p) a combination of a heavy chain variable region of the amino acid sequence of SEQ ID NO.:57 or a sequence substantially the same thereto and, a light chain variable region of the amino acid sequence of SEQ ID NO.:61 or a sequence substantially the same thereto, (q) a combination of a heavy chain variable region having CDR consisting of CDR1 of SEQ ID NO.:222, CDR2 of SEQ ID NO.:223, and CDR3 of SEQ ID NO.:224, or CDR substantially the same thereto and,
a light chain variable region having CDR consisting of CDR1 of SEQ ID NO.:226, CDR2 of SEQ ID NO.:227, and CDR3 of SEQ ID NO.:228, or CDR substantially the same thereto, (r) a combination of a heavy chain variable region having CDR consisting of CDR1 of SEQ ID NO.:230, CDR2 of SEQ ID NO.:231, and CDR3 of SEQ ID NO.:232, or CDR substantially the same thereto and,
a light chain variable region having CDR consisting of CDR1 of SEQ ID NO.:234, CDR2 of SEQ ID NO.:235, and CDR3 of SEQ ID NO.:236, or CDR substantially the same thereto, (s) a combination of a heavy chain variable region having CDR consisting of CDR1 of SEQ ID NO.:238, CDR2 of SEQ ID NO.:239, and CDR3 of SEQ ID NO.:240, or CDR substantially the same thereto and,
a light chain variable region having CDR consisting of CDR1 of SEQ ID NO.:242, CDR2 of SEQ ID NO.:243, and CDR3 of SEQ ID NO.:244, or CDR substantially the same thereto, (t) a combination of a heavy chain variable region of the amino acid sequence of SEQ ID NO.:221 or a sequence substantially the same thereto and, a light chain variable region of the amino acid sequence of SEQ ID NO.:225 or a sequence substantially the same thereto, (u) a combination of a heavy chain variable region of the amino acid sequence of SEQ ID NO.:229 or a sequence substantially the same thereto and, a light chain variable region of the amino acid sequence of SEQ ID NO.:233 or a sequence substantially the same thereto, (v) a combination of a heavy chain variable region of the amino acid sequence of SEQ ID NO.:237 or a sequence substantially the same thereto and, a light chain variable region of the amino acid sequence of SEQ ID NO.:241 or a sequence substantially the same thereto.

In one embodiment of the invention, there is provided a human antibody or a humanized antibody. Also, the antibody of the invention is constructed in a various configuration. For instance, the antibody of the invention is constructed as IgG, Fab, Fab', F(ab')$_2$, scFv, or dsFv antibody.

Further, the invention provides CDR of an anti-IgSF4 antibody. The CDR of the invention contains any one of the amino acid sequences of SEQ ID NOs.:2-4, 6-8, 10-12, 14-16, 18-20, 22-24, 26-28, 30-32, 34-36, 38-40, 42-44, 46-48, 50-52, 54-56, 58-60, 62-64, 222-224, 226-228, 230-232, 234-236, 238-240, and 242-244.

Furthermore, the present invention provides an isolated nucleic acid molecule encoding a heavy chain variable region or a light chain variable region of the antibody of the present invention or a CDR of the present invention.

The present invention further relates to a vector carrying the molecule in a way in which it can be expressed and to a transformant into which the nucleic acid molecule is introduced.

As another aspect, the present invention provides a cancer treatment drug including the antibody of the present invention as an active ingredient.

As a further aspect, the present invention provides a reagent including an anti-IgSF4 antibody and used for examination of liver cancer, examination of adult T cell leukemia, study of liver cancer, or study of adult T cell leukemia. Furthermore, the present invention also provides a kit including the reagent and an instruction, which is used for examination of liver cancer, examination of adult T cell leukemia, study of liver cancer, or study of adult T cell leukemia.

As a further aspect, the present invention provides a method for obtaining information for diagnosing liver cancer or adult T cell leukemia, the method comprising the steps:
(1) preparing subjected cells isolated from a living body; and
(2) detecting IgSF4 in the subjected cells.

Furthermore, the present invention also provides a method for determining a grade of malignancy of liver cancer cells, the method comprising the steps of:
(1) preparing subjected liver cells separated from a living body; and
(2) detecting IgSF4 in the subjected liver cells.

Furthermore, the present invention provides a method for screening a compound specifically bonded to liver cancer cells or adult T cell leukemia cells, the method comprising the steps:
(1) bringing IgSF4 into contact with a test compound;
(2) evaluating the binding property of the test compound to IgSF4.

Furthermore, the present invention provides a method for screening an IgSF4 binding compound efficacious in treating liver cancer, the method comprising the steps of:
(1) preparing cells expressing an IgSF4 gene;
(2) bringing the cells into contact with a test compound; and
(3) evaluating killing or decrease of cancer cells.

Furthermore, the present invention provides a method of screening an IgSF4 binding compound efficacious in treating adult T cell leukemia, the method comprising the steps of:
(1) preparing adult T cell leukemia cells;
(2) bringing the cells into contact with a test compound; and
(3) evaluating killing or decrease of cancer cells.

The present invention provides use of IgSF4 as an antigen. In this use, as an antigen for preparing a cancer treating antibody, IgSF4 is used. Herein, as the IgSF4, any one of the following IgSF4 can be used.
(1) IgSF4 generated by using an expression system of *E. coli*;
(2) IgSF4 secreted in a culture medium by using an expression system of animal cells;
(3) IgSF4 expressed on the cell surface by using an expression system of animal cells; and
(4) IgSF4 secreted in a culture medium or expressed on the cell surface by using an expression system of animal cells expressing T antigen and capable of transitional expression.

On the other hand, an extracellular region of the IgSF4 may be used as an antigen so as to prepare an antibody for treating cancer.

The present invention provides a method for treating cancer. The method includes administering an anti-IgSF4 antibody to a subject carrying cancer cells. As the anti-IgSF4 antibody, the antibody having an ADCC activity is preferably used. Furthermore, the present invention also provides a method for treating adult T cell leukemia. The method includes administering an anti-IgSF4 antibody to a subject carrying adult T cell leukemia cells.

BRIEF DESCRIPTION OF THE DRAWINGS

FIG. 3-1 is a diagram showing the base sequence (SEQ ID NO.: 171) of an insert section of pscFvCA9-E8VHdVLd and the amino acid sequence (SEQ ID NO.: 172) coded by the corresponding base sequence.

FIG. 3-2 is a continuation of FIG. 3-1.

FIG. 4-1 is a diagram showing the base sequence (SEQ ID NO.: 175) of an insert section of pscFvCA-E8VHd, and the restriction enzyme site and the amino acid sequence (SEQ ID NO.: 176) encoded by the corresponding base sequence.

FIG. 4-2 is a continuation of FIG. 4-1.

FIG. 5 is a view showing a process of screening an antibody clone specific to a liver cancer cells.

FIG. 6 is a view showing results of staining of tissues by using a selected antibody clone. Herein, antibody staining was carried out with respect to three kinds of tissues derived from patients and the staining was investigated for cancer specificity.

FIG. 11 is a view showing a result of cancer cell stained with antibody clone 035-273. The used cell is HepG2 cell, Nuk-1 cell and HLF cell in this order from the upper part in the left column, and HuH-7 cell and THLE-3 cell in this order from the upper part in the right column.

FIG. 12-1 is a diagram showing a sequence of the cp3 type antibody obtained as an antibody clone specific to liver cancer cells.

FIG. 12-2 is a continuation of FIG. 12-1.

FIG. 13 shows results of the western blotting of immunoprecipitated product obtained by using an antibody clone specific to liver cancer cells. After immunoprecipitation, SDS-PAGE was carried out and detection with a 035-283 antibody is carried out. Lane 1: sample obtained by immunoprecipitation (IP) using a iysate of a solid phased 035-283 antibody clone and HLF (poorly differentiated human liver cancer cell line). Lane 2: 035-283 antibody clone and HLF (replication of an experiment of lane 1). Lane 3: 035-283 antibody and HepG2 (cell line derived from human liver cancer). Lane 4: 035-283 antibody and HepG2 (replication of an experiment of lane 3). A band was excised from lanes 1 to 4 and the amino acid sequence of protein was determined by using a mass spectrometer.

FIG. 14 shows an amino acid sequence of the identified antigen. The portion written in italic (cf: NLMIDIQK) that is a sequence of a fragment obtained by MSMS is a sequence identified by the method using ESI-ionTRAP-MSMS. On the other hand, the underlined portion (cf: QTIYFR) shows a fragment identified by a PMF method using MALDI-TOF-MS. The portion shown in italic and provided with an under line (cf: GTYFTHEAK) is a portion identified by both MS/MS and PMF method. It was confirmed that this antigen underwent remarkable sugar chain modification. A candidate amino acid that undergoes the sugar chain modification is shown by N.

FIG. 15-1 is the sequence of the isolated IgSF4 cDNA clone (IgSF4N: cDNA1).

FIG. 15-2 is a continuation of FIG. 15-1.

FIG. 16-1 is the sequence of the isolated IgSF4 cDNA clone (IgSF4X: cDNA2).

FIG. 16-2 is a continuation of FIG. 16-1.

FIG. 17 is a graph showing results of IgSF4 expression experiment (FCM analysis result). Violet: no gene was transferred, red: cDNA1 was transferred; and green: cDNA2 was transferred. Left graph: detection results of 035-273 antibody. Right graph: detection results of an anti-influenza antibody YA14.

FIG. 18 is a view showing results of IgSF4 expression experiment (results of staining cells). Cell into which cDNA1 was transferred, cell into which cDNA2 was transferred and cell into which no genes were transferred are shown in this order from the left.

FIG. 21 shows FCM analysis results in RNAi experiment.

FIG. 25 shows the FCM reactivity of an isolated antibody clone against human kidney cancer derived cell line ACHN.

FIG. 26 shows the FCM reactivity of an isolated antibody clone against human ATL derived cell line KK1.

FIG. 28 shows the FCM reactivity of isolated antibody clone 035-212 against human ATL derived cell lines ED, Su9T, and SO4 in which the IgSF4 promoter is methylated and against human ATL derived cell lines KK1, KOB and ST1 in which the IgSF4 promoter is not methylated.

FIG. 29 shows the FCM reactivity of an isolated antibody clone against human non-ATL derived cell line MOLT4 (human T cell leukemia derived cell line) and Jurkat, and HUT102 and MT-2 derived from human T cell directive virus infected (HTLV infected cell line) T cell lymphoma.

FIG. 31 shows the FCM reactivity of IgG type antibody 035-029 against A431 cell line.

FIG. 32 shows the result of evaluation of the ADCC activity of antibody clone 035-029. Lung cancer derived cell nucleus VMRC-LCD was used as a target cell.

Figure 1:
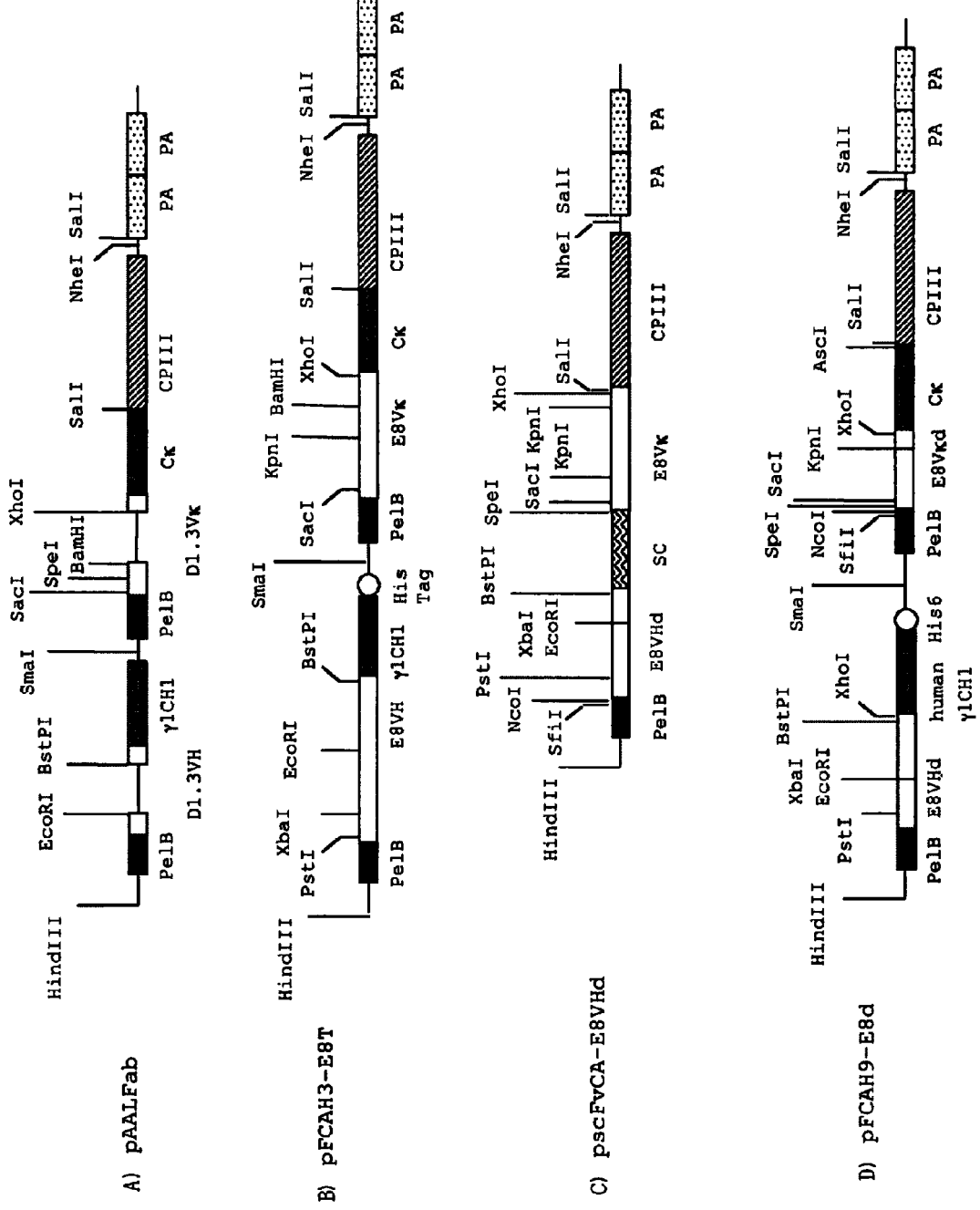
FIG. 1 is a schematical diagram showing the vector used in the preparation of a scFv antibody gene library.

THE BEST MODE OF CARRYING OUT THE INVENTION (Terms)

For convenience of description, definitions of certain terms employed in this specification are summarized below.

In this specification, the term "comprise" or "comprising" is used to refer to include the meaning of "consist of". Therefor, for example, the description: "a product (or method) comprising a plurality of elements (members)" is naturally considered to include the meaning: "a product (or method) consisting of a plurality of elements (members)."

An "isolated" signifies a state that is taken out from the original environment (for example, natural environment for natural materials), that is, a state that is different from the original state due to the artificial operation.

The term "isolated nucleic acid" is typically one which is separated from other nucleic acids co-existing in the natural state when the nucleic acid is a naturally occurring nucleic acid (for example, a nucleic acid in a living human body). However, an isolated nucleic acid may include a part of other nucleic acid components, for example, nucleic acid sequences flanking in the natural state. Preferably, an "isolated nucleic acid" is substantially free of other DNA components (including DNA sequences which naturally flank the nucleic acid) co-existing in a natural state in, for example, the genomic DNA.

Preferably, an "isolated nucleic acid" such as a cDNA molecule can be substantially free of other cellular components or culture medium when produced by recombinant techniques. Similarly, preferably, an "isolated nucleic acid" such as a dNTP can be substantially free of precursors (raw materials), other chemicals used in chemical synthesis, or the like, when chemically synthesized.

When a nucleic acid is present as a part of a vector or a composition, or a nucleic acid is present in a cell as an exogenous molecule, the nucleic acid may be an "isolated nucleic acid" as long as it is present as a result of an artificial operation. Unless otherwise mentioned, a "nucleic acid" simply described in the specification includes a "nucleic acid in an isolated state".

On the other hand, an "isolated antibody" does not include an antibody that is a naturally occurring antibody and that has not undergone any external operations (artificial operation), that is, an antibody that has been produced in an individual body and remains therein. Note here that the isolated antibody is typically an antibody that is free of other antibodies, that is, an antibody that is present as a single material (as an aggregate of homogenious). In the case of a CDR region, the "isolated" state includes a state in which the antibody is present together with other region of the antibody in addition to a state as a single material. That is to say, the term "isolated CDR" includes not only a CDR that is present as a single body but also a CDR that is present as a part of an isolated antibody.

The term "substantially identical" used regarding amino acid sequences signifies that the difference in sequence between two amino acid sequences to be compared is relatively small and the difference on the sequence does not give a substantial effect on the specific binding property against IgSF4. An amino acid sequence, which is thought to include a part of modification and may be provided to the reference amino acid sequence in the range which the specific binding property against IgSF4 is not effected, can be a substantially identical amino acid sequence. The "part of modification of the amino acid sequence" herein denotes that change occurs in an amino acid sequence due to deletion or substitution of one to several amino acids constituting the amino acid sequence, or addition or insertion of one to several amino acids constituting the amino acid sequence, or the combination thereof. The position of mutation of the amino acid sequence is not particularly limited and may occur in a plurality of positions. The plurality herein signifies a numerical value corresponding to one within, for example, 10% of total amino acids constituting the amino acid sequence. Preferably, it is a numerical value corresponding to one within, for example, 5% of total amino acids. Further preferably, it is a numerical value corresponding to one within, for example, 1% of total amino acids.

Whether or not two amino acids are substantially identical can be determined by comparing the binding specificity of an antibody including each amino acid sequence (the sequence of other region is identical) against IgSF4 (hereinafter, unless otherwise noted, "specificity" signifies "specificity against IgSF4"). For example, when the dissociation constant (Kd) of the reference antibody in the environment of physiological saline is denoted by A, if Kd of the antibody of the subject to be compared is in the range from $A \times 10^{-1}$ to $A \times 10$, substantially identical property can be recognized.

The term "nucleic acid" used herein includes DNA (including cDNA and genomic DNA), RNA (including mRNA), a DNA analogue and an RNA analogue. The form of nucleic acid of the present invention is not particularly limited. That is to say, it may be any of single stranded and double stranded. Preferably, it is a double stranded DNA. Furthermore, codon degeneracy is considered. That is to say, in the case of nucleic acid coding for protein, the nucleic acid may include any base sequences as long as the protein can be obtained as an expression product. In this specification, a "nucleic acid encoding a certain protein (for example, an antibody)" denotes a nucleic acid from which the protein is obtained when it is expressed. The nucleic acid includes not only a nucleic acid having a base sequence corresponding to the amino acid sequence of the protein but also a nucleic acid obtained by adding a sequence that encodes no amino acid sequence to the above-mentioned nucleic acid (for example, DNA including one or a plurality of introns).

"IgSF4" is an abbreviated name of Immunoglobulin super-family member 4 and also referred to as BL2, ST17, NECL2, TSLC1, IGSF4A, SYNCAM and sTSLC-1. IgSF4 is thought to be expressed from 11q23.2 of human chromosome No. 11. It has been reported that IgSF4 is expressed specifically in lung cancer as a suppressor gene and that IgSF4 is involved in the junction of brain nerves, and the like (Biederer T et al. Science. 2002 Aug 30;297(5586):1525-31). You can see the details of the sequence information of IgSF4 and the related reports issued to date in the homepage of NCBI (Accession No. NM_01433, Definition: *Homo sapiens* immunoglobulin superfamily, member 4 (IGSF4), mRNA). Note here that the amino acid sequence and the base sequence of IgSF4 are shown in SEQ ID NO.: 145 and SEQ ID NO.: 146, respectively.

In the present invention, a "method of determining the grade of malignancy" is a method for determining the grade of malignancy in the subjected liver cells. The term "determination of the grade of malignancy" is used to include the concept of discrimination between benign or malignant." In general, the grade of malignancy of cancers is evaluated by using the grade of differentiation. In general, the cancer cells are classified into well-differentiated cancer, moderately differentiated cancer, poorly differentiated cancer, and undifferentiated cancer. The lower the grade of differentiation is, the higher the grade of malignancy is. The index for measuring the grade of malignancy (differenciation) employs N/C ratio. The N/C ratio is a ratio of nucleus and cytoplasm. In general, the cancer cells with high grade of differentiation (well-differentiated cancer cells) have low N/C ratio and relatively large cell size. On the other hand, the cancer cells with low grade of differentiation (poorly differentiated cancer cells) have generally high N/C ratio. In general, undifferentiated cancer cells have high N/C ratio and small cell size.

Well-differentiated cancer cells hold many of the natures of the original tissue. In well-differentiated cancer cells, the infiltrating ability or the metastaticity is not so high. On the other hand, as the grade of differentiation becomes lower, it becomes more difficult to understand the origin of the cell and the infiltrating ability or the metastaticity is increased. Cancer cells with low grade of differentiation are difficult to be treated. In undifferentiated cancers, the prognosis is extremely bad.

In this specification, if necessary, the following abbreviations (in brackets) are used in accordance with the practice.

Heavy chain (H-chain), light chain (L-chain), heavy chain variable region (VH), light chain variable region (VL), complementarity determining region (CDR), first complementarity determining region (CDR1), second complementarity determining region (CDR2), third complementarity determining region (CDR3), first complementarity determining region of heavy chain (VH CDR1), second complementarity determining region of heavy chain (VH CDR2), third complementarity determining region of heavy chain (VH CDR3), first complementarity determining region of light chain (VL CDR1), second complementarity determining region of light chain (VL CDR2), and third complementarity determining region of light chain (VL CDR3).

The first aspect of the present invention relates to an antibody having a specific binding property against IgSF4, that is, an anti-IgSF4 antibody. In the preferable embodiment, the antibody of the present invention has an ADCC activity. As shown in the below mentioned Examples, the present inventors have succeeded in identifying IgSF4 that is a cell membrane surface antigen molecule specific to liver cancer by a unique method using a phage antibody library and obtaining eleven kinds of antibodies (035-029 antibody, 035-212 antibody, 035-215 antibody, 035-273 antibody, 035-283 antibody, 040-131 antibody, 051-054 antibody, 051-181 antibody, 051-129 antibody, 035-130 antibody, and 035-169 antibody) having high specificity against IgSF4. Since these antibodies recognize the extracellular domain of accessible IgSF4 that is in state in which it is expressed on the cell membrane surface, they can undergo cell/tissue staining. As a result of analysis of sequence of variable region of each antibody, the below-mentioned sequence information was obtained. Note here that following the names of antibodies, the amino acid sequence of the heavy chain variable region; the amino acid sequence of the heavy chain CDR1; the amino acid sequence of the heavy chain CDR2; the amino acid sequence of the heavy chain CDR3; the amino acid sequence of the light chain variable region; the amino acid sequence of the light chain CDR1; the amino acid sequence of the light chain CDR2; the amino acid sequence of the light chain CDR3 are sequentially shown in this order.

035-029 Antibody SEQ ID NO.: 1(VH);
SEQ ID NO.: 2(VH CDR1); SEQ ID NO.: 3(VH CDR2);
SEQ ID NO.: 4(VH CDR3); SEQ ID NO.: 5(VL);
SEQ ID NO.: 6(VL CDR1); SEQ ID NO.: 7(VL CDR2);
SEQ ID NO.: 8(VL CDR3)

035-212 Antibody SEQ ID NO.: 9(VH); SEQ ID NO.: 10
(VH CDRl); SEQ ID NO.: 11(VH CDR2); SEQ ID NO.:12
(VH CDR3); SEQ ID NO.: 13(VL); SEQ ID NO.: 14

-continued
(VL CDR1); SEQ ID NO.: 15(VL CDR2); SEQ ID NO.: 16
(VL CDR3)

035-215 Antibody SEQ ID NO.: 17(VH);
SEQ ID NO.: 18(VH CDR1); SEQ ID NO.: 19(VH CDR2);
SEQ ID NO.: 20(VH CDR3); SEQ ID NO.: 21(VL);
SEQ ID NO.: 22(VL CDR1); SEQ ID NO.: 23(VL CDR2);
SEQ ID NO.: 24(VL CDR3)

035-273 Antibody SEQ ID NO.: 25(VH);
SEQ ID NO.: 26( VH CDR1); SEQ ID NO.: 27(VH CDR2);
SEQ ID NO.: 28(VH CDR3); SEQ ID NO.: 29(VL);
SEQ ID NO.: 30(VL CDR1); SEQ ID NO.: 31(VL CDR2);
SEQ ID NO.: 32(VL CDR3)

035-283 Antibody SEQ ID NO.: 33(VH);
SEQ ID NO.: 34(VH CDR1); SEQ ID NO.: 35(VH CDR2);
SEQ ID NO.: 36(VH CDR3); SEQ ID NO.: 37(VL);
SEQ ID NO.: 38(VL CDR1); SEQ ID NO.: 39(VL CDR2);
SEQ ID NO.: 40(VL CDR3)

040-131 Antibody SEQ ID NO.: 41(VH);
SEQ ID NO.: 42(VH CDR1); SEQ ID NO.: 43(VH CDR2);
SEQ ID NO.: 44(VH CDR3); SEQ ID NO.: 45(VL);
SEQ ID NO.: 46 (VL CDR1); SEQ ID NO.: 47(VL CDR2);
SEQ ID NO.: 48(VL CDR3)

051-054 Antibody SEQ ID NO.: 49(VH);
SEQ ID NO.: 50(VH CDR1); SEQ ID NO.: 51(VH CDR2);
SEQ ID NO.: 52(VH CDR3); SEQ ID NO.: 53(VL);
SEQ ID NO.: 54(VL CDR1); SEQ ID NO.: 55(VL CDR2);
SEQ ID NO.: 56(VL CDR3)

051-181 Antibody SEQ ID NO.: 57(VH);
SEQ ID NO.: 58(VH CDR1); SEQ ID NO.: 59(VH CDR2);
SEQ ID NO.: 60(VH CDR3); SEQ ID NO.: 61(VL);
SEQ ID NO.: 62(VL CDR1); SEQ ID NO.: 63(VL CDR2);
SEQ ID NO.: 64(VL CDR3)

051-129 Antibody SEQ ID NO.: 221(VH);
SEQ ID NO.: 222(VH CDR1); SEQ ID NO.: 223(VH
CDR2); SEQ ID NO.: 224(VH CDR3); SEQ ID NO.: 225
(VL); SEQ ID NO.: 226(VL CDR1); SEQ ID NO.: 227(VL
CDR2); SEQ ID NO.: 228(VL CDR3)

035-130 Antibody SEQ ID NO.: 229(VH);
SEQ ID NO.: 230(VH CDR1);
SEQ ID NO.: 231(VH CDR2); SEQ ID NO.: 232( VH
CDR3); SEQ ID NO.: 233(VL); SEQ ID NO.: 234(VL
CDR1); SEQ ID NO.: 235(VL CDR2); SEQ ID NO.: 236
(VL CDR3)

035-169 Antibody SEQ ID NO.: 237(VH);
SEQ ID NO.: 238(VH CDR1); SEQ ID NO.: 239
(VH CDR2); SEQ ID NO.: 240(VH CDR3);
SEQ ID NO.: 241(VL); SEQ ID NO.: 242(VL CDR1);
SEQ ID NO.: 243(VL CDR2); SEQ ID NO.: 244(VL CDR3)

The variable region of the antibody of the present invention includes at least a part the CDR of the anti-IgSF4 antibody that has been successfully obtained by the present inventors or an amino acid sequence that is substantially identical thereto. Note here that in the following description, when a certain amino acid sequence is described, unless it is clear that the amino acid sequence itself is described, the amino acid sequence denotes "the certain amino acid or an amino acid that is substantially identical thereto." For example, the description of the amino acid sequence of SEQ ID NO.: 1 signifies "the amino acid sequence of SEQ ID NO.: 1 or amino acid substantially identical thereto."

Concretely, for instance, the heavy chain variable region of the antibody of the invention contains, as a part or a whole of CDR, at least one amino acid sequence (for instance, contains as CDR3), preferably at least two amino acid sequences (for instance, contained as CDR2 and CDR3), more preferably at least three amino acid sequences (namely, contains as CDR1-3), which is (are) selected from the group consisting of (1) the amino acid sequence of SEQ ID NO.:2, (2) the amino acid sequence of SEQ ID NO.:3, (3) the amino acid sequence of SEQ ID NO.:4, (4) the amino acid sequence of SEQ ID NO.:10, (5) the amino acid sequence of SEQ ID NO.:11, (6) the amino acid sequence of SEQ ID NO.:12, (7) the amino acid sequence of SEQ ID NO.:18, (8) the amino acid sequence of SEQ ID NO.:19, (9) the amino acid sequence of SEQ ID NO.:20, (10) the amino acid sequence of SEQ ID NO.:26, (11) the amino acid sequence of SEQ ID NO.:27, (12) the amino acid sequence of SEQ ID NO.:28, (13) the amino acid sequence of SEQ ID NO.:34, (14) the amino acid sequence of SEQ ID NO.:35, (15) the amino acid sequence of SEQ ID NO.:36, (16) the amino acid sequence of SEQ ID NO.:42, (17) the amino acid sequence of SEQ ID NO.:43, (18) the amino acid sequence of SEQ ID NO.:44, (19) the amino acid sequence of SEQ ID NO.:50, (20) the amino acid sequence of SEQ ID NO.:51, (21) the amino acid sequence of SEQ ID NO.:52, (22) the amino acid sequence of SEQ ID NO.:58, (23) the amino acid sequence of SEQ ID NO.:59, (24) the amino acid sequence of SEQ ID NO.:60, (49) the amino acid sequence of SEQ ID NO.:222, (50) the amino acid sequence of SEQ ID NO.:223, (51) the amino acid sequence of SEQ ID NO.:224, (52) the amino acid sequence of SEQ ID NO.:230, (53) the amino acid sequence of SEQ ID NO.:231, (54) the amino acid sequence of SEQ ID NO.:232, (55) the amino acid sequence of SEQ ID NO.:238, (56) the amino acid sequence of SEQ ID NO.:239, and (57) the amino acid sequence of SEQ ID NO.:240. Herein, the above-described (1), (4), (7), (10), (13), (16), (19), (22), (49), (52), and (55) are preferably contained as CDR1, in case that it is contained as CDR of a variable region. Similarly, the above-described (2), (5), (8), (11), (14), (17), (20), (23), (50), (53), and (56) are preferably contained as CDR2, and the above-described (3), (6), (9), (12), (15), (18), (21), (24), (51), (54), and (57) are preferably contained as CDR3.

On the other hand, the light chain variable region of the antibody of the invention contains, as a part or a whole of CDR, at least one amino acid sequence (for instance, contains as CDR3), preferably at least two amino acid sequences (for instance, contains as CDR2 and CDR3), more preferably at least three amino acid sequences (namely, contains as CDR1-3), which is (are) selected from the group consisting of (25) the amino acid sequence of SEQ ID NO.:6, (26) the amino acid sequence of SEQ ID NO.:7, (27) the amino acid sequence of SEQ ID NO.:8, (28) the amino acid sequence of SEQ ID NO.: 14, (29) the amino acid sequence of SEQ ID NO.:15, (30) the amino acid sequence of SEQ ID NO.:16, (31) the amino acid sequence of SEQ ID NO.:22, (32) the amino acid sequence of SEQ ID NO.:23, (33) the amino acid sequence of SEQ ID NO.:24, (34) the amino acid sequence of SEQ ID NO.:30, (35) the amino acid sequence of SEQ ID NO.:31, (36) the amino acid sequence of SEQ ID NO.:32, (37) the amino acid sequence of SEQ ID NO.:38, (38) the amino acid sequence of SEQ ID NO.:39, (39) the amino acid sequence of SEQ ID NO.:40, (40) the amino acid sequence of SEQ ID NO.:46, (41) the amino acid sequence of SEQ ID NO.:47, (42) the amino acid sequence of SEQ ID NO.:48, (43) the amino acid sequence of SEQ ID NO.:54, (44) the amino acid sequence of SEQ ID NO.:55, (45) the amino acid sequence of SEQ ID NO.:56, (46) the amino acid sequence of SEQ ID NO.:62, (47) the amino acid sequence of SEQ ID NO.:63, (48) the amino acid sequence of SEQ ID NO.:64, (58) the amino acid sequence of SEQ ID NO.:, (59) the amino acid sequence of SEQ ID NO.:, (60) the amino acid sequence of SEQ ID NO.:, (61) the amino acid sequence of SEQ ID NO.:, (62) the amino acid sequence of SEQ ID NO.:, (63) the amino acid sequence of SEQ ID NO.:, (64) the amino acid sequence of SEQ ID NO.:, (65) the amino acid sequence of SEQ ID NO.:, and (66) the amino acid sequence of SEQ ID NO.:. Herein, the above-described (25), (28), (31), (34), (37), (40), (43), (46), (58), (61), and (64) are preferably contained as CDR1, in case that it is contained as CDR of a variable region. Similarly, the above-described (26), (29), (32), (35), (38), (41), (44), (47), (59), (62), and (65) are preferably contained as CDR2, and the above-described (27), (30), (33), (36), (39), (42), (45), (48), (60), (63), and (66) are preferably contained as CDR3.

In the antibody of one preferable embodiment in the invention, CDR1 of the heavy chain variable region has any one of the amino acid sequences of the above-described (1), (4), (7), (10), (13), (16), (19), (22), (49), (52), and (55), CDR2 of the heavy chain variable region has any one of the amino acid sequences of the above-described (2), (5), (8), (11), (14), (17), (20), (23), (50), (53), and (56), CDR3 of the heavy chain variable region has any one of the amino acid sequences of the above-described (3), (6), (9), (12), (15), (18), (21), (24), (51), (54), and (57), CDR1 of the light chain variable region has any one of the amino acid sequences of the above-described (25), (28), (31), (34), (37), (40), (43), (46), (58), (61), and (64), CDR2 of the light chain variable region has any one of the amino acid sequences of the above-described (26), (29), (32), (35), (38), (41), (44), (47), (59), (62), and (65), and CDR3 of the light chain variable region has any one of the amino acid sequences of the above-described (27), (30), (33), (36), (39), (42), (45), (48), (60), (63), and (66).

In the antibody of one more preferable embodiment in the invention, CDR3 of the heavy chain variable region and the light chain variable region is any one of combinations of the following (a) to (k).

(a) The heavy chain CDR3: the amino acid sequence of SEQ ID NO.:4, the light chain CDR3: the amino acid sequence of SEQ ID NO.:8

(b) The heavy chain CDR3: the amino acid sequence of SEQ ID NO.:12, the light chain CDR3: the amino acid sequence of SEQ ID NO.:16

(c) The heavy chain CDR3: the amino acid sequence of SEQ ID NO.:20, the light chain CDR3: the amino acid sequence of SEQ ID NO.:24

(d) The heavy chain CDR3: the amino acid sequence of SEQ ID NO.:28, the light chain CDR3: the amino acid sequence of SEQ ID NO.:32

(e) The heavy chain CDR3: the amino acid sequence of SEQ ID NO.:36, the light chain CDR3: the amino acid sequence of SEQ ID NO.:40

(f) The heavy chain CDR3: the amino acid sequence of SEQ ID NO.:44, the light chain CDR3: the amino acid sequence of SEQ ID NO.:48

(g) The heavy chain CDR3: the amino acid sequence of SEQ ID NO.:52, the light chain CDR3: the amino acid sequence of SEQ ID NO.:56

(h) The heavy chain CDR3: the amino acid sequence of SEQ ID NO.:60, the light chain CDR3: the amino acid sequence of SEQ ID NO.:64

(i) The heavy chain CDR3: the amino acid sequence of SEQ ID NO.:224, the light chain CDR3: the amino acid sequence of SEQ ID NO.:228

(j) The heavy chain CDR3: the amino acid sequence of SEQ ID NO.:232, the light chain CDR3: the amino acid sequence of SEQ ID NO.:236

(k) The heavy chain CDR3: the amino acid sequence of SEQ ID NO.:240, the light chain CDR3: the amino acid sequence of SEQ ID NO.:244

These are combinations of CDR3, being described beginning at the top, in 035-029 antibody, 035-212 antibody, 035-215 antibody, 035-273 antibody, 035-283 antibody, 040-131 antibody, 051-054 antibody, 051-181 antibody, 051-129 antibody, 035-130 antibody, and 035-169 antibody, and can be expected high specificity against IgSF4.

In the antibody of one yet more preferable embodiment in the invention, CDR2 and CDR3 of the heavy chain variable region and the light chain variable region are any one of combinations of the following (l) to (v).

(l) The heavy chain CDR2: the amino acid sequence of SEQ ID NO.:3, the heavy chain CDR3: the amino acid sequence of SEQ ID NO.:4, the light chain CDR2: the amino acid sequence of SEQ ID NO.:7, the light chain CDR3: the amino acid sequence of SEQ ID NO.:8

(m) The heavy chain CDR2: the amino acid sequence of SEQ ID NO.:11, the heavy chain CDR3: the amino acid sequence of SEQ ID NO.: 12, the light chain CDR2: the amino acid sequence of SEQ ID NO.:15, the light chain CDR3: the amino acid sequence of SEQ ID NO.:16

(n) The heavy chain CDR2: the amino acid sequence of SEQ ID NO.:19, the heavy chain CDR3: the amino acid sequence of SEQ ID NO.:20, the light chain CDR2: the amino acid sequence of SEQ ID NO.:23, the light chain CDR3: the amino acid sequence of SEQ ID NO.:24

(O) The heavy chain CDR2: the amino acid sequence of SEQ ID NO.:27, the heavy chain CDR3: the amino acid sequence of SEQ ID NO.:28, the light chain CDR2: the amino acid sequence of SEQ ID NO.:31, the light chain CDR3: the amino acid sequence of SEQ ID NO.:32

(p) The heavy chain CDR2: the amino acid sequence of SEQ ID NO.:35, the heavy chain CDR3: the amino acid sequence of SEQ ID NO.:36, the light chain CDR2: the amino acid sequence of SEQ ID NO.:39, the light chain CDR3: the amino acid sequence of SEQ ID NO.:40

(q) The heavy chain CDR2: the amino acid sequence of SEQ ID NO.:43, the heavy chain CDR3: the amino acid sequence of SEQ ID NO.:44, the light chain CDR2: the amino acid sequence of SEQ ID NO.:47, the light chain CDR3: the amino acid sequence of SEQ ID NO.:48

(r) The heavy chain CDR2: the amino acid sequence of SEQ ID NO.:51, the heavy chain CDR3: the amino acid sequence of SEQ ID NO.:52, the light chain CDR2: the amino acid sequence of SEQ ID NO.:55, the light chain CDR3: the amino acid sequence of SEQ ID NO.:56

(s) The heavy chain CDR2: the amino acid sequence of SEQ ID NO.:59, the heavy chain CDR3: the amino acid sequence of SEQ ID NO.:60, the light chain CDR2: the amino acid sequence of SEQ ID NO.:63, the light chain CDR3: the amino acid sequence of SEQ ID NO.:64

(t) The heavy chain CDR2: the amino acid sequence of SEQ ID NO.:223, the heavy chain CDR3: the amino acid sequence of SEQ ID NO.:224, the light chain CDR2: the amino acid sequence of SEQ ID NO.:227, the light chain CDR3: the amino acid sequence of SEQ ID NO.:228

(u) The heavy chain CDR2: the amino acid sequence of SEQ ID NO.:231, the heavy chain CDR3: the amino acid sequence of SEQ ID NO.:232, the light chain CDR2: the amino acid sequence of SEQ ID NO.:235, the light chain CDR3: the amino acid sequence of SEQ ID NO.:236

(v) The heavy chain CDR2: the amino acid sequence of SEQ ID NO.:239, the heavy chain CDR3: the amino acid sequence of SEQ ID NO.:240, the light chain CDR2: the amino acid sequence of SEQ ID NO.:243, the light chain CDR3: the amino acid sequence of SEQ ID NO.:244

These are combinations of CDR2 and CDR3, being described beginning at the top, in 035-029 antibody, 035-212 antibody, 035-215 antibody, 035-273 antibody, 035-283 antibody, 040-131 antibody, 051-054 antibody, 051-181 antibody, 051-129 antibody, 035-130 antibody, and 035-169 antibody, and can be expected high specificity against IgSF4.

In the antibody of the most preferable embodiment in the invention, CDR1-CDR3 of the heavy chain variable region and the light chain variable region are any one of combinations of the following (A) to (K).

(A) The heavy chain CDR1: the amino acid sequence of SEQ ID NO.:2, the heavy chain CDR2: the amino acid sequence of SEQ ID NO.:3, the heavy chain CDR3: the amino acid sequence of SEQ ID NO.:4, the light chain CDR1: the amino acid sequence of SEQ ID NO.:6, the light chain CDR2: the amino acid sequence of SEQ ID NO.:7, the light chain CDR3: the amino acid sequence of SEQ ID NO.:8

(B) The heavy chain CDR1: the amino acid sequence of SEQ ID NO.:10, the heavy chain CDR2: the amino acid sequence of SEQ ID NO.:11, the heavy chain CDR3: the amino acid sequence of SEQ ID NO.:12, the light chain CDR1: the amino acid sequence of SEQ ID NO.:14, the light chain CDR2: the amino acid sequence of SEQ ID NO.:15, the light chain CDR3: the amino acid sequence of SEQ ID NO.:16

(C) The heavy chain CDR1: the amino acid sequence of SEQ ID NO.:18, the heavy chain CDR2: the amino acid sequence of SEQ ID NO.:19, the heavy chain CDR3: the amino acid sequence of SEQ ID NO.:20, the light chain CDR1: the amino acid sequence of SEQ ID NO.:22, the light chain CDR2: the amino acid sequence of SEQ ID NO.:23, the light chain CDR3: the amino acid sequence of SEQ ID NO.:24

(D) The heavy chain CDR1: the amino acid sequence of SEQ ID NO.:26, the heavy chain CDR2: the amino acid sequence of SEQ ID NO.:27, the heavy chain CDR3: the amino acid sequence of SEQ ID NO.:28, the light chain CDR1: the amino acid sequence of SEQ ID NO.:30, the light chain CDR2: the amino acid sequence of SEQ ID NO.:31, the light chain CDR3: the amino acid sequence of SEQ ID NO.:32

(E) The heavy chain CDR1: the amino acid sequence of SEQ ID NO.:34, the heavy chain CDR2: the amino acid sequence of SEQ ID NO.:35, the heavy chain CDR3: the amino acid sequence of SEQ ID NO.:36, the light chain CDR1: the amino acid sequence of SEQ ID NO.:38, the light chain CDR2: the amino acid sequence of SEQ ID NO.:39, the light chain CDR3: the amino acid sequence of SEQ ID NO.:40

(F) The heavy chain CDR1: the amino acid sequence of SEQ ID NO.:42, the heavy chain CDR2: the amino acid sequence of SEQ ID NO.:43, the heavy chain CDR3: the amino acid sequence of SEQ ID NO.:44, the light chain CDR1: the amino acid sequence of SEQ ID NO.:46, the light chain CDR2: the amino acid sequence of SEQ ID NO.:47, the light chain CDR3: the amino acid sequence of SEQ ID NO.:48

(G) The heavy chain CDR1: the amino acid sequence of SEQ ID NO.:50, the heavy chain CDR2: the amino acid sequence of SEQ ID NO.:51, the heavy chain CDR3: the amino acid sequence of SEQ ID NO.:52, the light chain CDR1: the amino acid sequence of SEQ ID NO.:54, the light chain CDR2: the amino acid sequence of SEQ ID NO.:55, the light chain CDR3: the amino acid sequence of SEQ ID NO.:56

(H) The heavy chain CDR1: the amino acid sequence of SEQ ID NO.:58, the heavy chain CDR2: the amino acid sequence of SEQ ID NO.:59, the heavy chain CDR3: the amino acid sequence of SEQ ID NO.:60, the light chain CDR1: the amino acid sequence of SEQ ID NO.:62, the light chain CDR2: the amino acid sequence of SEQ ID NO.:63, the light chain CDR3: the amino acid sequence of SEQ ID NO.:64

(I) The heavy chain CDR1: the amino acid sequence of SEQ ID NO.:222, the heavy chain CDR2: the amino acid sequence of SEQ ID NO.:223, the heavy chain CDR3: the amino acid sequence of SEQ ID NO.:224, the light chain CDR1: the amino acid sequence of SEQ ID NO.:226, the light chain CDR2: the amino acid sequence of SEQ ID NO.:227, the light chain CDR3: the amino acid sequence of SEQ ID NO.:228

(J) The heavy chain CDR1: the amino acid sequence of SEQ ID NO.:230, the heavy chain CDR2: the amino acid sequence of SEQ ID NO.:231, the heavy chain CDR3: the amino acid sequence of SEQ ID NO.:232, the light chain CDR1: the amino acid sequence of SEQ ID NO.:234, the light chain CDR2: the amino acid sequence of SEQ ID NO.:235, the light chain CDR3: the amino acid sequence of SEQ ID NO.:236

(K) The heavy chain CDR1: the amino acid sequence of SEQ ID NO.:238, the heavy chain CDR2: the amino acid sequence of SEQ ID NO.:239, the heavy chain CDR3: the amino acid sequence of SEQ ID NO.:240, the light chain CDR1: the amino acid sequence of SEQ ID NO.:242, the light chain CDR2: the amino acid sequence of SEQ ID NO.:243, the light chain CDR3: the amino acid sequence of SEQ ID NO.:244

These are combinations of CDR1-CDR3, being described beginning at the top, in 035-029 antibody, 035-212 antibody, 035-215 antibody, 035-273 antibody, 035-283 antibody, 040-131 antibody, 051-054 antibody, 051-181 antibody, 051-129 antibody, 035-130 antibody, and 035-169 antibody, and can be expected higher specificity against IgSF4.

The sequence of the framework region (FR region) in a variable region of the antibody of the present invention is not particularly limited as long as it does not substantially affect the specific binding property against IgSF4. For example, when the antibody of the present invention is constructed as a humanized antibody, a FR region of the well-known human antibody can be used. Furthermore, for example, when an antibody used as a reagent for detection or an antibody applied to non-human animal species is constructed, in some cases, expected effects can be obtained even if a human antibody FR region is not used or a case where it is not appropriate to use a human antibody FR region. In such cases, it is possible to use a FR region of non-human animal species (for example, mouse or rat).

In one embodiment of the present invention, the antibody includes a constant region in addition to a variable region (for example, in the case of an IgG type antibody). The sequence of the constant region of this embodiment is not particularly limited. For example, as mentioned below, when the antibody of the present invention is constructed as a humanized antibody, it is possible to use a constant region of the well-known human antibody. Furthermore, similar to the above-mentioned FR region, it is possible to use a constant region of the non-human animal species (for example, mouse or rat).

The antibody of one embodiment of the present invention is a humanized antibody. The "humanized antibody" herein denotes an antibody that is constructed to have a structure similar to that of the human antibody and includes a human type chimera antibody in which only a constant region of the antibody is substituted by that of a human antibody, a human type CDR-grafted antibody in which a part other than CDR (complementarity determining region) existing in the constant region and the variable region is substituted by that of the human antibody (P. T. Johons et al., Nature 321,522 (1986)). In order to enhance the antigen binding activity of the human type CDR-grafted antibody, improved technologies of a method of selecting a human antibody FR with high homology to a mouse antibody, a method of preparing a humanized type antibody with high homology, a method of transplanting a mouse CDR into a human antibody and then substituting the amino acids of the FR region have already been developed (see, for example, U.S. Pat. No. 5,585,089, U.S. Pat. No. 5,693,761, U.S. Pat. No. 5,693,762, U.S. Pat. No. 6,180,370, European patent No. 451216, European patent No. 682040, U.S. Pat. No. 2,828,340), and can be used for preparing the human type antibody of the present invention.

The human type chimera antibody can be produced by, for example, by substituting the constant region of an antibody having the structure of the H-chain variable region and/or the structure of the L-chain variable region by the constant region of the human antibody. As the constant region of the human antibody, the well-known antibodies can be employed. Hereinafter, one example of the method of producing the human type chimera antibody is described.

Firstly, mRNA is extracted from a hybridoma producing a mouse anti-IgSF4 antibody, and cDNA is synthesized according to the routine method. The synthesized cDNA is integrated into a vector so as to construct a cDNA library. From this cDNA library, by using a H-chain gene fragment and a L-chain gene fragment as a probe, a vector containing the H-chain gene and the L-chain gene is selected. By carrying out sequencing of the insertion sequence of the selected vector, the sequence of the H-chain variable region and the L-chain variable region is determined. Based on the thus obtained sequence data, DNA encoding the H-chain variable region is produced by chemical synthesis, biochemical cutting/recombination, and the like. DNA encoding the obtained H-chain variable region is ligated with DNA encoding the human H-chain constant region, which is integrated into an expression vector. Thus, the H-chain expression vector is produced. An example of the expression vector may include a SV40 virus based vector, an EB virus based vector, a BPV (papilloma virus) based vector, and the like. However, the expression vector is not limited thereto. On the other hand, the L-chain expression vector is produced by the same method. These H-chain expression vector and L-chain expression vector co-transform a host cell. As the host cell, CHO (Chinese hamster ovary) cell (A. Wright & S. L. Morrison, J. Immunol. 160, 3393-3402 (1998)), SP2/0 cell (mouse myeloma) (K. Motmans et al., Eur. J. Cancer Prev. 5, 512-519 (1996), R. P. Junghans et al., Cancer Res. 50, 1495-1502 (1990)), and the like, can be preferably used. Furthermore, for transformation, a Lipofectin method (R. W. Malone et al., Proc. Natl. Acad. Sci. USA 86,6077 (1989), P. L. Feigner et al., Proc. Natl. Acad. Sci. USA 84,7413 (1987), electroporation method, calcium phosphate method (F. L. Graham & A. J. van der Eb, Virology 52, 456-467 (1973)), DEAE-Dextran method and the like can be preferably used.

After the transformant is cultured, human type chimera antibodies are separated from the transformant cell or the culture medium. For separation and purification of antibodies, any appropriate combination of centrifugation, ammonium sulfate fractionation, salting out, ultra-filtration, affinity chromatography, ion exchange chromatography, gel filtration chromatography, and the like, can be used.

On the other hand, a human-type CDR graft antibody can be prepared, for instance, as the following manner. First of all, by the method described in the column of the above-described preparation method of the chimeric antibody, an amino acid sequence and a corresponding base sequence are determined, which is an amino acid sequence of a H chain variable region and a L chain variable region of a mouse anti-IgSF4 antibody. In addition, an amino acid sequence of each CDR region and a corresponding base sequence are determined.

Examples of the base sequence of CDR include the following base sequences.

H chain CDR1 (VH CDR1): any one of the base sequences of SEQ ID NO.:66, 74, 82, 90, 98, 106, 114, 122, 246, 254, and 262

H chain CDR2 (VH CDR2): any one of the base sequences of SEQ ID NO.:67, 75, 83, 91, 99, 107, 115, 123, 247, 255, and 263

H chain CDR3 (VH CDR3): any one of the base sequences of SEQ ID NO.:68, 76, 84, 92, 100, 108, 116, 124, 248, 256, and 264

L chain CDR1 (VL CDR1): any one of the base sequences of SEQ ID NO.:70, 78, 86, 94, 102, 110, 118, 126, 250, 258, and 266

L chain CDR2 (VL CDR2): any one of the base sequences of SEQ ID NO.:71, 79, 87, 95, 103, 111, 119, 127, 251, 259, and 267

L chain CDR3 (VL CDR3): any one of the base sequences of SEQ ID NO.:72, 80, 88, 96, 104, 112, 120, 128, 252, 260, and 268

As the base sequence of CDR, any one of the following combinations can be preferably used.

(1) The combination of VH CDR1: the base sequence of SEQ ID NO.:66, VH CDR2: the base sequence of SEQ ID NO.:67, VH CDR3: the base sequence of SEQ ID NO.:68, VL CDR1: the base sequence of SEQ ID NO.:70, VL CDR2: the base sequence of SEQ ID NO.:71, and VL CDR3: the base sequence of SEQ ID NO.:72

(2) The combination of VH CDR1: the base sequence of SEQ ID NO.:74, VH CDR2: the base sequence of SEQ ID NO.:75, VH CDR3: the base sequence of SEQ ID NO.:76, VL CDR1: the base sequence of SEQ ID NO.:78, VL CDR2: the base sequence of SEQ ID NO.:79, and VL CDR3: the base sequence of SEQ ID NO.:80

(3) The combination of VH CDR1: the base sequence of SEQ ID NO.:82, VH CDR2: the base sequence of SEQ ID NO.:83, VH CDR3: the base sequence of SEQ ID NO.:84, VL CDR1: the base sequence of SEQ ID NO.:86, VL CDR2: the base sequence of SEQ ID NO.:87, and VL CDR3: the base sequence of SEQ ID NO.:88

(4) The combination of VH CDR1: the base sequence of SEQ ID NO.:90, VH CDR2: the base sequence of SEQ ID NO.:91, VH CDR3: the base sequence of SEQ ID NO.:92, VL CDR1: the base sequence of SEQ ID NO.:94, VL CDR2: the base sequence of SEQ ID NO.:95, and VL CDR3: the base sequence of SEQ ID NO.:96

(5) The combination of VH CDR1: the base sequence of SEQ ID NO.:98, VH CDR2: the base sequence of SEQ ID NO.:99, VH CDR3: the base sequence of SEQ ID NO.:100, VL CDR1: the base sequence of SEQ ID NO.:102, VL CDR2: the base sequence of SEQ ID NO.:103, and VL CDR3: the base sequence of SEQ ID NO.:104

(6) The combination of VH CDR1: the base sequence of SEQ ID NO.:106, VH CDR2: the base sequence of SEQ ID NO.:107, VH CDR3: the base sequence of SEQ ID NO.:108, VL CDR1: the base sequence of SEQ ID NO.:110, VL CDR2: the base sequence of SEQ ID NO.: 111, and VL CDR3: the base sequence of SEQ ID NO.: 112

(7) The combination of VH CDR1: the base sequence of SEQ ID NO.:114, VH CDR2: the base sequence of SEQ ID NO.:115, VH CDR3: the base sequence of SEQ ID NO.:116, VL CDR1: the base sequence of SEQ ID NO.:118, VL CDR2:

the base sequence of SEQ ID NO.:119, and VL CDR3: the base sequence of SEQ ID NO.:120

(8) The combination of VH CDR1: the base sequence of SEQ ID NO.:122, VH CDR2: the base sequence of SEQ ID NO.:123, VH CDR3: the base sequence of SEQ ID NO.:124, VL CDR1: the base sequence of SEQ ID NO.:126, VL CDR2: the base sequence of SEQ ID NO.:127, and VL CDR3: the base sequence of SEQ ID NO.:128

(9) The combination of VH CDR1: the base sequence of SEQ ID NO.:246, VH CDR2: the base sequence of SEQ ID NO.:247, VH CDR3: the base sequence of SEQ ID NO.:248, VL CDR1: the base sequence of SEQ ID NO.:250, VL CDR2: the base sequence of SEQ ID NO.:251, and VL CDR3: the base sequence of SEQ ID NO.:252

(10) The combination of VH CDR1: the base sequence of SEQ ID NO.:254, VH CDR2: the base sequence of SEQ ID NO.:255, VH CDR3: the base sequence of SEQ ID NO.:256, VL CDR1: the base sequence of SEQ ID NO.:258, VL CDR2: the base sequence of SEQ ID NO.:259, and VL CDR3: the base sequence of SEQ ID NO.:260

(11) The combination of VH CDR1: the base sequence of SEQ ID NO.:262, VH CDR2: the base sequence of SEQ ID NO.:263, VH CDR3: the base sequence of SEQ ID NO.:264, VL CDR1: the base sequence of SEQ ID NO.:266, VL CDR2: the base sequence of SEQ ID NO.:267, and VL CDR3: the base sequence of SEQ ID NO.:268

In addition, these are equal to combinations of each CDR, being described beginning at the top, in 035-029 antibody, 035-212 antibody, 035-215 antibody, 035-273 antibody, 035-283 antibody, 040-131 antibody, 051-054 antibody, 051-181 antibody, 051-129 antibody, 035-130 antibody, and 035-169 antibody.

Next, FR (framework region) that is present surrounding the CDR region is selected. As a method for selecting FR, approximately three methods can be employed. The first method is a method of using a human antibody frame such as NEWM, REI, and the like, whose three dimensional structure has been clarified (Riechmann L. et al., Nature 332, 323-3Z7 (1988); Tempst, P R. et al., Protein Engineering 7, 1501-1507 (1994); Ellis J H. et al., J. Immunol. 155, 925-937 (1995)). The second method is a method of selecting the human antibody variable region having the highest homology to the objective mouse antibody variable region from database, and using the FR thereof (Queen C. et al., Proc Natl Acad SciUSA 86, 10029-10033 (1989); Rozak M J. et al., J Biol Chem 271, 22611-22618 (1996); Shearman C W. et al., J. Immunol 147, 4366-4373 (1991)). The third method is a method of selecting amino acid used most commonly to the FR of the human antibody (Sato K. et al., Mol Immunol 31, 371-381 (1994); Kobinger F. et al., Protein Engineering 6, 971-980 (1993); Kettleborough CA. et al., Protein Engineering 4, 773-783 (1991)). In the present invention, any one of these methods can be used.

Note here that an amino acid sequence in which the amino acid sequence of the selected human FR is modified can be also used as the amino acid sequence of FR as long as a finally produced human type CDR-grafted antibody has a specific binding property against IgSF4. In particular, when a part of the amino acids of the selected human FR is changed into the amino acids of FR of the antibody that is an origin of the CDR, the probability that the property of the antibody can be maintained is high. The number of amino acids to be modified is not more than 30% with respect to an entire FR. Further preferably, the number is not more than 20% with respect to an entire FR. Yet further preferably, the number is not more than 10% with respect to an entire FR.

Next, by combining the FR selected by any of the methods mentioned above and the above-mentioned CDR, DNA encoding the H-chain variable region and the L-chain variable region is designed. Based on this design, DNA encoding the H-chain variable region and DNA encoding the L-chain variable region are produced by chemical synthesis, biochemical cutting/recombination, and the like, respectively. DNA encoding the H-chain variable region is integrated into an expression vector together with DNA encoding the human immunoglobulin H-chain constant region. Thus, the H-chain expression vector is constructed. Similarly, DNA encoding the L-chain variable region is integrated into an expression vector together with DNA encoding the human immunoglobulin L-chain constant region. Thus, the L-chain expression vector is constructed. An example of the expression vector may include a SV40 virus based vector, an EB virus based vector, a BPV (papilloma virus) based vector, and the like. However, the expression vector is not limited thereto.

The H-chain expression vector and L-chain expression vector, which have been produced by the above-mentioned method, co-transform a host cell. As the host cell, CHO (Chinese hamster ovary) cell (A. Wright & S. L. Morrison, J. Immunol. 160, 3393-3402 (1998)), SP2/0 cell (mouse myeloma) (K. Motmans et al., Eur. J. Cancer Prev. 5, 512-519 (1996), R. P. Junghans et al., Cancer Res. 50, 1495-1502 (1990)), and the like, can be preferably used. Furthermore, for transformation, a Lipofectin method (R. W. Malone et al., Proc. Natl. Acad. Sci. USA 86,6077 (1989), P. L. Feigner et al., Proc. Natl. Acad. Sci. USA 84,7413 (1987), an electroporation method, a calcium phosphate method (F. L. Graham & A. J. van der Eb, Virology 52, 456-467 (1973)), a DEAE-Dextran method and the like can be preferably used.

After the transformant is cultured, human type CDR-grafted antibodies are separated from the transformant cell or the culture medium. For separation and purification of antibodies, any appropriate combination of centrifugation, ammonium sulfate fractionation, salting out, ultra-filtration, affinity chromatography, ion exchange chromatography, gel filtration chromatography, and the like, can be used.

Based on the antibody of the present invention or based on the sequence information of gene encoding the antibody of the present invention, an antibody fragment can be produced. An example of the antibody fragment may include Fab, Fab', F(ab')$_2$, scFv, and dsFv antibodies, and the like.

Fab can be obtained by digesting IgG with papain in the presence of cysteine. Fab is a fragment having a molecular weight of about 50000, which includes L-chain and H-chain variable regions as well as an H-chain fragment including a $C_H1$ domain and a part of the hinge portion. In the present invention, it can be obtained by digesting the above-mentioned antibodies with papain. Furthermore, DNA encoding a part of the H-chain and L-chain of the above-mentioned antibody is integrated into an appropriate vector, and Fab can be prepared from the transformant transformed by using this vector.

Fab' is a fragment having a molecular weight of about 50000, which can be obtained by cutting disulfide linkage between H-chains of the below mentioned F(ab')$_2$. In the present invention, it can be obtained by digesting the antibody with pepsin and cutting the disulfide linkage by using a reducing agent. Furthermore, similar to Fab, Fab' can be prepared by using DNA encoding Fab' by genetic engineering.

F(ab')$_2$ can be obtained by digesting IgG with pepsin. F(ab')$_2$ is a fragment having a molecular weight of about 100000, which includes L-chain and H-chain variable regions as well as an H-chain fragment including a $C_H1$ domain and a part of the hinge portion, and in which the fragment (Fab') is bonded by disulfide linkage. In the present invention, it can be obtained by digesting the above-mentioned antibodies with pepsin. Furthermore, similar to Fab, it can be prepared by using DNA encoding F(ab')$_2$ by genetic engineering.

ScFv is a single stranded antibody fragment in which Fv including an H-chain variable region and an L-chain variable region are linked to each other by linking the C terminal of one chain and the N terminal of the other chain with an appropriate peptide linker. As the peptide linker, for example, (GGGGS)$_3$ having high flexibility and the like can be used. For example, by using DNA encoding the H-chain variable region and the L-chain variable region of the above-mentioned antibody and DNA encoding the peptide linker, DNA encoding scFv antibody is constructed. This is integrated into an appropriate vector. ScFv can be prepared from the transformant, which has been transformed by using this vector.

DsFv is an Fv fragment in which a Cys residue is introduced into appropriate positions of the H-chain variable region and the L-chain variable region, and the H-chain variable region and the L-chain variable region are stabilized by disulfide linkage. The position of each chain into which the Cys residue is introduced can be determined based on the three-dimensional structure predicted by molecule modeling. In the present invention, for example, the three-dimensional structure is predicted from the amino acid sequence of the H-chain variable region and the L-chain variable region of the above-mentioned antibody, and based on the prediction, DNA encoding each of the H-chain variable region and the L-chain variable region into which mutation is introduced is constructed. This is integrated into an appropriate vector, and dsFv can be prepared from the transformant transformed by using this vector.

By using an appropriate linker, antibody fragments can be polymerized by linking the scFv antibody, the dcFv antibody and the like to each other, or fusing them with streptavidin.

By fusing or binding the antibody (including an antibody fragment) of the present invention to a low molecular weight compound, protein, a labeling material, or the like, a fused antibody or labeled antibody can be formed. An example of the labeling material can include a radioactive material such as $^{125}$I, peroxidase, β-D-galactosidase, microperoxidase, horseradish peroxidase (HRP), fluorescein isothiocyanate (FITC), rhodamine isothiocyanate (RITC), alkaline phosphatase, biotin, and the like.

Since the antibody (including an antibody fragment) of the present invention has a specific binding property against IgSF4, the antibody can be specifically bonded to a cancer cell (for example, a lung cancer cell, a liver cancer cell) specifically expressing IgSF4. By using this property, labeling, detection, and the like of a cancer cell (or cancer tissue) can be carried out. Furthermore, it can be expected that the cytotoxicity can be exerted via binding to cancer cells. Actually, as shown in the below-mentioned Examples, 035-029 antibody, 035-273 antibody and 051-054 antibody show the ADCC activity. Therefore, the antibodies themselves can be used for damaging (killing) the cancer cell. Herein, when the humanized antibody of the present invention is used, attack and elimination by the immune system do not easily occur, the expected effect can be exerted efficiently and occurrence of severe side effect can be avoided.

In addition, the antibody of the present invention can be used as a medium (carrier) for allowing drugs and the like to be delivered specifically to a liver cancer cell. That is to say, it is assumed that the application of the antibody of the present invention includes DDS (Drug delivery system) for targeting a liver cancer cell.

Herein, the experiment using the antibody successfully obtained by the present inventors has clarified that the 035-273 antibody and the 051-054 antibody can specifically recognize a liver cancer cell having a low grade of differentiation. In general, it is difficult to treat a liver cancer with low grade of differentiation, and the prognosis of such a cancer is extremely poor. The 035-273 antibody and the like can specifically recognize such cancer cells that is difficult to be treated and has high value in treating application and diagnosis application. For example, when the 035-273 antibody is used as a carrier of drugs, the drugs can be delivered specifically to a poorly-differentiated liver cancer. Thus, a high treatment effect can be expected. Furthermore, when the antibody is used as an immunostaining antibody, it is possible to obtain the staining effect reflecting the grade of differentiation. That is to say, when the antibody is used, it is possible to determine the grade of differentiation of a cancer cell with high accuracy. Thus, the antibody is very useful also in diagnosis application.

Note here that each application of the antibody of the present invention is described in detail hereinafter.

(Diagnosis Application)

Another aspect of the present invention relates to the use of IgSF4 as a diagnosis marker based on the finding that IgSF4 is expressed specifically to a liver cancer cell. One embodiment of this aspect relates to a method of obtaining information for diagnosing a liver cancer or adult T cell Leukemia and includes the following steps:

Step (1): step of preparing a subjected cell separated from a living body.

Step (2): step of detecting IgSF4 as the subjected cell.

The information (detected results) obtained in the method can be used for determining whether or not the subjected cell corresponds to a liver cancer cell, or whether or not the subjected cell corresponds to adult T cell Leukemia.

Herein, as shown in the below-mentioned Examples, when a plurality of liver cancer cells having different grades of malignancy (grades of differentiation) are subjected to immunostaining by using an anti-IgSF4 antibody, significant difference in the staining property can be found. That is to say, it is clear that there is a strong relation between the grade of malignancy and the expression amount of IgSF4. Thus, it is determined that IgSF4 is also effective as a marker for determining the grade of malignancy of liver cancer cells. Based on this finding, another aspect of the present invention provides a method using the detected results in the above-mentioned step for determining the grade of malignancy of the subjected liver cells, that is to say, a method for determining the grade of malignancy of liver cancer cells.

The detection results according to the present invention is useful for diagnosing liver cancer or adult T cell Leukemia. For example, the information obtained by carrying out the above-mentioned method with respect to patients with liver cancer can be used for evaluating and grasping the evaluation of the conditions of the patients or evaluating the treating effect. For example, by carrying out the method of the present invention in parallel with the treatment of liver cancer, treatment effect can be evaluated based on the information obtained as a result. Specifically, when the method of the present invention is carried out after administering a drug, the change of the expression amount of IgSF4 in the liver cells is examined and the treatment effect can be determined from the increase and decrease of the expression amount. Thus, the method of the present invention may be used for monitoring the treatment effect.

On the other hand, information obtained in the case where the experiment is carried out to persons other than patients, that is, persons who are not recognized to have a liver cancer can be used for determination of whether or not a patient has a liver cancer, evaluation of incidence risk, and the like. According to the method of the present invention, since the diagnosis of liver cancer can be carried out based on the objective index, that is, an expression amount, the value is extremely high.

Hereinafter, the steps constituting the present invention are described.

1. Step (1)

In the step (1), cells separated from a subject (subjected person, living body) are prepared. The subject herein includes not only patients (patients with liver cancer or adult T cell Leukemia) but also healthy persons (including persons having a risk of developing liver cancer or adult T cell Leukemia). For example, a part of liver of the subject collected by biopsy may be used for the method of the present invention as the subjected cell.

The "subjected cell (subjected liver cell or subjected T cell)" in the present invention is a cell that is used as a sample (subject) for detection in the method of the present invention. The subjected cells are separated from a living body. That is to say, to the subjected cells in the state in which they are separated from a living body, the present invention is applied. The "separated from a living body" shows a state in which the subjected cells are completely separated from the living body of origin of the subjected cells by extracting a part of the living tissue including the subjected cells. In step (2), when an immunological detection method is employed, the subjected cells are usually prepared in a state in which they are present in the living body, that is, in a state in which they are connected to the surrounding cells (as a tissue piece) and used for the present invention. Note here that the method of the present invention may be used after the cells are separated (isolated) from the surrounding cells.

When liver cells are used as the subjected cells and the detection result is used for determining the grade of malignancy of the subjected cells, as the subjected cells, liver cells that are determined to be a cancer by other diagnosis methods, liver cells that are determined to have high possibility of liver cancer, or liver cells having a probability of liver cancer are suitably employed. Preferably, liver cells that are determined to be a cancer by other diagnosis methods, liver cells that are determined to have high possibility of liver cancer are used. The other diagnosis methods herein include, for example, X-ray photography, endoscopy, ultrasonography, CT examination, MRI examination, PET examination, and a diagnosis method using a tumor marker, and the like. In general, by using one or more of them, subjected cells (subjected liver cells) are collected from the tissue that may have liver cancer.

In the present invention, "liver cancer" can be interpreted in the wide sense and includes liver carcinoma and liver sarcoma. Furthermore, in the present invention, the term "cancer" can be used interchangeably with "tumor." Furthermore, a stage before the diagnosis is pathologically determined, that is, before whether a tumor is benign or malignant, the term may generally include benign tumor, boundary lesion of being benign and malignant, and malignant tumor.

2. Step (2)

In step (2), from the prepared subjected cells, IgSF4 is detected. The term "IgSF4 is detected" signifies examining whether or not IgSF4 is expressed (presence of expression), or obtaining the expression amount of IgSF4 as an absolute amount or a relative amount. Herein, the reference of the relative amount can be defined as, for example, the amount of IgSF4 of the standard sample prepared according to the grade of malignancy. In general, the presence of expression of IgSF4, and the amount of the expressed IgSF4 if any are examined. When IgSF4 is detected, it is not essential to strictly measure the amount of IgSF4. For example, when liver cells are used as the subjected cells and the detection of IgSF4 is carried out for determining the grade of malignancy of the subjected cells (subjected cancer cells), the amount of IgSF4 may be measured in a level that the grade of malignancy of the subjected cancer cells can be determined by making a comparison with the amount of IgSF4 of control that is used as an index of the grade of malignancy.

One embodiment of the present invention carries out a detection method by using mRNA that is a transcriptional product of IgSF4 as a target. For the detection (measurement) of mRNA, general methods, for example, an RT-PCR method, various hybridization methods using a specific probe (for example, northern hybridization, in situ hybridization), and the like, can be used. Another aspect of the present invention carries out a detection method using an expression product (protein) of IgSF4 as a target.

Preferably, IgSF4 is detected by an immunological technique (for example, immunohistochemical staining method). The immunological technique uses an anti-IgSF4 antibody and detects IgSF4 protein as an index of the binding property (binding amount) of the antibodies. According to the immunological detection method, rapid and sensitive detection can be achieved. In addition, operation is simple. Note here that an example of the detection method may include an ELISA method, radioimmunoassay, FCM, an immunoprecipitation method, immunoblotting, and the like.

According to the immunohistochemical staining method, rapid and sensitive detection of IgSF4 can be achieved. In addition, operation is simple. Therefore, burden, when IgSF4 is detected, to a subject (patient) is reduced.

In the immunohistochemical staining method, in general, firstly, a step of bringing an anti-IgSF4 antibody into contact with the subjected cells is carried out, followed by examining the binding amount of anti-IgSF4. Concretely, in accordance with the below-mentioned immunohistochemical staining method, the method of the present invention can be carried out.

The immunohistochemical staining method with respect to the living tissue is generally carried out by the following procedures (1) to (9). Note here that the immunohistochemical staining method with respect to the living tissue can be referred to various documents and publications (see, for example, "Koso Koutai hou (Emzyme Antibody Technique), the third revised edition" edited by Keiichi Watanabe, Kazuko Nakane, GAKUSAI KIKAKU LTD).

(1) Fixation—Paraffin Embedding Method

Tissue surgically collected from a living body is fixed by using formalin, paraformamide, absolute ethanol, and the like, and thereafter, embedded in paraffin. In general, dehydration with alcohol is carried out, treated with xylene, and finally embedded in paraffin. The specimen embedded in paraffin is cut into a predetermined thickness (for example, 3 to 5 μm) and expanded on a slide glass. Instead of paraffin embedded specimen, an alcohol fixed specimen, a dry sealed specimen, a frozen specimen, and the like may be use.

(2) Deparaffinization

Treatment is generally carried out with xylene, alcohol and purified water.

(3) Pre-Treatment (Antigen Activation)

For antigen activation, enzyme treatment, heat treatment and/or pressurization treatment is carried out if necessary.

(4) Removing of Endogenous Peroxidase

When peroxidase is used as a labeling material for staining, treatment of hydrogen peroxide solution is carried out so as to remove endogenous peroxidase activity.

(5) Inhibition of Nonspecific Reaction

The section is treated with a bovine serum albumin solution (for example, 1% solution) for several minutes to several tens minutes so as to inhibit the nonspecific reaction. Note here that by using an antibody solution containing bovine serum albumin, the following primary antibody reaction is carried out. This process may be omitted.

(5) Primary Antibody Reaction

An antibody that has been diluted to an appropriate concentration is dropped on a section on the slide glass so as to carry out a reaction for several tens to several hours. After reaction, washing with an appropriate buffer solution such as a phosphate buffer solution or the like can be carried out.

(6) Addition of Labeling Reagent

As the labeling material, peroxidase is frequently used. A secondary antibody combined to peroxidase is dropped on a section on the slide glass and then reacted for several tens minutes to several hours. After reaction, washing with an appropriate buffer solution such as a phosphate buffer solution or the like can be carried out.

(7) Color Reaction

DAB (3,3'-diaminobenzidine) is dissolved in Tris buffer. Then, hydrogen peroxide solution is added thereto. Thus prepared coloring solution is permeated into the section for several minutes (for example, 5 minutes) so as to be colored. After coloring, the section is fully washed with tap water so as to remove DAB.

(8) Nuclear Staining

A reaction with Mayer's hematoxylin is carried out for several seconds to several tens seconds so as to carry out nuclear staining. Washing with running water is performed so as to carry out saddening (in general, several minutes).

(9) Dehydration, Penetration, and Encapsulation

Dehydration with alcohol is carried out, then penetration with xylene is carried out, and finally encapsulation with synthetic resin, glycerine, gum syrup, or the like, is carried out.

The kind and origin of the anti-IgSF4 antibody used in the immunological staining method are not particularly limited as long as the antibody has a specific binding property against IgSF4. The anti-IgSF4 antibody may be any one of a polyclonal antibody, an oligoclonal antibody (mixture of several kinds to several tens kinds of antibodies), and a monoclonal antibody. As the polyclonal antibody or the oligoclonal antibody, in addition to an IgG fraction derived from antiserum obtained by immunizing an animal, it is possible to use an antibody obtained by affinity-purifying with antigen. The anti-IgSF4 antibody may be any antibody fragments such as Fab, Fab', F(ab')$_2$, scFv, and dsFv antibodies, and the like.

The anti-IgSF4 antibody may be prepared by using an immunological technique, a phage display method, a ribosome display method, and the like.

A polyclonal antibody by an immunological technique can be prepared by the following procedures. Antigen (IgSF4 or a part thereof) is prepared and an animal such as a rabbit is immunized with this prepared antigen. As the antigen, besides human IgSF4, IgSF4 of non-human animal species such as mouse IgSF4 can be used. Such an IgSF4 can be obtained by purifying living samples. Furthermore, recombinant IgSF4 can be used. The recombinant human IgSF4 can be prepared by introducing, for example, a gene (a part of a gene may be included) encoding IgSF4 into an appropriate host by using a vector and expressing the gene within the obtained recombinant cell.

In order to enhance an immunization provoking effect, an antigen to which carrier protein is bonded may be used. As the carrier protein, KLH (Keyhole Limpet Hemocyanin), BSA (Bovine Serum Albumin), OVA (Ovalbumin), and the like, can be used. For the binding of the carrier protein, a carbodiimide method, a glutaraldehyde method, a diazo condensation method, an MBS (maleimide benzoyloxysuccinimide) method, and the like, can be used. On the other hand, it is also possible to use an antigen in which IgSF4 (or a part thereof) is expressed as a fused protein with GST, β galactosidase, maltose binding protein, or histidine (His) tag, and the like, can be used. Such a fused protein can be purified by a general method in a simple way.

Immunization is repeated if necessary. At the time when the antibody titer is sufficiently increased, blood is collected and centrifuged so as to obtain serum. The obtained antiserum is affinity-purified so as to obtain a polyclonal antibody.

On the other hand, the monoclonal antibody may be prepared by the following procedures. Firstly, by the same procedure as mentioned above, immunization operation is carried out. If necessary, immunization is repeated. At the time when the antibody titer is sufficiently increased, antibody production cells are extracted from the immunized animal. Next, the obtained antibody production cells and myeloma cells are fused, so that hybridoma is obtained. Subsequently, this hybridoma is made into monoclones, followed by selecting a clone capable of producing antibody having a high specificity against an objective protein. By purifying the culture medium of the selected clone, the objective antibody can be obtained. On the other hand, after the hybridoma is proliferated into a predetermined number or more, this can be transplanted into the peritoneal cavity of an animal (for example, a mouse) and proliferated in the ascites. Also by purifying the ascites, the objective antibody can be obtained. For the purification of the above-mentioned culture medium or the purification of the ascites, affinity chromatography using the protein G, protein A, and the like, is preferably used. Furthermore, an affinity chromatography in which antigen is made into a solid phase can be used. Furthermore, an ion exchange chromatography, a gel filtration chromatography, ammonium sulfate fractionation, and centrifugation, and the like, can be used. These methods can be used alone or in a combination of any of them.

As long as the specific binding property with respect to IgSF4 is maintained, various modifications can be provided to the antibody. In the present invention, such a modified antibody can be used.

If a labeled antibody is used as the anti-IgSF4 antibody, it is possible to directly detect the amount of binding antibody by using the labeled amount as an index. Therefore, the method become simpler. On the other hand, it is necessary to prepare an anti-IgSF4 antibody to which a labeling material is bonded. In addition, detection sensitivity is generally lowered. Therefore, it is preferable to use an indirect detection method such as a method of using a secondary antibody to which a labeling material is bonded, a method of using a polymer in which a secondary antibody and a labeling material are bonded, and the like. Herein, the secondary antibody is an antibody having a specific binding property against an anti-IgSF4 antibody. For example, in the case where an anti-IgSF4 antibody is prepared as a rabbit antibody, anti-rabbit IgG antibody can be used. Labeled secondary antibodies that can be used for antibodies of various species such as rabbit, goat, mouse, and the like, are commercially available (for example, products from Funakoshi Co., Ltd., COSMO BIO CO., LTD, and the like). In accordance with an anti-IgSF4 antibody used in the present invention, an appropriate labeled antibodies can be appropriately selected.

As the labeling material, any of peroxidase, β-D-galactosidase, microperoxidase, horseradish peroxidase (HRP), fluorescein isothiocyanate (FITC), rhodamine isothiocyanate (RITC), alkaline phosphatase, biotin, and a radioactive material can be preferably selected and used. In particular, when biotin is used as the labeling material and a method for reacting avidin peroxidase is used, highly sensitive detection can be carried out.

The above-described antibody of the invention may be used as IgSF4 antibody herein. As examples of the antibody, for instance, the antibodies can be used which have been successfully obtained by the inventors (035-029 antibody, 035-212 antibody, 035-215 antibody, 035-273 antibody, 035-283 antibody, 040-131 antibody, 051-054 antibody, 051-181 antibody, 051-129 antibody, 035-130 antibody, or 035-169 antibody). As shown in the examples described below, in the successfully obtained antibodies, in case of using 035-273 antibody or the like, it was possible to clearly dye cancers having different degrees of malignancy in different tones. Therefore, the antibody of the invention has a great deal of potential especially in a method for judging degree of malignancy in hepatic cancer cells.

In the method of determining the grade of malignancy in accordance with the present invention, typically, it is determined which segment of a plurality of segments corresponding to the expression amount of IgSF4 the subjected cells (the subjected liver cells) are classified in. Herein, the number of segments is not particularly limited. For example, three segments may be provided (concretely, the grade of malignancy 1 (well-differentiated): no IgSF4 is detected, the grade of malignancy 2 (moderately differentiated): expression amount of IgSF4 is small, and the grade of malignancy 3 (poorly-differentiated or undifferentiated): expression amount of IgSF4 is large).

(Treatment Application)

A further aspect of the present invention relates to a use of IgSF4 in the application of treatment of cancer based on the finding that IgSF4 is specifically expressed in cancer cells and that it becomes a target for the cytotoxicity when an ADCC is used. Furthermore, based on the finding that there is found a relation between adult T cell Leukemia and IgSF4, the aspect of the present invention relates to the use of IgSF4 in the treatment application of adult T cell leukemia. The fact that IgSF4 is effective as the target for the cytotoxicity by ADCC activity has not been determined before the process for identifying an antigen against the antibody specific to liver cancer specific antibody which the present inventors have successfully obtained. With this result, it is determined that the anti-IgSF4 antibody is a drug effective to damages specific to cancer cells.

In this aspect, firstly, by using IgSF4 as a target, a drug capable of specifically affecting cancer cells and damaging thereof (cancer treatment drug) and a treatment method using the drug, or a drug capable of affecting adult T cell leukemia cells and damaging thereof (adult T cell leukemia treatment drug) and the treatment method using the drug are provided. In one embodiment, the drug of the present invention contains an anti-IgSF4 antibody as an effective component. In a preferable embodiment, the drug of the present invention contains an anti-IgSF4 antibody having an ADCC activity as an effective component. In the drug of this embodiment, the treatment effect can be obtained by the cytotoxic property by using an ADCC activity. As the anti-IgSF4 antibody having the ADCC activity, 035-029 antibody, 035-273 antibody, 051-054 antibody, and the like, shown in the below-mentioned Examples (any antibodies in which a part thereof may be modified as long as they maintain a specific binding property against IgSF4 and an ADCC activity). Alternatively, based on this, the constructed antibodies of different kinds (for example, IgG type) are used. These antibodies have both specific binding property against IgSF4 and the ADCC activity. Therefore, they can be specifically bound to cancer cells expressing IgSF4 and then exert the ADCC activity so as to damage the cancer cells. The cancer cell used as a target of the drug of the present invention is not particularly limited, and, for example, a liver cancer cell, a lung cancer cell, and the like, can be used.

In another embodiment, the drug of the present invention uses an anti-IgSF4 antibody as a carrier for DDS. That is to say, this embodiment provides an immunocomplex obtained by combining a drug (cytotoxin and the like), radioactive isotope, or the like (these are also referred to as "active ingredient" together) to anti-IgSF4 antibody. The immunocomplex containing a drug (cytotoxin) having a cell-killing activity or a cytotoxic activity is generally referred to as immunotoxin. An example of the cytotoxin may include Taxol, cytochalasin B, gramicidin D, ethidium bromide, emetine, mitomycin, etoposide, tenoposide, vincristine, vinblastine, colchicines, doxorubicin, daunorubicin, dihydroxy-anthracene-dione, mitoxantrone, methramycin, actinomycin D, 1-dehydrotestosterone, glucocorticoid, procaine, tetracaine, lidocaine, propranolol, and puromycin as well as analogue or homologue thereof.

As the active ingredient contained in the immunocomplex of the present invention, protein or peptide having a desirable biological activity may be used. An example of the candidate for protein and the like that can be used for such a purpose may include abrin, ricin A, *Pseudomonas*—exotoxin, diphteria toxin, tumor necrosis factor, interferon-γ, interleukin 1 (IL-1), interleukin 2 (IL-2), interleukin 6 (IL-6), a granulocyte macrophage colony stimulating factor (GM-CSF), a granulocyte colony stimulating factor (G-CSF) lymphokine.

A technology for combining an active component to an antibody is well known and you can see in, for example, Monoclonal Antibodies And Cancer Therapy, Reisfeld et al. (eds.), pp. 243-56 (Alan R. Liss, Inc. 1985), Controlled Drug Delivery (2nd edition.), Robinson et al. (eds.), pp. 623-53 (Marcel Dekker, Inc. 1987), Monoclonal Antibodies For Cancer Detection And Therapy, Baldwin et al. (eds.), pp. 303-16 (Academic Press 1985), Thorpe et al., "The Preparation And Cytotoxic Properties Of antibody-Toxin Conjugates", Immunol. Rev., 62:119-58 (1982).

The present invention further provides a method for urging to reduce or normalize the grade of malignancy of the target cells by inhibiting and suppressing the expression of IgSF4 in the target cells (that is to say, cancer cells such as liver cancer cells or adult T cell leukemia cells). The inhibition or suppression of the expression of IgSF4 can be carried out by an antisense method or RNA interference or by using ribozyme.

In the case where expression inhibition by the antisense method is carried out, for example, when transcription is carried out in the target cell, an antisense-construct for generating RNA that is complementary to a portion peculiar to mRNA encoding this protein is used. Such an antisense—construct is introduced into the target cells, for example, in a form of an expression plasmid. On the other hand, when it is introduced in to the target cells as the antisense—construct, it is possible to employ an oligonucleotide—probe that is hybridized with mRNA or genome DNA sequence encoding this protein and inhibits the expression thereof. As such an oligonucleotide—probe, one having a resistance to endogenous nuclease such as exonuclease and/or endonuclease is preferably used.

When DNA molecule is used as an antisense nucleic acid, it is preferable that oligodeoxyribonucleotide derived from a region (for example, a region from −10 to +10) including a translation initiation site of mRNA encoding this protein is used.

It is preferable that the complementation between the antisense nucleic acid and the target nucleic acid is strict. However, some mismatch may be accepted. The hybridization performance of the antisense nucleic acid with respect to the target nucleic acid is generally dependent upon both the degree of complementation of both nucleic acids and the length thereof. In general, as the antisense nucleic acid to be used is longer, even if the number of mismatch is increased, a stable double strand (or triple strand) can be formed between the antisense nucleic acid and the target nucleic acid. Persons skilled in the art can confirm the degree of permissible degree of the mismatch by using a standard technique.

The antisense nucleic acid may be DNA, RNA or a chimera mixture thereof, or derivative or modified type thereof. Furthermore, it may be single stranded or double stranded. By modifying a base portion, a sugar portion or a skeleton portion of phosphoric acid, the stability and hybridization performance and the like of the antisense nucleic acid can be improved. Furthermore, to the antisense nucleic acid, materials for urging the cell membrane transportation (for example, see Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or materials capable of enhancing the affinity with respect to certain cells may be added.

The antisense nucleic acid can be synthesized by a usual method, for example, by using commercially available automated DNA synthesizer (for example, Applied Biosystems, and the like). For producing the modulated product or derivative of nucleic acid, you can see, for example, Stein et al. (1988), Nucl. Acids Res. 16:3209, or Sarin et al., (1988), Proc. Natl. Acad. Sci. U.S.A. 85:7448-7451.

In order to enhance the effect of the antisense nucleic acid in the target cells, a strong promoter such as pol II or pol III can be used. That it to say, if a construct including the antisense nucleic acid disposed under control of such a promoter is introduced into the target cells, it is possible to secure the transcription of sufficient amount of the antisense nucleic acid by the effect of the promoter.

The antisense nucleic acid can be expressed by using arbitrary promoters (derivative promoters or constitutive promoters) known to function in the mammalian cells (preferably, human cells). For example, promoters such as a SV40 early promoter region (Bernoist and Chambon, 1981, Nature 290: 304-310), a promoter derived from the 3'-terminal region of Rous sarcoma virus (Yamamoto et al., 1980, Cell 22:787-797), a Herpetic Thymidine Kinase promoter (Wagner et al., 1981, Proc. Natl. Acad. Sci. U.S.A. 78: 1441-1445), and the like, can be used.

In one embodiment of the present invention, the expression of the protein is inhibited by RNA interference (RNAi). RNAi is a process of a sequence specific post-transcriptional gene suppression that can be caused in the eukaryote. In the RNA interference, double stranded RNA (dsRNA) having a sequence corresponding to the sequence of the target mRNA is used. It is known that mammalian cells have two routes (a sequence specific route and a sequence nonspecific route) affected by dsRNA. In the sequence specific route, relatively long dsRNA is divided into short interference RNAs (siRNAs). Each of the siRNAs has sense and antisense chains of about 21 nucleotides that form siRNA of about 19 nucleotides having protruding portions at the 3' terminal portion. On the other hand, it is thought that a sequence nonspecific route can be caused by arbitrary dsRNA regardless of the sequence as long as it has a predetermined length or longer. In this route, dsRNA, two enzymes, that is, PKR, which becomes an active form and stops whole synthesis of proteins by phosphorylating the translation initiation factor eIF2, and 2', 5' oligoadenylate synthetase, which is involved in the synthesis of an RNAase L activated molecule are activated. In the method of the present invention, in order to minimize the progress of this nonspecific route, it is preferable to use dsRNA including less than 30 base pairs (see, for example, Hunter et al. (1975) J Biol Chem 250: 409-17; Manche et al. (1992) Mol Cell Biol 12: 5239-48; Minks et al. (1979) J Biol Chem 254: 10180-3; and Elbashir et al. (2001) Nature 411: 494-8).

Note here that it is confirmed that RNAi is an effective means for reducing the gene expression in various cells (for example, a HeLa cell, a NIH/3T3 cell, a COS cell, a 293 cell, and the like). Furthermore, in general, it can inhibit expression more effectively than by the antisense method.

The dsRNA used in RNAi can be prepared in vitro or in vivo by chemical synthesis or by using an appropriate expression vector. In the latter method, it is particularly effective to prepare a relatively long dsRNA. For designing dsRNA, in general, sequence peculiar to the target nucleic acid (continuous sequence) is used. Note here that a program and algorithm for selecting an appropriate target sequence have been developed.

In another embodiment of the present invention, the expression of IgSF4 is carried out by using ribozyme. By using ribozyme for cleave mRNA at the site specific recognition sequence, it is possible to destroy mRNA encoding the protein. However, preferably, a hammerhead ribozyme is used. A method for constructing the hammerhead ribozyme can be seen in, for example, Haseloff and Gerlach, 1988, Nature, 334: 585-591.

Similar to the antisense method, for example, for the purpose of the stability and target performance, by using a modified oligonucleotide, ribozyme may be constructed. In order to produce an effective amount of ribozyme in the target cells, for example, under the control of a strong promoter (for example, pol II and pol III), it is preferable that the nucleic acid construct in which DNA encoding ribozyme is disposed is used.

Drugs used for the treatment method (including a method of urging to reducing or normalizing the grade of malignancy of cancer cells, and the like) of the present invention can be formulated according to the usual method. In formulation, other ingredients acceptable for formulation (for example, carrier, vehicle, disintegrating agents, buffer agent, emulsifying agent, suspending agent, soothing agent, stabilizer, preservative, antiseptic, physiological saline, and the like) can be contained. An example of the vehicle may include lactose, starch, sorbitol, D-mannitol, sucrose, and the like. An example of the disintegrating agent may include starch, carboxymethyl cellulose, calcium carbonate, and the like. An example of the buffer agent may include phosphate, citrate, acetate, and the like. An example of the emulsifying agent may include gum Arabic, alginate sodium, tragacanth, and the like. An example of the suspending agent may include glyceryl monostearate, aluminum monostearate, methylcellulose, carboxymethyl cellulose, hydroxymethyl cellulose, sodium lauryl sulfate, and the like. An example of the soothing agent may include benzyl alcohol, chlorobutanol, sorbitol, and the like. An example of the stabilizer may include propylene glycol, diethylene sulfite, ascorbic acid, and the like. An example of the antiseptic may include phenol, benzalkonium chloride, benzyl alcohol, chlorobutanol, methylparaben, and the like. An example of the preservative may include benzalkonium chloride, parahydroxybenzoate, chlorobutanol, and the like.

The dosage form in the formulation is not particularly limited. An example of the dosage form may include tablet, powdered drug, fine subtilae, granule, capsule, syrup, injectable drug, external preparation, and suppository.

In the treatment using the drug of the present invention, the drug of the present invention is administered to a subject (patient) with a cancer cell or adult T cell leukemia. The drug of the present invention can be administered to a subject (patient) by oral administration or parenteral administration (intravenous, intra-arterial, subcutaneous, intramuscular, intraperitoneal injection, direct introduction to the target cell, and the like) depending upon the dosage form.

The dosage amount of the drug of the present invention will vary depending on the symptoms, age, sex, body weight, and the like, of the patient, but the person skilled in the art can set an appropriate dosage amount. For example, the dosage amount can be set so that the dosage amount of effective ingredient for adult (body weight: about 60 kg) per day is about 0.001 mg to about 100 mg. The administration schedule can include, for example, once to several times a day, once per two days, or once per three days. For setting the administration schedule, conditions of a patient, efficacy duration time of the drug, and the like, can be considered.

(Screening Method)

The present invention further provides a screening method of a compound that is specifically bound to a liver cancer cell or an adult T cell leukemia. The screening method of the present invention includes the following steps:

(1) bringing IgSF4 into contact with a test compound;
(2) evaluating the binding property of the test compound to IgSF4.

Hereinafter, detail of each step is described.

1. Step (1)

In the step (1), IgSF4 is brought into contact with the test compound. Concretely, for example, a test compound is brought into contact with IgSF4 fixed on the insoluble support such as a plate, membrane, beads, or the like, in a reaction solution. After a predetermined time has passed, washing with an appropriate solution is carried out so as to remove components nonspecifically bounded thereto.

The reaction solution is not particularly limited, and it is possible to use well-known and commercially available buffers, physiological saline, and the like. The reaction conditions (composition and pH of the reaction solution, as well as reaction temperature, reaction time, and the like) can be easily set, for example, based on the results of binding experiment using IgSF4 and an anti-IgSF4 antibody that is one of the specific biding molecules against IgSF4. For example, as the reaction solution, a phosphate buffer solution, a citrate buffer solution, Tris chloride buffer, Tris acetate buffer, and the like, can be used. The pH is, for example, in the range from pH 6.0 to pH 8.0. Preferably, it is in the range from pH 6.5 to pH 7.5. Furthermore, the reaction temperature is, for example, in the range from 4° C. to 45° C. and preferably in the range from 4° C. to 40° C. The reaction time can be set in the range from, for example, 1 minute to 24 hours (concretely, reaction is carried out overnight).

The test compound may be brought into contact with IgSF4 competitively with respect to the anti-IgSF4 antibody. That is to say, an experiment system may be employed in which IgSF4 and anti-IgSF4 antibody are brought into contact with each other in the presence and absence of the test compound. If the test compound has the binding activity with respect to IgSF4, by the presence of the test compound, the binding of the anti-IgSF4 antibody to IgSF4 is inhibited. Therefore, when the amount of anti-IgSF4 antibody bonded to IgSF4 is compared between the case where the test compound is brought into contact with the anti-IgSF4 antibody in the presence of the compound and the case where the test compound is brought into contact with the anti-IgSF4 antibody in the absence of the compound, the binding activity of the test compound to IgSF4 can be determined indirectly.

The test compound used for the screening method of the present invention may include organic compounds having various molecular sizes (nucleic acid, peptide, protein, lipid (simple lipid, complex lipid (phosphoglyceride, sphingolipid, glycosyl glyceride, cerebroside, and the like), prostaglandin, isoprenoid, terpene, steroid, and the like) or inorganic compounds can be used. The test compound may be naturally occurring or may be synthesized. In the latter case, for example, by using a combinatorial synthesizing technique, an effective screening system can be constructed. Note-here that cell extract, culture supernatant, and the like, may be used as the test compound.

2. Step (2)

The step (2) evaluates the binding property of the test compound with respect to IgSF4. That is to say, the amount of the test compound bonded to IgSF4 is measured. Then, based on the measurement results, the binding activity is determined. The measurement of the binding amount with respect to IgSF4 is carried out by an appropriate method in accordance with, for example, kinds and properties of the test compounds. For example, when the test compound is a protein molecule, the amount of the test compounds bound to IgSF4 can be calculated by measuring the amount of protein after components bound to IgSF4 are collected, or by using an immunological technique using an antibody having a specific binding property to the test compound. These methods are just an example and any measurement methods can be employed as long as the binding amount of IgSF4 can be measured.

As mentioned above, when an experiment system using an anti-IgSF4 antibody is employed, the amount of the anti-IgSF4 antibody bound to IgSF4 becomes a measurement subject. Then, from the measurement results (the binding amount of the anti-IgSF4 antibody), the binding activity of the test compound can be obtained.

In the screening method of the present invention, a test compound that is recognized to have a high binding activity with respect to IgSF4 is selected as a promising compound. The compound selected in the screening method of the present invention has a binding activity with respect to IgSF4. Therefore, it can be used as a transporting product for DDS for a cancer cell specifically expressing IgSF4 (that is to say, a liver cancer cell, an adult T cell leukemia cell, and the like) as a target. On the other hand, if the compound itself is recognized to have the cytotoxicity to a cancer cell, the compound itself can be used as a therapeutic drug to a cancer cell. Thus, the compound that is selected in the screening method of the present invention is effective to medical treatment with respect to cancer. Thus, it can be a potential candidate of the cancer therapeutic drug or useful materials for developing the cancer therapeutic drug. When the selected compound has a sufficient drug efficacy to cancer, it can be used as an effective ingredient of the drug as it is. On the other hand, when the selected compound does not have a sufficient drug efficacy, it can be used as an effective ingredient of the drug after it has undergone a chemical modification to enhance the efficacy.

Needless to say, even if it has a sufficient drug efficacy, for the purpose of further improving the drug efficacy, the modification may be carried out similarly.

The present invention further provides a screening method of an IgSF4 binding compound that is efficacious in treating liver cancer. By this screening method, by the contact (administration, addition) of the test compound, it can be examined whether or not cancer cells are killed (or whether the number of cells is reduced). Concretely, the following step is carried out:

(1) preparing cells expressing IgSF4 genes;
(2) bringing the cells into contact with a test compound; and
(3) evaluating killing or decrease of cancer cells.

Hereinafter, each step is described in detail.

1. Step (1)

In the step (1), cells expressing an IgSF4 gene (the base sequence of the standard human IgSF4 gene is shown in SEQ ID NO.: 146) are prepared. Preferably, cells expressing a human IgSF4 gene is used. However, cells expressing an IgSF4 gene of non-human species (for example, IgSF4 gene of mouse or rat) can be used.

Herein, as the "cell," mammalian cells are preferably used. An example of the mammalian cell may include cells of rodents such as mouse, rat, guinea pig, and the like, and primates such as human, monkey, chimpanzee, and the like. The origin of cells is not particularly limited. However, the cells derived from the liver is preferred. It is particularly preferable to use liver cancer cells. As the liver cancer cell line, HepG2 cells, Nuk-1 cells, and HLF cells are established. Then, any of the cells may be used in the method of the present invention.

As long as cells are non-human animal cells (for example, mouse, rat, rabbit, chicken, and the like), cells in a state in which they are not separated from the living body (that is to say, a state of cells constituting the body) may be used.

Instead of dispersed cells, a cell group in which network is found to be formed between cells (for example, cells constituting a certain tissue) can be used for screening. Furthermore, by using cells of two different kinds, the screening method of the present invention can be carried out.

In addition to cells capable of naturally expressing an IgSF4 gene, cells capable of expressing an IgSF4 gene as a result of an artificial operation can be used. For example, transformed cells in which an IgSF4 gene is integrated expressably may be used. An example of cells which can be used for transformation may include HeLa cells, COS cells, and CHO cells. These cells are easily available from a cell bank such as ATCC.

The number of cells to be used is not particularly limited, and it can be determined while considering the detection sensitivity, experimental facility, and the like. For example, 1 to $10^5$ cells can be used. Preferably, 10 to $10^4$ cells can be used. More preferably, $10^2$ to $10^3$ cells can be used.

2. Step (2)

In the step (2), a test compound is brought into contact with the prepared cells. Contact of the test compound is carried out by, for example, culturing cells in a condition in which the test compound is present in the culture medium in a predetermined time. Alternatively, the test compound or the solution including thereof may be brought into contact with the cells directly.

The administration amount may be set arbitrarily. For example, the maximum possible amount can be administered in the range that does not lethally affect the cells.

The contact time is not particularly limited. For example, the contact time may be set in the range from one minute to ten days. Contact is carried out continuously with some intervals.

The test compound used for the screening method of the present invention may include organic compounds having various molecular sizes (nucleic acid, peptide, protein, lipid (simple lipid, complex lipid (phosphoglyceride, sphingolipid, glycosyl glyceride, cerebroside, and the like), prostaglandin, isoprenoid, terpene, steroid, and the like)) or inorganic compounds can be used. The test compound may be naturally occurring or may be synthesized. In the latter case, for example, by using a combinatorial synthesizing technique, an effective screening system can be constructed. Note here that cell extract, culture supernatant, and the like, may be used as the test compound.

3. Step (3)

In the step (3), after the test compound is brought into contact with cancer cells, the killing or decrease of the cancer cells is evaluated. For example, cells (test group) with which the test compound is brought into contact and cells (control group) with which the test compound is not brought into contact are prepared. The numbers of cancer cells are measured for the test group and the control group, respectively, and compared with each other. When the number of survival cells in the test group is smaller than that of the control group, that is to say, when it is found that the test compound has a cancer cell killing effect, it can be determined that the test compound is effective to liver cancer. Therefore, such a compound is selected as a candidate of a liver cancer therapeutic drug. When significant killing effect of cells is found in the test group, it is determined that the test compound is a particularly effective compound to liver cancer. Therefore, such a compound is selected as a very promising candidate of a liver cancer therapeutic drug.

As mentioned above, according to the screening method of the present invention, it is possible to select a candidate compound of a liver cancer therapeutic drug. When the selected compound has a sufficient drug efficacy to liver cancer, it can be used as an effective ingredient of the drug as it is. On the other hand, when the selected compound does not have a sufficient drug efficacy, it can be used as an effective ingredient of the drug after it has undergone a chemical modification to enhance the efficacy. Needless to say, even if it has a sufficient drug efficacy, for the purpose of further improving the drug efficacy, the modification may be carried out similarly.

The present invention further provides a screening method of IgSF4 binding compound that is efficacious in treating adult T cell leukemia. By this screening method, by the contact (administration, addition) of the test compound, it can be examined whether or not adult T cell leukemia cells are killed (or whether the number of cells is reduced). Concretely, the following step is carried out:

(1) preparing adult T cell leukemia cells;
(2) bringing the cells into contact with a test compound; and
(3) evaluating killing or decrease of cancer cells.

Hereinafter, each step is described in detail. Note here that unless otherwise noted, the explanation corresponding to the above-mentioned "a screening method of IgSF4 binding compound that is efficacious in treating liver cancer" is applied.

1. Step (1)

In the step (1), adult T cell leukemia cells are prepared. As the adult T cell leukemia cell line, KK1, KOB, and ST1 are established. Any one of them can be used for the method of the present invention. Cells derived from a patient can be used.

2. Step (2)

In the step (2), a test compound is brought into contact with the prepared cells. The contact method or administration amount of the test compounds, contact time, the test compound to be used, and the like, employ the above-mentioned explanation.

3. Step (3)

In the step (3), after the test compound is brought into contact with adult T cell leukemia cells, the killing or decrease of the cancer cells is evaluated. For example, cells (test group) with which the test compound is brought into contact and cells (control group) with which the test compound is not brought into contact are prepared. The numbers of adult T cell leukemia cells are measured for the test group and the control group, respectively, and compared with each other. When the number of survival cells in the test group is smaller than that of the control group, that is to say, when it is found that the test compound has an adult T cell leukemia cell killing effect, it can be determined that the test compound is effective to adult T cell leukemia. Therefore, such a compound is selected as a candidate of an adult T cell leukemia therapeutic drug. When significant killing effect of cells is found in the test group, it is determined that the test compound is a particularly effective compound to adult T cell leukemia. Therefore, such a compound is selected as a very promising candidate of an adult T cell leukemia therapeutic drug.

As mentioned above, according to the screening method of the present invention, it is possible to select a candidate compound of an adult T cell leukemia therapeutic drug. When the selected compound has a sufficient drug efficacy to adult T cell leukemia, it can be used as an effective ingredient of the drug as it is. On the other hand, when the selected compound does not have a sufficient drug efficacy, it can be used as an effective ingredient of the drug after it has undergone a chemical modification to enhance the efficacy. Needless to say, even if it has a sufficient drug efficacy, for the purpose of further improving the drug efficacy, the modification may be carried out similarly.

(Application for Study)

The present invention further relates to an application for study of IgSF4 gene that has been clarified to specifically express in liver cancer cells. One embodiment of this aspect provides a reagent for liver cancer study, which includes isolated nucleic acid having a base sequence of SEQ ID NO.: 146 or the homologous nucleic acid thereof. Another embodiment of this aspect provides a reagent for liver cancer study, which includes isolated protein having an amino acid sequence of SEQ ID NO.: 145 or the homologous protein thereof.

The reagent of the present invention can be used as an experiment tool for studying the onset mechanism or developing mechanism of symptom of liver cancer. Furthermore, it can be used as a reagent for carrying out the method of the present invention (a method of obtaining information for diagnosing liver cancer, a method of determining the grade of malignancy of liver cancer, a screening method, and the like), or can be used as a component constituting the drug of the present invention. The reagent of the present invention can be used for producing a chimera mouse or a transgenic mouse as a model animal of liver cancer.

The reagent of the present invention contains nucleic acid in a state in which, for example, it is inserted into an appropriate vector (for example, an expression vector).

The "homologous nucleic acid" herein is referred to as nucleic acid in which the function of the encoded protein is equal to that of the reference nucleic acid but a part of the base sequence is different from that of the reference base sequence as compared with the reference nucleic acid (nucleic acid having a base sequence of SEQ ID NO.: 146). An example of the homologous nucleic acid may include DNA encoding a protein having a feature that it has a base sequence including substitution, deletion, insertion, addition or inversion in one or a plurality of bases when the base sequence of SEQ ID NO.: 146 is made to be a reference base sequence, and that the expression amount is increased relating to the grade of malignancy of liver cancer. The substitution, deletion, or the like, of the base may occur in a plurality of sites. Herein, "plurality" denotes, for example, 2 to 40 bases, preferably 2 to 20 bases, and more preferably 2 to 10 bases, although it depends upon the positions or kinds of the amino acid residue in the three-dimensional structure of the protein encoded by the nucleic acid. The above-mentioned homologous nucleic acid can be obtained by modifying nucleic acid having a sequence of SEQ ID NO.: 146 so that a certain site may include substitution, deletion, insertion, addition or inversion of base by using a site specific mutation method. Furthermore, homologous nucleic acid can be obtained by other method such as irradiation with ultraviolet ray.

Another example of the homologous nucleic acid can include nucleic acid that hybridizes to the complementary strand of the nucleic acid of any base sequence of SEQ ID NO.: 146 under stringent conditions. Herein, "stringent conditions" are referred to as conditions in which a so-called specific hybrid can be formed and a nonspecific hybrid cannot be formed. Such stringent conditions are known to the person skilled in the art. Such stringent conditions can be set by referred to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formaldehyde, 10×SSC (0.15M NaCl, 15 mM sodium citrate, pH 7.0), 5×Denhardt solution, 1% SDS, 10% dextran sulfate, and 10 μg/ml modified salmon sperm DNA, 50 mM phosphate buffer (pH 7.5)) is used and incubated at about 42° C. to about 50° C., thereafter, 0.1×SSC and 0.1% SDS are used and washed at about 65° C. to about 70° C. Further preferable stringent conditions can include conditions in which, for example, a hybridization solution (50% formaldehyde, 5×SSC (0.15M NaCl, 15 mM sodium citrate, pH 7.0), 1×Denhardt solution, 1% SDS, 10% dextran sulfate, 10 μg/ml modified salmon sperm DNA and 50 mM phosphate buffer (pH 7.5)) is used.

Further example of the homologous nucleic acid can include nucleic acid in which the above-mentioned difference in the base is recognized due to the polymorphism represented by SNP.

(Kit Used in the Present Invention)

Each method of the present invention (a screening method, a method for obtaining information for diagnosis, and the like) may be carried out by using a kit of reagent and the like. Another aspect of the present invention provides a kit used for such a purpose. For example, nucleic acid (probe and primer), reaction reagent, dilution, a reactor vessel, and the like, which are used for the method of the present invention can be contained in the kit. Note here that the kit of the present invention is generally includes instruction.

The user of a kit makes it possible to allow the method of the present invention to be carried out in a simple way and for a short time.

The configuration of the kit is described in detail taking a case in which the kit is used for determining the grade of malignancy of liver cancer cells by using an immunological technique as an example. The kit of this embodiment includes a reagent having a specific binding property to IgSF4. An appropriate example of this reagent is an anti-IgSF4 antibody but it is not particularly limited to this alone. In the case of a kit used for the method of directly detecting the binding amount of the anti-IgSF4 antibody, a labeled anti-IgSF4 antibody is used. On the other hand, in the case of a kit for the indirect detection method, unlabeled anti-IgSF4 antibody is used. In this case, a secondary antibody labeled with a labeling material (a labeled secondary antibody) may be used. In the case of the kit using a polymer to which the secondary antibody and a labeling material are bonded, the polymer may be included in the kit.

On the other hand, the kit may include IgSF4 (antigen). The IgSF4 is not always full length IgSF4 as long as it can recognize an anti-IgSF4 antibody contained in the kit. Furthermore, recombinant IgSF4 may be used. IgSF4 is used for confirming that the staining property obtained by using a kit is based on the specific binding between the anti-IgSF4 antibody and IgSF4. Specifically, firstly, an anti-IgSF4 antibody is treated with this IgSF4. Immunostaining is carried out by using the treated anti-IgSF4 antibody. The obtained stained image is compared with the stained image obtained by using an untreated anti-IgSF4 antibody. If the latter stained image shows a stronger staining property, it can be confirmed that the staining property is based on the specific binding between the anti-IgSF4 antibody and IgSF4.

Furthermore, on the other hand, when an anti-IgSF4 antibody produced using a fused protein of a tag and a carrier protein (hereinafter, referred to as "tag and the like") as antigen, furthermore, the used tag and the like may be contained in the kit. This tag is necessary when an antibody having a reactivity with respect to the tag and the like used during the production process may be mixed in the anti-IgSF4 antibody constituting the kit. When the tag and the like is used as mentioned below, it can be confirmed that the staining property obtained by using a kit is based on the specific binding between the anti-IgSF4 antibody and the IgSF4 antibody. Firstly, the anti-IgSF4 antibody is treated with the tag and the like. Then, immunostaining of the specimen is carried out by using the treated anti-IgSF4 antibody. The obtained stained image is compared with the stained image obtained by using an untreated anti-IgSF4 antibody. If there is no difference in the staining property between the both stained images, it can be confirmed that the staining property of the latter stained image is based on the specific binding between the anti-IgSF4 antibody and the IgSF4.

The kit of the present invention may further include one or more reagents, instrument, or the like, which are necessary to carry out immunostaining such as an antigen antibody reaction or staining, and the like (for example, formalin or paraffin for fixing or embedding tissue, color reagent such as BSA, DAB, and the like, for inhibiting the nonspecific binding, a hematoxylin solution and the like for nuclear staining). Furthermore, in general, the kit of the present invention includes an instruction manual.

(Use of IgSF4 as Antigen)

The aspect of the present invention relates to a use of IgSF4 as an antigen. That is to say, by using IgSF4 as antigen, a method of obtaining an antibody having a specific binding property to IgSF4 is provided. For example, as an immunological antigen by a classical immunological technique, or a screening antigen in an antibody production method using a genetic engineering technique such as a phage display method, and the like, IgSF4 is used.

As IgSF4 as an antigen, any of the following IgSF4 can be used:

(1) IgSF4 produced by using an expression system of *E. coli;*

(2) IgSF4 secreted in a culture medium by using an expression system of an animal cell;

(3) IgSF4 expressed on a cell surface by using an expression system of an animal cell;

(4) IgSF4 secreted in a culture medium or expressed on a cell surface by using an expression system of an animal cell that expresses T antigen and is capable of carrying out a transitional expression.

Furthermore, when being used as an antigen, since IgSF4 is membrane protein, it is preferable that a partial protein of an extracellular domain is used as an antigen. Further preferably, a membrane fraction expressed in a cell is used, and most preferably, an IgSF4 high expression cell itself as an antigen for obtaining the IgSF4 antibody. The antibodies recognizing these IgSF4 extracellular domains are used not only for immunostaining. In addition, because they have a potential for presenting an ADCC activity, a method for obtaining a binding antibody using IgSF4 as an antigen is useful for obtaining a treating antibody.

EXAMPLE

1. Preparation of Vector for Preparing scFv Antibody Gene Library 1-1 Preparation of Vector for Preparing scFv Antibody Gene Library As conceptually shown in FIG. 1, a pAALFab vector was prepared by incorporating pelB (signal sequence) of M13 phage, His 6 tag sequence, cp3 protein of M13 phage (Δcp3 (198aa-406aa) N-end deleted capsid protein 3) sequence, and protein A protein sequence in pTZ19R phagemid vector (Pharmacia) at an appropriate restriction enzyme site (see Iba, Y. et al., Gene 194: 35-46, 1997). From this pAALFab, pFCAH9-E8d for an integration vector was prepared.

An actual antibody protein expression vector is to be completed by inserting a heavy chain gene and a light chain gene at the predetermined locations of this vector. The shape of the antibody expressed by the completed vector is in a scFv type. A light chain constant region CL gene has been bound to the above-described cp3 gene, as a result, the expression protein is to be in a shape of scFv-CL-cp3. Concretely, the following operations were carried out:

Primers which have been used:

```
527 Reverse (SEQ ID NO.: 147):
5'-CAGGAAACAGCTATGAC-3'

599 E8VHf-PstR: (SEQ ID NO.: 148)
3'-CGGCTCCAAGTCGACGTCGTCA-5'

544 E8VHf-PstF: (SEQ ID NO.: 149)
5'-CAGCTGCAGCAGTCTGGGGCAGAGCTTGTGAAGCCAGGGGCCTCAGT
CAAGTTGTCCTGCACAGCTTCTGGCTTCAACATTAA-3'

545 E8VHf-XbaR: (SEQ ID NO.: 150)
3'-AGACCGAAGTTGTAATTTCTGTGGATATACGTGACCCACTTCGTCTC
CGGACTTTTCCCAGATCTCACCTAACCTTCCTAA-5'

546 E8VHf-XbaF: (SEQ ID NO.: 151)
5'-AAGGGTCTAGAGTGGATTGGAAGGATTGATCCTGCGAGTGGTAATAC
TAAATATGACCCGAAGGACAAGGCCACTATAACAGCA-3'
```

-continued

547 E8VHf-EcoR (SEQ ID NO.: 152)
3'-TTCCTGTTCCGGTGATATTGTCGTCTGTGTAGGAGGTTGTGTCGGAT
GGATGTCGACTTAAGGGAC-5'

548 E8VHf-EcoF (SEQ ID NO.: 153)
5'-CAGCTGAATTCCCTGACATCTGAGGACACTGCCGTCTATTACTGTGC
TGGT-3'

549 E8VHf-BstR (SEQ ID NO.: 154):
3'-CAGATAATGACACGACCAATACTAATGCCGTTGAAACTGATGACCCC
GGTTCCGTGGTGCCAGTGGCACAAGG-5'

590 His6-SmaR (SEQ ID NO.: 155):
3'-GGTTCTCTAACAGTAGTGGTAGTAGTGGTAATTATTCTCGATAGGGC
CCTCGAA-5'

542 E8VLf-SacF (SEQ ID NO.: 156):
5'-GACATCGAGCTCACCCAGTCTCCAGCCTCCCTTTCTGCGTCTGTGGG
AGAAACTGTCACCATCACATGT-3'

539 E8VLf-KpnR (SEQ ID NO.: 157):
3'-TGACAGTGGTAGTGTACAGCTCGTTCACCCTTATAAGTGTTAATAAA
TCGTACCATGGTCGTC-5'

542 E8VLf-KpnF (SEQ ID NO.: 158):
5'-GCATGGTACCAGCAGAAACCAGGGAAATCTCCTCAGCTCCTGGTCTA
T-3'

543 E8VLf-BamR (SEQ ID NO.: 159):
3'-GGAGTCGAGGACCAGATATTACGTTTTTGGAATCGTCTACCACACGG
TAGTTCCAAGTCACCGTCACCTAGGCCTTGTGTT-5'

562 E8VLf-XhoR (SEQ ID NO.: 160):
3'-TCATGAGGCACCTGCAAGCCACCTCCGTGGTTCGAGCTCTAGTT
T-5'

563 E8VLf-XhoF (SEQ ID NO.: 161):
5'-AGTACTCCGTGGACGTTCGGTGGAGGCACCAAGCTCGAGATCAA
A-3'

613 NheR (SEQ ID NO.: 162):
3'-ATCGACAGCT-5'

600 E8VLKpnXboR (SEQ ID NO.: 163):
3'-AAGCCACCTCCATGGTTCGAGCTCTAGTTT-5'

LCP3ASC (SEQ ID NO.: 164):
3'-TCGAAGTTGTCCTTACTCACAAGCCGCGCGGTCAGCTGAGGTAA-5' hCH1Bst (SEQ ID NO.: 165):
5'-ACCCTGGTCACCGTCTCCTCAGCCTCCACCAAGGGCCCATCGGTCTT
CCCCCTGG-3' hCH1midAS (SEQ ID NO.: 166):
3'-GGGAGTCGTCGCAGCACTGGCACGGGAGGTCGTCGAA-5' hCH1midS (SEQ ID NO.: 167):
5'-GGACTCTACTCCCTCAGCAGCGTCGTGACCGTGCCC-3' hCH1H6 (SEQ ID NO.: 168):
3'-GGGTCGTTGTGGTTCCACCTGTTCTTTCAACTCGGGTTTAGAACAGT
AGTGGTAGTAGTGGTA-5' hCH1H6Sma (SEQ ID NO.: 169):
3'-GGGTTTAGAACAGTAGTGGTAGTAGTGGTAATTATTCTCGATAGGGC
CCTCGAACG-5'

702 BstXhoF (SEQ ID NO.: 170):
5'-GGCACCACGGTCACCGTCTCGAGCGCCTCCACC-3'

<Preparation of pFCAH3-E8T H Chain Portion>
1) A DNA fragment was prepared by carrying out PCR using 527-599 and PCR using 547-590 by making pAALFab as a template.
2) A DNA fragment was prepared by carrying out PCR using 544-545, 546-547, 548-549.
3) 1) and 2) were mixed, PCR was carried out using 527, 590 and this was cloned into HindIII-SmaI site of pAALFab.
<pFCAH3-E8T L Chain Portion>

Figure 2:
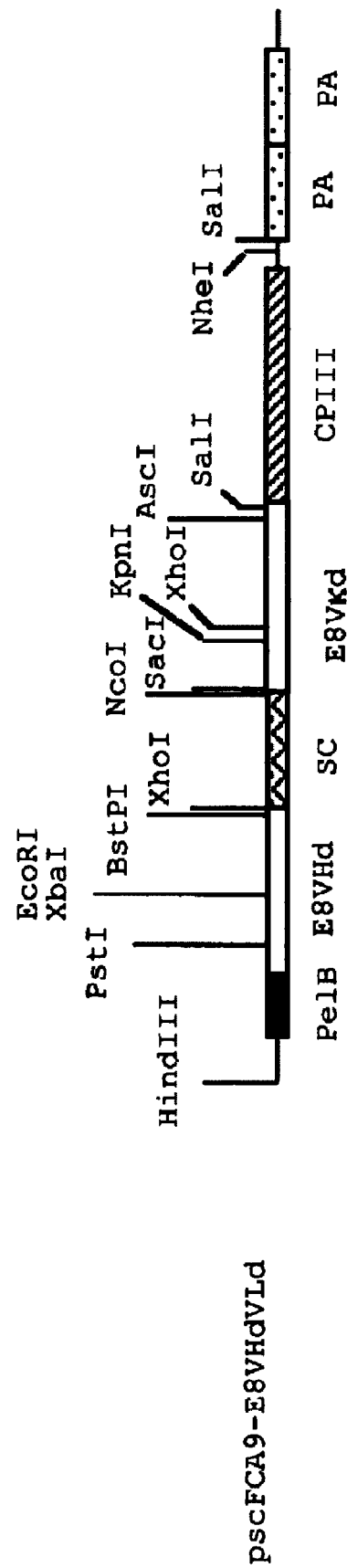
FIG. 2 is a diagram schematically showing the structure of pscFvCA9-E8VHdVLd.

4) A DNA fragment was prepared by carrying out PCR using 542-562, 561-613.
5) A DNA fragment was prepared by carrying out PCR using 538-539, 542-543.
6) 4) and 5) were mixed, PCR was carried out using 538, 562 and this was cloned into SacI-NheI site of pAALFab.
<pFCAH9-E8d>
7) Preparation of VH stuffer portion
After pFCAH3-E8T was digested with XbaI, EcoRI and changed into a blunt end by being acted with a klenow fragment, self ligation was carried out, thereby preparing a stuffer of a VH portion.
8) Preparation of VL stuffer portion
PCR was carried out using 527-600 by making pFCAH3-E8T as a template, and cloned into HindIII-XhoI site of 7).
9) This was digested with KpnI, the self ligation was carried out and a stuffer of the VL portion was prepared.
10) Introduction of SfiI, NcoI, SpeI sites
PCR was carried out using 527-663 by making pFCAH3-E8T as a template, and cloned into HindIII-SacI site of 1).
11) Introduction of AscI site
PCR was carried out using 527-LCP3ASC by making pFCAH3-E8T as a template, this was cloned into 2) by completely digesting it with SacI and partially digesting it with SalII.
12) Conversion of γCH1 portion into human gene
Since BstPI site exists in the human γCH1 portion, cloning was carried out by designing this being deleted. By making tonsil cDNA as a template, after PCR was carried out using hCH1Bst-hCH1midS, hCH1midAS-hCH1H6, these were mixed, then PCR was carried out using hCH1Bst-hCH16Sma, and its DNA fragment was cloned into BstPI-Sma site of 3).
13) Introduction of Xho site
By making 12) as a template, PCR was carried out using 702-663, this was cloned into BstPI-SacI site of 12).
<Preparation of pscFvCA9-E8VHdVLd>
3 μg (3 μL) of pFCAH9-E8d (see FIG. 1D) was mixed with 3 μL of BstPI (3 U/μL), 5 μL of 10×H buffer, 39 μL of DW, and treated with restriction enzyme at 37° C. for 2 hours. After the treatment, the precipitation obtained by carrying out the precipitation with ethanol was dissolved in 10 μL of TE buffer. 1 μL of SacI (10 U/μL), 5 μL of 10×L buffer, 34 μL of DW were mixed into this, and after treated with restriction enzyme at 37° C. for 2 hours, agarose gel electrophoresis was carried out, then 4.7 kb fragment was collected. The recovered matter was precipitated with ethanol and made it into 10 μL (pFCAH9-E8d BstPI-SacI fragment).
On the other hand, 5 μL of primer linF (100 μmol/μL) and 5 μL of primer linR (100 pmol/μL) were mixed, and after heated at 94° C. for 5 minutes, and annealed by being heated at 80° C. for 5 minutes, at 70° C. for 5 minutes and left at room temperature for 30 minutes. 2 μL was taken, then 1 μL of pFCAH9-E8d BstPI-SacI fragment obtained above, 1.5 μL of 10× ligation buffer, 9.5 μL of DW and 1 μL of T4DNA ligase were mixed, and reacted at 16° C. for 16 hours. After the reaction the precipitation was carried out with ethanol resulting in being condensed into 3 μL, and out of this, using 1.5 μL, 20 μL of E. coli DH12S competent cell was transformed by electroporation. The plasmid of the obtained clone was extracted, the base sequence was confirmed and named as pscFvCA9-E8VHdVLd. In FIG. 2, the structure of is pscFvCA9-E8VHdVLd schematically shown. Moreover, in FIG. 3-1-FIG. 3-2, the base sequence of the insert portion of pscFvCA9-E8VHdVLd (SEQ ID No.: 171) and amino acid sequence (SEQ ID No.: 172) coded by it are shown.

Primer IinF
(SEQ ID NO.: 173)
GTCACCGTCTCGAGAGGCGGTGGCGGATCAGGTGGCGGTGGAAGTGGCGG
TGGTGGGTCCATGGCCGACATCGAGCT Primer IinR
(SEQ ID NO.: 174)
CGATGTCGGCCATGGACCCACCACCGCCACTTCCACCGCCACCTGATCCG
CCACCGCCTCTCGAGACG

1-2 Preparation of Vector for Temporarily Cloning Heavy Chain Variable Region (VH)

First, according to the known technique (see Iba, Y. et al., Gene 194: 35-46, 1997), pAALFab vector (FIG. 1A) was prepared. A pscFvCA-E8VHd vector (FIG. 1C) in which XbaI through EcoRI of pAALFab vector was deleted, restriction enzyme cut sites Kpn I, Sfi I, Nco I and Spe I were newly added, and a VH (heavy chain variable region) is capable of cloning via pFCAH3-E8T (FIG. 1B) was prepared, and was made a vector for temporarily cloning a heavy chain variable region. The base sequence (SEQ ID NO.: 175) of an insert of pscFvCA-E8VHd is shown in FIGS. 4-1 to 4-2, restriction enzyme sites and the amino acid sequence (SEQ ID NO.: 176) coded by the base sequence are shown.

Concretely, Primer 610 and primer 611 were annealed, which was cloned into BstPI-SacI site of pFCAH3-E8T, thereby preparing a single chain. Furthermore, PCR was carried out using primer 527 and primer 619, which was further cloned into HindIII-PstI site, and the introduction of SfiI, NcoI sites was carried out. The sequences of primers used in the preparation of the vector are shown bellow.

610 scBstSpeSacF (SEQ ID NO.: 177):
5'-CACCACGGTCACCGTCTCCTCAGGCGGTGGCGGATCAGGTGGCGGTG
GAAGTGGCGGTGGTGGGTCTACTAGTGACATCGAGCTCACCCAG-3'

611 scBstSpeSacR (SEQ ID NO.: 178):
3'-GTGGTGCCAGTGGCAGAGGAGTCCGCCACCGCCTAGTCCACCGCCAC
CTTCACCGCCACCACCCAGATGATCACTGTAGCTCGAGTGGGTC-5'

527 Reverse (SEQ ID NO.: 179):
5'-CAGGAAACAGCTATGAC-3'

619 E8VHf-SfiNcoPstR (SEQ ID NO.: 180):
3'-GACGCCGGGTCGGCCGGTACCGGCTCCAAGTCGACGTCGTCA-5'

2. Preparation of Immunoglobulin Light Chain Library

2-1 Isolation of Immunoglobulin Light Chain Gene Using PCR 2.6 μg of mRNA was obtained using commercially available kit (QuickPrep Micro mRNA purification kit; made by Pharmacia Biotech) from 4×10⁷ bone marrow cells (specimen No. 59) and lymphocytes collected from umbilical blood and peripheral blood. A cDNA was prepared from this mRNA. The cDNA was prepared by SuperScript Preamplification System made by GibcoBRL. An oligo dT was used for primer. By making the obtained cDNA as a template, PCR was carried out using 5'primer (κ1-κ6, λ1-λ6) and 3' primer (hCKASC primer or hCLASC primer) for acquiring a light chain gene. After phenol treatment, the PCR product was precipitated with ethanol and suspended in 10 μL of TE buffer. The base sequence of primer employed and PCR conditions are as follows:

Note that the underlined portions in the base sequences of primers for acquiring a light chain gene indicate NcoI site, AscI site.

5'-primer κ1-κ6
hVK1a (SEQ ID NO.: 181):
GTCCTCGCAACTGCGGCCCAGCCGGCCATGGCCGACATCCAGATGACCCA
GTCTCC hVK2a (SEQ ID NO.: 182:
GTCCTCGCAACTGCGGCCCAGCCGGCCATGGCCGATGTTGTGATGACTCA
GTCTCC hVK3a (SEQ ID NO.: 183):
GTCCTCGCAACTGCGGCCCAGCCGGCCATGGCCGAAATTGTGTTGACGCA
GTCTCC hVK4a (SEQ ID NO.: 184):
GTCCTCGCAACTGCGGCCCAGCCGGCCATGGCCGACATCGTGATGACCCA
GTCTCC hVK5a (SEQ ID NO.: 185):
GTCCTCGCAACTGCGGCCCAGCCGGCCATGGCCGAAACGACACTCACGCA
GTCTCC hVK6a (SEQ ID NO.: 186):
GTCCTCGCAACTGCGGCCCAGCCGGCCATGGCCGAAATTGTGCTGACTCA
GTCTCC 5'-primerλ1-λ6
hVL1 (SEQ ID NO.: 187):
GTCCTCGCAACTGCGGCCCAGCCGGCCATGGCCCAGTCTGTGTTGACGCA
GCCGCC hVL2 (SEQ ID NO.: 188):
GTCCTCGCAACTGCGGCCCAGCCGGCCATGGCCCAGTCTGCCCTGACTCA
GCCTGC hVK3a (SEQ ID NO.: 189):
GTCCTCGCAACTGCGGCCCAGCCGGCCATGGCCTCCTATGTGCTGACTCA
GCCACC hVL3b (SEQ ID NO.: 190):
GTCCTCGCAACTGCGGCCCAGCCGGCCATGGCCTCTTCTGAGCTGACTCA
GGACCC hVL4 (SEQ ID NO.: 191):
GTCCTCGCAACTGCGGCCCAGCCGGCCATGGCCCACGTTATACTGACTCA
ACCGCC hVL5 (SEQ ID NO.: 192):
GTCCTCGCAACTGCGGCCCAGCCGGCCATGGCCCAGGCTGTGCTCACTCA
GCCGCC hVL6 (SEQ ID NO.: 193):
GTCCTCGCAACTGCGGCCCAGCCGGCCATGGCCAATTTTATGCTGACTCA
GCCCCA 3'-primer hCKASC (SEQ ID NO.: 194):
TCGACTGGCGCGCCGAACACTCTCCCTGTTGAAGCTCTTTGTG 3'-primer HCLASC (SEQ ID NO.: 195):
TCGACTGGCGCGCCGAACATTCTGTAGGGGCCACTGTCTTCTC Conditions of PCRμ

| | |
|---|---|
| cDNA | 2 μL |
| 10 x buffer #1 (Attached to KOD) | 10 μL |
| dNTP mix (2.0 mM) | 10 μL |
| 25 mM MgCl₂ | 4 μL |
| 5'end side primer (100 pmol/μL) | 1 μL |
| 3'end side primer (100 pmol/μL) | 1 μL |
| Already sterilized MilliQ | 71 μL |
| KOD DNA polymerase (2.5 U/μL; made by Toyobo) | 1 μL |

35 cycles of PCR carrying out one cycle at 94° C. for one minute, at 55° C. for 2 minutes and at 74° C. for one minute.

2-2-1 Incorporation of Light Chain Gene into Phagemid

The PCR product obtained in 1 was treated with restriction enzymes under the following conditions:

| | |
|---|---|
| PCR product | 10 μL |
| 10 x NEB4 (Attached to AscI) | 5 μL |
| Already sterilized MilliQ | 33 μL |
| AscI (10 U/μL; made by NEB) | 1 μL |
| NcoI (10 U/μL; made by Takara) | 1 μL |

After reacting at 37° C. for one hour and at 50° C. for one hour, the portion of 10 μL out of it was subjected to agarose electrophoresis, the band nearby 600 bp was cut out, and purified by Gene Clean II Kit (made by Funakoshi). pscFvCA9-E8VHdVLd, which had been treated with restriction enzymes in the same manner as the PCR product, was purified with Gene Clean II Kit and then ligated by reacting it with the PCR product treated by restriction enzymes at 16° C. for 4 hours to over night under the following conditions:

| | |
|---|---|
| pscFvCA9-E8VHdVLd treated with restriction enzymes | 2 μL |
| PCR product treated with restriction enzymes | 1 μL |
| 10 x ligation buffer (Attached to T4 DNA ligase) | 1.5 μL |
| 10 mM ATP | 1.5 μL |
| Already sterilized MilliQ | 8 μL |
| T4 DNA ligase (10 U/μL; made by Takara) | 1 μL |

2-2-2 Introduction of Phagemid into *E. coli*

*E. coli* DH12S was transformed using the obtained ligated DNA as follows:

Specifically, the ligated DNA was once precipitated with ethanol, and dissolved in 3 μL of ⅕TE (TE diluted 5-fold with already sterilized MilliQ). Out of it, 1.5 μL was suspended in 20 μL of competent cell DH12S (made by GIBCO BRL), the electroporation was carried out under the following conditions:

| Electroporator Cell-Porator (Cat. series 1600) made by BRL | | |
|---|---|---|
| Setting conditions; | voltage booster | 4 kΩ |
| | capacitance | 330 μF |
| | DC volts | Low Ω |
| | charge rate | Fast |

The above-described transformed *E. coli* was inputted in 2 mL of the medium for transformation (SOB), after shaken and cultured at 37° C. for one hour, one portion of it plated on the agar medium (Amp plate), the remains were cultured in 1% glucose, 100 μg/mL ampicilin containing 2×TY medium and stocked with glycerin. The agar medium was incubated at 30° C., the growing colony was separated by picking at it with a stick, a plasmid was prepared, respectively, and the base sequence of the light chain gene was examined.

SOB medium: the following components were added to 950 mL of the purified water and shaken, after completely dissolved, 10 mL of KCl solution in 250 mM was added, and adjusted at pH 7.0 with 5N NaOH. After the purified water was added to adjust the volume into 1000 mL, it was sterilized using autoclave for 20 minutes, and 5 mL of $MgCl_2$ in 2M sterilized immediately before the use was added.

| | |
|---|---|
| Bacto-tryptone | 20 g |
| Bacto-yeast extract | 5 g |
| NaCl | 0.5 g |

2×YT medium: the following components were added to 900 mL of the purified water and shaken, after completely dissolved, it was adjusted at pH 7.0 with 5N NaOH, the purified water was added to make the volume into 1000 mL. Sterilized by autoclave for 20 minutes, and used.

| | |
|---|---|
| Bacto-tryptone | 16 g |
| Bacto-yeast extract | 10 g |
| NaCl | 5 g |

The other reagents were purchased from the followings:

| Maker | Name of product |
|---|---|
| Sigma | Ampicillin sodium |
| Wako Junyaku | Phenol |
| Sigma | BSA |
| DIFCO | 2 x YT medium |
| Wako Junyaku | kanamycin sulfate |
| Nacalai tesque | polyethylene glycol 6000 |
| Nacalai tesque | Tween 20 |
| Katayama Chemical | NaCl |
| Wako Junyaku | IPTG |
| Wako Junyaku | skimmed milk |
| Wako Junyaku | sodium azide |
| Wako Junyaku | triethylamine |
| Wako Junyaku | hydrogen peroxide |
| Wako Junyaku | OPD tablet |
| Wako Junyaku | ethanol |

The above-described operations were carried out with respect to all of κ1, κ2, κ3, κ4, κ5 and κ6, and λ1, λ2, λ3a, λ3b, λ4, λ5, λ6, λ7, λ8, λ9 and λ10, and whether or not the clone of interest was obtained was confirmed. Subsequently, clones of the respective groups such as κ1, κ2 and the like were mixed so as to become equivalent ratio of the usage frequency in vivo. As for the groups of these light chains, it was already known at what ratio these actually express in vivo. These gene clones amplified by PCR and incorporated in a vector were mixed so as to become at a ratio nearby the usage frequency in vivo, and made VL library. The constitutive ratio of the respective families in VL library is indicated as follows:

TABLE 1

| family | Usage frequency in vivo(%)* | Constitutive ratio in VL library (%) | Constitutive ratio in KL200 (%) |
|---|---|---|---|
| Vκ1 | 39 | 37 | 30.7 |
| Vκ2 | 12 | 12 | 19.8 |
| Vκ3 | 36 | 35 | 33.7 |
| Vκ4 | 12 | 12 | 10.9 |
| Vκ5 | 1 | 2 | 5.0 |
| Vκ6 | —** | 2*** | 0.0 |

*Griffith AD et al. EMBO J. (1994) 13, 3245-60.
**No description when published.
***Equal quantities of cDNA prepared with primer VK6-2 and cDNA prepared with primer VK6-3 were mixed.

TABLE 2

| family | Usage frequency in vivo(%)* | Constitutive ratio in VL library (%) | Constitutive ratio in KL200 (%) |
|---|---|---|---|
| Vλ1 | 43 | 41 | 34.1 |
| Vλ2 | 15 | 15*[3] | 15.2 |
| Vλ3 | 34 | 32*[4] | 25.3 |
| Vλ4 | 0 | 1.5*[5] | 0.0 |
| Vλ5 | 0 | 1.0*[6] | 11.1 |
| Vλ6 | 0 | 1 | 14.1 |
| Vλ7 | 6 | 6 | 0.0 |
| Vλ8 | 1 | 1 | 0.0 |
| Vλ9 | 1 | 1 | 0.0 |
| Vλ10 | —*[2] | 1 | 0.0 |

*Griffith AD et al. EMBO J. (1994) 13, 3245-60.
*[2]No description when published.
*[3]5% of cDNA prepared with primer VL2 and 10% of cDNA prepared with primer VL2-2 were mixed.
*[4]17% of cDNA prepared with primer VL3a-2 and 15% of cDNA prepared with primer VL3b were mixed.
*[5]0.5% of cDNA prepared with primer VL4a and 0.5% of cDNA prepared with primer VL4b and 0.5% of cDNA prepared with VL4c were mixed.
*[6]0.5% of cDNA prepared with primer VL5abde and 0.5% of cDNA prepared with primer VL5c were mixed.

3. Preparation of Combination Library (scFv Antibody Gene Library) of Light Chain Gene library and heavy chain gene library 3-1-1 Isolation of Immunoglobin Heavy Chain Gene Using PCR cDNAs were prepared from umbilical blood, bone marrow liquid, lymphocyte in peripheral blood and tonsil using human μ primer (primer 634 shown in the following) or random hexamer by the procedure similar to 2-1, by making each cDNA as a template, and PCR was carried out using 5' primer for acquiring human antibody heavy chain gene (VH1-VH7) and 3' primer (primer in which equal quantities of 4 species of human JH primers were mixed, primer 697-700 shown in the following or human μ primer (primer 634 shown in the following). In Table, the portions underlined are indicated as SfiI sites. Since hVH2a did not correspond to germ line VH2 family, VH2a-2 was newly designed. Moreover, since hVH4a did not correspond to the whole of VH4 family, hVH4a-2 was newly designed. Since VH5a neither corresponded to germ line VH5 subfamily, VH5a-2 was newly designed. Moreover, as a primer corresponding to VH7, hVH7 was designed. These genes were also amplified, then incorporated into pscFvCA-E8VHd, and what kinds of genes were obtained were confirmed by a base sequence. As for hVH5a-2, its sequence is extremely similar to hVH1a, since a gene product similar to a gene product amplified by hVH1a was expected to obtain, it was not used. The PCR product was suspended in 10 μL of TE buffer by precipitating with ethanol following phenol treatment.

634 humμCH1R (SEQ ID NO.: 196):
ATGGAGTCGGGAAGGAAGTC

Primers Used for the Amplification of Each VH Family Human VH Primer SfiI Sites are Indicated by Underlines.

628 hVH1a (SEQ ID NO.: 197):
GTCCTCGCAACTGCGGCCCAGCCGGCCATGGCCCAGGTGCAGCTGGTGCA
GTCTGG 629 hVH2a (SEQ ID NO.: 198):
GTCCTCGCAACTGCGGCCCAGCCGGCCATGGCCCAGGTCAACTTAAGGGA
GTCTGG 630 hVH3a (SEQ ID NO.: 199):
GTCCTCGCAACTGCGGCCCAGCCGGCCATGGCCGAGGTGCAGCTGGTGGA
GTCTGG 631 hVH4a (SEQ ID NO.: 200):
GTCCTCGCAACTGCGGCCCAGCCGGCCATGGCCCAGGTGCAGCTGCAGGA
GTCGGG 632 hVH5a (SEQ ID NO.: 201):
GTCCTCGCAACTGCGGCCCAGCCGGCCATGGCCCAGGTGCAGCTGTTGCA
GTCTGC 633 hVH6a (SEQ ID NO.: 202):
GTCCTCGCAACTGCGGCCCAGCCGGCCATGGCCCAGGTACAGCTGCAGCA
GTCAGG 629-2 hVH2a-2 (SEQ ID NO.: 203):
GTCCTCGCAACTGCGGCCCAGCCGGCCATGGCCCAGRTCACCTTGAAGGA
GTCTGGTCC 63 1-2 hVH4a-2 (SEQ ID NO.: 204):
GTCCTCGCAACTGCGGCCCAGCCGGCCATGGCCCAGGTGCAGCTACAGCA
GTGGGG 632-2 hVH5a-2 (SEQ ID NO.: 205):
GTCCTCGCAACTGCGGCCCAGCCGGCCATGGCCGAGGTGCAGCTGGTGCA
GTCTGG 712 hVH7 (SEQ ID NO.: 206):
GTCCTCGCAACTGCGGCCCAGCCGGCCATGGCCCAGGTGCAGCTGGTGCA
ATCTGGGTCTGAGT

Human JH primer BstPI, XhoI sites are shown by an underline.
697 hJH1-2 (SEQ ID NO.: 207):
GGTGGAGGCACTCGAGACGGTGACCAGGGTGC 698 hJH3 (SEQ ID NO.: 208):
GGTGGAGGCACTCGAGACGGTGACCATTGTCC 699 hJH4-5 (SEQ ID NO.: 209):
GGTGGAGGCACTCGAGACGGTGACCAGGGTTC 700 hJH6 (SEQ ID NO.: 210):
GGTGGAGGCACTCGAGACGGTGACCGTGGTCC

| | |
|---|---|
| cDNA | 2 μL |
| 10 x buffer #1(Attached to KOD) | 10 μL |
| dNTP mix (2.0 mM) | 10 μL |
| 25 m MgCl$_2$ | 4 μL |
| 5'end side primer (100 pmol/μL) | 1 μL |
| 3'end side primer (100 pmol/μL) | 1 μL |
| Already sterilized MilliQ | 71 μL |
| KOD DNA polymerase (2.5 U/μL; made by Toyobo) | 1 μL |

PCR conditions: 35 cycles of PCR carrying out one cycle at 94° C. for one minute, at 55° C. for 2 minutes and at 74° C. for one minute.

3-1-2 Preparation of Heavy Chain Gene Library

The PCR product obtained in 3-1-1 was treated with restriction enzymes under the following conditions:

| | |
|---|---|
| PCR product | 10 μL |
| 10 x K buffer (made by Takara) | 5 μL |
| Already sterilized MilliQ | 33 μL |
| SfiI (10 U/μL; made by NEB) | 1 μL |
| XhoI (12 U/μL; made by Takara) | 1 μL |

After reacting at 37° C. for 2 hours, the portion of 10 μL out of it was subjected to agarose electrophoresis, the band nearby 400 bp was cut out, and purified by Gene Clean II Kit (made by Funakoshi). pscFvCA-E8VHd, which had been treated with restriction enzymes in the same manner as the PCR product, was purified with Gene Clean II Kit. The ligation was carried out by reacting it with the PCR product treated by restriction enzymes at 16° C. for 4 hours to over night under the following conditions:

| | |
|---|---|
| pscFvCA-E8VHd treated with restriction enzymes | 2 μL |
| PCR product treated with restriction enzymes | 1 μL |
| 10 x ligation buffer (Attached to T4 DNA ligase) | 1.5 μL |
| 10 mM ATP | 1.5 μL |
| Already sterilized MilliQ | 8 μL |
| T4 DNA ligase (10 U/μL; made by Takara) | 1 μL |

3-1-3 Introduction of Phagemid into *E. Coli*

The obtained DNA was transformed into *E. coli* DH12S. Concretely, the DNA was once precipitated with ethanol, and dissolved in 3 μL of ⅕TE (TE diluted 5-fold with already sterilized MilliQ). Out of this, 1.5 μL was suspended in 20 μL of competent cell DH12S (made by GIBCO BRL), and transformation was carried out by an electroporation method.

| Electroporator Cell-Porator (Cat. series 1600) made by BRL | | |
|---|---|---|
| Setting conditions: | voltage booster | 4 kΩ |
| | capacitance | 330 μF |
| | DC volts | Low Ω |
| | charge rate | Fast |

The above-described transformed *E. coli* that the above-described operation were terminated was put in 2 mL of the medium for transformation (SOB), after shaken and cultured at 37° C. for one hour, one portion of it was plated on the agar medium (Amp plate), the remains were cultured in 0.1% glucose, 100 μg/mL ampicillin containing 2×YT medium and stocked with glycerin. The agar medium was incubated at 30° C., the grown colony was separated by picking at it with a stick, a plasmid was prepared, respectively, and the base sequence of the heavy chain gene was examined. These operations were carried out with respect to all of VH1-VH7 and whether or not the clone of interest was obtained was confirmed. The clones of the respective groups (families) were mixed so as to become nearby ratio of the usage frequency in vivo and made it as VH library. The constitutive ratio of the respective families in VH library is indicated as follows:

TABLE 3

| family | Usage frequency in vivo (%)* | Constitutive ratio in VL library (%) |
|---|---|---|
| VH1 | 25 | 29** |
| VH2 | 6.6 | 7 |
| VH3 | 40 | 40 |
| VH4 | 19 | 19*** |
| VH5 | 5 | —** |
| VH6 | 3.8 | 4 |
| VH7 | 1.2 | 2 |

*Griffith AD et al. EMBO J. (1994) 13, 3245-60.
**Actually, since VH1 and VH5 are amplified with the same primers, these cannot be separated and totaled.
***cDNA prepared with primer VH4 and cDNA prepared with primer VH4-2 were mixed and made this ratio.

3-2 Preparation of Combination Gene Library

200 μg of VH library was digested with HindIII and XhoI under the following conditions, the heavy chain gene was cut out and purified by Gene Clean II Kit.

| | |
|---|---|
| 200 μg of VH library | 100 μL |
| 10 x K buffer (made by Takara) | 40 μL |
| Already sterilized MilliQ | 205 μL |
| HindIII (40 U/μL; made by Takara) | 30 μL |
| XhoI (50 U/μL; made by Takara) | 25 μL |

The vector pscFvCA9-E8VHdVLd into which VL library was inserted was also digested with HindIII and XhoI under the following conditions, and the fragment containing the light chain gene was purified by Gene Clean II Kit.

| | |
|---|---|
| pscFvCA9-E8VHdVLd into which VL library was inserted 100 μg | 100 μL |
| 10 x K buffer (made by Takara) | 40 μL |
| Already sterilized MilliQ | 230 μL |
| HindIII (40 U/μL; made by Takara) | 15 μL |
| XhoI (50 U/μL; made by Takara) | 15 μL |

Next, the ligation was carried out by reacting VH gene library fragment and pscFvCA9-E8VHdVLd vector into which the light chain gene was inserted at 16° C. over night under the following conditions:

| | |
|---|---|
| VH library fragment treated with restriction enzymes 10 μg | 50 μL |
| pscFvCA9-E8VHdVLd containing VL library fragments treated with restriction enzymes 40 μg | 50 μL |
| 10 x ligation buffer (Attached to T4 DNA ligase) | 100 μL |
| 10 mM ATP | 100 μL |
| Already sterilized MilliQ | 670 μL |
| T4 DNA ligase (10 U/μL; made by Takara) | 30 μL |

*E. coli* DH12S was transformed using the DNA whose reaction was terminated. Concretely, the DNA was once precipitated with ethanol, and dissolved in 30 μL of ⅕TE (TE diluted 5-fold with already sterilized MilliQ). This was suspended in 500 μL of competent cell DH12S (made by GIBCO BRL), and the electroporation was carried out.

| Electroporator Cell-Porator (Cat. series 1600) made by BRL | | |
|---|---|---|
| Setting conditions: | voltage booster | 4 kΩ |
| | capacitance | 330 μF |
| | DC volts | Low Ω |
| | charge rate | Fast |

The *E. coli* that the above-described operation were terminated was put in 12 mL of the medium for transformation (SOB), after shaken and cultured at 37° C. for one hour, one portion of it was plated on the agar medium (Amp plate), the remains were cultured in 500 mL of 0.1% glucose, 100 μg/mL ampicillin containing 2×YT medium and stocked with glycerin. The agar medium was incubated at 30° C., and the number of clones was estimated from the number of the grown colonies. $8.5 \times 10^{10}$ clones were obtained.

4. Preparation of scFv-CL Antibody Phage Library from scFv-CL Antibody Gene Library 2.5 mL each of AIMS-5 suspension was added to 16 bottles of flasks of 5 L into which 300 mL of 2×YT medium has been inputted and then 1% glucose and 100 μg/mL ampicillin were added, then it was shaken and cultured at 37° C. and grown until the absorbance became 1.0 while the absorbance at 600 nm of wavelength was measured every hour. 12 mL per one bottle of flask of helper phage solution (M13KO7) was added to the culture medium, infected with the helper phage, cultured at 37° C. for 2 hours, and made it DH12S already infected with helper phage.

600 mL of 2×YT medium, 0.6 mL of ampicillin (100 μg/mL), 0.8 mL of Kanamycin (50 μg/mL) and 200 mL of DH12S already infected with helper phage were added to 24 bottles of flasks of 5 L and shaken and cultured at 37 C° for 20 hours.

The bacterial cells were centrifuged at 8000 rpm at 4° C. for 10 minutes, and supernatant was recovered. 4 L of 20% polyethylene glycol/2.5M NaCl was added to the supernatant, after it was quietly stirred for about 20 minutes, centrifuged at 8000 rpm at 4° C. for 20 minutes. The precipitate was dissolved in 1 L of PBS, 200 mL of 20% polyethylene glycol/2.5M NaCl was added thereto, after it was quietly stirred for about 20 minutes, and centrifuged at 800 rpm at 4° C. for 20 minutes. The supernatant was discarded and further, centrifuged at 8000 rpm at 4° C. for 3 minutes, and the precipitate was recovered. The precipitate was dissolved in PBS to which 0.05% NaN$_3$ was added, after it was centrifuged at 1000 rpm at 4° C. for 15 minutes and the supernatant was recovered, further, centrifuged at 800 rpm at 4° C. for 3 minutes and the supernatant was recovered.

The titer of the recovered phage solution was checked as followings: the phage solution was diluted with PBS in $10^6$, $10^7$ and $10^8$-fold, out of these, 10 L was infected with 990 μL of DH12S, cultured at 37° C. for one hour. 100 μL of this was plated on LBGA plate and cultured at 30° C. for 18 hours. The titer of the stock solution before dilution was calculated by counting the number of colonies. The stock solution of the phage solution was suspended in PBS containing 0.05% NaN$_3$ so as to be $2 \times 10^{14}$/mL.

5. Obtaining of Antibody Clone Specific to Liver Cancer Cell 5-1 Screening using Liver Cancer Cell Line HepG2, Nuk-1

Firstly, HepG2 cells were cultured in a 15 cm-dish and dissociated from the dish by using 2 mg/ml collagenase I (Gibco BRL)/cell dissociation buffer (Gibco BRL). They were washed with cooled PBS and $4 \times 10^7$ cells were used. They were mixed with $1 \times 10^{13}$ cfu of human antibody phage library, so that the final concentration of the reaction mixture was made to be 1% BSA-0.1% NaN$_3$/MEM, the volume was made to be 1.6 ml. The reaction was carried out while rotating slowly at 4° C. for four hours. After the reaction was completed, the reaction mixture was divided into two parts and each part was stratified on 0.6 ml of organic solution (dibutyl phtalate cycloheximide 9:1) and subjected to centrifugation at centrifugal force of 3000 rpm by using a micro-centrifugal machine for two minutes, so that cells were allowed to precipitate at the bottom of the tube. From each tube, the solution was discarded and cells were suspended in 0.7 ml of 1% BSA/MEM, stratified on 0.7 ml of organic solvent and subjected to centrifugation. This operation was repeated again. Then the solution was discarded and cells were suspended in 0.3 ml of PBS, frozen with liquid nitrogen and melted at 37° C.

After this was infected with 20 ml of *E. coli* DH12S (OD 0.5) for one hour, the part of it was plated on an Ampicillin plate and the titer of the collected phage was calculated. Phage infected *E. coli* was cultured over night in 600 ml of 2×YTGA culture medium (2×YT, 200 μg/ml ampicillin sulfate, 1% glucose) at 30° C. The cultured product (10 ml) that had been cultured over night was mixed with 200 ml of 2×YTA culture medium (2×YT, 200 μg/ml ampicillin sulfate) and cultured at 37° C. for 1.5 hours. Thereafter, helper phage KO7 ($1 \times 10^{11}$) was placed and cultured at 37° C. for one hour. Then, 800 ml of 2×YTGAK (2×YT, 200 μg/ml ampicillin sulfate, 0.05% glucose, 50 μg/ml kanamycin) was placed and cultured over night at 30° C. This was centrifuged at 8000 rpm for ten minutes so as to prepare supernatant 11. With supernatant 11, 200 ml of PEG solution (20% polyetyleneglycol 6000, 2.5M NaCl) was mixed and fully agitated. Thereafter, centrifugation was carried out at 8000 rpm for 10 minutes so as to precipitate phage. This was suspended in 10 ml of PBS and the part of it was used so as to examine the number of infected *E. coli*. This is the phase of the 1st screening.

For the 2nd screening, $2 \times 10^7$ cultured cells and $1 \times 10^{10}$ of the 1st phages were used, so that the volume of the reaction mixture was made to be 0.8 ml. The reaction mixture was 1% BSA-0.1% NaN$_3$/MEM and the entire scale was carried out as half as that of the 1st screening.

The 3rd screening was carried out in the same conditions as those of the 2nd screening except that $1 \times 10^9$ of the 2nd phages were used.

The screening of the liver cancer cell line derived from patient with hepatitis C was carried out by the same method as that of the screening with respect to HepG2.

5-2 Selection of Antibody Clones and Immunostaining with Selected Antibody Clones Because the recovering rate of HepG2 was increased in the 3rd screening (FIG. 5), it was judged that HepG2 cell specific antibody clone was concentrated in this state, and 480 clones were picked up. These clones were checked for antibody expression and 225 expression positive clones were selected. Next, when the base sequence of H-chain portions of these positive clones were analyzed, it was shown that clones were divided into 130 kinds. Antibody samples of these 130 clones were prepared and operation materials obtained from three patients were subjected to tissue staining in liver cancer portion and non-liver cancer portion. Then, staining specific to cancer was observed in 33 antibodies. In 19 antibodies of them, the cancer membrane portion was stained (FIG. 6). Similarly, when a liver cancer cell line NUK-1 derived from hepatitis C patient was subjected to screening (FIG. 5), eight antibody clones specifically staining a cell membrane of the liver cancer portion were obtained (FIG. 6). In these antibody clones, cell staining of immortalized liver cells THLE-3, liver cancer cell line HepG2, and HLF was carried out and antibody clones showing the recognition specific to cancer cell membrane were selected. As a result, it was shown that 035-029, 035-212, 035-215, 035-273, 035-283, 040-131, 051-054, 051-181, 051-129, 035-130 and 035-169 have particularly high specificity to cancers.

Figure 7:
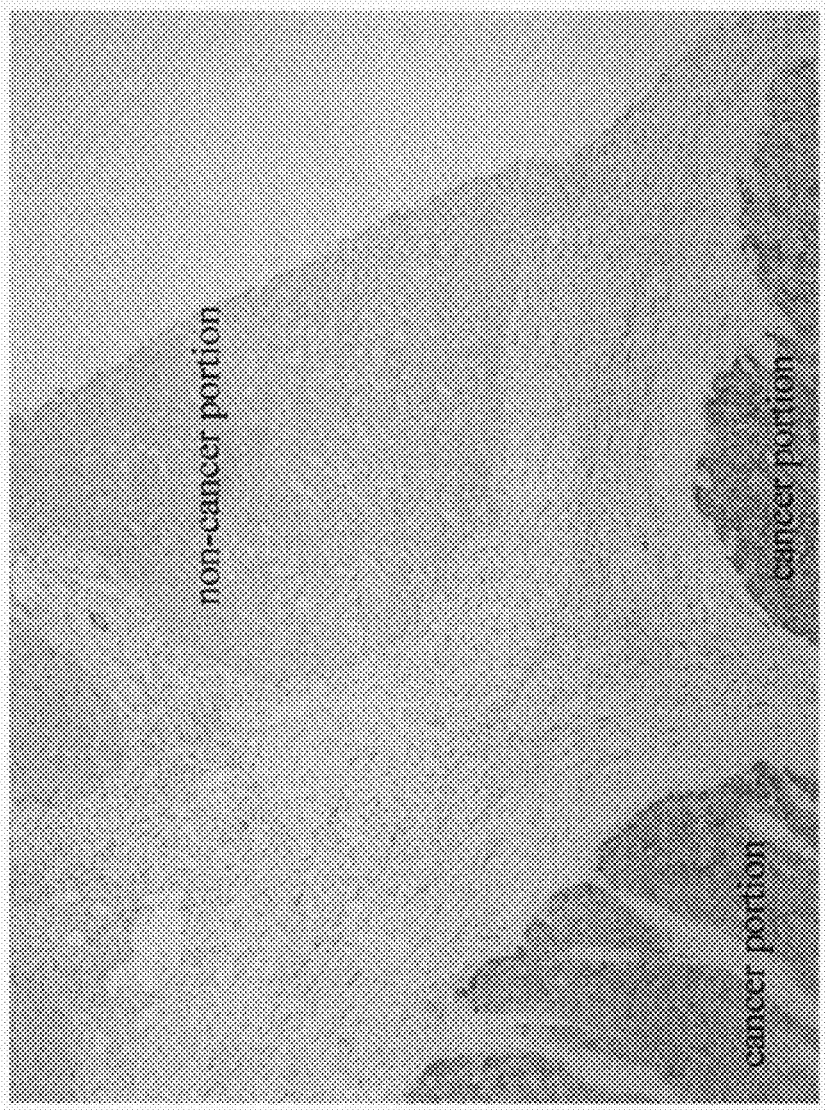
FIG. 7 is a view showing a result of cancer tissue stained with antibody clone 035-273.
Figure 8:
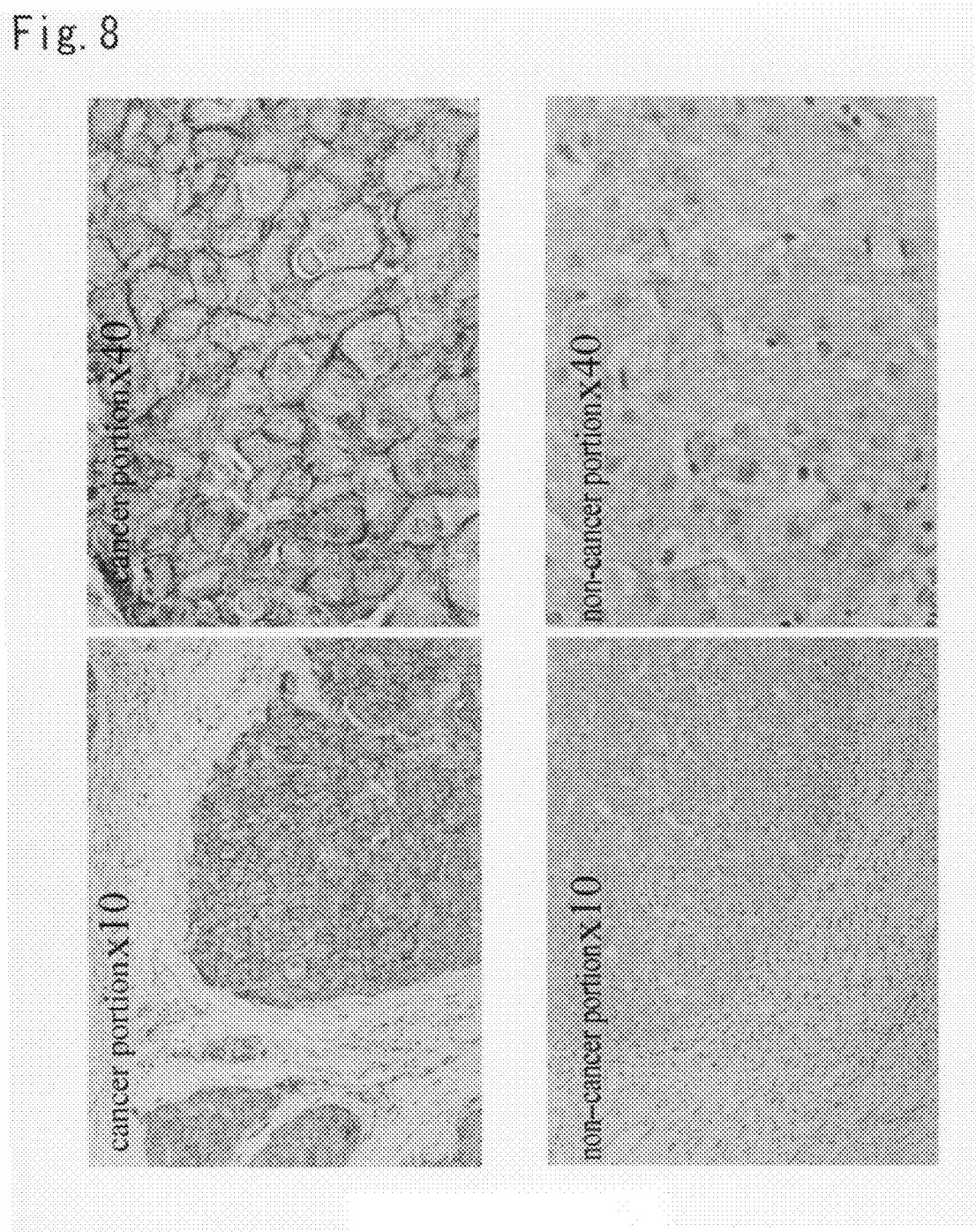
FIG. 8 is a view showing a result of cancer tissue stained with antibody clone 035-273. Upper columns show the stained results of a cancer portion; and lower columns show the stained results of a non-cancer portion.
Figure 9:
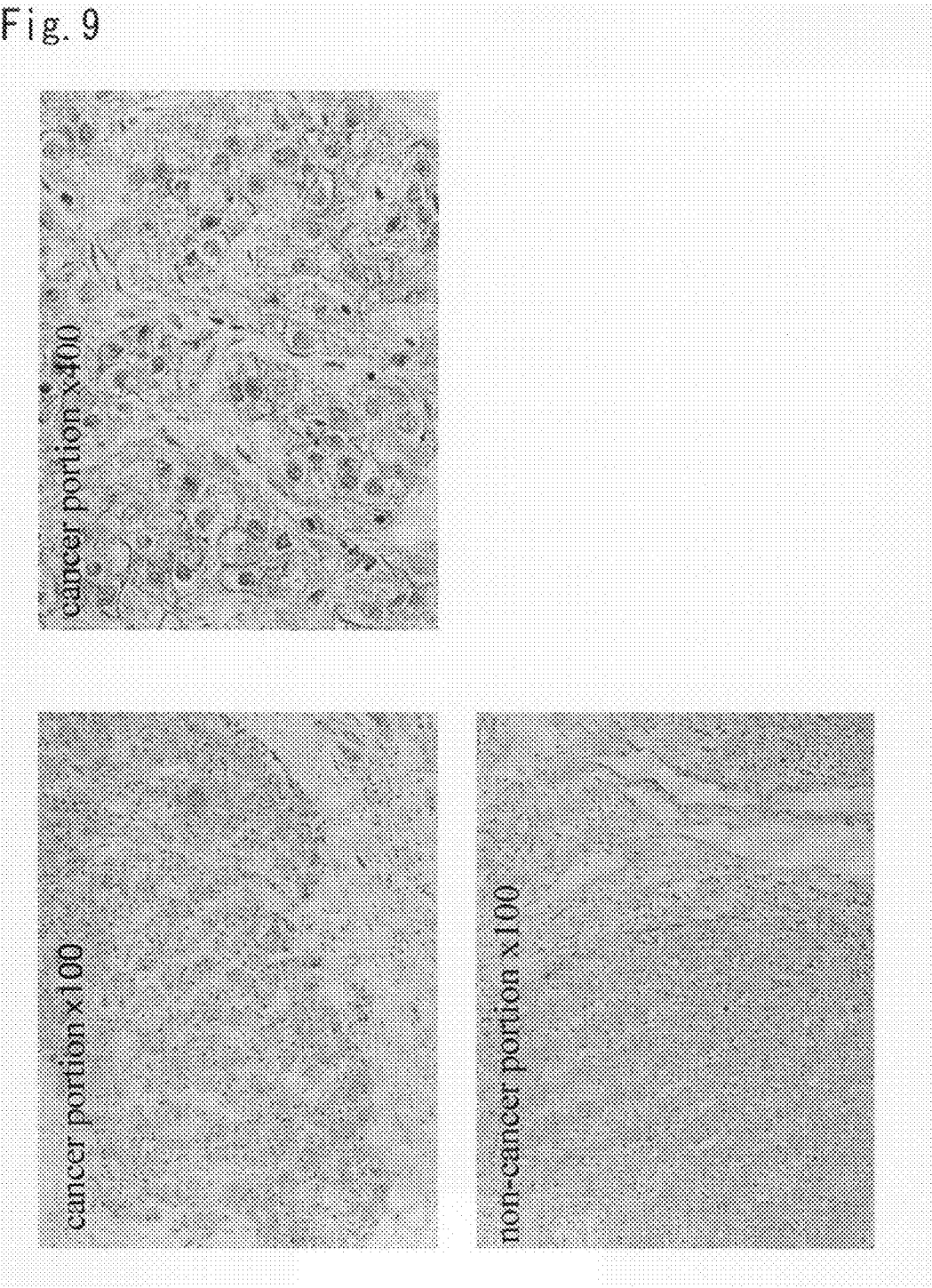
FIG. 9 is a view showing a result of cancer tissue stained with antibody clone 051-129. Upper columns show the stained results of a cancer portion; and lower columns show the stained results of a non-cancer portion.
Figure 10:
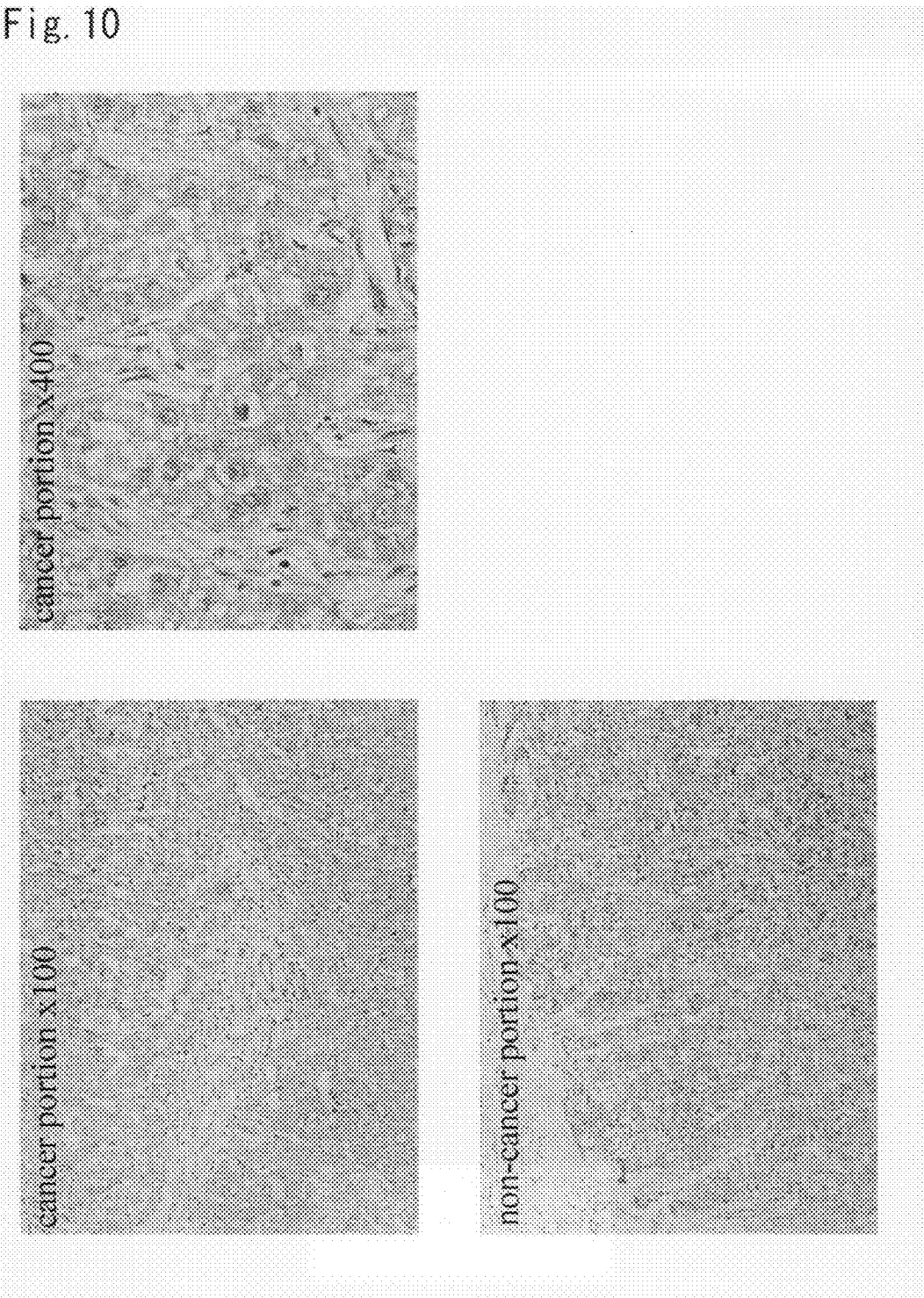
FIG. 10 is a view showing a result of cancer tissue stained with antibody clone 035-169. Upper columns show the stained results of a cancer portion; and lower columns show the stained results of a non-cancer portion.

FIGS. 7 and 8 show images of liver cancer tissue stained with antibody clone 035-273. Similarly, FIG. 9 shows an image of liver cancer tissue stained with antibody clone 051-129, and FIG. 10 shows an image of liver cancer tissue stained with antibody clone 035-169. As is apparent from FIGS. 7 to 10, these antibodies specifically stain the cell membrane of the cancer portion and do not stain the tissue of the non-cancer portion. Furthermore, as shown in FIG. 11, antibody 035-273 stained poorly-differentiated liver cancer cell line HepG2, undifferentiated liver cancer cell line HLF, and cell line Nuk-1 derived from a hepatitis C patient, but hardly stained well-differentiated liver cancer cell line HuH-7 and immortalized liver cell THLE-3. Note here that antibody clones 035-029, 035-212, 035-215, 035-283, 040-131, 051-054, and 051-181 showed the same staining results (the results are not shown).

Note here that cell staining and tissue staining were carried out by the following procedure.

5-2-1 Cell Staining

Cells were dissociated from a dish by using 2 mg/ml collagenase I (Gibco BRL)/cell dissociation buffer (Gibco BRL), then collected by using 10% FBS/D MEM, and 1×10$^5$ of the cells were used. These were washed with 2.5% BSA, 0.05% NaN$_3$/PBS (BSA solution), then suspended in 100 μl of 2.5% normal goat serum/BSA solution and left on ice for 30 minutes. Thereafter, cp3 type antibodies were added so that the concentration was 5 μg/ml and left on ice for one hour. This was washed with a BSA solution once, then suspended in 100 μl of 5 μg/ml BSA solution of anti-cp3 mouse monoclonal antibody (Medical & Biological Laboratories Co., Ltd.) and left on ice for one hour. This was washed with a BSA solution once, then suspended in 100 μl of 5 μg/ml BSA solution of Alexa 488 binding anti-mouse IgG goat antibody (Molecularprobe), and left on ice for one hour. This was washed with a BSA solution twice, and then supernatant was discarded. To this, 50 μl of OptiLyse B (BECKMAN COULTER) was added and left at room temperature for ten minutes so as to fix the cells. To this, 950 μl of 1 ng DAPI/BSA solution was added, left at room temperature for 10 minutes, and subjected to centrifugation for collecting cells. The cells were filled in MULTITEST SLIDE (ICN) and observed under microscopy.

5-2-2 Tissue Staining (1) Preparation of Antibody Sample

*E. coli* culture medium cultured overnight (0.5 ml) was planted in 10 ml of 2×YTAI (2×YT, 200 μg/ml ampicillin sulfate, 0.5 mM IPTG), cultured overnight at 30° C. and centrifuged at 15000 rpm for 5 minutes by using a microcentrifugal machine, and supernatant was recovered. To this, an equal amount of saturated ammonium sulfate was added and left at room temperature for 30 minutes. Then, it was centrifuged at room temperature at 10000 rpm for 5 minutes and supernatant was discarded. The obtained precipitate was suspended in 1 ml of PBS-0.05% NaN$_3$, protease inhibitor solution and centrifuged at 4° C. at 15000 rpm for 5 minutes, and supernatant was recovered.

(2) Production of Tissue Staining Section

The extracted tissue was cut into about 5 mm×5 mm×10 mm, placed in 4% PFA/0.01% glutaraldehyde/0.1 M cacodylic acid buffer (4° C.) (PFA is a product by Wako Junyaku (Wako Pure Chemical Institute), glutaraldehyde is a product by KANTO CHEMICAL CO., INC., sodium cacodylate is a product by SIGMA). By using a microwave oven (SHARP), it was microwave-fixed. Then, it was fixed again in this fixation solution at 4° C. for one hour. Then, it was transferred into 10% sucrose/PBS and immersed therein at 4° C. for four hours, then substituted by 15% sucrose/PBS and immersed therein at 4° C. for four hours, and then substituted by 20% sucrose/PBS and immersed at 4° C. over night. It was embedded in an OTC compound and rapidly frozen in dry ice/hexane. This was thinly cut into 4 μm thickness by using cryostat (Reichert-Jung 2800 FRIGCUT E), attached to silane coated slide glass (MATSUNAMI) and dried by using a cold wind drier for 30 minutes.

(3) Tissue Staining

The slide glass to which a section was attached was immersed in PBS three times for five minutes each so as to make hydrophilic. Next, 50 μl of 0.3% H$_2$O$_2$/0.1% NaN$_3$ was dropped so as to cause a reaction at room temperature for ten minutes and blocking of endogenous peroxidase was carried out. Then, it was washed with PBS three times for five minutes each. Then, it was reacted in 2% BSA/PBS at room temperature for 10 minutes, and blocking of a non-specific reaction was carried out. Then, excess liquid was dropped off and 50 μl of antibody sample was dropped thereto so as to cause a reaction at room temperature for one hour, followed by washing with PBS three times for 5 minutes each. Next, 50 μl of anti-CP3 rabbit antibody (5 μg/ml) was dropped to cause a secondary antibody reaction at room temperature for 45 minutes, followed by washing with PBS three times for 5 minutes each. Then, 50 μl of peroxidase labeled dextran binding anti-rabbit immunoglobulin—goat polyclonal antibody (DAKO) was dropped so as to cause a tertiary antibody reaction at room temperature for 30 minutes. This was washed with PBS three times for 5 minutes each, and the 50 μl of DAB-H$_2$O$_2$ coloring solution was dropped. After the color became brown, this was transferred to a vat filled with distilled water so as to terminate the reaction. Thereafter, obtained product was washed with water for 10 minutes, followed by staining nuclear with hematoxylin. Thereafter, dehydration and penetration were carried out, encapsulation with marinol and observation under microscopy were carried out.

6. Determination of Base Sequence and Expression of Confirmation of Antibody Clone

*E. coli* obtained by screening was diluted and plated on a nutrient agar medium containing 100 μg/ml of ampicillin. The obtained colonies were picked up and cultured in 2×YTGA culture medium at 30° C. overnight. DNA was extracted by using KURABO PI-50 and the base sequence was determined by a dideoxy method. Furthermore, this culture medium cultured overnight (0.05 ml) was plated on 1.2 ml of 2×YTAI (2×YT, 200 μg/ml ampicillin sulfate, 0.5 mM IPTG) and cultured overnight at 30° C., centrifuged by using a micro-centrifugal machine at 15000 rpm for 5 minutes, and supernatant was obtained.

Since the antibody was expressed as a cp3 fused protein, the expression using the protein was examined. That is to say, firstly, the obtained supernatant was reacted in Maxisorp (NUNC) at 37° C. for two hours, liquid was discarded, and blocking was carried out by reacting 5% BSA at 37° C. for two hours. The liquid was discarded and a rabbit anti-cp3 antibody (Medical & Biological Laboratories Co., Ltd.) that had been diluted 2000-fold with 0.05% Tween/PBS was reacted at room temperature for one hour, followed by washing with PBS. Then, a HRP labeled goat anti-rabbit IgG antibody (Medical & Biological Laboratories Co., Ltd.) that had been diluted 2000-fold with 0.05% Tween/PBS was reacted at room temperature for one hour, followed by washing with PBS. Then, 100 μl of OPD solution was reacted at room temperature for 15 minutes, and the reaction was terminated by using 2M ammonium sulfate, and by using SPECTRAmax 340PC (Molecular Devices), the absorbance at 492 nm of wavelength was measured.

In this process, antibody clones which have the same base sequence or expression antibody were removed, and finally 11 antibody clones (035-029 antibody, 035-212 antibody, 035-215 antibody, 035-273 antibody, 035-283 antibody, 040-131 antibody, 051-054 antibody, 051-181 antibody, 051-129 antibody, 035-130 antibody, and 035-169 antibody) were obtained. The amino acid sequence of each antibody clone is shown bellow.

(1) 035-029 Antibody
VH: SEQ ID NO.: 1, VH CDR1: SEQ ID NO.: 2,
VH CDR2: SEQ ID NO.: 3, VH CDR3: SEQ ID NO.: 4
VL: SEQ ID NO.: 5, VL CDR1: SEQ ID NO.: 6,
VL CDR2: SEQ ID NO.: 7, VL CDR3: SEQ ID NO.: 8,
VLCL: SEQ ID NO.: 129

(2) 035-212 Antibody
VH: SEQ ID NO.: 9, VH CDR1: SEQ ID NO.: 10,
VH CDR2: SEQ ID NO.: 11, VH CDR3: SEQ ID NO.: 12
VL: SEQ ID NO.: 13, VL CDR1: SEQ ID NO.: 14,
VL CDR2: SEQ ID NO.: 15, VL CDR3: SEQ ID NO.: 16,
VLCL: SEQ ID NO.: 131

(3) 035-215 Antibody
VH: SEQ ID NO.: 17, VH CDR1: SEQ ID NO.: 18,
VH CDR2: SEQ ID NO.: 19, VH CDR3: SEQ ID NO.: 20
VL: SEQ ID NO.: 21, VL CDR1: SEQ ID NO.: 22,
VL CDR2: SEQ ID NO.: 23, VL CDR3: SEQ ID NO.: 24,
VLCL: SEQ ID NO.:133

(4) 035-273 Antibody
VH: SEQ ID NO.: 25, VH CDR1: SEQ ID NO.: 26,
VH CDR2: SEQ ID NO.: 27, VH CDR3: SEQ ID NO.: 28
VL: SEQ ID NO.: 29, VL CDR1: SEQ ID NO.: 30,
VL CDR2: SEQ ID NO.: 31, VL CDR3: SEQ ID NO.: 32,
VLCL: SEQ ID NO.: 135

(5) 035-283 Antibody
VH: SEQ ID NO.: 33, VH CDR1: SEQ ID NO.: 34,
VH CDR2: SEQ ID NO.: 35, VH CDR3: SEQ ID NO.: 36
VL: SEQ ID NO.: 37, VL CDR1: SEQ ID NO.: 38,
VL CDR2: SEQ ID NO.: 39, VL CDR3: SEQ ID NO.: 40,
VLCL: SEQ ID NO.: 137

(6) 040-131 Antibody
VH: SEQ ID NO.: 41, VH CDR1: SEQ ID NO.: 42,
VH CDR2: SEQ ID NO.: 43, VH CDR3: SEQ ID NO.: 44
VL: SEQ ID NO.: 45, VL CDR1: SEQ ID NO. : 46,
VL CDR2: SEQ ID NO.: 47, VL CDR3: SEQ ID NO.: 48,
VLCL: SEQ ID NO.: 139

(7) 051-054 Antibody
VH: SEQ ID NO.: 49, VH CDR1: SEQ ID NO.: 50,
VH CDR2: SEQ ID NO.: 51, VH CDR3: SEQ ID NO.: 52
VL: SEQ ID NO.: 53, VL CDR1: SEQ ID NO.: 54,
VL CDR2: SEQ ID NO.: 55, VL CDR3: SEQ ID NO.: 56,
VLCL: SEQ ID NO.: 141

(8) 051-181 Antibody
VH: SEQ ID NO.: 57, VH CDR1: SEQ ID NO.: 58,
VH CDR2: SEQ ID NO.: 59, VH CDR3: SEQ ID NO.: 60
VL: SEQ ID NO.: 61, VL CDR1: SEQ ID NO.: 62,
VL CDR2: SEQ ID NO.: 63, VL CDR3: SEQ ID NO.: 64,
VLCL: SEQ ID NO.: 143
On the other hand, the base sequence of each antibody clone is shown below.

(1) 035-029 Antibody
VH: SEQ ID NO.: 65, VH CDR1: SEQ ID NO.: 66,
VH CDR2: SEQ ID NO.: 67, VH CDR3: SEQ ID NO.: 68
VL: SEQ ID NO.: 69, VL CDR1: SEQ ID NO.: 70,
VL CDR2: SEQ ID NO.: 71, VL CDR3: SEQ ID NO.: 72,
VLCL: SEQ ID NO.: 130

(2) 035-212 Antibody
VH: SEQ ID NO.: 73, VH CDR1: SEQ ID NO.: 74,
VH CDR2: SEQ ID NO.: 75, VH CDR3: SEQ ID NO.: 76
VL: SEQ ID NO.: 77, VL CDR1: SEQ ID NO.: 78,
VL CDR2: SEQ ID NO.: 79, VL CDR3: SEQ ID NO.: 80,
VLCL: SEQ ID NO.: 132

(3) 035-215 Antibody
VH: SEQ ID NO.: 81, VH CDR1: SEQ ID NO.: 82,
VH CDR2: SEQ ID NO.: 83, VH CDR3: SEQ ID NO.: 84
VL: SEQ ID NO.: 85, VL CDR1: SEQ ID NO.: 86,
VL CDR2: SEQ ID NO.: 87, VL CDR3: SEQ ID NO.: 88,
VLCL: SEQ ID NO.: 134

-continued (4) 035-273 Antibody
VH: SEQ ID NO.: 89, VH CDR1: SEQ ID NO.: 90,
VH CDR2: SEQ ID NO.: 91, VH CDR3: SEQ ID NO.: 92
VL: SEQ ID NO.: 93, VL CDR1: SEQ ID NO.: 94,
VL CDR2: SEQ ID NO.: 95, VL CDR3: SEQ ID NO.: 96,
VLCL: SEQ ID NO.: 136

(5) 035-283 Antibody
VH: SEQ ID NO.: 97, VH CDR1: SEQ ID NO.: 98,
VH CDR2: SEQ ID NO.: 99, VH CDR3: SEQ ID NO.: 100
VL: SEQ ID NO.: 101, VL CDR1: SEQ ID NO.: 102,
VL CDR2: SEQ ID NO.: 103,
VL CDR3: SEQ ID NO.: 104, VLCL: SEQ ID NO.: 138

(6) 040-131 Antibody
VH: SEQ ID NO.: 105, VH CDR1: SEQ ID NO.: 106,
VH CDR2: SEQ ID NO.: 107, VH CDR3: SEQ ID NO.:108
VL: SEQ ID NO.: 109, VL CDR1: SEQ ID NO.: 110,
VL CDR2: SEQ ID NO.: 111,
VL CDR3: SEQ ID NO.: 112, VLCL: SEQ ID NO.: 140

(7) 051-054 Antibody
VH: SEQ ID NO.: 113, VH CDR1: SEQ ID NO.: 114,
VH CDR2: SEQ ID NO.: 115, VH CDR3: SEQ ID NO.: 116
VL: SEQ ID NO.: 117, VL CDR1: SEQ ID NO.: 118,
VL CDR2: SEQ ID NO.: 119, VL CDR3: SEQ ID NO.: 120,
VLCL: SEQ ID NO.:142

(8) 051-181 Antibody
VH: SEQ ID NO.: 121, VH CDR1: SEQ ID NO.: 122,
VH CDR2: SEQ ID NO.: 123, VH CDR3: SEQ ID NO.: 124
VL: SEQ ID NO.: 125, VL CDR1: SEQ ID NO.: 126,
VL CDR2: SEQ ID NO.: 127,
VL CDR3: SEQ ID NO.: 128, VLCL: SEQ ID NO.: 144

(9) 051-129 Antibody
VH: SEQ ID NO.: 221, VH CDR1: SEQ ID NO.: 222,
VH CDR2: SEQ ID NO.: 223, VH CDR3: SEQ ID NO.: 224
VL: SEQ ID NO.: 225, VL CDR1: SEQ ID NO.: 226,
VL CDR2: SEQ ID NO.: 227, VL CDR3: SEQ ID NO.: 228

(10) 035-130 Antibody
VH: SEQ ID NO.: 229, VH CDR1: SEQ ID NO.: 230,
VH CDR2: SEQ ID NO.: 231, VH CDR3: SEQ ID NO.: 232
VL: SEQ ID NO.: 233, VL CDR1: SEQ ID NO.: 234,
VL CDR2: SEQ ID NO.: 235, VL CDR3: SEQ ID NO.: 236

(11) 035-169 Antibody
VH: SEQ ID NO.: 237, VH CDR1: SEQ ID NO.: 238,
VH CDR2: SEQ ID NO.: 239, VH CDR3: SEQ ID NO.: 240
VL: SEQ ID NO.: 241, VL CDR1: SEQ ID NO.: 242,
VL CDR2: SEQ ID NO.: 243, VL CDR3: SEQ ID NO.: 244

7. Identification of Protein (Antigen) Recognized by Antibody Clone 7-1 Production of pp Type Antibody Expressing *E. coli*

The obtained antibody clone is cp3 type and the construct is shown in FIGS. 12-1 and 12-2 (this Figures show a structure common to all the antibodies). A VH sequence and a VLCL sequence shown in FIGS. 12-1 and 12-2 are inserted into a VH region and a VLCL region, respectively. This DNA was extracted by using KURABO PI-50, digested with a restriction enzyme SalI, self reconnected, then, introduced into *E. coli* DH12S for transformation. Then, it was plated on a LBGA plate and cultured at 30° C. overnight. The obtained *E. coli* colonies were cultured in 2×YTGA overnight and a pp type antibody expressing *E. coli* culture medium was obtained.

7-2 Preparation of Antibody for Immunoprecipitation

*E. coli* (10 ml) into, which a plasmid expressing pp type antibody clones was introduced was plated on YTGA and cultured while shaking at 30° C. one day and one night (pre-culture medium). This was added to 4l of 2×YT, 0.05% glucose, 100 μg/ml Ampicillin and cultured at 30° C. When O.D. of the bacterial cells became 0.5, 4 ml of 1M IPTG was added and cultured while shaking at 30° C. one day and one night. After the culture was terminated, the bacterial cells were centrifuged by using a cooling centrifugal machine at 10000 g, 4° C. for 10 minutes. To the obtained culture supernatant, an equal amount of saturated ammonium sulfate aqueous solution was added and stirred at room temperature for one hour. This solution was centrifuged by using a cooling centrifugal machine at 10000 g, 4° C. for 15 minutes, then supernatant was discarded, the obtained precipitate was suspended in 20 ml of PBS-NaN$_3$ solution, centrifuged by using a cooling centrifugal machine at 10000 g, 4° C. for 5 minutes, and supernatant was recovered. This was dialyzed with PBS one day and one night. To this, 2 ml of IgG sepharose 6 Fast Flow (Amersham Biosciences) balanced with 0.05% NaN$_3$/PBS was added and reacted while shaking at 4° C. one day and one night. This mixture was transferred to a column and naturally dropped. The components that were not reacted with beads were allowed to pass through the column. This column was washed with 100 ml of PBS twice, washed with 0.1% Tween 20/PBS (30 ml) four times, and washed with 100 ml of PBS twice. To this, 0.2M Glycine-HCl (pH 3, 4 ml) was slowly added three times and the eluted component was recovered. Then, 3M Tris (80 μl) was added thereto for neutralization (antibody solution). This was filtrated through a MILLEX-GP 0.22 μm filter, O.D. was measured, and the yield of antibodies was calculated.

7-3 Preparation of Solid Phased Antibody for Immunoprecipitation

Firstly, an antibody solution was dialyzed with a coupling buffer solution (0.1M NaHCO$_3$—NaOH, pH 9). That is to say, an antibody solution was enclosed with a dialysis membrane (Snake Skin Pleated Dialysis Tubing 10,000 MWCO) and this was allowed to be sunk in 1.5 L of the coupling buffer solution (0.1M NaHCO$_3$—NaOH, pH 9) and stirred by using a stirrer at 4° C. for two to three hours. Then, the buffer solution was replaced with new one and dialyzed for two to three hours. Thereafter, the buffer solution was replaced with new one again and dialyzed one day and one night.

Next, activated CNBr-activated Sepharose 4B used for making solid phase was adjusted. That is to say, CNBr-activated Sepharose 4B (Amersham Biosciences) was swollen with 1 mM HCl, then sucked by using an aspirator. To this, 50 ml of coupling buffer solution was added, stirred, and then sucked by using an aspirator. In this sucked state, a coupling buffer solution was added.

An antibody was made to be solid phased as follows. That is to say, to 5 mg antibody solution (10 ml), activated gel (1 ml) was added to cause a reaction at room temperature for two hours. After the reaction was terminated, the gel was transferred to a column and washed with a coupling buffer solution (1 ml) ten times. The presence of non-reacted antibodies was confirmed by measuring the O.D. The solid phased gel was substituted by 0.2M Glycine-NaOH pH8 solution (5 ml) twice, the same solution (5 ml) was further added and left at room temperature for two hours, this solution was naturally dropped, to this, 0.2M Glycine-HCl (pH 3, 5 ml) was added and substituted, the same solution (5 ml) was further added and left for 5 minutes, and then naturally dropped. Finally, the column was substituted by 20 ml of PBS, then naturally dropped, and 1% NP40, a protease inhibitor, and 0.05% NaN$_3$/PBS were added, and the gel was recovered.

7-4 Biotin Label of Protein on Cell Membrane and Production of Cell Lysate

Biotin labeling of the cultured liver cancer cell line was carried out as follows. That is to say, cultured cells HLF that had been cultured in five 15 cm-dishes were washed with PBS twice, and collagenase I (GIBCO) whose concentration had been adjusted to 5 mg/ml by using a cell dissociation buffer (GIBCO) was added and reacted in a CO$_2$ incubator at 37° C., so that cells were liberated. Thereafter, cells were recovered in a culture medium and washed with PBS(−) twice. Then, the number of cells was counted by using a hemocytometer. The cells were suspended in PBS(−) so that the counted number became about 5×10$^7$/ml. To this, an equal amount of EZ-Link Sulfo-NHS-LC-Biotinylation Kit (PIERCE) was added so that the concentration had been adjusted to 1 mg/ml with PBS, left at room temperature for 30 minutes and then washed with PBS twice.

The cell lysate of biotin labeled cells was adjusted as follows. That is to say, to the above-mentioned biotin labeled cells, 4 ml of lysis buffer (1% NP40/detergent base solution, the composition of the detergent base solution: 20 mM HEPES, pH 8.0, 140 mM NaCl, a protease inhibitor) was added and cells were suspended. This suspension was placed and homogenized in a cooled Dounce homogenizer. To the solution, ½ amount (2 ml) of a detergent mix solution (1% NP40, tritonX-100, b-D-Maltoside, n-Octyl b-D-Glucoside, n-Octyl b-D-Maltoside, n-Decyl b-D-Maltoside, deoxycholic acid, each 0.5%/detergent base solution) was added and mixed at 4° C. for four hours while rotating. This solution was centrifuged at 100,000 rpm for 30 minutes and filtrated through MILLEX-GP 0.22 μm filter.

7-5 Immunoprecipitation Reaction

Firstly, about 60 μl parts (about 150 μl solution parts) of the solid-phased antibodies (hereinafter, referred to as "antibody beads") were placed in a 2 ml-tube and 1/10 volume (about 15 μl) of 4 mM biotin was added to the tube. A mixture of 0.5 dishes of lysate (600 μl) and 60 μl of biotin solution was added to the tube and reacted while stirring at 4° C. for several hours. Then, the tube was centrifuged (5500 g, one minute, 4° C.) and supernatant was removed. To this, 800 μl of washing biotin/lysis-T buffer (0.5 mM biotin, 0.1% Tween 20/PBS) was added and mixed while falling two or three times, then the tube was centrifuged (5500 g, one minute, 4° C.), and supernatant was removed. This washing operation was carried out again, then 30 μl of citric acid solution (50 mM citric acid, pH 2.5) for elution was added to the antibody beads and stirred. Then, the tube was centrifuged (5500 g, 1 min, 4° C.) and supernatant was recovered. To the remaining antibody beads, 30 μl of citric acid solution for elution was added and stirred. The tube was centrifuged (5500 g, 1 min, 4° C.) and supernatant was recovered. This elution operation was repeated further three times, and a sample solution was recovered and 3M Tris was added to the solution for neutralization. This sample was migrated by SDS-PAGE so as to confirm the band by silver staining. At the same time, this sample was subjected to western blotting by using streptavidin—HRP (Anti-Streptavidin, IgG Fraction, Conjugated to Peroxidase CORTEX biochem) so as to detect a band of the biotin membrane protein (FIG. 13).

7-6 Mass Spectrometry of Cut-Out Band 7-6-1 Trypsin Digestion in Gel

A portion corresponding to detected membrane protein was digested with trypsin in a gel and peptide was recovered. SDS polyacrylamide gel electrophoresis was carried out in accordance with a usual method and a band that had been obtained by staining with Coomassie Brilliant Blue was cut out. This was soaked in 200 mM ammonium bicarbonate 50% acetonitrile solution, shaken at 37° C. for 45 minutes. Then, the solution was discarded and the operation was repeated twice, thereby removing the Coomassie Brilliant Blue. This gel was dried under reduced pressure, and 4 μl of trypsin (20 μg/ml) dissolved in 40 mM ammonium bicarbonate (pH 8.1)

−10% acetonitrile was added per unit area (mm$^2$) of gel slice, and left at room temperature for one hour and sufficiently infiltrated. To this, a trypsin solution was added in an amount that was 2.5 times as much as the previously added amount, and left at 37° C. for 18 hours. This was filtrated by a tube having a filter whose power size was 0.22 μm, and peptide in which an antigen had been cut with trypsin was recovered.

7-6-2 Identification of Antigen by Mass Spectrometry

A specimen obtained by in-gel trypsin digestion was subjected to HPLC linked with an electrospray ionization type ion trap quadrupole-mass spectrometer. From the reversed phase chromatography column of HPLC, according to the change of linear concentration gradient of 0% to 80% acetonitrile containing 0.1% TFA, each peptide that had been eluted sequentially depending upon the hydrophobic property was ionized by an electrosparay method. The mass of each peptide was analyzed.

At the same time, the mass of limited digested product of each peptide generated by collision with helium atoms placed in the middle of the flight route of ions was analyzed. When one amino acid is removed by limited digestion, since ion that is smaller by a part of the mass of the removed amino acid is observed, the kind of the removed amino acid can be identified according to the difference in mass. Furthermore, another amino acid is removed, since ion that is smaller by a part of the mass of the removed amino acid is observed, the kind of the removed amino acid can be identified according to the difference in mass. By proceeding the same analysis of the experimental data, an inner amino acid sequence can be determined. The set of the inner sequence of the obtained amino acid was retrieved by using a published amino acid sequence database and antigen was identified. As a result, it was determined that IgSF4 (Accession No. NM_01433, Definition: *Homo sapiens* immunoglobulin superfamily, member 4 (IGSF4), mRNA) was antigen (FIG. 14). In the identification results, it was confirmed that the total amount of the identified protein that had been analogized from the amino acid sequence is not contradictory to the experimental data of the molecular weight of the SDS polyacrylamide electrophoresis of antigen before carrying out the trypsin digestion.

8. IgSF4 Expression Experiment 8-1 Isolation of IgSF4 cDNA Fragment (1) RNA Purification HLF cells were cultured in seven 15 cm-dishes, liberated in TRYSIN-EDTA (1×) (GIBCO), recovered in the culture medium, and washed with PBS (−) twice. Then, total RNA was extracted by RNA Extraction Kit (Amersham Pharmacia). That is to say, 5 ml of extraction buffer was added to the cells and allowed 21 G needle to pass through ten times, stratified on 5 ml of CsTFA placed in 13PA tube (HITACHI), centrifuged by using himac CP80beta (HITACHI) at 15° C. at 36000 rpm and for 20 hours. The obtained precipitate was suspended in RNase free TE, and 822 μg of total RNA was obtained.

(2) Reverse Transcription Reaction

For a reverse transcription reaction, Superscript First-Strand Synthesis System For RT-PCR (Invitrogen) was used. The reaction conditions were as follows.

| HLF total RNA | 10 μg |
| 200 pmol/μl hIgSF4B | 1.2 μl |
| 10 mM dNTP | 2 μl |
| QW | 20.8 μl | hIgSF4B:
(SEQ ID NO.: 211)
5'-GTGTGCGGCCGCCTAGATGAAGTACTCTTTCTTTTC-3'

These were mixed well, treated at 65° C. for 5 minutes, and left on ice for 2 minutes. Next, the following reagents were added, and the mixture was left at 42° C. for 2 minutes.

| 5x First Strand buffer | 8 μl |
| 1M DTT | 4 μl |
| Rnase inhibitor | 2 μl |

Subsequently, 2 μl of Superscript II was added and reacted at 42° C. for 50 minutes, followed by treating at 70° C. for 15 minutes so as to terminate a reverse transcription reaction. To this, 2 μl of RibonucleaseH was added, treated at 37° C. for 15 minutes, then phenol/chloroform extraction and ethanol precipitation were carried out, and finally suspended in 80 μl of QW.

8-2 Construct of Expression Vector (1) Vector

A vector pCMVSalNot for expressing cDNA of IgSF4 was constructed. For constructing the vector, pCMV-Script (Clontech) was used. This was digested with SacI and KpnI and subjected to electrophoresis by using 0.7% agarose gel so as to cut out 4.3 kb band. A DNA fragment was extracted by using suprec01 (TAKARA) and subjected to phenol/chloroform treatment. Then, ethanol precipitation of DNA was carried out, and the obtained DNA was suspended in QW.

(2) Insert

Synthesized DNAs, CMKM-SacIF and CMKM-KpnIR were treated at 95° C. for 5 minutes. Then, the temperature was reduced to room temperature and the synthesized DNAs were digested with SacI and KpnI, and extracted by phenol/chloroform treatment. Then, ethanol precipitation of DNA was carried out, and the obtained DNAs were suspended in QW.

```
CMKM-SacIF:
5'caaaagctggagctcgtcgactacccagaattcaagcttattcgcgcggccgcggtaccaggtaa    (SEQ ID NO.: 212)
gtg3'

CMKM-KpnIR:
5'cacttacctggtaccgcggccgcgcgaataatctttccttctgggtagtcgacgagctccagcttt    (SEQ ID NO.: 213)
tg3'
```

(3) Binding Reaction

The above-mentioned vector and insert were mixed to cause a binding reaction. By using the obtained reaction mixture, E. coli DH12S was transformed, plated on a LBGK plate, and cultured at 30° C. overnight so as to obtain E. coli colonies. These were cultured in 2 ml of 2×YTK at 30° C. overnight. Then, the obtained bacterial medium was treated with KURABO PI-50 and a DNA solution was obtained. Next, this DNA (4 μl) was treated at 85° C. for 5 minutes. Thereto, 3.2 pmol/μl T7 primer (2 μl) and DTCS Quick Start Mix (4 μl) were added, and 40 cycles of treatment were carried out (96° C., 20 seconds; 50° C., 20 seconds; and 60° C., 4 minutes). Then, the obtained reaction solution was analyzed by using SEQ 2000 DNA Analysis System (Beckman) and the base sequence was determined.

8-3 PCR Reaction, Recombination into Expression Vector

In order to isolate cDNA clone of IgSF4, PCR reaction was carried out by using KOD (Toyobo). The reaction conditions were as follows.

| | |
|---|---|
| 200 pmol/μl hIgSF4A | 0.25 μl |
| 200 pmol/μl hIgSF4B | 0.25 μl |
| cDNA | 1 μl |
| 10xKOD buffer | 5 μl |
| 25 mM MgSO$_4$ | 2 μl |
| 2 mM dNTP | 1 μl |
| KOD plus | 1 μl |
| QW | 35.5 μl |

```
hIgSF4A:
                                        (SEQ ID NO.: 214)
5'-GAGAGTCGACGCCACCATGGCGAGTGTAGTGCTGCCGAGC-3' hIgSF4B:
                                        (SEQ ID NO.: 211)
5'-GTGTGCGGCCGCCTAGATGAAGTACTCTTTCTTTTC-3'
```

These were mixed on ice, mineral oil was stratified and treated at 94° C. for 3 minutes. Next, the following cycle was carried out 33 times.

| | |
|---|---|
| 94° C. | 30 seconds |
| 68° C. | 3 minutes |

The reaction product was subjected to electrophoresis on 0.8% agarose gel and about 1.4 kb band was cut out. This was recovered by using Gel Extraction Kit (QIAGEN) and then digested with restriction enzymes SalI and NotI. The obtained DNA fragment was integrated into a vector pCMV-SalNot for expression animal cells. By using this, E. coli DH12S was transformed and the transformant was plated on a LBGK plate and cultured at 30° C. overnight so as to obtain E. coli colonies. These were cultured in 2×YTK (2 ml) at 30° C. overnight and the obtained bacterial medium was treated with KURABO PI-50 so as obtain DNA. The reaction of DNA was carried out in SEQ DTCK-Quick Start Kit (Beckman). The reaction was as follows. DNA (4 μl) was treated at 85° C. for 5 minutes, 3.2 pmol/μl primer (T3 or T7 primer) (2 μl) and DTCS Quick Start Mix (4 μl) were added thereto and 40 cycles of treatment were carried out (96° C., 20 sec; 50° C., 20 sec; and 60° C., 4 sec).

```
Primer
T3primer:   AATTAACCCTCACTAAAGGG   (SEQ ID NO.: 215)

T7primer:   TAATACGACTCACTATAGGG   (SEQ ID NO.: 216)
```

The obtained reaction solution was analyzed by using SEQ 2000 DNA Analysis System (Beckman) and the base sequence was determined. As a result, as IgSF4 cDNA clone, two kinds, that is, IgSF4N (cDNA1: FIGS. 15-1 and 15-2: SEQ ID NO. 217) and IgSF4X (cDNA2: FIGS. 16-1 and 16-2: SEQ ID NO. 218), were isolated.

8-4 Introduction of IgSF4 Expression Vector into NIH3T3-13C7 Cells

Firstly, introduced DNA (12 μg) and Opti-MEM (GIBCO) (0.75 ml) were mixed and left at room temperature for 5 minutes. To the mixture, a mixture in which Opti-MEM (GIBCO) (0.75 ml) and lipofectamine 2000 (30 μl) were mixed and left at room temperature for 5 minutes, was added and left at room temperature for 20 minutes. This was added to NIH3T3-13C7 cells that had been cultured in a 10 cm-dish and cultured in a $CO_2$ incubator at 37° C. for one day.

8-5 FCM, Cell Staining

Cells were dissociated from a dish by using 2 mg/ml of collagenase I (Gibco BRL)/cell dissociation buffer (Gibco BRL), and recovered by 10% FBS/D MEM. This was washed with 2.5% BSA, 0.05% $NaN_3$/PBS (BSA solution), then suspended in 100 μl of 2.5% normal goat serum/BSA solution and left on ice for 30 minutes. Then, cp3 type antibodies (035-029, 035-212, 035-215, 035-273, 035-283, 040-131, 051-054, 051-181, and YA14) were added thereto so that the concentration became 5 μg/ml and left on ice for one hour. This was washed with a BSA solution once, then suspended in 100 μl of 5 μg/ml BSA solution of anti-cp3 mouse monoclonal antibody (Medical & Biological Laboratories Co., Ltd.) and left on ice for one hour. This was washed with a BSA solution once, then suspended in 100 μl of 5 μg/ml BSA solution of Alexa 488 binding anti-mouse IgG goat antibody (Molecularprobe) and left on ice for one hour. This was washed with BSA solution twice, suspended in 500 μl of BSA solution, treated by using Cell Strainer (Becton Dickinson), and then the fluorescence intensity of the group of cells was analyzed by using FACScaliver (FCM) (Becton Dickinson).

FIG. 17 shows the results of FCM. NIH3T3-13C7, into which gene had not been introduced, was hardly stained. On the other hand, in NIH3T3-13C7, in which IgSF4 (cDNA1 or cDNA2) had been forcedly expressed, it was observed that the fluorescence intensity became about 2 times.

FIG. 18 shows the results of immunostaining of cells that had forcedly expressed IgSF4. In the group of cells that had forcedly expressed IgSF4 (cDNA1 or cDNA2), clear staining was observed. The results coincided with the FCM results.

9. Expression Inhibiting Experiment (RNAi)

9-1 Production of d-siRNA

As a template, an 880 bp DNA fragment that had been amplified from cDNA of HepG2 by using hIGSF4C and hIGSF4D primers was used.

```
                                        (SEQ ID NO.: 219)
hIGSF4C (24mer):   5'-TTCAGGGACTTCAGGCCTTTGAAG-3'

(SEQ ID NO.: 220)
hIGSF4D (24mer):   5'-CACCGATCACGGCATGATCCACTG-3'
```

The production method of siRNA was carried out according to the protocol of INVITROGEN. That is to say, a T7 linker was bonded to the template DNA (100 ng), which was divided into two tubes. One was subjected to a PCR reaction by using hIGSF4C and T7 primer so as to produce a DNA fragment for antisense expression and another was subjected to a PCR reaction by using hIGSF4D primer and T7 primer so as to produce a DNA fragment for sense expression. Each of these DNA fragments was subjected to a reaction by T7 RNA polymerase and then synthesized RNA was recovered by using RNAi Purification Kit. Thus, RNA products of about 30 μg was obtained, respectively. A tube in which these were mixed was placed in boiling water for annealing and double strand RNA was produced. To this, Dicer was added and reaction was carried out at 37° C. for 17 hours. Thereafter, by using RNAi Purification Kit, 21 μg of d-siRNA was recovered.

9-2 RNAi Reaction

As cells, well-differentiated liver cancer cell line HLF was used. Cells, which had been subcultured in a 6-well plate (Falcon 3516) the day before, were used. Firstly, 10 μg of lipofectamine 2000 (Invitrogen) and 500 μg of Opti-MEM (GIBCO) were mixed with each other, then, to the mixture, d-siRNA (1 μg) was slowly added and mixed slowly, then left at room temperature for 15 minutes. This was added to cells and the mixed cells were cultured in a $CO_2$ incubator for two days.

9-3 FCM, Cell Staining

Cells were dissociated from a dish by using 2 mg/ml of collagenase I (Gibco BRL)/cell dissociation buffer (Gibco BRL), and recovered by 10% FBS/D MEM. This was washed with 2.5% BSA, 0.05% $NaN_3$/PBS (BSA solution), then suspended in 100 μl of 2.5% normal goat serum/BSA solution and left on ice for 30 minutes. Then, cp3 type antibodies (035-029, 035-212, 035-215, 035-273, 035-283, 040-131, 051-054, and 051-181) were added thereto so that the concentration became 5 μg/ml and left on ice for one hour. This was washed with a BSA solution once, then suspended in 100 μl of 5 μg/ml BSA solution of anti-cp3 mouse monoclonal antibody (Medical & Biological Laboratories Co., Ltd.) and left on ice for one hour. This was washed with a BSA solution once, then suspended in 100 μl of 5 μg/ml BSA solution of Alexa 488 binding anti-mouse IgG goat antibody (Molecularprobe) and left on ice for one hour. This was washed with a BSA solution twice, suspended in 500 μl of BSA solution, treated by using Cell Strainer (Becton Dickinson), and then the fluorescence intensity of the group of cells was analyzed by using FACScaliver (FCM) (Becton Dickinson).

Cells labeled with a fluorescent antibody were collected by centrifugation and then, supernatant was discarded. To this, 50 μl of OptiLyse B (BECKMAN COULTER) was added and left at room temperature for ten minutes so as to fix the cells. To this, 950 μl of 10 ng DAPI/ml PBS solution was added, left at room temperature for 10 minutes, and subjected to centrifugation for collecting cells. The cells were filled in MULTITEST SLIDE (ICN) and observed under microscopy.

Figure 19:
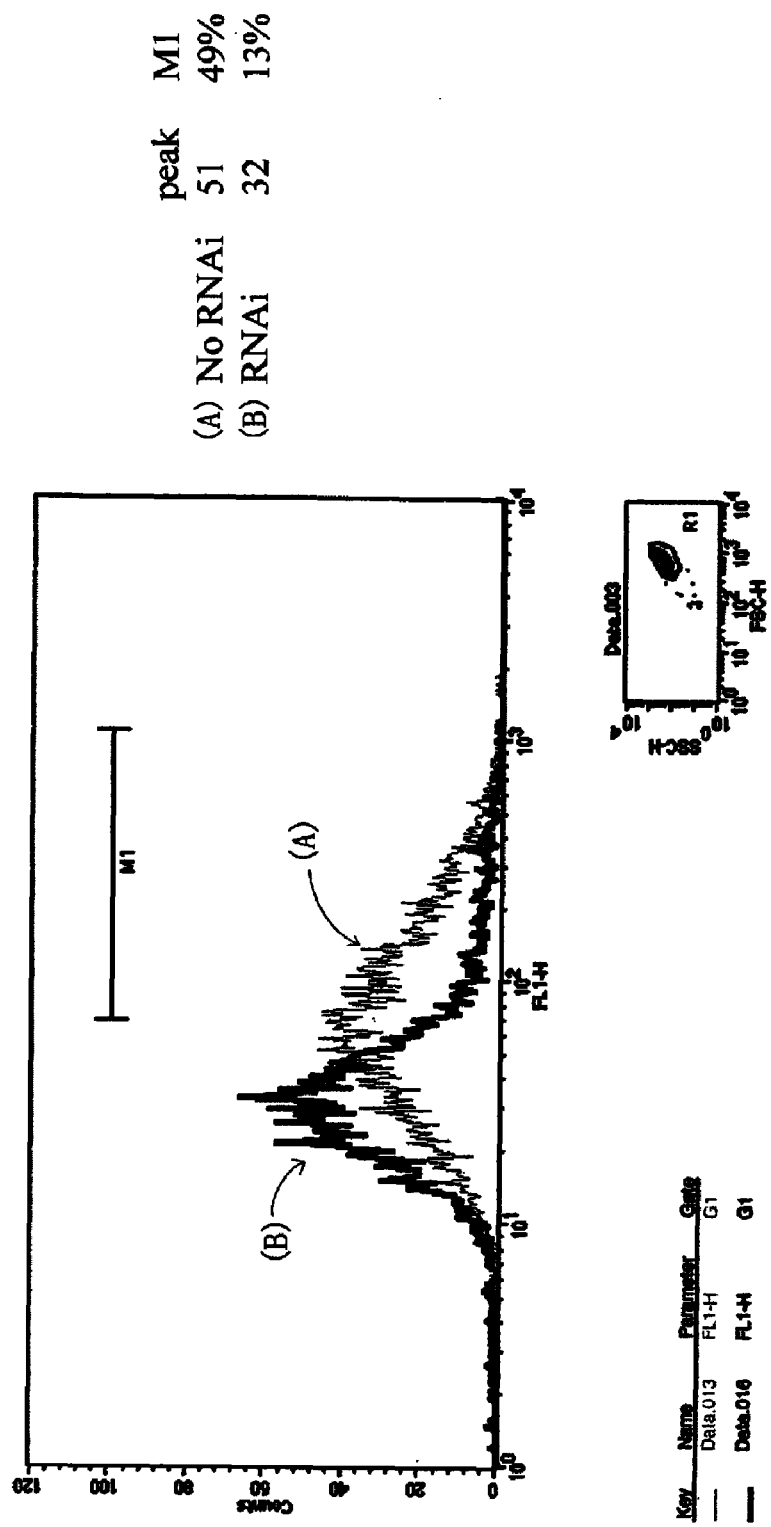
FIG. 19 shows results of RNAi experiment using HLF cells. (A): no RNAi. (B) IgSF4 RNAi. Based on the peak position in (A), the rate of cells having stronger fluorescence intensity than the peak position in (A) is defined as M1.
Figure 20:
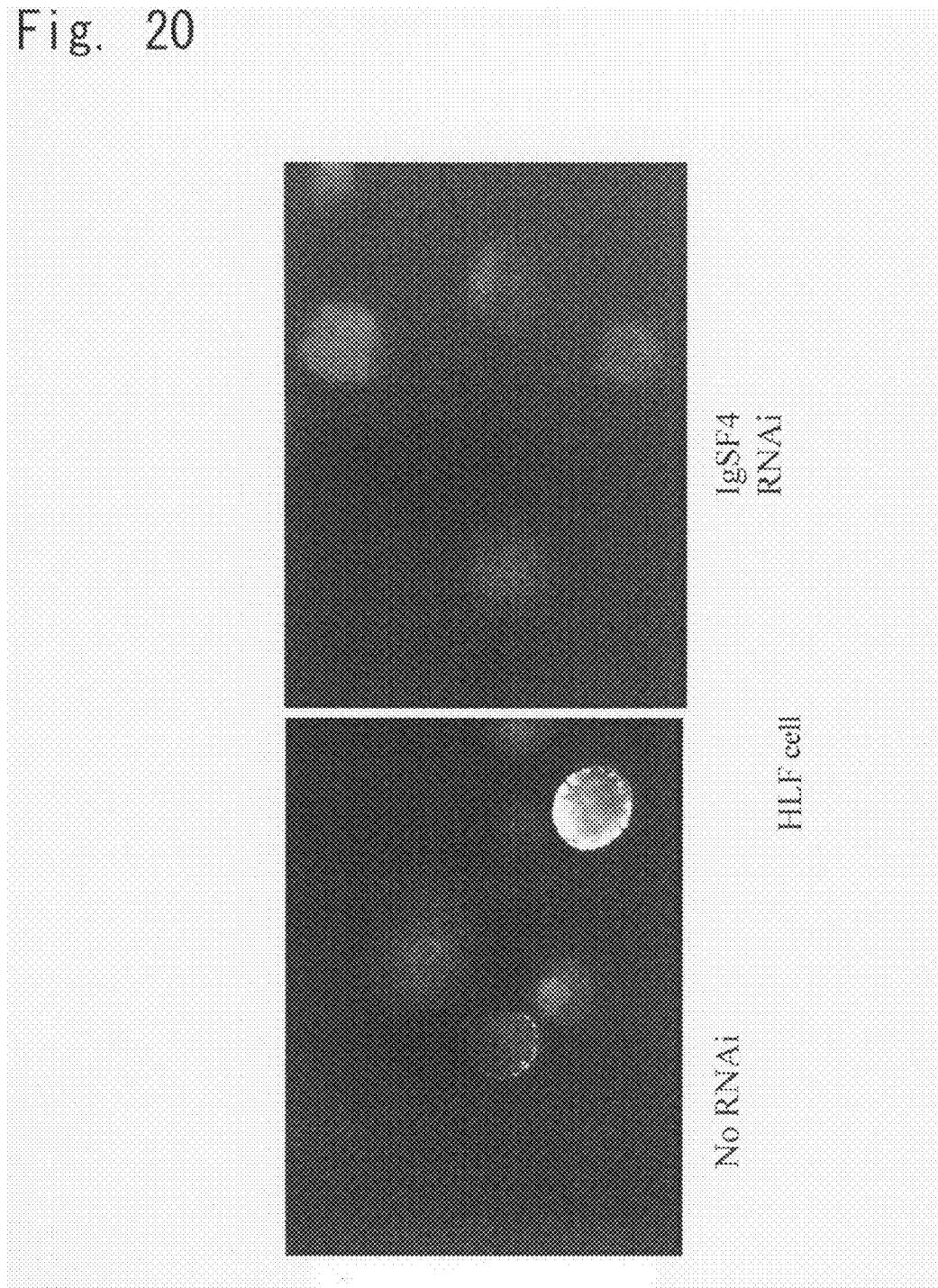
FIG. 20 shows results of RNAi experiment using HLF cells. Left side: treatment with IgSF4 RNAi was not carried out. Right side: treatment with IgSF4 RNAi was carried out.

The results of RNAi experiment mentioned above are shown in FIGS. 19 and 20. According to the FCM analysis, in cells that had been subjected to RNAi treatment, the fluorescence intensity was reduced to about 1/1.6 as a whole. Clear reduction in recognition of antibodies was observed (FIG. 19). The results of cell staining showed that membrane staining had been reduced (FIG. 20). From these results, it was strongly suggested that the antigen recognized by a sample antibody was IgSF4.

10. Expression Inhibition Experiment 2 (RNAi)

10-1 Construction of Induction Type RNAi Vector

By using a system capable of expressing an interference RNA in RNAi in the presence of tetracycline in cell culture medium and knocking down and controlling a subjected gene expression, an RNAi experiment of IgSF4 was carried out.

A part of the sequence of IgSF4 translation region, GGC-CCAACCTGTTCATCAATA (SEQ ID NO.: 269) was defined as an RNAi target. A vector was constructed according to the manual of Block-iT Inducible Lentiviral RNAi System (Invitrogen). That is to say, under 1× annealing buffer conditions, synthesized DNA 832 (5'-CACCAGGCT-CAACTTGTTCGTCAATATTCAA-GAGATATTGATGAACAGGTT GGGCC-3': SEQ ID NO.: 270) and 833 (5'-GGCCCAACCTGTTCATCAATATCTCT-TGAATATTGACGAACAAGTTGAGCCT-3': SEQ ID NO.: 271) were mixed with each other so that each concentration became 50 μM, thermally treated at 95° C. for 4 minutes, and left at room temperature for 5 minutes. This was 10000-fold diluted with 1× annealing buffer. The double strand ds oligo (5 μl) and pENTR/H1/TO (1 μl) were mixed with each other, and a binding reaction was carried out by using an attached ligation system. Thereafter, by using attached One Shot TOP10 Competent *E. coli*, transformation was carried out. It was plated on a 50 mM Kanamycin plate and transformant colonies were obtained. These were cultured in an LB culture medium containing 50 mM Kanamycinn, DNA was prepared in QIAprep Spin Miniprep kit (Qiagen), and a sequence reaction was carried out by using a H1 forward primer and a V5 reverse primer in GenomeLab DTCS-Quick Start Kit (Beckman Coulter). Then, the obtained sequence was analyzed. Thus, the targeted clone (Entry clone) including synthesized DNA 832 sequence from 2138 of pENTR/H1/TO was obtained. This Entry clone (100 ng) and a pLenti4/BLOCK-iT-DEST vector (150 ng) were mixed with each other and the volume was adjusted to 8 μl by TE buffer (pH 8.0), then attached LR clonase II enzyme mix (2 μl) was mixed and left at 25° C. for one hour. The obtained reacted product was transformed with One Shot Stb13 Competent *E. coli* and plated on a 100 mg/ml ampicillin plate so as to obtain transformant colonies. This was cultured in 100 mM of ampicillin-containing LB culture medium, the DNA was prepared by using a QIAprep Spin Miniprep kit (Qiagen), by using H1 forward primer (5'-TGTTCTGGGAAATCACCATA-3': SEQ ID NO.: 272) and V5 reverse primer (5'-ACCGAG-GAGAGGGTTAGGGAT-3': SEQ ID NO.: 273), the sequence reaction was carried out by using GenomeLab DTCS-Quick Start Kit (Beckman Coulter) and the obtained sequence was analyzed. Since the sequence that is the same as that of the entry vector was obtained, it was judged that the following sequence portion (underlined portion shows an insertion sequence by synthesized DNA (SEQ ID NO.: 274)) was integrated into pLenti4/BLOCK-iT-DEST (pLenti4/BLOCK-iT-DEST expression construct).

2087-GAAATCCCTATCAGTGATAGAGACTTATAAGTTCCCTATCAGTGA

TAGACA<u>CACCAGGCTCAACTTGTTCGTCAATATTCAAGAGATATTGATGA</u>

<u>ACAGGTTGGGCC</u> TTTTTTGTCGAGCTT 10-2 Confirmation of RNAi Effect of Entry Clone RNAi effect in the stage of Entry clone was confirmed by the following method. The day before, the following repressor expression HLF host cell line had been subcultured in two 10 cm-dishes to 50% confluent (the culture medium includes 3 μg/ml Blasticidin, 10% FBS and 1% penicillin/streptomycin-D MEM). Since cells were 80 to 90% confluent at the day, the culture medium was replaced by 10% FBS-D MEM culture medium (without containing antibiotics).

Into the Entry clone plasmid (10 μg), 1.5 ml of Opti-MEM (Gibco BRL) was placed and mixed with each other slowly. In another tube, 36 μl of lipofectamine 2000 (Invitrogen) and 1.5 ml of Opti-MEM were placed and mixed with each other slowly. The mixtures were left at room temperature for 5 minutes, mixed, and left at room temperature for 20 minutes. This was added to a repressor expression HLF host cell line, mixed slowly, and then cultured in a $CO_2$ incubator. Six hours later, the culture medium was replaced by 3 μg/ml Blasticidin, 10% FBS (tetracycline tested), and 1% penicillin/streptomycin-D MEM. The next day, in one dish, the culture medium was replaced by 1 μg/ml tetracycline, 3 μg/ml Blasticidin, 10% FBS (tetracycline tested), 1% penicillin/streptomycin-D MEM culture medium (with tetracycline). In another dish, 3 μg/ml Blasticidin, 10% FBS (tetracycline tested), 1% penicillin/streptomycin-D MEM culture medium (without tetracycline). 48 hours after tetracycline was acted on, cells were recovered, and RNAi effect was confirmed by FCM.

10-3 FCM Analysis

Cells were dissociated from a dish by using 2 mg/ml of collagenase I (Gibco BRL)/cell dissociation buffer (Gibco BRL), and recovered by 10% FBS/D MEM. This was washed with 5% BSA, 0.05% $NaN_3$/PBS (BSA solution), then suspended in 100 μl of 2.5% normal goat serum/BSA solution and left on ice for 30 minutes. Then, 35-273 cp3 was added thereto so that the concentration became 5 μg/ml and left on ice for one hour. This was washed with a BSA solution once, then suspended in 100 μl of 5 μg/ml BSA solution of anti-cp3 rabbit polyclonal antibody (MBL, special order) and left on ice for one hour. This was washed with a BSA solution once, then suspended in 100 μl of 5 μg/ml BSA solution of Alexa 488 binding anti-rabbit IgG goat antibody (Molecularprobe), and left on ice for one hour. This was washed with a BSA solution twice, suspended in 1 ml of PBS, treated by using Cell Strainer (Becton Dickinson), and then the fluorescence intensity of the group of cells was analyzed by using FACScaliver (FCM) (Becton Dickinson). As a result, it was observed that the fluorescence intensity of the group of cells was significantly reduced in the case where tetracycline was acted on as compared with the case where tetracycline was not acted on.

10-4 Preparation of Lentivirus

Lentivirus was prepared in tetracycline repressor expression plasmid pLenti6/TR and the above-mentioned pLenti4/BLOCK-iT-DEST expression construct. The method as follows. 293FT cells had been subcultured so that the cells became about 90% confluent on the day of the experiment. On the day of the experiment, before DNA sensitization experiment, the culture medium was replaced by a culture medium without containing antibiotic. A plasmid (3 μg) and attached ViraPower Packaging Mix (9 μg) were mixed with each other. To the mixture, 1.5 ml of Gibco BRL Opti-MEM was placed and mixed with each other slowly. In another tube, 36 μl of lipofectamine 2000 (Invitrogen) and 1.5 ml of Opti-MEM were place and mixed with each other slowly. These mixtures were left at room temperature for 5 minutes, mixed, and left at room temperature for 20 minutes. To this mixture, 293FT cells ($1.2\times10^6$ cells) removed with trypsin were added and mixed slowly, then transferred to a 10 cm-dish, and cultured in a $CO_2$ incubator. The next day, the culture medium was replaced by D MEM containing 10% FBS, 2 mM L-glutamine, 0.1 mM MEM Non Essential Amino Acids, 1% penicillin/streptomycin, and 1 mM MEM Sodium Pyruvate, and cultured for further two days. On 72 hours after the DNA sensitization, the culture medium was recovered, filtrated and sterilized by a 0.22 μm filter.

10-5 Titer Check of Lentivirus

HLF cells were cultured and subcultured in a 6 well-plate so that they were about 25% confluent the day before the experiment and made to be about 30 to 50% confluent on the day of the experiment. On the day of the experiment, 1 ml of virus medium diluted with the culture medium (10% FBS, 1% penicillin/streptomycin-D MEM) was prepared and this was allowed to act on each well and Polyblene was placed so that the final concentration became 6 μg/ml and cultured in a $CO_2$ incubator for one day. On the next day, the culture medium was replaced by a new one. On two days later, the culture medium was replaced by a selection medium. As to pLenti6/TR virus, 3 μg/ml Blasticidin, 10% FBS, 1% penicillin/streptomycin-D MEM were used. As to the pLenti4/BLOCK-iT-DEST expression construct, firstly, cells were removed with trypsin, then 100 μg/ml Zeocin, 10% FBS, 1% penicillin/streptomycin-D MEM culture medium was cultured in a 10 cm-dish. Two weeks after the culture medium had been replaced, formed colonies were counted. Thus, the titer of the virus medium was calculated. During this time, the culture medium was replaced by another one every two days.

10-6 Construction of Tetracycline Repressor Expression Host Cell Line

Ten colonies of the colonies that had been obtained by the titer check of the above-mentioned pLenti6/TR virus were picked up, and individually cultured in 3 μg/ml Blasticidin, 10% FBS, 1% penicillin/streptomycin-D MEM culture medium. Then, cells were recovered by using trypsin and washed with PBS and suspended in PBS. This was subjected to ultrasonic treatment by using Sonifier, the amount of protein was measured by Micro BCA, 20 μg of the amount was subjected to SDS-PAGE migration, western blot was carried out by using an anti-tetracycline repressor rabbit polyclonal antibody (Mo Bi Tec), and clones well expressing a repressor were obtained.

10-7 Selection of hsRNAi Cell Line

The above-mentioned tetracycline repressor expression host cell line was cultured in 3 μg/ml Blasticidin, 10% FBS, and 1% penicillin/streptomycin-D MEM culture medium, and subcultured in a 10 cm-dish so that they became 25% confluent the day before. On the day of the experiment, to the culture, about 200 colonies of pLenti4/BLOCK-iT-DEST expression construct viruses were infected and allowed polybrane to act on. The next day, the culture medium was replaced with new one. On two days later, cells were removed with trypsin and recovered, and three-levels of dilute lines were made and subcultured in 15 cm-dishes. The culture medium included 50 mM HEPES, 3 μg/ml blasticidin, 100 μg/ml Zeocin, 10% FBS, and 1% penicillin/streptomycin-D MEM. Firstly, they were treated at 4° C. for two hours, and cultured in a $CO_2$ incubator at 37° C. Later, the culture medium was replaced by 100 μg/ml Zeocin, 10% FBS and 1% penicillin/streptomycin-D MEM culture medium every two days. On day 14, 24 colonies were isolated. These were individually cultured and 12 clones were obtained.

10-8 Tetracycline Induction Experiment

On the day before, each of the above-mentioned cell clones was subcultured in a 6 well-plate 2 wells each so that they were about 25% confluent. The culture medium included 3 μg/ml blasticidin, 100 μg/ml Zeocin, 10% FBS, and 1% penicillin/streptomycin-D MEM. As FBS, tetracycline tested FBS (Invitrogen) was used. On the day, cells were 50 to 60% confluent. By the culture medium containing 1 μg/ml tetracycline and by the culture medium without containing it, the culture medium was replaced. On 48 hours after the culture medium was replaced by new one, cells were recovered and subjected to FCM analysis.

10-9 FCM Analysis

Cells were dissociated from a dish by using 2 mg/ml of collagenase I (Gibco BRL)/cell dissociation buffer (Gibco BRL), and recovered by 10% FBS/D MEM. This was washed with 5% BSA, 0.05% $NaN_3$/PBS (BSA solution), then suspended in 100 µl of 2.5% normal goat serum/BSA solution, and left on ice for 30 minutes. Then, 35-273 cp3 type antibody was added thereto so that the concentration became 5 µg/ml and left on ice for one hour. This was washed with a BSA solution once, then suspended in 100 µl of 5 µg/ml BSA solution of anti-cp3 rabbit polyclonal antibody (MBL, special order) and left on ice for one hour. This was washed with a BSA solution once, then suspended in 100 µl of 5 µg/ml BSA solution of Alexa 488 binding anti-rabbit IgG goat antibody (Molecularprobe), and left on ice for one hour. This was washed with a BSA solution twice, suspended in 1 ml of a PBS solution, treated by using Cell Strainer (Becton Dickinson), and then the fluorescence intensity of the group of cells was analyzed by using FACScaliver (FCM) (Becton Dickinson). As is apparent from FIG. 21, to the cells cultured in a culture medium containing tetracycline, RNAi acted on. In this case, similar to the case where the antibody is not allowed to act on, no FCM shift was observed. It was confirmed that the recognition targeting molecule of 035-273 antibody was IgSF4.

11. Reactivity of Antibody Clone with Respect to Various Cell Lines

The reactivity of isolated various antibody clones with respect to various cell lines was confirmed by FCM as follows.

Figure 22:
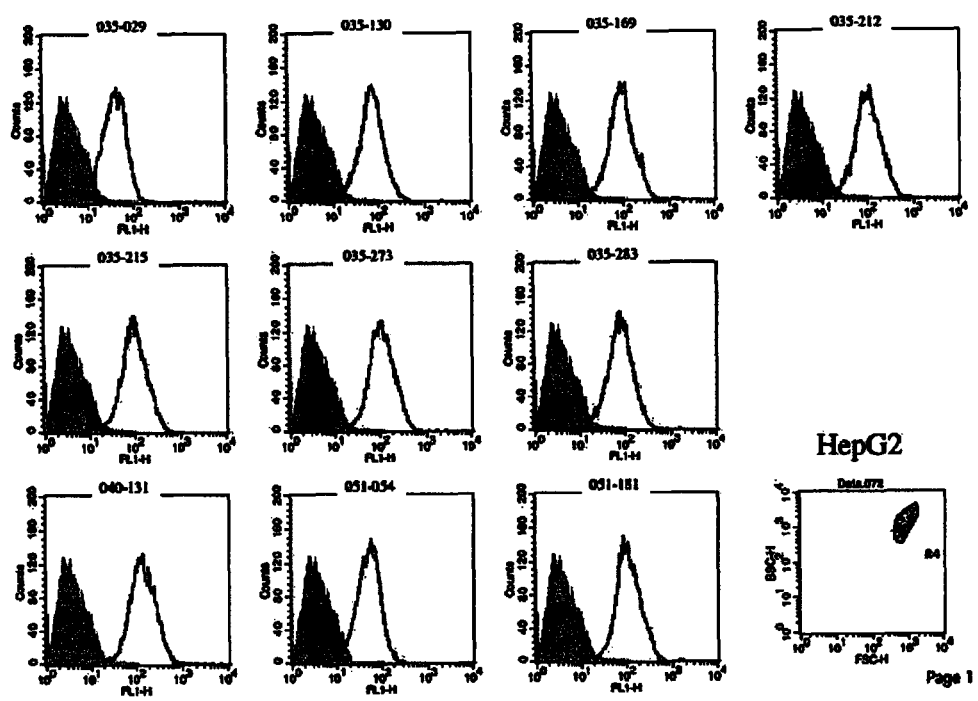
FIG. 22 shows the FCM reactivity of an isolated antibody clone against liver cancer derived cell line HEPG2.
Figure 23:
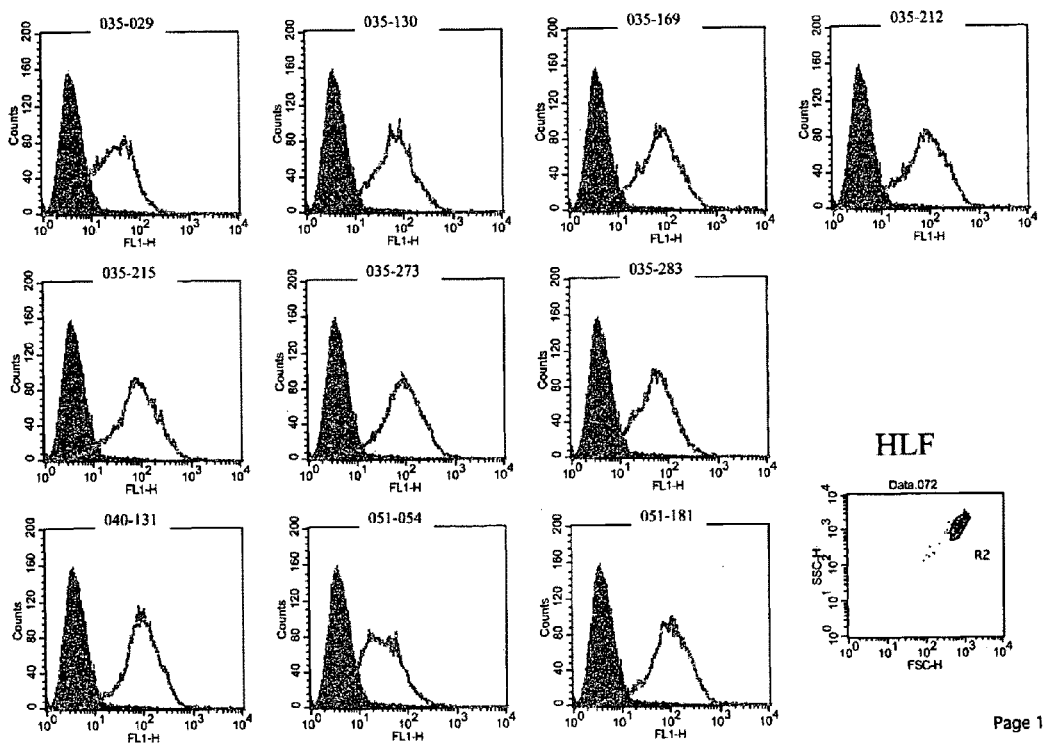
FIG. 23 shows the FCM reactivity of an isolated antibody clone against liver cancer derived cell line HLF.

(1) Examined FCM reactivity with respect to cell lines derived from liver cancer HEPG2 (FIG. 22) and HLF (FIG. 23).

Figure 24:
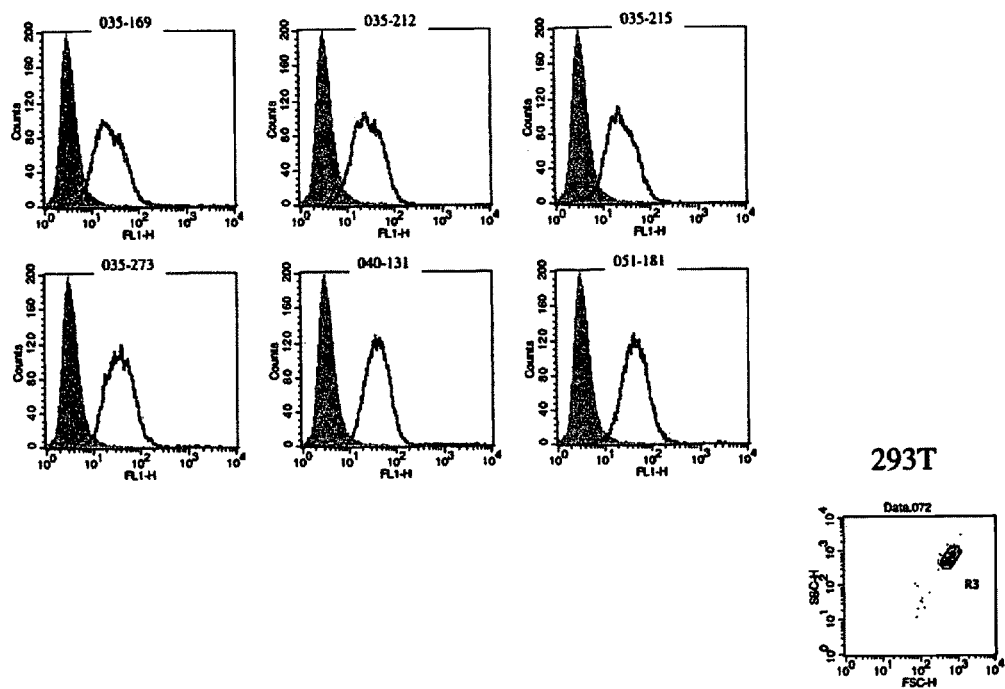
FIG. 24 shows the FCM reactivity of an isolated antibody clone against human embryo kidney epithelium derived cell line 293T.

(2) Examined FCM reactivity with respect to cell line 293T derived from human embryonic renal epitherium (FIG. 24).

(3) Examine FCM reactivity with respect to cell line ACHN derived from human renal cancer (FIG. 25).

(4) Carried out FCM analysis by using KK1 as a human ATL-derived cell line (FIG. 26).

Figure 27:
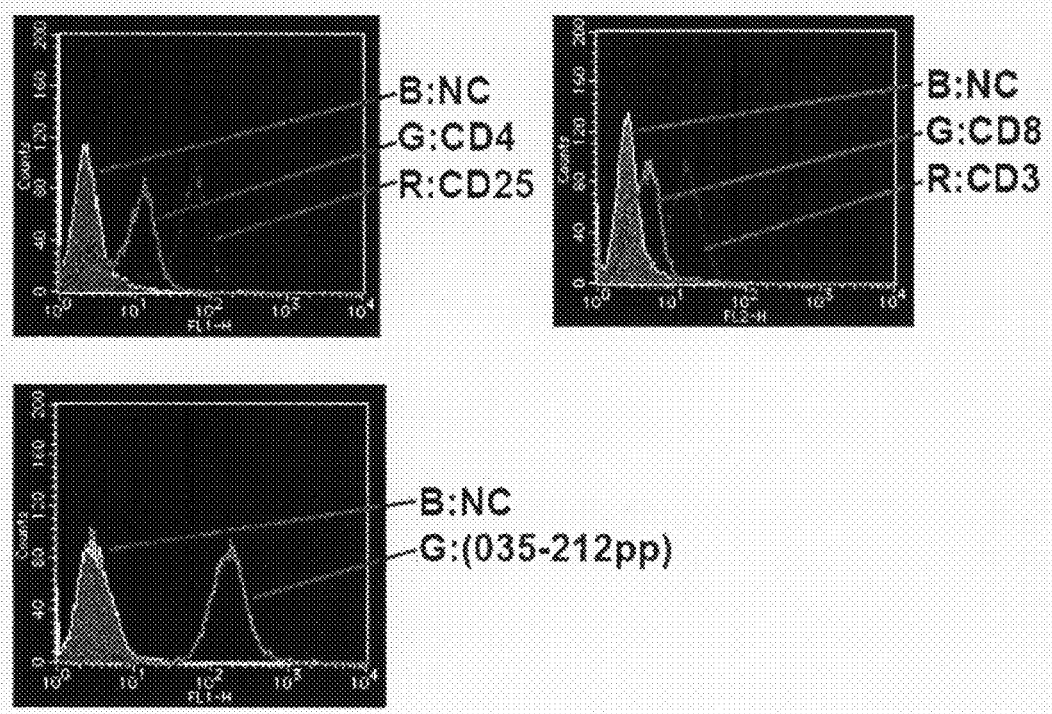
FIG. 27 shows the comparison in the FCM between the reactivity of an isolated antibody clone 035-212 and the reactivity of ATL cell surface markers (anti-CD3, anti-CD4, anti-CD8, and anti-CD25 antibodies).

(5) Compared the reactivity of 035-212 antibody that had been thought to have the highest reactivity from the above-mentioned results with the reactivities of other ATL cell surface markers (various antibodies such as anti-CD3, anti-CD4, anti-CD8, anti-CD25) by FCM (FIG. 27).

(6) As the comparison between non-expression ATL cell line and expression ATL cell line of IgSF4, compared be FCM between cell lines ED, Su9T and SO4 derived from human ATL in which a promoter of IgSF4 is methylated and cell lines KK1, KOB and ST1 derived from human ATL in which a promoter of IgSF4 is not methylated (FIG. 28).

(7) ATL is thought to be a specific leukemia caused by HTLV infection. Therefore, as the comparison between non-HTLV infected T cell line and HTLV infected T cell line, compared by FCM between a cell line MOLT4 derived from human non-ATL (derived from human T cell leukemia) and Jurkat, and HUT102 and MT-2 derived from human T cell directive virus infection (HTLV infection line) T cell lymphoma (FIG. 29).

FCM experiment operations in (1) to (7) were carried out as follows.

Firstly, as adhesive cell lines, a cell line that had been cultured in a 6-well plate (Falcon 3516) and as suspended cell lines such as ATL-derived cell line, a cell line that had been cultured in a suspended cell culture flask (70 ml (Slant Neck)), by using a culture medium (RPMI-1640: Sigma-Aldrich, 10% fetal bovine serum and a solution of 1% penicillin-streptomycin), were cultured in a $CO_2$ incubator at 37° C. and used, respectively.

i) Adhesive cell lines were dissociated from a dish by using 2 mg/ml collagenase I (Gibco BRL)/cell dissociation buffer (Gibco BRL) and recovered by using 10% FBS/D MEM. On the other hand, in the case of suspended cells, in order to remove the culture medium, intact cells were centrifuged (400×g, 4° C., 2 minutes). After such an operation, each cell was washed with 2.5% BSA, 0.05% $NaN_3$/PBS (BSA solution), suspended in 2.5% normal goat serum/BSA solution (100 µl), left on ice for 30 minutes, dispensed so that number became $10^6$ cells/well, centrifuged (400×g, 4° C., 2 minutes) and supernatant was removed.

ii-1) In the case of cp3 antibodies, they were added so that the concentration became 5 µg/ml and left on ice for one hour. This was washed with a BSA solution once, suspended in 100 µl of 5 µg/ml BSA solution of anti-cp3 mouse monoclonal antibody (Medical & Biological Laboratories Co., Ltd.) and left on ice for one hour. This was washed with a BSA solution once, then suspended in 100 µl of 5 µg/ml BSA solution of Alexa 488 binding anti-mouse IgG goat antibody (Molecularprobe) and left on ice for one hour. This was washed with a BSA solution twice, and then suspended in 500 µl of a BSA solution. To this solution, 50 µl of a fixation solution (formaldehyde) was added and it was left for 10 minutes. Thereafter, 150 µl of PBS was added, treated by using Cell Strainer (Becton Dickinson), and then the fluorescence intensity of the group of cells was analyzed by using FACScaliver (FCM) (Becton Dickinson) ((1) to (3)).

ii-2) In the case of the pp type (protein A type) antibodies, they were added so that the concentration became 5 µg/ml and left on ice for one hour. This was washed with a BSA solution once, then suspended in 100 µl of 5 µg/ml BSA solution of Alexa 488 binding anti-mouse IgG goat antibody (Molecularprobe) and left on ice for one hour. This was washed with a BSA solution twice, and then suspended in 500 µl of BSA solution. To this solution, 50 µl of a fixation solution (formaldehyde) was added and it was left for 10 minutes. Thereafter, 150 µl of PBS was added, treated by using Cell Strainer (Becton Dickinson), and then the fluorescence intensity of the group of cells was analyzed by using FACScaliver (FCM) (Becton Dickinson) ((4) to (7)).

ii-3) Furthermore, as to KK1 cells, other ATL cell surface marker antibodies (anti-human CD3-mouse antibody (Becton Dickinson), anti-human CD4-mouse antibody (Becton Dickinson), anti-human CD8-mouse antibody (Becton Dickinson), and anti-human CD25-mouse antibody (Becton Dickinson)) were used, and made to be a control by the following procedure in order to compare with the obtained antibody. The above-mentioned antibodies were added so that the concentration became 5 µg/ml and left on ice for one hour. This was washed with a BSA solution once, suspended in 100 µl of 5 µg/ml BSA solution of Alexa 488 binding anti-mouse IgG goat antibody (Molecularprobe) and left on ice for one hour. This was washed with a BSA solution twice, and then suspended in 500 µl of a BSA solution. To this solution, 50 µl of fixation solution (formaldehyde) was added and it was left for 10 minutes. Thereafter, 150 µl of PBS was added, treated by using Cell Strainer (Becton Dickinson), and then the fluorescence intensity of the group of cells was analyzed by using FACScaliver (FCM) (Becton Dickinson) (in the case where the anti-CD antibody of (5) was used).

In the analysis, detection antibody was labeled with fluorescent dye (Alexa 488, etc.) in advance. After a sample antibody and cells were reacted, it was reacted with the detection antibody. The difference in the binding antibody amount occurs depending upon the amount of antigen existing on the surface of the cells, and as a result, the fluorescence intensity became different. Thus, the affinity with respect to the antigen existing on the surface of the cells and the amount of antigen can be estimated. Furthermore, in order to remove dead cells and debris, and the like from the measurement, Forward Scatter: FSC is expressed in X-axis and Side Scatter: SSC is expressed in Y-axis, and a group of living cells (substantially the same group because cultured cells were used) in data obtained by dot plot expansion were gated, the fluorescence intensity only in this gate was measured.

As is apparent from the experiment results (1) to (4) mentioned above (FIG. 22 to FIG. 26), since various antibodies show substantially the same shift, it was clarified that was possible to obtain a large number of antibodies capable of capturing IgSF4 on the surface of the cell membrane found in renal cancer, liver cancer and ATL as a marker. Furthermore, from the experiment result of (5) (FIG. 27), IgSF4 can be an ATL cell surface marker that is comparable with or superior to ATL cell surface markers CD3, CD4, CD8, and CD25 as a control. Furthermore, this experiment supported that an antibody that specifically recognizes IgSF4 that is a molecule on the membrane surface and a new ATL cell surface marker was obtained.

Figure 30:
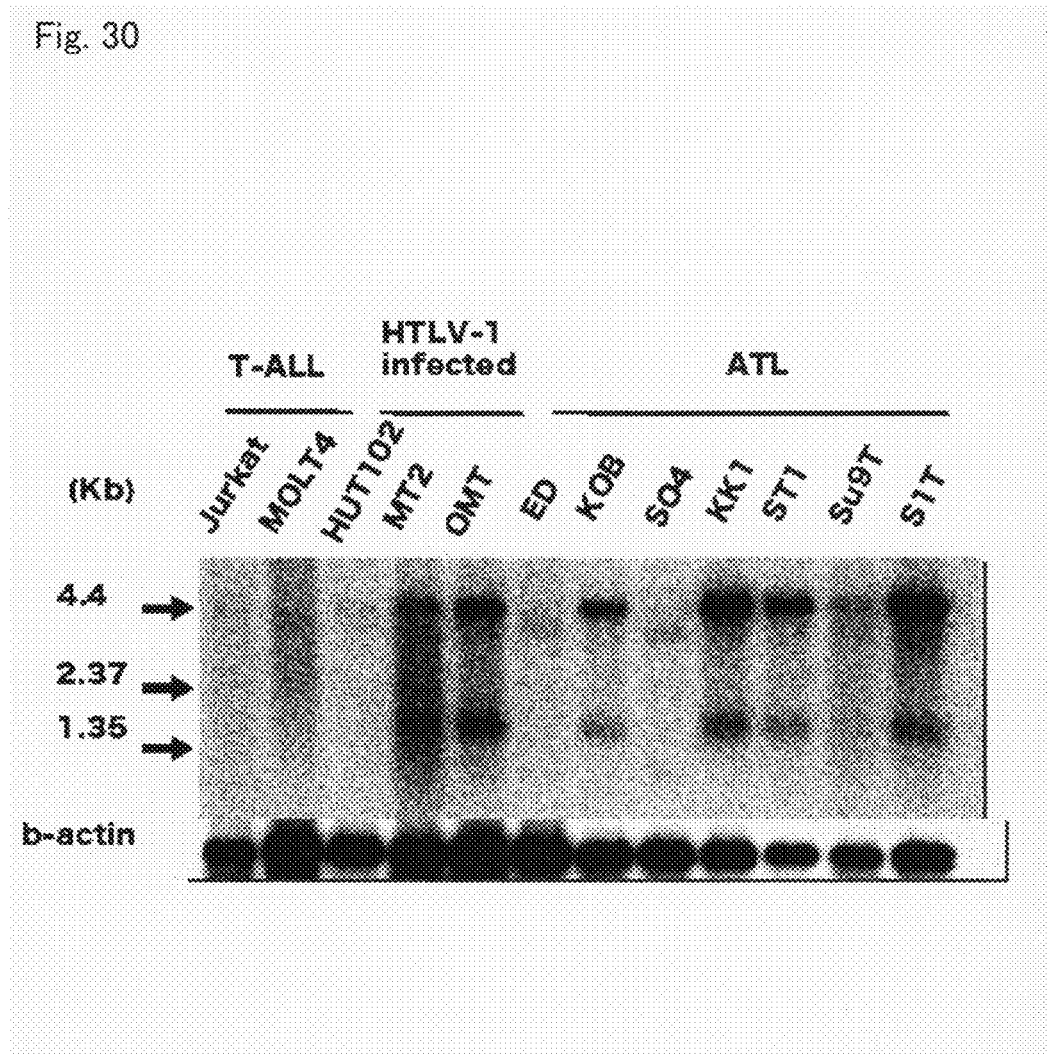
FIG. 30 shows results of mRNA expression analysis of IgSF4 by Northern Blot. Expression states of IgSF4 in HTLV-1 infected cell or ATL derived cell are shown.

(8) Northern Blot Analysis of mRNA expression of IgSF4 (FIG. 30)

From each cell, mRNA was extracted by using FastTrack 2.0 (Invitrogen, Carlsbad, Calif.). Thereafter, the obtained mRNA (3 µg) was subjected to electrophoresis on 1% agarose gel in MOPS buffer solution, then transferred to a nylon membrane (BIODYNE Pall BioSupport, East Hills, N.Y.). Then, by using 961 bp of p32 labeled probe in the position 411 to 1371 of IgSF4, Northern blot was carried out. For the label of the probe, Prime-It II Random Primer Labeling Kit (Stratagene, La Jolla, Calif.) was used.

Considering the experiment results of (6) and (7) (FIG. 28 and FIG. 29) and results of Northern Blot (FIG. 30) together, it was shown that it was possible to obtain antibodies capable of recognizing ATL-derived cell line (KK1, KOB and ST1) and HTLV infected cells (HUT102 and MT-2) in which IgSF4 molecules were expressed on the cell surface (cells in which IgSF4 expression is not observed due to the mutilation of the promoter and HTLV non-infected cells cannot be recognized by this antibody).

12. FCM Analysis and ADCC Activity Measurement of Anti-IgSF4 Antibody

Antibody-Dependent Cell-mediated Cytotoxicity (hereinafter, referred to as "ADCC") is an immune reaction for killing and attacking cells such as virus infected cells, which are harmful to human body. In the mechanism of ADCC, cells in which antibodies are widely bounded to the membrane surface is regarded as a target and attacked by the "effector cells" mainly including natural killer cells or monocytes. The cytotoxic property by ADCC occurs depending upon the combination of antibodies specifically binding to the cell membrane surface antigen and the effector cells.

Some of the antibodies specifically bounded to the tumor surface antigen show anti-tumor effect, cancer treating effect, and sold as an antibody pharmaceutical agent. It has been reported that the main action mechanism of these antibodies is ADCC. As a method for evaluating whether or not a cancer antigen specific antibody successfully isolated by the present inventors has an anti-tumor effect, that is, whether or not it is promising as a cancer treatment antibody, the detection of ADCC has been tried. In the following experiment, a method of allowing target cells to react with human IgG type antibody clone recognizing IgSF4 and presenting it to effector cells was used. The detection of ADCC was carried out by calculating the degree of damage by using a cytotoxic detection kit for detecting the enzyme activity of lactate dehydrogenase leaking from target cancer cells attacked by effector cells into the culture medium based on the color of the reagent.

12-1 FCM Analysis of IgG Antibody i) A431 cell lines were dissociated from a dish by using 2 mg/ml collagenase I (Gibco BRL)/cell dissociation buffer (Gibco BRL), and recovered by 10% FBS/D MEM. It was washed with 2.5% BSA, 0.05% $NaN_3$/PBS (BSA solution), suspended in 2.5% normal goat serum/BSA solution (100 µl), left on ice for 30 minutes, and dispensed so that number became $10^6$ cells/well.

The prepared IgG type antibody 035-029 was added so that the concentration became 5 µg/ml, and left on ice for one hour. This was washed with a BSA solution once, suspended in 100 µl of 5 µg/ml BSA solution of Alexa 488 binding anti-mouse IgG goat antibody (Molecularprobe) and left on ice for one hour. This was washed with a BSA solution twice, and then suspended in 500 µl of a BSA solution. Thereto, 50 µl of a fixation solution (formaldehyde) was added and it was left for 10 minutes. Thereafter, 150 µl of PBS was added, treated by using Cell Strainer (Becton Dickinson), and then the fluorescence intensity of the group of cells was analyzed by using FACScaliver (FCM) (Becton Dickinson) (FIG. 31).

12-2 Preparation of IgG Antibody

Chinese hamster cell line CHO-K1 including a gene fragment encoding IgG antibody (clone No.: 035-029, YA14 (anti-influenza virus antibody), and HR1-007 (anti-habu venom antibody)) used for ADCC activity measurement experiment was cultured in a serum-free culture medium (CHO-S-SFM II: Invitrogen, 1% (v/v) Penicillin-Streptomycin Solution: Sigma-Aldrich, 700 µg/ml G418: Sigma-Aldrich) large volume culture flask (Becton Dickinson, CELLine 1000 Flask) for 2 weeks, and culture supernatant was recovered. It was reacted with Protein G binding affinity column. After it was washed with PBS, eluted from the column with glycine-hydrochloric acid buffer (pH 2.7), and neutralized with Tris-HCl buffer (pH 8.9). For the purified antibody samples, samples that has been substituted and concentrated in PBS by using a dialyzing and concentrating tube (Millipore, Amicon Ultra-15) were used for experiment.

12-3 Preparation of Target Cells

As target cells to be used, lung cancer derived cultured cells VMRC-LCD (provided from Japanese Collection of Research Bioresources) was grown in a liquid culture medium 1 (Minimum Essential Medium Alpha Medium: Invitrogen, 10% (v/v) fetal bovine serum: Equitic-Bio, 1% (v/v) Penicillin-Streptomycin Solution: Sigma-Aldrich) on a culture dish having a diameter of 150 mm. The liquid culture medium was removed, cells were washed with 10 ml of PBS twice, and liquid was removed. To this, 5 ml of 4% (w/v) collagenase Type IV (Invitrogen) was added and maintained at 37° C. for 10 minutes, thereby peeling the cells off from the culture dish. Furthermore, 5 ml of liquid culture medium 2 (RPMI-1640, 10% (v/v) fetal bovine serum, 1% (v/v) Penicillin-Streptomycin Solution: Sigma-Aldrich) (RPMI-1640: Sigma-Aldrich, 10% fetal bovine serum, 1% penicillin streptomycin solution) was added so as to terminate the collagenase reaction. Suspended cells (6.7×10⁶ cells) were recovered, centrifuged (200×g, 4° C., 3 minutes) and supernatant was removed. Thereafter, it was suspended in a cytotoxicity test culture medium (Cytotoxic Medium, hereinafter, referred to as "CTM". RPMI-1640 culture medium, 1% (v/v) fetal bovine serum, 1% (v/v) Penicillin—Streptomycin Solution, 1% (v/v) 1M HEPES buffer (pH7.0): Invitrogen) so that the cell density became 3×10⁵ cells/ml and used for the experiment.

12-4 Preparation of Peripheral Blood Mononuclear Leukocyte Containing Effector Cell Heparin-added peripheral blood (30 ml) collected from a volunteer was diluted with PBS to 80 ml, 10 ml of lymphocyte isolation reagent Ficoll Paque Plus (Amersham Bioscience) was dispensed into four centrifugation tubes and it was stratified quietly and centrifuged (400×g, 20° C., 40 minutes). A mononuclear leukocyte fraction (including lymphocyte and monocyte) was recovered and diluted with cooled PBS to 80 ml. It was centrifuged (200×g, 4° C., 15 minutes) and precipitated. The precipitate was suspended in CTM so that the cell density became 7.5×10⁶ cells/ml.

12-5 ADCC Reaction

Into a U-bottom 96-well multiplate (Becton Dickinson), 66 µl/well of target cells (2×10⁴ cells) were placed. To this, 66 µl of IgG antibody (3 µg/ml) was added, and then 66 µl of peripheral blood mononuclear leukocyte suspension (7.5×10⁵ cells) was added. The E/T ratio (ratio of the effector cells and target cells) was made to be 20. In order to prompt to associate cells, centrifugation (60×g, 4° C., 5 minutes) was carried out so as to precipitate cells in the bottom. Then, the cells were incubated for 240 minutes in a culture device under conditions of 37° C. and 5% $CO_2$, and thus the ADCC reaction was induced. Each antibody sample was prepared as a CTM solution. Furthermore, in each sample, as a negative control, CTM is used and as a control of maximum liberation amount of lactate dehydrogenase, a mixture of target cells and 100 µl of 2% Triton X-100-CTM solution was used (cells had been destroyed by Triton X-100 in advance). Furthermore, in each experiment group, three wells were used.

12-6 Cytotoxicity Test

After the ADCC reaction, according to the method of cytotoxicity detection kit (Roche Diagnostics), an operation was carried out as follows. Centrifugation was carried out (350×g, 4° C., 10 minutes), 100 µl of supernatant was recovered, and transferred to a flat-bottomed 96-well multiplate (TPP). In each sample, a reaction solution (100 µl) of the cytotoxicity detection kit was added and left at room temperature so as to induce coloring of a coloring agent. The degree of coloring is proportional to the concentration of lactate dehydrogenase that is free in the culture supernatant and functions as an index of damage of the target cells. After 30 minutes from start of coloring, the absorbance (OD490-OD620 (background absorbance)) was measured by using a spectrophotometer. In each experiment group, the average absorbance of three wells was calculated and the Cytotoxic Index was calculated. In advance, the absorbance of only the culture medium was subtracted and the calculation was carried out as the following equation.

A) Experiment group without effector cells [Equation 1]

$$\text{Cytotoxic Index}(\%) = \frac{[\text{experimental value}] - [\text{control of only target cells (natural liberation)}]}{[\text{control of maximum liberation amount}] - [\text{control of only target cells (natural liberation)}]} \times 100$$

B) Experiment group including effector cells $$\text{Cytotoxic Index}(\%) = \frac{[\text{experimental value}] - [\text{control of only target cells (natural liberation)}] - [\text{control of only effector cells}]}{[\text{control of maximum liberation amount}] - [\text{control of only target cells (natural liberation)}]} \times 100$$

In the case of IgG antibody clone 035-029 that is specifically bonded to membrane molecule IgSF4, in the experiment group into which effector cells were added, the cytotoxic property was significantly increased (FIG. 32). That is to say, it was shown that the effector cell recognized an antibody clone specifically bonded to a target cell VMRC-LCD and attacked the target. In the anti-habu venom IgG antibody, clone HR1-007 and anti-influenza antibody YA14 (the results are not shown) which are regarded as not being related to surface antigen of VMRC-LCD, and in the experiment group in which no antibody clones were added, the increase in the cytotoxic property was not observed. Also in other antibody clones (035-273 and 051-054), after cp3 type antibody was subjected to primary reaction, when the same ADCC activity measurement test was carried out by using an anti-cp3 rabbit polyclonal antibody as a secondary antibody, similar to the antibody clone 035-029, the ADCC activity was confirmed (data are not shown).

From the above-mentioned results, it has been confirmed that it was possible to successfully obtain an antibody capable of specifically recognizing cancer cells via IgSF4 and exerting the damaging effect by ADCC activity. Therefore, such antibodies are effective as an antibody drug for targeting cancer cells.

Industrial Applicability

In accordance with the present invention, based on the discovery of a molecule expressing specific to cancer and capable of treating cancer or used as a target for diagnosing cancer, means that is effective to treatment or diagnosis of cancer, or study of development mechanism of cancer and the like are provided. It is expected that an anti-IgSF4 antibody provided in the present invention can be used as a treatment antibody, diagnosis antibody, study antibody, and the like, targeting cancer cell specifically expression IgSF4.

The present invention is not limited by the descriptions of Embodiments and Examples of the above-described invention at all. The present invention also includes a variety of modified aspects in the scope where those skilled in the art can easily conceive without departing the scope of the claims.

Each of the theses, Publication of patent applications, patent Publications, and other published documents mentioned or referred to in this specification is herein incorporated by reference in its entity.

The invention claimed is:

1. An isolated antibody having specific binding property against IgSF4, which comprises:
   a heavy chain variable region having CDR containing the amino acid sequences of SEQ ID NO.:58-60, and;
   a light chain variable region having CDR containing the amino acid sequences of SEQ ID NO.:62-64.

2. The isolated antibody according to claim 1, which is a human antibody or a humanized antibody.

3. The isolated antibody according to claim 1, which is IgG, Fab, Fab', F(ab')$_2$, cFv, or dsFv antibody.

4. A therapeutic agent for cancer comprising an antibody as claimed in claim 1 as an active ingredient.

5. A reagent comprising an antibody as claimed in claim 1, which is used for examination of liver cancer, examination of adult T cell leukemia, study of liver cancer, or study of adult T cell leukemia.

6. The isolated antibody according to claim 1, which comprises:
   a heavy chain variable region and a light chain variable region in a combination of a heavy chain variable region having CDR consisting of CDR1 of SEQ ID NO.:58, CDR2 of SEQ ID NO.:59, and CDR3 of SEQ ID NO.:60, and a light chain variable region having CDR consisting of CDR1 of SEQ ID NO.:62, CDR2 of SEQ ID NO.:63, and CDR3 of SEQ ID NO.:64.

* * * * *

SEQUENCE LISTING

<160> NUMBER OF SEQ ID NOS: 274

<210> SEQ ID NO 1
<211> LENGTH: 116
<212> TYPE: PRT
<213> ORGANISM: Homo sapiens

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Asp Asn Trp Tyr Phe Asp Leu Trp Gly Arg Gly Thr Leu Val
            100                 105                 110

Thr Val Ser Ser
        115

<210> SEQ ID NO 2
<211> LENGTH: 5
<212> TYPE: PRT
<213> ORGANISM: Homo sapiens

<400> SEQUENCE: 2

Ser Tyr Ala Met Ser
1               5

<210> SEQ ID NO 3
<211> LENGTH: 17
<212> TYPE: PRT
<213> ORGANISM: Homo sapiens

<400> SEQUENCE: 3

Ala Ile Ser Gly Ser Gly Gly Ser Thr Tyr Tyr Ala Asp Ser Val Lys
1               5                   10                  15

Gly

<210> SEQ ID NO 4
<211> LENGTH: 9
<212> TYPE: PRT
<213> ORGANISM: Homo sapiens

<400> SEQUENCE: 4

Ala Arg Asp Asn Trp Tyr Phe Asp Leu
1               5

<210> SEQ ID NO 5
<211> LENGTH: 109
<212> TYPE: PRT
<213> ORGANISM: Homo sapiens

<400> SEQUENCE: 5

Ser Ser Glu Leu Thr Gln Asp Pro Ala Val Ser Val Ala Leu Gly Gln

```
                1               5                   10                  15
Thr Val Arg Ile Thr Cys Gln Gly Asp Ser Leu Arg Ser Tyr Tyr Ala
                    20                  25                  30

Ser Trp Tyr Gln Gln Lys Pro Gly Gln Ala Pro Val Leu Val Ile Tyr
            35                  40                  45

Gly Lys Asn Asn Arg Leu Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly
            100                 105
```

<210> SEQ ID NO 6
<211> LENGTH: 11
<212> TYPE: PRT
<213> ORGANISM: Homo sapiens

<400> SEQUENCE: 6

```
Gln Gly Asp Ser Leu Arg Ser Tyr Tyr Ala Ser
1               5                   10
```

<210> SEQ ID NO 7
<211> LENGTH: 7
<212> TYPE: PRT
<213> ORGANISM: Homo sapiens

<400> SEQUENCE: 7

```
Gly Lys Asn Asn Arg Leu Ser
1               5
```

<210> SEQ ID NO 8
<211> LENGTH: 11
<212> TYPE: PRT
<213> ORGANISM: Homo sapiens

<400> SEQUENCE: 8

```
Asn Ser Arg Asp Ser Ser Gly Asn His Val Val
1               5                   10
```

<210> SEQ ID NO 9
<211> LENGTH: 121
<212> TYPE: PRT
<213> ORGANISM: Homo sapiens

<400> SEQUENCE: 9

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                    20                  25                  30

Ser Val Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Gly Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Tyr Tyr Gly Met Asp Val Trp Gly
```

```
                100             105             110
Gln Gly Thr Thr Val Thr Val Ser Ser
        115             120

<210> SEQ ID NO 10
<211> LENGTH: 7
<212> TYPE: PRT
<213> ORGANISM: Homo sapiens

<400> SEQUENCE: 10

Ser Asn Ser Val Ala Trp Asn
1               5

<210> SEQ ID NO 11
<211> LENGTH: 18
<212> TYPE: PRT
<213> ORGANISM: Homo sapiens

<400> SEQUENCE: 11

Arg Thr Tyr Tyr Arg Ser Lys Trp Tyr Asn Asp Tyr Ala Gly Ser Val
1               5                   10                  15

Lys Ser

<210> SEQ ID NO 12
<211> LENGTH: 9
<212> TYPE: PRT
<213> ORGANISM: Homo sapiens

<400> SEQUENCE: 12

Asp Ser Tyr Tyr Tyr Gly Met Asp Val
1               5

<210> SEQ ID NO 13
<211> LENGTH: 109
<212> TYPE: PRT
<213> ORGANISM: Homo sapiens

<400> SEQUENCE: 13

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Arg Pro Gly Gln Ala Pro Leu Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Phe His
                85                  90                  95

Arg Val Phe Gly Thr Gly Thr Lys Val Thr Val Leu Gly
            100                 105

<210> SEQ ID NO 14
<211> LENGTH: 11
<212> TYPE: PRT
<213> ORGANISM: Homo sapiens

<400> SEQUENCE: 14

Gln Gly Asp Ser Leu Arg Ser Tyr Tyr Ala Ser
1               5                   10
```

```
<210> SEQ ID NO 15
<211> LENGTH: 7
<212> TYPE: PRT
<213> ORGANISM: Homo sapiens

<400> SEQUENCE: 15

Gly Lys Asn Asn Arg Pro Ser
1               5

<210> SEQ ID NO 16
<211> LENGTH: 11
<212> TYPE: PRT
<213> ORGANISM: Homo sapiens

<400> SEQUENCE: 16

Asn Ser Arg Asp Ser Ser Gly Phe His Arg Val
1               5                   10

<210> SEQ ID NO 17
<211> LENGTH: 121
<212> TYPE: PRT
<213> ORGANISM: Homo sapiens

<400> SEQUENCE: 17

Gln Val Gln Leu Gln Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Tyr Gly Ile Trp Tyr Phe Asp Leu Trp Gly
            100                 105                 110

Arg Gly Thr Leu Val Thr Val Ser Ser
        115                 120

<210> SEQ ID NO 18
<211> LENGTH: 7
<212> TYPE: PRT
<213> ORGANISM: Homo sapiens

<400> SEQUENCE: 18

Ser Asn Ser Ala Ala Trp Asn
1               5

<210> SEQ ID NO 19
<211> LENGTH: 18
<212> TYPE: PRT
<213> ORGANISM: Homo sapiens

<400> SEQUENCE: 19

Arg Thr Tyr Tyr Arg Ser Lys Trp Tyr Asn Asp Tyr Ala Val Ser Val
1               5                   10                  15

Lys Ser

<210> SEQ ID NO 20
```

```
<211> LENGTH: 9
<212> TYPE: PRT
<213> ORGANISM: Homo sapiens

<400> SEQUENCE: 20

Glu Tyr Gly Ile Trp Tyr Phe Asp Leu
1               5

<210> SEQ ID NO 21
<211> LENGTH: 108
<212> TYPE: PRT
<213> ORGANISM: Homo sapiens

<400> SEQUENCE: 21

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Val
                85                  90                  95

Val Phe Gly Gly Gly Thr Lys Leu Thr Val Leu Gly
            100                 105

<210> SEQ ID NO 22
<211> LENGTH: 11
<212> TYPE: PRT
<213> ORGANISM: Homo sapiens

<400> SEQUENCE: 22

Gln Gly Asp Ser Leu Arg Ser Tyr Tyr Ala Ser
1               5                   10

<210> SEQ ID NO 23
<211> LENGTH: 7
<212> TYPE: PRT
<213> ORGANISM: Homo sapiens

<400> SEQUENCE: 23

Gly Lys Asn Asn Arg Pro Ser
1               5

<210> SEQ ID NO 24
<211> LENGTH: 10
<212> TYPE: PRT
<213> ORGANISM: Homo sapiens

<400> SEQUENCE: 24

Asn Ser Arg Asp Ser Ser Gly Asn Val Val
1               5                   10

<210> SEQ ID NO 25
<211> LENGTH: 115
<212> TYPE: PRT
<213> ORGANISM: Homo sapiens

<400> SEQUENCE: 25

Glu Val Gln Leu Val Glu Ser Gly Gly Gly Leu Ile Gln Pro Gly Gly
```

```
                1               5                   10                  15
Ser Leu Arg Leu Ser Cys Ala Ala Ser Gly Phe Thr Val Ser Ser Asn
                    20                  25                  30

Tyr Met Ser Trp Val Arg Gln Ala Pro Gly Lys Gly Leu Glu Trp Val
                    35                  40                  45

Ser Val Ile Tyr Ser Gly Gly Ser Thr Tyr Tyr Ala Asp Ser Val Lys
                    50                  55                  60

Gly Arg Phe Thr Ile Ser Arg Asp Asn Ser Lys Asn Thr Leu Tyr Leu
    65                  70                  75                  80

Gln Met Asn Ser Leu Arg Ala Glu Asp Thr Ala Val Tyr Tyr Cys Ala
                    85                  90                  95

Arg Gly Thr Trp Tyr Met Asp Val Trp Gly Lys Gly Thr Thr Val Thr
                    100                 105                 110

Val Ser Ser
        115
```

<210> SEQ ID NO 26
<211> LENGTH: 5
<212> TYPE: PRT
<213> ORGANISM: Homo sapiens

<400> SEQUENCE: 26

```
Ser Asn Tyr Met Ser
1               5
```

<210> SEQ ID NO 27
<211> LENGTH: 16
<212> TYPE: PRT
<213> ORGANISM: Homo sapiens

<400> SEQUENCE: 27

```
Val Ile Tyr Ser Gly Gly Ser Thr Tyr Tyr Ala Asp Ser Val Lys Gly
1               5                   10                  15
```

<210> SEQ ID NO 28
<211> LENGTH: 7
<212> TYPE: PRT
<213> ORGANISM: Homo sapiens

<400> SEQUENCE: 28

```
Gly Thr Trp Tyr Met Asp Val
1               5
```

<210> SEQ ID NO 29
<211> LENGTH: 109
<212> TYPE: PRT
<213> ORGANISM: Homo sapiens

<400> SEQUENCE: 29

```
Ser Ser Glu Leu Thr Gln Asp Pro Ala Val Ser Val Ala Ser Gly Gln
1               5                   10                  15

Thr Val Arg Ile Thr Cys Gln Gly Asp Ser Leu Arg His Tyr Tyr Pro
                20                  25                  30

Ser Trp Tyr Gln Gln Lys Pro Arg Gln Ala Pro Val Leu Val Phe Phe
                35                  40                  45

Gly Glu Asn Asn Arg Pro Ser Gly Ile Pro Asp Arg Phe Ser Gly Ser
            50                  55                  60

Ala Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Gly Asn Asp Asp Arg
```

```
                    85                  90                  95

Trp Leu Phe Gly Gly Gly Thr Lys Val Thr Val Leu Gly
                100                 105

<210> SEQ ID NO 30
<211> LENGTH: 11
<212> TYPE: PRT
<213> ORGANISM: Homo sapiens

<400> SEQUENCE: 30

Gln Gly Asp Ser Leu Arg His Tyr Tyr Pro Ser
1               5                   10

<210> SEQ ID NO 31
<211> LENGTH: 7
<212> TYPE: PRT
<213> ORGANISM: Homo sapiens

<400> SEQUENCE: 31

Gly Glu Asn Asn Arg Pro Ser
1               5

<210> SEQ ID NO 32
<211> LENGTH: 11
<212> TYPE: PRT
<213> ORGANISM: Homo sapiens

<400> SEQUENCE: 32

Ser Ser Arg Asp Gly Asn Asp Asp Arg Trp Leu
1               5                   10

<210> SEQ ID NO 33
<211> LENGTH: 121
<212> TYPE: PRT
<213> ORGANISM: Homo sapiens

<400> SEQUENCE: 33

Gln Val Gln Leu Gln Gln Ser Gly Pro Gly Leu Leu Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Asp Asn Tyr Tyr Gln Gly Met Asp Val Trp Gly
            100                 105                 110

Gln Gly Thr Thr Val Thr Val Ser Ser
        115                 120

<210> SEQ ID NO 34
<211> LENGTH: 7
<212> TYPE: PRT
<213> ORGANISM: Homo sapiens

<400> SEQUENCE: 34

Ser Asn Ser Ala Ala Trp Asn
1               5
```

<210> SEQ ID NO 35
<211> LENGTH: 18
<212> TYPE: PRT
<213> ORGANISM: Homo sapiens

<400> SEQUENCE: 35

Arg Thr Tyr Tyr Arg Ser Lys Trp Tyr Asn Asp Tyr Ala Val Ser Val
1               5                   10                  15

Lys Ser

<210> SEQ ID NO 36
<211> LENGTH: 11
<212> TYPE: PRT
<213> ORGANISM: Homo sapiens

<400> SEQUENCE: 36

Asp Asn Tyr Tyr Gln Gly Met Asp Val Trp Gly
1               5                   10

<210> SEQ ID NO 37
<211> LENGTH: 109
<212> TYPE: PRT
<213> ORGANISM: Homo sapiens

<400> SEQUENCE: 37

Ser Ser Glu Leu Thr Gln Asp Pro Thr Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Asn Ser Gly Tyr His
                85                  90                  95

Arg Val Phe Gly Thr Gly Thr Lys Val Thr Val Leu Gly
            100                 105

<210> SEQ ID NO 38
<211> LENGTH: 11
<212> TYPE: PRT
<213> ORGANISM: Homo sapiens

<400> SEQUENCE: 38

Gln Gly Asp Ser Leu Arg Ser Tyr Tyr Ala Ser
1               5                   10

<210> SEQ ID NO 39
<211> LENGTH: 7
<212> TYPE: PRT
<213> ORGANISM: Homo sapiens

<400> SEQUENCE: 39

Gly Lys Asn Asn Arg Pro Ser
1               5

<210> SEQ ID NO 40
<211> LENGTH: 9
<212> TYPE: PRT

<213> ORGANISM: Homo sapiens

<400> SEQUENCE: 40

Asn Ser Arg Asp Asn Ser Gly Tyr His
1               5

<210> SEQ ID NO 41
<211> LENGTH: 115
<212> TYPE: PRT
<213> ORGANISM: Homo sapiens

<400> SEQUENCE: 41

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Gly Gly Tyr
            20                  25                  30

Tyr Trp Gly Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Pro Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Trp Tyr Pro Asp Pro Trp Gly Gln Gly Thr Leu Val Thr
            100                 105                 110

Val Ser Ser
        115

<210> SEQ ID NO 42
<211> LENGTH: 5
<212> TYPE: PRT
<213> ORGANISM: Homo sapiens

<400> SEQUENCE: 42

Gly Tyr Tyr Trp Gly
1               5

<210> SEQ ID NO 43
<211> LENGTH: 16
<212> TYPE: PRT
<213> ORGANISM: Homo sapiens

<400> SEQUENCE: 43

Glu Ile Asn His Ser Gly Ser Thr Asn Tyr Asn Pro Ser Leu Lys Ser
1               5                   10                  15

<210> SEQ ID NO 44
<211> LENGTH: 7
<212> TYPE: PRT
<213> ORGANISM: Homo sapiens

<400> SEQUENCE: 44

Gly Gly Trp Tyr Pro Asp Pro
1               5

<210> SEQ ID NO 45
<211> LENGTH: 108
<212> TYPE: PRT
<213> ORGANISM: Homo sapiens

<400> SEQUENCE: 45

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Val
                85                  90                  95

Val Phe Gly Gly Gly Thr Lys Leu Thr Val Leu Gly
                100                 105
```

<210> SEQ ID NO 46
<211> LENGTH: 11
<212> TYPE: PRT
<213> ORGANISM: Homo sapiens

<400> SEQUENCE: 46

```
Gln Gly Asp Ser Leu Arg Ser Tyr Tyr Ala Ser
1               5                   10
```

<210> SEQ ID NO 47
<211> LENGTH: 7
<212> TYPE: PRT
<213> ORGANISM: Homo sapiens

<400> SEQUENCE: 47

```
Gly Lys Asn Asn Arg Pro Ser
1               5
```

<210> SEQ ID NO 48
<211> LENGTH: 10
<212> TYPE: PRT
<213> ORGANISM: Homo sapiens

<400> SEQUENCE: 48

```
Asn Ser Arg Asp Ser Ser Gly Asn Val Val
1               5                   10
```

<210> SEQ ID NO 49
<211> LENGTH: 115
<212> TYPE: PRT
<213> ORGANISM: Homo sapiens

<400> SEQUENCE: 49

```
Gln Val Gln Leu Gln Gln Trp Gly Ala Gly Leu Leu Lys Pro Ser Glu
1               5                   10                  15

Thr Leu Ser Leu Thr Cys Ala Phe Tyr Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95
```

Arg Ser Ser Trp Tyr Phe Asp Leu Trp Gly Arg Gly Thr Leu Val Thr
            100                 105                 110

Val Ser Ser
        115

<210> SEQ ID NO 50
<211> LENGTH: 5
<212> TYPE: PRT
<213> ORGANISM: Homo sapiens

<400> SEQUENCE: 50

Gly Tyr Tyr Trp Ser
1               5

<210> SEQ ID NO 51
<211> LENGTH: 16
<212> TYPE: PRT
<213> ORGANISM: Homo sapiens

<400> SEQUENCE: 51

Glu Ile Asn His Ser Gly Ser Thr Asn Tyr Asn Pro Ser Leu Lys Ser
1               5                   10                  15

<210> SEQ ID NO 52
<211> LENGTH: 7
<212> TYPE: PRT
<213> ORGANISM: Homo sapiens

<400> SEQUENCE: 52

Ser Ser Trp Tyr Phe Asp Leu
1               5

<210> SEQ ID NO 53
<211> LENGTH: 109
<212> TYPE: PRT
<213> ORGANISM: Homo sapiens

<400> SEQUENCE: 53

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Met Leu Thr Val Leu Gly
            100                 105

<210> SEQ ID NO 54
<211> LENGTH: 11
<212> TYPE: PRT
<213> ORGANISM: Homo sapiens

<400> SEQUENCE: 54

Gln Gly Asp Ser Leu Arg Ser Tyr Tyr Ala Ser
1               5                   10

```
<210> SEQ ID NO 55
<211> LENGTH: 7
<212> TYPE: PRT
<213> ORGANISM: Homo sapiens

<400> SEQUENCE: 55

Gly Lys Asn Asn Arg Pro Ser
1               5

<210> SEQ ID NO 56
<211> LENGTH: 11
<212> TYPE: PRT
<213> ORGANISM: Homo sapiens

<400> SEQUENCE: 56

Asn Ser Arg Asp Ser Ser Gly Asn His Val Val
1               5                   10

<210> SEQ ID NO 57
<211> LENGTH: 116
<212> TYPE: PRT
<213> ORGANISM: Homo sapiens

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Pro Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Arg His Asp Tyr Trp Gly Gln Gly Thr Leu Val
            100                 105                 110

Thr Val Ser Ser
        115

<210> SEQ ID NO 58
<211> LENGTH: 5
<212> TYPE: PRT
<213> ORGANISM: Homo sapiens

<400> SEQUENCE: 58

Ser Tyr Trp Met Ser
1               5

<210> SEQ ID NO 59
<211> LENGTH: 17
<212> TYPE: PRT
<213> ORGANISM: Homo sapiens

<400> SEQUENCE: 59

Asn Ile Lys Gln Asp Gly Ser Glu Lys Tyr Tyr Val Asp Ser Val Lys
1               5                   10                  15

Gly

<210> SEQ ID NO 60
<211> LENGTH: 7
```

```
<212> TYPE: PRT
<213> ORGANISM: Homo sapiens

<400> SEQUENCE: 60

Gly Gly Gly Arg His Asp Tyr
1               5

<210> SEQ ID NO 61
<211> LENGTH: 111
<212> TYPE: PRT
<213> ORGANISM: Homo sapiens

<400> SEQUENCE: 61

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gly Thr Trp Asp Ser Ser Leu
                85                  90                  95

Ser Ala Gly Val Phe Gly Thr Gly Thr Lys Val Thr Val Leu Gly
            100                 105                 110

<210> SEQ ID NO 62
<211> LENGTH: 13
<212> TYPE: PRT
<213> ORGANISM: Homo sapiens

<400> SEQUENCE: 62

Ser Gly Ser Ser Ser Asn Ile Gly Ser Asn Thr Val Asn
1               5                   10

<210> SEQ ID NO 63
<211> LENGTH: 7
<212> TYPE: PRT
<213> ORGANISM: Homo sapiens

<400> SEQUENCE: 63

Ser Asn Asn Gln Arg Pro Ser
1               5

<210> SEQ ID NO 64
<211> LENGTH: 11
<212> TYPE: PRT
<213> ORGANISM: Homo sapiens

<400> SEQUENCE: 64

Gly Thr Trp Asp Ser Ser Leu Ser Ala Gly Val
1               5                   10

<210> SEQ ID NO 65
<211> LENGTH: 348
<212> TYPE: DNA
<213> ORGANISM: Homo sapiens

<400> SEQUENCE: 65
gaggtgcagc tggtggagtc tgggggaggc ctggtcaagc ctggggggtc cctgagactc        60
```

```
tcctgtgcag cctctggatt cacctttagc agctatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccttgt attactgtgc gagggacaac      300
tggtacttcg atctctgggg ccgtggcacc ctggtcaccg tctcgagc                   348
```

<210> SEQ ID NO 66
<211> LENGTH: 15
<212> TYPE: DNA
<213> ORGANISM: Homo sapiens

<400> SEQUENCE: 66

```
agctatgcca tgagc                                                       15
```

<210> SEQ ID NO 67
<211> LENGTH: 51
<212> TYPE: DNA
<213> ORGANISM: Homo sapiens

<400> SEQUENCE: 67

```
gctattagtg gtagtggtgg tagcacatac tacgcagact ccgtgaaggg c                51
```

<210> SEQ ID NO 68
<211> LENGTH: 27
<212> TYPE: DNA
<213> ORGANISM: Homo sapiens

<400> SEQUENCE: 68

```
gcgagggaca actggtactt cgatctc                                           27
```

<210> SEQ ID NO 69
<211> LENGTH: 327
<212> TYPE: DNA
<213> ORGANISM: Homo sapiens

<400> SEQUENCE: 69

```
tcttctgagc tgactcagga ccctgctgtg tctgtggcct tgggacagac agtcaggatc      60
acatgccaag agacagcct cagaagctat tatgcaagct ggtaccagca gaagccagga      120
caggcccctg tacttgtcat ctatggtaaa aacaaccggc ctcagggat cccagaccga       180 ttctctggct ccagctcagg aaacacagct tccttgacca tcactggggc tcaggcggaa      240
gatgaggctg actattactg taactcccgg gacagcagtg gtaaccatgt ggtattcggc      300
ggagggacca gctgaccgt cctaggt                                           327
```

<210> SEQ ID NO 70
<211> LENGTH: 33
<212> TYPE: DNA
<213> ORGANISM: Homo sapiens

<400> SEQUENCE: 70

```
caaggagaca gcctcagaag ctattatgca agc                                   33
```

<210> SEQ ID NO 71
<211> LENGTH: 21
<212> TYPE: DNA
<213> ORGANISM: Homo sapiens

<400> SEQUENCE: 71

```
ggtaaaaaca accggctctc a                                                21
```

<210> SEQ ID NO 72
<211> LENGTH: 33
<212> TYPE: DNA
<213> ORGANISM: Homo sapiens

<400> SEQUENCE: 72
aactcccggg acagcagtgg taaccatgtg gta                                    33

<210> SEQ ID NO 73
<211> LENGTH: 363
<212> TYPE: DNA
<213> ORGANISM: Homo sapiens

<400> SEQUENCE: 73
caggtacagc tgcagcagtc aggtccagga ctggtgaagc cctcgcagac cctctcactc        60
acctgtgcca tctccgggga cagtgtctct agcaacagtg ttgcttggaa ctggatcagg       120
cagtccccat cgagaggcct tgagtggctg gaaggacat actacaggtc caagtggtat        180
aatgattatg caggatctgt gaaaagtcga ataaccatca cccagacac atccaagaac         240 caattctccc tgcagctgaa ctctgtgact cccgaggaca cggctgtgta ttactgtgca        300
agagattcgt actactacgg tatggacgtc tggggccaag ggaccacggt caccgtctcg        360
agc                                                                    363

<210> SEQ ID NO 74
<211> LENGTH: 21
<212> TYPE: DNA
<213> ORGANISM: Homo sapiens

<400> SEQUENCE: 74
agcaacagtg ttgcttggaa c                                                21

<210> SEQ ID NO 75
<211> LENGTH: 54
<212> TYPE: DNA
<213> ORGANISM: Homo sapiens

<400> SEQUENCE: 75
aggacatact acaggtccaa gtggtataat gattatgcag gatctgtgaa aagt             54

<210> SEQ ID NO 76
<211> LENGTH: 27
<212> TYPE: DNA
<213> ORGANISM: Homo sapiens

<400> SEQUENCE: 76
gattcgtact actacggtat ggacgtc                                          27

<210> SEQ ID NO 77
<211> LENGTH: 327
<212> TYPE: DNA
<213> ORGANISM: Homo sapiens

<400> SEQUENCE: 77
tcttctgagc tgactcagga ccctgctgtg tctgtggcct tgggacagac agtcaggatc        60
acatgccaag agacagcct cagaagctat tatgcaagct ggtaccagca gaggccagga       120
caggcccctc tacttgtcat ttatggtaaa aataaccggc cctcagggat cccagaccga       180
ttctctggct ccagctcagg aaacacagct tccttgacca tcactggggc tcaggcggaa       240
gatgaggccg actattactg taactcccgg gacagcagtg gtttccatcg ggtcttcgga       300

```
actgggacca aggtcaccgt cctaggt                                         327
```

<210> SEQ ID NO 78
<211> LENGTH: 33
<212> TYPE: DNA
<213> ORGANISM: Homo sapiens

<400> SEQUENCE: 78

```
caaggagaca gcctcagaag ctattatgca agc                                   33
```

<210> SEQ ID NO 79
<211> LENGTH: 21
<212> TYPE: DNA
<213> ORGANISM: Homo sapiens

<400> SEQUENCE: 79

```
ggtaaaaata accggccctc a                                                21
```

<210> SEQ ID NO 80
<211> LENGTH: 33
<212> TYPE: DNA
<213> ORGANISM: Homo sapiens

<400> SEQUENCE: 80

```
aactcccggg acagcagtgg tttccatcgg gtc                                   33
```

<210> SEQ ID NO 81
<211> LENGTH: 363
<212> TYPE: DNA
<213> ORGANISM: Homo sapiens

<400> SEQUENCE: 81

```
caggtgcagc tgcaggagtc gggtccagga ctggtgaagc cctcgcagac cctctcactc       60
acctgtgcca tctccgggga cagtgtctct agcaacagtg ctgcttggaa ctggatcagg      120
cagtccccat cgagaggcct tgagtggctg ggaaggacat actacaggtc caagtggtat      180
aatgattatg cagtatctgt gaaaagtcga ataaccatca acccagacac atccaagaac      240
cagttctccc tgcagctgaa ctctgtgact cccgaggaca cggctgtgta ttactgtgca      300
agagagtacg ggatctggta cttcgatctc tggggccgtg gcaccctggt caccgtctcg      360
agc                                                                   363
```

<210> SEQ ID NO 82
<211> LENGTH: 21
<212> TYPE: DNA
<213> ORGANISM: Homo sapiens

<400> SEQUENCE: 82

```
agcaacagtg ctgcttggaa c                                                21
```

<210> SEQ ID NO 83
<211> LENGTH: 54
<212> TYPE: DNA
<213> ORGANISM: Homo sapiens

<400> SEQUENCE: 83

```
aggacatact acaggtccaa gtggtataat gattatgcag tatctgtgaa aagt            54
```

<210> SEQ ID NO 84
<211> LENGTH: 27
<212> TYPE: DNA
<213> ORGANISM: Homo sapiens

```
<400> SEQUENCE: 84
gagtacggga tctggtactt cgatctc                                          27

<210> SEQ ID NO 85
<211> LENGTH: 324
<212> TYPE: DNA
<213> ORGANISM: Homo sapiens

<400> SEQUENCE: 85
tcttctgagc tgactcagga ccctgctgtg tctgtggcct tgggacagac agtcaggatc      60
acatgccaag agacagcct cagaagctat tatgcaagct ggtaccagca gaagccagga      120
caggcccctg tacttgtcat ctatggtaaa acaaccggc cctcagggat cccagaccga      180
ttctctggct ccagctcagg aaacacagct tccttgacca tcactgggc tcaggcggaa      240 gatgaggctg actattactg taactcccgg gacagcagtg gtaacgtggt attcggcgga     300
gggaccaagc tgaccgtcct aggt                                             324

<210> SEQ ID NO 86
<211> LENGTH: 33
<212> TYPE: DNA
<213> ORGANISM: Homo sapiens

<400> SEQUENCE: 86
caaggagaca gcctcagaag ctattatgca agc                                   33

<210> SEQ ID NO 87
<211> LENGTH: 21
<212> TYPE: DNA
<213> ORGANISM: Homo sapiens

<400> SEQUENCE: 87
ggtaaaaaca accggccctc a                                                21

<210> SEQ ID NO 88
<211> LENGTH: 30
<212> TYPE: DNA
<213> ORGANISM: Homo sapiens

<400> SEQUENCE: 88
aactcccggg acagcagtgg taacgtggta                                       30

<210> SEQ ID NO 89
<211> LENGTH: 345
<212> TYPE: DNA
<213> ORGANISM: Homo sapiens

<400> SEQUENCE: 89
gaggtgcagc tggtggagtc tggaggaggc ttgatccagc ctgggggtc cctgagactc       60 tcctgtgcag cctctgggtt caccgtcagt agcaactaca tgagctgggt ccgccaggct     120
ccagggaagg ggctggagtg ggtctcagtt atttatagcg gtggtagcac atactacgca     180
gactccgtga aggccgatt caccatctcc agagacaatt ccaagaacac gctgtatctt      240
caaatgaaca gcctgagagc cgaggacacg gccgtgtatt actgtgcgag aggtacttgg    300
tacatggacg tctggggcaa agggaccacg gtcaccgtct cgagc                     345

<210> SEQ ID NO 90
<211> LENGTH: 15
<212> TYPE: DNA
<213> ORGANISM: Homo sapiens
```

```
<400> SEQUENCE: 90
agcaactaca tgagc                                                      15

<210> SEQ ID NO 91
<211> LENGTH: 48
<212> TYPE: DNA
<213> ORGANISM: Homo sapiens

<400> SEQUENCE: 91
gttatttata gcggtggtag cacatactac gcagactccg tgaagggc                  48

<210> SEQ ID NO 92
<211> LENGTH: 21
<212> TYPE: DNA
<213> ORGANISM: Homo sapiens

<400> SEQUENCE: 92
ggtacttggt acatggacgt c                                               21

<210> SEQ ID NO 93
<211> LENGTH: 327
<212> TYPE: DNA
<213> ORGANISM: Homo sapiens

<400> SEQUENCE: 93
tcttctgagc tgactcagga ccctgctgtg tctgtggcct cggggcagac agtcaggatc     60
acatgccaag agacagcct  cagacattat tatccaagct ggtaccagca gaagccacga   120
caggcccctg tacttgtctt ctttggtgaa acaaccggc  cctcagggat cccagaccga   180
ttctctggct ccgcctcagg aaacacagct tctttgacca tcgctggggc acaggcagaa   240
gatgacgctg actattattg ttcttcgcgg gacggcaatg atgaccgctg gctattcggc   300
ggagggacca aagtgaccgt cctgggt                                       327

<210> SEQ ID NO 94
<211> LENGTH: 33
<212> TYPE: DNA
<213> ORGANISM: Homo sapiens

<400> SEQUENCE: 94
caaggagaca gcctcagaca ttattatcca agc                                 33

<210> SEQ ID NO 95
<211> LENGTH: 21
<212> TYPE: DNA
<213> ORGANISM: Homo sapiens

<400> SEQUENCE: 95
ggtgaaaaca accggccctc a                                               21

<210> SEQ ID NO 96
<211> LENGTH: 33
<212> TYPE: DNA
<213> ORGANISM: Homo sapiens

<400> SEQUENCE: 96
tcttcgcggg acggcaatga tgaccgctgg cta                                 33

<210> SEQ ID NO 97
<211> LENGTH: 363
<212> TYPE: DNA
<213> ORGANISM: Homo sapiens
```

<400> SEQUENCE: 97

```
caggtacagc tgcagcagtc aggtccagga ctgctgaagc cctcgcagac cctctcactc      60
acctgtgcca tctccgggga cagtgtctct agcaacagtg ctgcttggaa ctggatcagg     120
cagtccccat cgagaggcct tgagtggctg gggaggacat actacaggtc caagtggtat     180
aatgattatg cagtatctgt gaaaagtcga ataaccatca acccagacac atccaagaac     240
cagttctccc tgcagctgag ctctgtgact cccgaggaca cggctgtata ttactgtgca     300
agagataact actaccaagg tatggacgtc tggggccagg ggaccacggt caccgtctcg     360
agc                                                                   363
```

<210> SEQ ID NO 98
<211> LENGTH: 21
<212> TYPE: DNA
<213> ORGANISM: Homo sapiens

<400> SEQUENCE: 98

```
agcaacagtg ctgcttggaa c                                                21
```

<210> SEQ ID NO 99
<211> LENGTH: 54
<212> TYPE: DNA
<213> ORGANISM: Homo sapiens

<400> SEQUENCE: 99

```
aggacatact acaggtccaa gtggtataat gattatgcag tatctgtgaa aagt            54
```

<210> SEQ ID NO 100
<211> LENGTH: 33
<212> TYPE: DNA
<213> ORGANISM: Homo sapiens

<400> SEQUENCE: 100

```
gataactact accaaggtat ggacgtctgg ggc                                   33
```

<210> SEQ ID NO 101
<211> LENGTH: 327
<212> TYPE: DNA
<213> ORGANISM: Homo sapiens

<400> SEQUENCE: 101

```
tcttctgagc tgactcagga ccctactgtg tctgtggcct tgggacagac agtcaggatc      60
acatgccaag agacagcct cagaagctat tatgcaagct ggtaccagca gaagccagga     120
caggcccctg tacttgtcat ctatggtaaa aacaaccggc cctcagggat cccagaccga     180
ttctctggct ccagctcagg aaacacagct tccttgacca tcactgggc tcaggcggaa     240
gatgaggctg actattactg taactcccgg gacaacagtg gttaccatcg tgtcttcgga     300
actggtacca aggtcaccgt cctgggt                                         327
```

<210> SEQ ID NO 102
<211> LENGTH: 33
<212> TYPE: DNA
<213> ORGANISM: Homo sapiens

<400> SEQUENCE: 102

```
caaggagaca gcctcagaag ctattatgca agc                                   33
```

<210> SEQ ID NO 103
<211> LENGTH: 21
<212> TYPE: DNA

<213> ORGANISM: Homo sapiens

<400> SEQUENCE: 103
ggtaaaaaca accggccctc a                                            21

<210> SEQ ID NO 104
<211> LENGTH: 27
<212> TYPE: DNA
<213> ORGANISM: Homo sapiens

<400> SEQUENCE: 104
aactcccggg acaacagtgg ttaccat                                      27

<210> SEQ ID NO 105
<211> LENGTH: 345
<212> TYPE: DNA
<213> ORGANISM: Homo sapiens

<400> SEQUENCE: 105
caggtgcagc tacagcagtg gggcgccgga ctgttgaagc cttcggagac cctgtccctc    60
acctgcgctg tctatggtgg gtccttcggt ggttactact ggggctggat ccgccagccc   120
ccagggaagg ggctggagtg gattggggaa atcaatcata gtggaagcac caactacaac   180
ccgtccctca agagtcgagt caccatatca gtagacacgc caagaaccca gttctccctg   240
aagctgagct ctgtgaccgc cgcggacacg gctgtgtatt actgtgcgag agggggctgg   300
taccccgacc cctggggcca gggaaccctg gtcaccgtct cgagc                   345

<210> SEQ ID NO 106
<211> LENGTH: 15
<212> TYPE: DNA
<213> ORGANISM: Homo sapiens

<400> SEQUENCE: 106
ggttactact ggggc                                                   15

<210> SEQ ID NO 107
<211> LENGTH: 48
<212> TYPE: DNA
<213> ORGANISM: Homo sapiens

<400> SEQUENCE: 107
gaaatcaatc atagtggaag caccaactac aacccgtccc tcaagagt                48

<210> SEQ ID NO 108
<211> LENGTH: 21
<212> TYPE: DNA
<213> ORGANISM: Homo sapiens

<400> SEQUENCE: 108
gggggctggt accccgaccc c                                            21

<210> SEQ ID NO 109
<211> LENGTH: 324
<212> TYPE: DNA
<213> ORGANISM: Homo sapiens

<400> SEQUENCE: 109
tcttctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa aacaaccggc cctcagggat cccagaccga   180

```
ttctctggct ccagctcagg aaacacagct tccttgacca tcactggggc tcaggcggaa      240
gatgaggctg actattactg taactcccgg gacagcagtg gtaacgtggt attcggcgga      300
gggaccaagc tgaccgtcct aggt                                            324
```

<210> SEQ ID NO 110
<211> LENGTH: 33
<212> TYPE: DNA
<213> ORGANISM: Homo sapiens

<400> SEQUENCE: 110

```
caaggagaca gcctcagaag ctattatgca agc                                   33
```

<210> SEQ ID NO 111
<211> LENGTH: 21
<212> TYPE: DNA
<213> ORGANISM: Homo sapiens

<400> SEQUENCE: 111

```
ggtaaaaaca accggccctc a                                                21
```

<210> SEQ ID NO 112
<211> LENGTH: 30
<212> TYPE: DNA
<213> ORGANISM: Homo sapiens

<400> SEQUENCE: 112

```
aactcccggg acagcagtgg taacgtggta                                       30
```

<210> SEQ ID NO 113
<211> LENGTH: 345
<212> TYPE: DNA
<213> ORGANISM: Homo sapiens

<400> SEQUENCE: 113

```
caggtgcagc tacagcagtg gggcgcagga ctgttgaagc cttcggagac cctgtccctc      60
acctgcgctt tctatggtga gtcgttcagt ggttactact ggagctggat ccgccagccc     120
ccagggaagg ggctggagtg gattgggaaa atcaatcata gtggaagcac caactacaac     180
ccgtccctca agagtcgagt caccatatca gtagacacgt ccaagaatca gttctccctg     240
aagctgaact ctgtgaccgc cgcggacacg gctgtgtatt actgtgcgag aagcagttgg     300
tacttcgatc tctggggccg tggcaccctg gtcaccgtct cgagc                     345
```

<210> SEQ ID NO 114
<211> LENGTH: 15
<212> TYPE: DNA
<213> ORGANISM: Homo sapiens

<400> SEQUENCE: 114

```
ggttactact ggagc                                                       15
```

<210> SEQ ID NO 115
<211> LENGTH: 48
<212> TYPE: DNA
<213> ORGANISM: Homo sapiens

<400> SEQUENCE: 115

```
gaaatcaatc atagtggaag caccaactac aacccgtccc tcaagagt                   48
```

<210> SEQ ID NO 116
<211> LENGTH: 21
<212> TYPE: DNA

-continued

<213> ORGANISM: Homo sapiens

<400> SEQUENCE: 116
agcagttggt acttcgatct c                                                21

<210> SEQ ID NO 117
<211> LENGTH: 327
<212> TYPE: DNA
<213> ORGANISM: Homo sapiens

<400> SEQUENCE: 117
tcttctgagc tgactcagga ccctgctgtg tctgtggcct tgggacagac agtcaggatc     60
acatgccaag agacagcct cagaagctat tatgcaagct ggtaccagca gaagccagga    120
caggcccctg tacttgtcat ctatggtaaa acaaccggc cctcagggat cccagaccga    180
ttctctggct ccagctcagg aaacacagct tccttgacca tcactggggc tcaggcggaa    240
gatgaggctg actattactg taactcccgg gacagcagtg gtaaccatgt ggtattcggc    300
ggagggacca tgctgaccgt cctaggt                                      327

<210> SEQ ID NO 118
<211> LENGTH: 33
<212> TYPE: DNA
<213> ORGANISM: Homo sapiens

<400> SEQUENCE: 118
caaggagaca gcctcagaag ctattatgca agc                                33

<210> SEQ ID NO 119
<211> LENGTH: 21
<212> TYPE: DNA
<213> ORGANISM: Homo sapiens

<400> SEQUENCE: 119
ggtaaaaaca accggccctc a                                             21

<210> SEQ ID NO 120
<211> LENGTH: 33
<212> TYPE: DNA
<213> ORGANISM: Homo sapiens

<400> SEQUENCE: 120
aactcccggg acagcagtgg taaccatgtg gta                                33

<210> SEQ ID NO 121
<211> LENGTH: 348
<212> TYPE: DNA
<213> ORGANISM: Homo sapiens

<400> SEQUENCE: 121
gaggtgcagc tggtggagtc tgggggaggc ttggtccagc ctgggggtc cctgagactc      60 tcctgtgcag cctctggatt cacctttagt agctattgga tgagctgggt ccgccaggct   120
ccagggaagg ggccggagtg ggtggccaac ataaagcaag atggaagtga gaaatactat   180
gtggactctg tgaagggccg attcaccatc tccagagaca cgccaagaa ctcactgtat   240 ctgcaaatga acagcctgag agccgaggac acggccgtgt attactgtgc gagaggagga   300
gggagacatg actactgggg ccaggaacc ctggtcaccg tctcgagc                348

<210> SEQ ID NO 122
<211> LENGTH: 15
<212> TYPE: DNA

<213> ORGANISM: Homo sapiens

<400> SEQUENCE: 122
agctattgga tgagc                                            15

<210> SEQ ID NO 123
<211> LENGTH: 51
<212> TYPE: DNA
<213> ORGANISM: Homo sapiens

<400> SEQUENCE: 123
aacataaagc aagatggaag tgagaaatac tatgtggact ctgtgaaggg c    51

<210> SEQ ID NO 124
<211> LENGTH: 21
<212> TYPE: DNA
<213> ORGANISM: Homo sapiens

<400> SEQUENCE: 124
ggaggaggga gacatgacta c                                     21

<210> SEQ ID NO 125
<211> LENGTH: 333
<212> TYPE: DNA
<213> ORGANISM: Homo sapiens

<400> SEQUENCE: 125
cagtctgtgt tgacgcagcc gccctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc agggtccct    180 gaccgattct ctggctccaa gtctggcacc tcagcctccc tggccatcag tgggctccag   240
tctgaggatg aggctgatta ttactgcgga acatgggata gcagcctgag tgctggcgtc   300
ttcggaactg ggaccaaggt caccgtccta ggt                               333

<210> SEQ ID NO 126
<211> LENGTH: 39
<212> TYPE: DNA
<213> ORGANISM: Homo sapiens

<400> SEQUENCE: 126
tctggaagca gctccaacat cggaagtaat actgtaaac                  39

<210> SEQ ID NO 127
<211> LENGTH: 21
<212> TYPE: DNA
<213> ORGANISM: Homo sapiens

<400> SEQUENCE: 127
agtaataatc agcggccctc a                                     21

<210> SEQ ID NO 128
<211> LENGTH: 33
<212> TYPE: DNA
<213> ORGANISM: Homo sapiens

<400> SEQUENCE: 128
ggaacatggg atagcagcct gagtgctggc gtc                        33

<210> SEQ ID NO 129
<211> LENGTH: 213
<212> TYPE: PRT

<213> ORGANISM: Homo sapiens

<400> SEQUENCE: 129

```
Ser Ser Glu Leu Thr Gln Asp Pro Ala Val Ser Val Ala Leu Gly Gln
 1               5                  10                  15
Thr Val Arg Ile Thr Cys Gln Gly Asp Ser Leu Arg Ser Tyr Tyr Ala
            20                  25                  30
Ser Trp Tyr Gln Gln Lys Pro Gly Gln Ala Pro Val Leu Val Ile Tyr
        35                  40                  45
Gly Lys Asn Asn Arg Leu Ser Gly Ile Pro Asp Arg Phe Ser Gly Ser
    50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Ser Gly Asn His
                85                  90                  95
Val Val Phe Gly Gly Gly Thr Lys Leu Thr Val Leu Gly Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys
    210
```

<210> SEQ ID NO 130
<211> LENGTH: 639
<212> TYPE: DNA
<213> ORGANISM: Homo sapiens

<400> SEQUENCE: 130

```
tcttctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctatggtaaa aacaaccggc tctcagggat cccagaccga   180
ttctctggct ccagctcagg aaacacagct tccttgacca tcactggggc tcaggcggaa   240
gatgaggctg actattactg taactcccgg gacagcagtg gtaaccatgt ggtattcggc   300
ggagggacca agctgaccgt cctaggtcag cccaaggctg cccctcggt cactctgttc    360
ccgccctcct ctgaggagct tcaagccaac aaggccacac tggtgtgtct cataagtgac   420
ttctaccccgg gagccgtgac agtggcctgg aaggcagata gcagccccgt caaggcggga   480
gtggagacca ccacaccctc caaacaaagc aacaacaagt acgcggccag cagctatctg   540
agcctgacgc ctgagcagtg gaagtcccac agaagctaca gctgccaggt cacgcatgaa   600
gggagcaccg tggagaagac agtggcccct acagaatgt                           639
```

<210> SEQ ID NO 131
<211> LENGTH: 212
<212> TYPE: PRT

<213> ORGANISM: Homo sapiens

<400> SEQUENCE: 131

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210
```

<210> SEQ ID NO 132
<211> LENGTH: 639
<212> TYPE: DNA
<213> ORGANISM: Homo sapiens

<400> SEQUENCE: 132

```
tcttctgagc tgactcagga ccctgctgtg tctgtggcct tgggacagac agtcaggatc    60
acatgccaag agacagcct cagaagctat tatgcaagct ggtaccagca gaaggccagga   120
caggcccctc tacttgtcat ttatggtaaa aataaccggc cctcagggat cccagaccga   180
ttctctggct ccagctcagg aaacacagct tccttgacca tcactggggc tcaggcggaa   240
gatgaggccg actattactg taactcccgg gacagcagtg gtttccatcg gtcttcgga   300
actgggacca aggtcaccgt cctaggtcag cccaaggcca accccactgt cactctgttc   360
ccgccctcct ctgaggagct ccaagccaac aaggccacac tagtgtgtct gatcagtgac   420
ttctaccccgg agctgtgac agtggcctgg aaggcagatg cagcccccgt caaggcggga   480
gtggagacca ccaaaccctc caaacagagc aacaacaagt acgcggccag cagctacctg   540
agcctgacgc ccgagcagtg gaagtcccac agaagctaca gctgccaggt cacgcatgaa   600
gggagcaccg tggagaagac agtggcccct acagaatgt                           639
```

<210> SEQ ID NO 133
<211> LENGTH: 212
<212> TYPE: PRT

<213> ORGANISM: Homo sapiens

<400> SEQUENCE: 133

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 134
<211> LENGTH: 636
<212> TYPE: DNA
<213> ORGANISM: Homo sapiens

<400> SEQUENCE: 134
tcttctgagc tgactcagga ccctgctgtg tctgtggcct tgggacagac agtcaggatc      60
acatgccaag agacagcct cagaagctat tatgcaagct ggtaccagca gaagccagga     120
caggcccctg tacttgtcat ctatggtaaa aacaaccggc cctcagggat cccagaccga     180
ttctctggct ccagctcagg aaacacagct tccttgacca tcactgggc tcaggcggaa     240
gatgaggctg actattactg taactcccgg gacagcagtg gtaacgtggt attcggcgga     300
gggaccaagc tgaccgtcct aggtcagccc aaggctgccc cctcggtcac tctgttcccg     360
ccctcctctg aggagcttca agccaacaag gccacactgg tgtgtctcat aagtgacttc     420
tacccgggag ccgtgacagt ggcctggaag gcagatagca gccccgtcaa ggcgggagtg     480
gagaccacca cacctccaa acaaagcaac aacaagtacg cggccagcag ctatctgagc     540
ctgacgcctg agcagtggaa gtcccacaga agctacagct gccaggtcac gcatgaaggg     600
agcaccgtgg agaagacagt ggcccctaca gaatgt                              636

<210> SEQ ID NO 135
<211> LENGTH: 213
<212> TYPE: PRT

<213> ORGANISM: Homo sapiens

<400> SEQUENCE: 135

Ser Ser Glu Leu Thr Gln Asp Pro Ala Val Ser Val Ala Ser Gly Gln
1               5                   10                  15

Thr Val Arg Ile Thr Cys Gln Gly Asp Ser Leu Arg His Tyr Tyr Pro
            20                  25                  30

Ser Trp Tyr Gln Gln Lys Pro Arg Gln Ala Pro Val Leu Val Phe Phe
        35                  40                  45

Gly Glu Asn Asn Arg Pro Ser Gly Ile Pro Asp Arg Phe Ser Gly Ser
    50                  55                  60

Ala Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Gly Asn Asp Asp Arg
                85                  90                  95

Trp Leu Phe Gly Gly Gly Thr Lys Val Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys
    210

<210> SEQ ID NO 136
<211> LENGTH: 639
<212> TYPE: DNA
<213> ORGANISM: Homo sapiens

<400> SEQUENCE: 136
tcttctgagc tgactcagga ccctgctgtg tctgtggcct cggggcagac agtcaggatc      60
acatgccaag agacagcct cagacattat tatccaagct ggtaccagca gaagccacga     120
caggcccctg tacttgtctt ctttggtgaa acaaccggc cctcagggat cccagaccga     180
ttctctggct ccgcctcagg aaacacagct tctttgacca tcgctgggc acaggcagaa     240 gatgacgctg actattattg ttcttcgcgg gacggcaatg atgaccgctg ctattcggc     300 ggagggacca aagtgaccgt cctgggtcag cccaaggctg cccctcggt cactctgttc     360 ccgccctcct ctgaggagct tcaagccaac aaggccacac tggtgtgtct cataagtgac     420 ttctaccgg gagccgtgac agtggcctgg aaggcagata gcagcccgt caaggcggga     480 gtggagacca ccacaccctc aaacaaagc aacaacaagt acgcggccag cagctatctg     540
agcctgacgc ctgagcagtg gaagtcccac agaagctaca gctgccaggt cacgcatgaa     600
gggagcaccg tggagaagac agtggcccct acagaatgt                           639

<210> SEQ ID NO 137
<211> LENGTH: 213
<212> TYPE: PRT

<213> ORGANISM: Homo sapiens

<400> SEQUENCE: 137

```
Ser Ser Glu Leu Thr Gln Asp Pro Thr Val Ser Val Ala Leu Gly Gln
1               5                   10                  15
Thr Val Arg Ile Thr Cys Gln Gly Asp Ser Leu Arg Ser Tyr Tyr Ala
            20                  25                  30
Ser Trp Tyr Gln Gln Lys Pro Gly Gln Ala Pro Val Leu Val Ile Tyr
        35                  40                  45
Gly Lys Asn Asn Arg Pro Ser Gly Ile Pro Asp Arg Phe Ser Gly Ser
    50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Asn Ser Gly Tyr His
                85                  90                  95
Arg Val Phe Gly Thr Gly Thr Lys Val Thr Val Leu Gly Gln Pro Lys
            100                 105                 110
Ala Asn Pro Thr Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Gly Ser Pro Val Lys Ala Gly
145                 150                 155                 160
Val Glu Thr Thr Lys Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys
    210
```

<210> SEQ ID NO 138
<211> LENGTH: 591
<212> TYPE: DNA
<213> ORGANISM: Homo sapiens

<400> SEQUENCE: 138

```
tcttctgagc tgactcagga ccctactgtg tctgtggcct tgggacagac agtcaggatc      60
acatgccaag agacagcct cagaagctat tatgcaagct ggtaccagca gaagccagga     120
caggcccctg tacttgtcat ctatggtaaa aacaaccggc cctcagggat cccagaccga     180
ttctctggct ccagctcagg aaacacagct tccttgacca tcactggggc tcaggcggaa     240
gatgaggctg actattactg taactcccgg gacaacagtg gttaccatcg tgtcttcgga     300
actggtacca aggtcaccgt cctgggtcag cccaaggcca accccactgt cactctgttc     360
ccgccctcct ctgaggagct ccaagccaac aaggccacac tagtgtgtct gatcagtgac     420
ttctaccgg gagctgtgac agtggcctgg aaggcagatg gcagcccgt caaggcggga     480
gtggagacca ccaaaccctc caaacagagc aacaacaagt acgcggccag cagctacctg     540
agcctgacgc ccgagcagtg gaagtcccac agaagcgccc tacagaatg t              591
```

<210> SEQ ID NO 139
<211> LENGTH: 212
<212> TYPE: PRT
<213> ORGANISM: Homo sapiens

<400> SEQUENCE: 139

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 140
<211> LENGTH: 636
<212> TYPE: DNA
<213> ORGANISM: Homo sapiens

<400> SEQUENCE: 140
tcttctgagc tgactcagga ccctgctgtg tctgtggcct tgggacagac agtcaggatc     60
acatgccaag agacagcct cagaagctat tatgcaagct ggtaccagca gaagccagga    120
caggcccctg tacttgtcat ctatggtaaa aacaaccggc cctcagggat cccagaccga   180
ttctctggct ccagctcagg aaacacagct tccttgacca tcactggggc tcaggcggaa   240
gatgaggctg actattactg taactcccgg gacagcagtg gtaacgtggt attcggcgga   300
gggaccaagc tgaccgtcct aggtcagccc aaggctgccc cctcggtcac tctgttcccg   360
ccctcctctg aggagcttca agccaacaag gccacactgg tgtgtctcat aagtgacttc   420
tacccgggag ccgtgacagt ggcctggaag gcagatagca gccccgtcaa ggcgggagtg   480
gagaccacca cacctccaa acaaagcaac aacaagtacg cggccagcag ctatctgagc    540
ctgacgcctg agcagtggaa gtcccacaga agctacagct gccaggtcac gcatgaaggg   600
agcaccgtgg agaagacagt ggcccctaca gaatgt                             636

<210> SEQ ID NO 141
<211> LENGTH: 213
<212> TYPE: PRT
<213> ORGANISM: Homo sapiens

<400> SEQUENCE: 141

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Met Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205

Ala Pro Thr Glu Cys
    210

<210> SEQ ID NO 142
<211> LENGTH: 639
<212> TYPE: DNA
<213> ORGANISM: Homo sapiens

<400> SEQUENCE: 142
tcttctgagc tgactcagga ccctgctgtg tctgtggcct tgggacagac agtcaggatc      60
acatgccaag agacagcct cagaagctat tatgcaagct ggtaccagca gaagccagga     120
caggcccctg tacttgtcat ctatggtaaa aacaaccggc cctcagggat cccagaccga     180
ttctctggct ccagctcagg aaacacagct tccttgacca tcactggggc tcaggcggaa     240
gatgaggctg actattactg taactcccgg gacagcagtg gtaaccatgt ggtattcggc     300
ggagggacca tgctgaccgt cctaggtcag cccaaggctg ccccctcggt cactctgttc     360
ccaccctcct ctgaggagct tcaagccaac aaggccacac tggtgtgtct cataagtgac     420
ttctacccgg gagccgtgac agtggcctgg aaggcagata gcagccccgt caaggcggga     480
gtggagacca ccacaccctc aaacaaagc aacaacaagt acgcggccag cagctacctg     540
agcctgacgc ctgagcagtg gaagtcccac aaaagctaca gctgccaggt cacgcatgaa     600
gggagcaccg tggagaagac agtggcccct acagaatgt                           639

<210> SEQ ID NO 143
<211> LENGTH: 215
<212> TYPE: PRT
<213> ORGANISM: Homo sapiens

<400> SEQUENCE: 143

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gly Thr Trp Asp Ser Ser Leu
                85                  90                  95

Ser Ala Gly Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Glu
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 144
<211> LENGTH: 645
<212> TYPE: DNA
<213> ORGANISM: Homo sapiens

<400> SEQUENCE: 144
cagtctgtgt tgacgcagcc gccctcagcg tctgggaccc ccgggcagag ggtcaccatc        60
tcttgttctg gaagcagctc caacatcgga agtaatactg taaactggta ccagcagctc       120
ccaggaacgg ccccaaact cctcatctat agtaataatc agcggccctc aggggtccct        180
gaccgattct ctggctccaa gtctggcacc tcagcctccc tggccatcag tgggctccag       240
tctgaggatg aggctgatta ttactgcgga acatgggata gcagcctgag tgctggcgtc       300
ttcggaactg ggaccaaggt caccgtccta ggtcagccca aggccaaccc cactgtcact       360
ctgttcccgc cctcctctga ggagctccaa gccaacaagg ccacactagt gtgtctgata       420
agtgacttct acccgggagc cgtgacagtg gcctggaagg cagatagcag ccccgtcgag       480
gcgggagtgg agaccaccac accctccaaa caaagcaaca acaagtacgc ggccagcagc       540
tacctgagcc tgacgcctga gcagtggaag tcccacagaa gctacagctg ccaggtcacg       600
catgaaggga gcaccgtgga agacagtg gcccctacag aatgt                         645

<210> SEQ ID NO 145
<211> LENGTH: 442
<212> TYPE: PRT
<213> ORGANISM: Homo sapiens -continued

<400> SEQUENCE: 145

```
Met Ala Ser Val Val Leu Pro Ser Gly Ser Gln Cys Ala Ala Ala Ala
1               5                   10                  15

Ala Ala Ala Ala Pro Pro Gly Leu Arg Leu Arg Leu Leu Leu Leu Leu
            20                  25                  30

Phe Ser Ala Ala Ala Leu Ile Pro Thr Gly Asp Gly Gln Asn Leu Phe
        35                  40                  45

Thr Lys Asp Val Thr Val Ile Glu Gly Glu Val Ala Thr Ile Ser Cys
    50                  55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
                85                  90                  95

Phe Gln Leu Leu Asn Phe Ser Ser Glu Leu Lys Val Ser Leu Thr
            100                 105                 110

Asn Val Ser Ile Ser Asp Glu Gly Arg Tyr Phe Cys Gln Leu Tyr Thr
            115                 120                 125

Asp Pro Pro Gln Glu Ser Tyr Thr Thr Ile Thr Val Leu Val Pro Pro
        130                 135                 140

Arg Asn Leu Met Ile Asp Ile Gln Arg Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
        195                 200                 205

Val His Lys Glu Asp Asp Gly Val Pro Val Ile Cys Gln Val Glu His
210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Pro Thr Thr
                325                 330                 335

Ile Pro Pro Pro Thr Thr Thr Thr Thr Thr Thr Thr Thr Thr Thr Thr
            340                 345                 350

Thr Ile Leu Thr Ile Ile Thr Asp Ser Arg Ala Gly Glu Glu Gly Ser
        355                 360                 365

Ile Arg Ala Val Asp His Ala Val Ile Gly Gly Val Ala Val Val
    370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
                405                 410                 415
```

```
Ala Ala Asp Ala Asp Thr Ala Ile Ile Asn Ala Glu Gly Gly Gln Asn
            420                 425                 430

Asn Ser Glu Glu Lys Lys Glu Tyr Phe Ile
        435                 440

<210> SEQ ID NO 146
<211> LENGTH: 3512
<212> TYPE: DNA
<213> ORGANISM: Homo sapiens

<400> SEQUENCE: 146
gacatggcga gtgtagtgct gccgagcgga tcccagtgtg cggcggcagc ggcggcggcg        60
gcgcctcccg ggctccggct ccggcttctg ctgttgctct tctccgccgc ggcactgatc       120
cccacaggtg atgggcagaa tctgtttacg aaagacgtga cagtgatcga gggagaggtt       180
gcgaccatca gttgccaagt caataagagt gacgactctg tgattcagct actgaatccc       240
aacaggcaga ccatttattt cagggacttc aggcctttga aggacagcag gtttcagttg       300
ctgaattttt ctagcagtga actcaaagta tcattgacaa acgtctcaat ttctgatgaa       360
ggaagatact tttgccagct ctataccgat cccccacagg aaagttacac caccatcaca       420
gtcctggtcc caccacgtaa tctgatgatc gatatccaga gagacactgc ggtggaaggt       480
gaggagattg aagtcaactg cactgctatg gccagcaagc cagccacgac tatcaggtgg       540
ttcaaaggga cacagagct aaaggcaaa tcggaggtgg aagagtggtc agacatgtac       600
actgtgacca gtcagctgat gctgaaggtg cacaaggagg acgatggggt cccagtgatc       660
tgccaggtgg agcaccctgc ggtcactgga aacctgcaga cccagcggta tctagaagta       720
cagtataagc cacaagtgca cattcagatg acttatcctc tacaaggctt aacccgggaa       780
ggggacgcgc ttgagttaac atgtgaagcc atcgggaagc cccagcctgt gatggtaact       840
tgggtgagag tcgatgatga aatgcctcaa cacgccgtac tgtctgggcc caacctgttc       900
atcaataacc taaacaaaac agataatggt acataccgct gtgaagcttc aaacatagtg       960
gggaaagctc actcggatta tatgctgtat gtatacgatc cccccacaac tatccctcct      1020
cccacaacaa ccaccaccac caccaccacc accaccacca ccatccttac catcatcaca      1080
gattcccgag caggtgaaga aggctcgatc agggcagtgg atcatgccgt gatcggtggc      1140
gtcgtggcgg tggtggtgtt cgccatgctg tgcttgctca tcattctggg cgctattttt      1200
gccagacata aagtacata cttcactcat gaagccaaag agccgatga cgcagcagac      1260 gcagacacag ctataatcaa tgcagaagga ggacagaaca ctccgaaga aaagaaagag      1320 tacttcatct agatcagcct ttttgtttca atgaggtgtc caactggccc tatttagatg      1380
ataaagagac agtgatattg gaacttgcga gaaattcgtg tgtttttttta tgaatgggtg      1440 gaaaggtgtg agactgggaa ggcttgggat ttgctgtgta aaaaaaaaaa aaaatgttct      1500
ttggaaagta cactctgctg tttgacacct ctttttttcgt ttgtttgttt gtttaattt      1560 tatttcttcc taccaagtca aacttggata cttggattta gtttcagtag attgcagaaa      1620
attctgtgcc ttgttttttg tttgtttgtt gcgttccttt cttttccccc tttgtgcaca      1680
tttatttcct ccctctaccc caatttcgga ttttttccaa aatctcccat tttggaattt      1740
gcctgctggg attccttaga ctcttttcct tcccttttct gttctagttt tttacttttg      1800
tttattttta tggtaactgc tttctgttcc aaattcagtt tcataaaagg agaaccagca      1860
cagcttagga tttcatagtt cagaatttag tgtatccata atgcattctt ctctgttgtc      1920
gtaaagattt gggtgaacaa acaatgaaaa ctctttgctg ctgcccatgt ttcaaatact      1980
```

```
tagagcagtg aagactagaa aattagactg tgattcagaa aatgttctgt ttgctgtgga    2040
actacattac tgtacagggt tatctgcaag tgaggtgtgt cacaatgaga ttgaatttca    2100
ctgtctttaa ttctgtatct gtagacggct cagtatagat accctacgct gtccagaaag    2160
gtttggggca gaaaggactc ctccttttc catgccctaa acagacctga caggtgaggt    2220
ctgttccttt tatataagtg gacaaatttt gagttgccac aggaggggaa gtagggaggg    2280
gggaaataca gttctgctct ggttgtttct gttccaaatg attccatcca cctttcccaa    2340
tcggccttac ttctcactaa tttgtaggaa aaagcaagtt cgtctgttgt gcgaatgact    2400
gaatgggaca gagttgattt ttttttttt tttcctttgt gcttagttag gaaggcagta    2460
ggatgtggcc tgcatgtact gtatattaca gatatttgtc atgctgggat ttccaactcg    2520
aatctgtgtg aaactttcat tccttcagat ttggcttgac aaaggcagga ggtacaaaag    2580
aagggctggt attgttctca cactggtctg ctgtcgctct cagttctcga taggtcagag    2640
cagaggtgga aaaacagcat gtacggattt tcagttactt aatcaaaact caaatgtgag    2700 tgttttatc ttttaccttt tcatacacta gccttggcct ctttcctcag ccttaagaac    2760
catctgccaa aaattactga tcctcgcatg atggcagcca tagtgcatag ctactaaaat    2820
cagtgacctt gaacatatct tagatgggga gcctcgggaa aaggtagagg agtcacgtta    2880
ccatttacat gttttaaaga aagaagtgtg gggattttca ctgaaacgtc taggaaatct    2940
agaagtagtc ctgaaggaca gaaactaaac tcttaccata tgtttggtaa gactccagac    3000
tccagctaac agtccctatg gaaagatggc atcaaaaaag atagatctat atatatatat    3060
aaatatatat tctattacat tttcagtgag taattttgga ttttgcaagg tgcatttta    3120 ctattgttac attatgtgga aaacttatgc tgatttattt aaggggggaaa aagtgtcaac    3180 tctttgttat ttgaaaacat gtttattttt cttgtcttta ttttaacctt tgatagaacc    3240
attgcaatat gggggccttt tgggaacgga ctggtatgta aaagaaaatc cattatcgag    3300
cagcatttta tttacccctc ccctatccct aggcacttaa ccaagacaaa aagccacaat    3360
gaacatccct ttttcaatga attttataat ctgcagctct attccgagcc cttagcaccc    3420
attccgacca tagtataatc atatcaaagg gtgagaatca tttagcatgt tgttgaaagg    3480 tttttttca gttgttcttt ttagaaaaaa ag                                  3512
```

<210> SEQ ID NO 147
<211> LENGTH: 17
<212> TYPE: DNA
<213> ORGANISM: Artificial
<220> FEATURE:
<223> OTHER INFORMATION: An artificially synthesized primer sequence

<400> SEQUENCE: 147
caggaaacag ctatgac                                                  17

<210> SEQ ID NO 148
<211> LENGTH: 22
<212> TYPE: DNA
<213> ORGANISM: Artificial
<220> FEATURE:
<223> OTHER INFORMATION: An artificially synthesized primer sequence

<400> SEQUENCE: 148
cggctccaag tcgacgtcgt ca                                            22

<210> SEQ ID NO 149
<211> LENGTH: 83
<212> TYPE: DNA

<213> ORGANISM: Artificial
<220> FEATURE:
<223> OTHER INFORMATION: An artificially synthesized primer sequence

<400> SEQUENCE: 149

```
cagctgcagc agtctggggc agagcttgtg aagccagggg cctcagtcaa gttgtcctgc    60
acagcttctg gcttcaacat taa                                            83
```

<210> SEQ ID NO 150
<211> LENGTH: 81
<212> TYPE: DNA
<213> ORGANISM: Artificial
<220> FEATURE:
<223> OTHER INFORMATION: An artificially synthesized primer sequence

<400> SEQUENCE: 150

```
agaccgaagt tgtaatttct gtggatatac gtgacccact tcgtctccgg acttttccca    60
gatctcacct aaccttccta a                                              81
```

<210> SEQ ID NO 151
<211> LENGTH: 84
<212> TYPE: DNA
<213> ORGANISM: Artificial
<220> FEATURE:
<223> OTHER INFORMATION: An artificially synthesized primer sequence

<400> SEQUENCE: 151

```
aagggtctag agtggattgg aaggattgat cctgcgagtg gtaatactaa atatgacccg    60
aaggacaagg ccactataac agca                                           84
```

<210> SEQ ID NO 152
<211> LENGTH: 66
<212> TYPE: DNA
<213> ORGANISM: Artificial
<220> FEATURE:
<223> OTHER INFORMATION: An artificially synthesized primer sequence

<400> SEQUENCE: 152

```
ttcctgttcc ggtgatattg tcgtctgtgt aggaggttgt gtcggatgga tgtcgactta    60
agggac                                                               66
```

<210> SEQ ID NO 153
<211> LENGTH: 51
<212> TYPE: DNA
<213> ORGANISM: Artificial
<220> FEATURE:
<223> OTHER INFORMATION: An artificially synthesized primer sequence

<400> SEQUENCE: 153

```
cagctgaatt ccctgacatc tgaggacact gccgtctatt actgtgctgg t             51
```

<210> SEQ ID NO 154
<211> LENGTH: 73
<212> TYPE: DNA
<213> ORGANISM: Artificial
<220> FEATURE:
<223> OTHER INFORMATION: An artificially synthesized primer sequence

<400> SEQUENCE: 154

```
cagataatga cacgaccaat actaatgccg ttgaaactga tgaccccggt tccgtggtgc    60
cagtggcaca agg                                                       73
```

<210> SEQ ID NO 155

```
<211> LENGTH: 54
<212> TYPE: DNA
<213> ORGANISM: Artificial
<220> FEATURE:
<223> OTHER INFORMATION: An artificially synthesized primer sequence

<400> SEQUENCE: 155
ggttctctaa cagtagtggt agtagtggta attattctcg atagggccct cgaa          54

<210> SEQ ID NO 156
<211> LENGTH: 69
<212> TYPE: DNA
<213> ORGANISM: Artificial
<220> FEATURE:
<223> OTHER INFORMATION: An artificially synthesized primer sequence

<400> SEQUENCE: 156
gacatcgagc tcacccagtc tccagcctcc ctttctgcgt ctgtgggaga aactgtcacc    60
atcacatgt                                                           69

<210> SEQ ID NO 157
<211> LENGTH: 63
<212> TYPE: DNA
<213> ORGANISM: Artificial
<220> FEATURE:
<223> OTHER INFORMATION: An artificially synthesized primer sequence

<400> SEQUENCE: 157
tgacagtggt agtgtacagc tcgttcaccc ttataagtgt taataaatcg taccatggtc    60
gtc                                                                 63

<210> SEQ ID NO 158
<211> LENGTH: 48
<212> TYPE: DNA
<213> ORGANISM: Artificial
<220> FEATURE:
<223> OTHER INFORMATION: An artificially synthesized primer sequence

<400> SEQUENCE: 158
gcatggtacc agcagaaacc agggaaatct cctcagctcc tggtctat                 48

<210> SEQ ID NO 159
<211> LENGTH: 81
<212> TYPE: DNA
<213> ORGANISM: Artificial
<220> FEATURE:
<223> OTHER INFORMATION: An artificially synthesized primer sequence

<400> SEQUENCE: 159
ggagtcgagg accagatatt acgttttttgg aatcgtctac cacacggtag ttccaagtca   60
ccgtcaccta ggccttgtgt t                                             81

<210> SEQ ID NO 160
<211> LENGTH: 45
<212> TYPE: DNA
<213> ORGANISM: Artificial
<220> FEATURE:
<223> OTHER INFORMATION: An artificially synthesized primer sequence

<400> SEQUENCE: 160
tcatgaggca cctgcaagcc acctccgtgg ttcgagctct agttt                    45

<210> SEQ ID NO 161
<211> LENGTH: 45
<212> TYPE: DNA
```

```
<213> ORGANISM: Artificial
<220> FEATURE:
<223> OTHER INFORMATION: An artificially synthesized primer sequence

<400> SEQUENCE: 161
agtactccgt ggacgttcgg tggaggcacc aagctcgaga tcaaa           45

<210> SEQ ID NO 162
<211> LENGTH: 10
<212> TYPE: DNA
<213> ORGANISM: Artificial
<220> FEATURE:
<223> OTHER INFORMATION: An artificially synthesized primer sequence

<400> SEQUENCE: 162
atcgacagct                                                  10

<210> SEQ ID NO 163
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 163
aagccacctc catggttcga gctctagttt                            30

<210> SEQ ID NO 164
<211> LENGTH: 44
<212> TYPE: DNA
<213> ORGANISM: Artificial
<220> FEATURE:
<223> OTHER INFORMATION: An artificially synthesized primer sequence

<400> SEQUENCE: 164
tcgaagttgt ccttactcac aagccgcgcg gtcagctgag gtaa            44

<210> SEQ ID NO 165
<211> LENGTH: 55
<212> TYPE: DNA
<213> ORGANISM: Artificial
<220> FEATURE:
<223> OTHER INFORMATION: An artificially synthesized primer sequence

<400> SEQUENCE: 165
accctggtca ccgtctcctc agcctccacc aagggcccat cggtcttccc cctgg    55

<210> SEQ ID NO 166
<211> LENGTH: 37
<212> TYPE: DNA
<213> ORGANISM: Artificial
<220> FEATURE:
<223> OTHER INFORMATION: An artificially synthesized primer sequence

<400> SEQUENCE: 166
gggagtcgtc gcagcactgg cacgggaggt cgtcgaa                    37

<210> SEQ ID NO 167
<211> LENGTH: 36
<212> TYPE: DNA
<213> ORGANISM: Artificial
<220> FEATURE:
<223> OTHER INFORMATION: An artificially synthesized primer sequence

<400> SEQUENCE: 167
ggactctact ccctcagcag cgtcgtgacc gtgccc                     36
```

<210> SEQ ID NO 168
<211> LENGTH: 63
<212> TYPE: DNA
<213> ORGANISM: Artificial
<220> FEATURE:
<223> OTHER INFORMATION: An artificially synthesized primer sequence

<400> SEQUENCE: 168
gggtcgttgt ggttccacct gttctttcaa ctcgggttta aacagtagt ggtagtagtg    60 gta                                                                 63

<210> SEQ ID NO 169
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 169
gggtttagaa cagtagtggt agtagtggta attattctcg atagggccct cgaacg       56

<210> SEQ ID NO 170
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 170
ggcaccacgg tcaccgtctc gagcgcctcc acc                                33

<210> SEQ ID NO 171
<211> LENGTH: 1916
<212> TYPE: DNA
<213> ORGANISM: Artificial
<220> FEATURE:
<223> OTHER INFORMATION: Insert sequence of pscFvCA9-E8VHdVLd

<400> SEQUENCE: 171
aagcttgcat gcaaattcta tttcaaggag acagtcataa tgaaatacct attgcctacg    60
gcagccgctg gattgttatt actcgctgcc caaccagcga tggcccaggt gcagctgcag   120
cagtctgggg cagagcttgt gaagccaggg gcctcagtca agttgtcctg cacagcttct   180
ggcttcaaca ttaaagacac ctatatgcac tgggtgaagc agaggcctga aaagggtcta   240
gaattccctg acatctgagg acactgccgt ctattactgt gctggttatg attacggcaa   300
cttttgacta ctggggccaag gcaccacggt caccgtctcg agaggcggtg gcggatcagg   360
tggcggtgga gtggcggtg gtgggtccat ggccgacatc gagctcaccc agtctccagc   420
ctccctttct gcgtctgtgg agaaaactgt caccatcaca tgtcgagcaa gtgggaatat   480
tcacaattat ttagcatggt accaagctcg agatcaaacg gctgatgct gcaccaactg   540 tatccatctt cccaccatcc agtgagcagt aacatctgg aggtgcctca gtcgtgtgct   600
tcttgaacag cttctacccc aaagacatca atgtcaagtg aagattgat ggcagtgaac   660 gacaaaatgg cgtcctgaac agttggactg atcaggacag caaagacagc acctacagca   720
tgagcagcac cctcacgttg accaaggacg agtatgaacg acataacagc tatacctgtg   780
aggccactca caagacatca acttcaccca ttgtcaagag cttcaacagg aatgagtgtt   840
cggcgcgcca gtcgactcca ttcgtttgtg aatatcaagg ccaatcgtct gacctgcctc   900
aacctcctgt caatgctggc ggcggctctg gtggtggttc tggtgcggc tctgagggtg   960

-continued

```
gtggctctga gggtggcggt tctgagggtg gcggctctga gggaggcggt tccggtggtg    1020
gctctggttc cggtgatttt gattatgaaa agatggcaaa cgctaataag ggggctatga    1080
ccgaaaatgc cgatgaaaac gcgctacagt cagacgctaa aggcaaactt gattctgtcg    1140
ctactgatta cggtgctgct atcgatggtt tcattggtga cgtttccggc cttgctaatg    1200
gtaatggtgc tactggtgat tttgctggct ctaattccca aatggctcaa gtcggtgacg    1260
gtgataattc acctttaatg aataatttcc gtcaatattt accttccctc cctcaatcgg    1320
ttgaatgtcg cccttttgtc tttggcgctg gtaaaccata tgaattttct attgattgtg    1380
acaaaataaa cttattccgt ggtgtctttg cgtttctttt atatgttgcc acctttatgt    1440
atgtattttc tacgtttgct aacatactgc gtaataagga gtcttaatca tgccagttct    1500
tttgggtgct agctgtcgac tgcgcaacac gatgaagccg tagacaacaa attcaacaaa    1560
gaacaacaaa acgcgttcta tgagatctta catttaccta acttaaacga gaacaacga     1620 aacgccttca tccaaagttt aaagatgac ccaagccaaa cgctaaccct tttagcagaa     1680
gctaaaaagc taaatgatgc tcaggcgccg aaagtagaca caaattcaa caagaacaa      1740 caaaacgcgt tctatgagat cttacattta cctaacttaa cgaagaaca acgaaacgcc    1800 ttcatccaaa gtttaaaaga tgacccaagc caaagcgcta accttttagc agaagctaaa  1860
aagctaaatg atgctcaggc gccgaaagta gacgcgaatt agctgggaat taattc        1916
```

<210> SEQ ID NO 172
<211> LENGTH: 66
<212> TYPE: PRT
<213> ORGANISM: Artificial
<220> FEATURE:
<223> OTHER INFORMATION: Amino acid sequence encoded by insert sequence of pscFvCA9-E8VHdVLd

<400> SEQUENCE: 172

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30

Leu Val Lys Pro Gly Ala Ser Val Lys Leu Ser Cys Thr Ala Ser Gly
        35                  40                  45

Phe Asn Ile Lys Asp Thr Tyr Met His Trp Val Lys Gln Arg Pro Glu
    50                  55                  60

Lys Gly
65
```

<210> SEQ ID NO 173
<211> LENGTH: 77
<212> TYPE: DNA
<213> ORGANISM: Artificial
<220> FEATURE:
<223> OTHER INFORMATION: An artificially synthesized primer sequence

<400> SEQUENCE: 173

```
gtcaccgtct cgagaggcgg tggcggatca ggtggcggtg aagtggcgg tggtgggtcc      60 atggccgaca tcgagct                                                    77
```

<210> SEQ ID NO 174
<211> LENGTH: 68
<212> TYPE: DNA
<213> ORGANISM: Artificial
<220> FEATURE:
<223> OTHER INFORMATION: An artificially synthesized primer sequence

<400> SEQUENCE: 174

```
cgatgtcggc catggaccca ccaccgccac ttccaccgcc acctgatccg ccaccgcctc    60
tcgagacg                                                              68
```

<210> SEQ ID NO 175
<211> LENGTH: 1774
<212> TYPE: DNA
<213> ORGANISM: Artificial
<220> FEATURE:
<223> OTHER INFORMATION: Insert sequence of pscFvCA-E8VHd

<400> SEQUENCE: 175

```
aagcttgcat gcaaattcta tttcaaggag acagtcataa tgaaatacct attgcctacg    60
gcagccgctg gattgttatt actcgcggcc cagccggcca tggcccaggt gcagctgcag   120
cagtctgggg cagagcttgt gaagccaggg gcctcagtca agttgtcctg cacagcttct   180
ggcttcaaca ttaaagacac ctatatgcac tgggtgaagc agaggcctga aaagggtcta   240
gaattccctg acatctgagg acactgccgt ctattactgt gctggttatg attacggcaa   300
ctttgactac tggggccaag gcaccacggt caccgtctcc tcaggcggtg gcggatcagg   360
tggcggtgga gtggcggtg gtgggtctac tagtgacatc gagctcaccc agtctccagc   420
ctcccttttct gcgtctgtgg gagaaactgt caccatcaca tgtcgagcaa gtgggaatat   480
tcacaattat ttagcatggt accagcagaa accagggaaa tctcctcagc tcctggtcta   540
taatgcaaaa accttagcag atggtgtgcc atcaaggttc agtggcagtg gatccggaac   600
acaatattct ctcaagatca acagcctgca gcctgaagat tttgggagtt attactgtca   660
acatttttgg agtactccgt ggacgttcgg tggaggtacc aagctcgagt cgactccatt   720
cgtttgtgaa tatcaaggcc aatcgtctga cctgcctcaa cctcctgtca atgctggcgg   780
cggctctggt ggtggttctg gtggcggctc tgagggtggt ggctctgagg gtggcggttc   840
tgagggtggc ggctctgagg gaggcggttc cgtggtggc tctggttccg gtgattttga   900
ttatgaaaag atggcaaacg ctaataaggg ggctatgacc gaaaatgccg atgaaaacgc   960
gctacagtca gacgctaaag gcaaacttga ttctgtcgct actgattacg gtgctgctat  1020
cgatggtttc attggtgacg tttccggcct tgctaatggt aatggtgcta ctggtgattt  1080
tgctggctct aattcccaaa tggctcaagt cggtgacgtt gataattcac ctttaatgaa  1140
taatttccgt caatatttac cttccctccc tcaatcggtt gaatgtcgcc cttttgtctt  1200
tggcgctggt aaaccatatg aattttctat tgattgtgac aaaataaact tattccgtgg  1260
tgtctttgcg tttcttttat atgttgccac ctttatgtat gtattttcta cgtttgctaa  1320
catactgcgt aataaggagt cttaatcatg ccagttcttt tgggtgctag ctgtcgactg  1380
cgcaacacga tgaagccgta gacaacaaat tcaacaaaga acaacaaaac gcgttctatg  1440
agatcttaca tttacctaac ttaaacgaag aacaacgaaa cgccttcatc caaagtttaa  1500
aagatgaccc aagccaaagc gctaaccttt tagcagaagc taaaaagcta atgatgctc   1560
aggcgccgaa agtagacaac aaattcaaca agaacaacaa aaacgcgttc tatgagatct  1620
tacatttacc taacttaaac gaagaacaac gaaacgcctt catccaaagt ttaaaagatg  1680
acccaagcca aagcgctaac cttttagcag aagctaaaaa gctaaatgat gctcaggcgc  1740
cgaaagtaga cgcgaattag ctgggaatta attc                              1774
```

<210> SEQ ID NO 176
<211> LENGTH: 66
<212> TYPE: PRT

<213> ORGANISM: Artificial
<220> FEATURE:
<223> OTHER INFORMATION: Amino acid sequence encoded by insert sequence of pscFvCA-E8VHd

<400> SEQUENCE: 176

```
Met Lys Tyr Leu Leu Pro Thr Ala Ala Ala Gly Leu Leu Leu Leu Ala
 1               5                  10                  15

Ala Gln Pro Ala Met Ala Gln Val Gln Leu Gln Gln Ser Gly Ala Glu
             20                  25                  30

Leu Val Lys Pro Gly Ala Ser Val Lys Leu Ser Cys Thr Ala Ser Gly
         35                  40                  45

Phe Asn Ile Lys Asp Thr Tyr Met His Trp Val Lys Gln Arg Pro Glu
     50                  55                  60

Lys Gly
 65
```

<210> SEQ ID NO 177
<211> LENGTH: 91
<212> TYPE: DNA
<213> ORGANISM: Artificial
<220> FEATURE:
<223> OTHER INFORMATION: An artificially synthesized primer sequence

<400> SEQUENCE: 177
caccacggtc accgtctcct caggcggtgg cggatcaggt ggcggtggaa gtggcggtgg    60
tgggtctact agtgacatcg agctcaccca g    91

<210> SEQ ID NO 178
<211> LENGTH: 91
<212> TYPE: DNA
<213> ORGANISM: Artificial
<220> FEATURE:
<223> OTHER INFORMATION: An artificially synthesized primer sequence

<400> SEQUENCE: 178
gtggtgccag tggcagagga gtccgccacc gcctagtcca ccgccacctt caccgccacc    60
acccagatga tcactgtagc tcgagtgggt c    91

<210> SEQ ID NO 179
<211> LENGTH: 17
<212> TYPE: DNA
<213> ORGANISM: Artificial
<220> FEATURE:
<223> OTHER INFORMATION: An artificially synthesized primer sequence

<400> SEQUENCE: 179
caggaaacag ctatgac    17

<210> SEQ ID NO 180
<211> LENGTH: 42
<212> TYPE: DNA
<213> ORGANISM: Artificial
<220> FEATURE:
<223> OTHER INFORMATION: An artificially synthesized primer sequence

<400> SEQUENCE: 180
gacgccgggt cggccggtac cggctccaag tcgacgtcgt ca    42

<210> SEQ ID NO 181
<211> LENGTH: 56
<212> TYPE: DNA
<213> ORGANISM: Artificial
<220> FEATURE:

<223> OTHER INFORMATION: An artificially synthesized primer sequence

<400> SEQUENCE: 181
gtcctcgcaa ctgcggccca gccggccatg gccgacatcc agatgaccca gtctcc    56

<210> SEQ ID NO 182
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 182
gtcctcgcaa ctgcggccca gccggccatg gccgatgttg tgatgactca gtctcc    56

<210> SEQ ID NO 183
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 183
gtcctcgcaa ctgcggccca gccggccatg gccgaaattg tgttgacgca gtctcc    56

<210> SEQ ID NO 184
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 184
gtcctcgcaa ctgcggccca gccggccatg gccgacatcg tgatgaccca gtctcc    56

<210> SEQ ID NO 185
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 185
gtcctcgcaa ctgcggccca gccggccatg gccgaaacga cactcacgca gtctcc    56

<210> SEQ ID NO 186
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 186
gtcctcgcaa ctgcggccca gccggccatg gccgaaattg tgctgactca gtctcc    56

<210> SEQ ID NO 187
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 187
gtcctcgcaa ctgcggccca gccggccatg gcccagtctg tgttgacgca gccgcc    56

<210> SEQ ID NO 188

```
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 188
gtcctcgcaa ctgcggccca gccggccatg gcccagtctg ccctgactca gcctgc        56

<210> SEQ ID NO 189
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 189
gtcctcgcaa ctgcggccca gccggccatg gcctcctatg tgctgactca gccacc        56

<210> SEQ ID NO 190
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 190
gtcctcgcaa ctgcggccca gccggccatg gcctcttctg agctgactca ggaccc        56

<210> SEQ ID NO 191
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 191
gtcctcgcaa ctgcggccca gccggccatg gcccacgtta tactgactca accgcc        56

<210> SEQ ID NO 192
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 192
gtcctcgcaa ctgcggccca gccggccatg gcccaggctg tgctcactca gccgcc        56

<210> SEQ ID NO 193
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 193
gtcctcgcaa ctgcggccca gccggccatg gccaatttta tgctgactca gccccca       56

<210> SEQ ID NO 194
<211> LENGTH: 44
<212> TYPE: DNA
<213> ORGANISM: Artificial
<220> FEATURE:
<223> OTHER INFORMATION: An artificially synthesized primer sequence

<400> SEQUENCE: 194
```

```
tcgactggcg cgccgaacac tctccctgt tgaagctctt tgtg            44
```

<210> SEQ ID NO 195
<211> LENGTH: 43
<212> TYPE: DNA
<213> ORGANISM: Artificial
<220> FEATURE:
<223> OTHER INFORMATION: An artificially synthesized primer sequence

<400> SEQUENCE: 195

```
tcgactggcg cgccgaacat tctgtagggg ccactgtctt ctc            43
```

<210> SEQ ID NO 196
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 196

```
atggagtcgg gaaggaagtc                                      20
```

<210> SEQ ID NO 197
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 197

```
gtcctcgcaa ctgcggccca gccggccatg gcccaggtgc agctggtgca gtctgg   56
```

<210> SEQ ID NO 198
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 198

```
gtcctcgcaa ctgcggccca gccggccatg gcccaggtca acttaaggga gtctgg   56
```

<210> SEQ ID NO 199
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 199

```
gtcctcgcaa ctgcggccca gccggccatg gccgaggtgc agctggtgga gtctgg   56
```

<210> SEQ ID NO 200
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 200

```
gtcctcgcaa ctgcggccca gccggccatg gcccaggtgc agctgcagga gtcggg   56
```

<210> SEQ ID NO 201
<211> LENGTH: 56
<212> TYPE: DNA
<213> ORGANISM: Artificial
<220> FEATURE:

<223> OTHER INFORMATION: An artificially synthesized primer sequence

<400> SEQUENCE: 201
gtcctcgcaa ctgcggccca gccggccatg gcccaggtgc agctgttgca gtctgc    56

<210> SEQ ID NO 202
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 202
gtcctcgcaa ctgcggccca gccggccatg gcccaggtac agctgcagca gtcagg    56

<210> SEQ ID NO 203
<211> LENGTH: 59
<212> TYPE: DNA
<213> ORGANISM: Artificial
<220> FEATURE:
<223> OTHER INFORMATION: An artificially synthesized primer sequence

<400> SEQUENCE: 203
gtcctcgcaa ctgcggccca gccggccatg gcccagrtca ccttgaagga gtctggtcc    59

<210> SEQ ID NO 204
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 204
gtcctcgcaa ctgcggccca gccggccatg gcccaggtgc agctacagca gtgggg    56

<210> SEQ ID NO 205
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 205
gtcctcgcaa ctgcggccca gccggccatg gccgaggtgc agctggtgca gtctgg    56

<210> SEQ ID NO 206
<211> LENGTH: 64
<212> TYPE: DNA
<213> ORGANISM: Artificial
<220> FEATURE:
<223> OTHER INFORMATION: An artificially synthesized primer sequence

<400> SEQUENCE: 206
gtcctcgcaa ctgcggccca gccggccatg gcccaggtgc agctggtgca atctgggtct    60
gagt    64

<210> SEQ ID NO 207
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 207
ggtggaggca ctcgagacgg tgaccagggt gc    32

```
<210> SEQ ID NO 208
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 208
ggtggaggca ctcgagacgg tgaccattgt cc                          32

<210> SEQ ID NO 209
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 209
ggtggaggca ctcgagacgg tgaccagggt tc                          32

<210> SEQ ID NO 210
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 210
ggtggaggca ctcgagacgg tgaccgtggt cc                          32

<210> SEQ ID NO 211
<211> LENGTH: 36
<212> TYPE: DNA
<213> ORGANISM: Artificial
<220> FEATURE:
<223> OTHER INFORMATION: An artificially synthesized primer sequence

<400> SEQUENCE: 211
gtgtgcggcc gcctagatga agtactcttt cttttc                      36

<210> SEQ ID NO 212
<211> LENGTH: 68
<212> TYPE: DNA
<213> ORGANISM: Artificial
<220> FEATURE:
<223> OTHER INFORMATION: An artificially synthesized primer sequence

<400> SEQUENCE: 212
caaaagctgg agctcgtcga ctacccagaa ttcaagctta ttcgcgcggc cgcggtacca   60
ggtaagtg                                                     68

<210> SEQ ID NO 213
<211> LENGTH: 68
<212> TYPE: DNA
<213> ORGANISM: Artificial
<220> FEATURE:
<223> OTHER INFORMATION: An artificially synthesized primer sequence

<400> SEQUENCE: 213
cacttacctg gtaccgcggc cgcgcgaata atctttcctt ctgggtagtc gacgagctcc   60
agcttttg                                                     68

<210> SEQ ID NO 214
<211> LENGTH: 40
<212> TYPE: DNA
```

```
<213> ORGANISM: Artificial
<220> FEATURE:
<223> OTHER INFORMATION: An artificially synthesized primer sequence

<400> SEQUENCE: 214
gagagtcgac gccaccatgg cgagtgtagt gctgccgagc                                40

<210> SEQ ID NO 215
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 215
aattaaccct cactaaaggg                                                      20

<210> SEQ ID NO 216
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 216
taatacgact cactataggg                                                      20

<210> SEQ ID NO 217
<211> LENGTH: 1323
<212> TYPE: DNA
<213> ORGANISM: Artificial
<220> FEATURE:
<223> OTHER INFORMATION: cDNA sequence

<400> SEQUENCE: 217
atggcgagtg tagtgctgcc gagcggatcc cagtgtgcgg cggcagcggc ggcggcggcg          60
cctcccgggc tccggcttct gctgttgctc ttctccgccg cggcactgat ccccacaggt         120
gatgggcaga atctgtttac gaaagacgtg acagtgatcg agggagaggt tgcgaccatc         180
agttgccaag tcaataagag tgacgactct gtgattcagc tactgaatcc caacaggcag         240
accatttatt tcagggactt caggcctttg aaggacagca ggtttcagtt gctgaatttt         300
tctagcagtg aactcaaagt atcattgaca aacgtctcaa tttctgatga aggaagatac         360
ttttgccagc tctataccga tccccacag gaaagttaca ccaccatcac agtcctggtc          420
ccaccacgta atctgatgat cgatatccag aaagacactg cggtggaagg tgaggagatt         480
gaagtcaact gcactgctat ggccagcaag ccagccacga ctatcaggtg gttcaaaggg         540
aacacagagc taaaaggcaa atcggagtg aagagtggt cagacatgta cactgtgacc           600
agtcagctga tgctgaaggt gcacaaggag gacgatgggg tcccagtgat ctgccaggtg         660
gagcaccctg cggtcactgg aaacctgcag acccagcggt atctagaagt acagtataag         720
cctcaagtgc acattcagat gacttatcct ctacaaggct taacccggga aggggacgcg         780
cttgagttaa catgtgaagc catcgggaag ccccagcctg tgatggtaac ttgggtgaga         840
gtcgatgatg aaatgcctca acacgccgta ctgtctgggc ccaacctgtt catcaataac         900
ctaaacaaaa cagataatgg tacataccgc tgtgaagctt caacacatgt ggggaaagct         960
cactcggatt atatgctgta tgtatacgat ccccccacaa ctatccctcc tccacaaca        1020 accaccacca ccaccaccac caccaccacc accatcctta ccatcatcac agattcccga        1080
gcaggtgaag aaggctcgat cagggcagtg gatcatgccg tgatcggtgg cgtcgtggcg        1140
```

-continued

| | |
|---|---|
| gtggtggtgt tcgccatgct gtgcttgctc atcattctgg ggcgctatttt tgccagacat | 1200 |
| aaaggtacat acttcactca tgaagccaaa ggagccgatg acgcagcaga cgcagacaca | 1260 |
| gctataatca atgcagaagg aggacagaac aactccgaag aaagaaaga gtacttcatc | 1320 |
| tag | 1323 |

<210> SEQ ID NO 218
<211> LENGTH: 1362
<212> TYPE: DNA
<213> ORGANISM: Artificial
<220> FEATURE:
<223> OTHER INFORMATION: cDNA sequence

<400> SEQUENCE: 218

| | |
|---|---|
| atggcgagtg tagtgctgcc gagcggatcc cagtgtgcgg cggcagcggc ggcggcggcg | 60 |
| cctcccgggc tccggctccg gcttctgctg ttgctcttct ccgccgcggc actgatcccc | 120 |
| acaggtgatg ggcagaatct gtttacgaaa gacgtgacag tgatcgaggg agaggttgcg | 180 |
| accatcagtt gccaagtcaa taagagtgac gactctgtga ttcagctact gaatcccaac | 240 |
| aggcagacca tttatttcag ggacttcagg cctttgaagg acagcaggtt tcagttgctg | 300 |
| aatttttcta gcagtgaact caaagtatca ttgacaaacg tctcaatttc tgatgaagga | 360 |
| agatactttt gccagctcta taccgatccc ccacaggaaa gttacaccac catcacagtc | 420 |
| ctggtcccac cacgtaatct gatgatcgat atccagaaag acactgcggt ggaaggtgag | 480 |
| gagattgaag tcaactgcac tgctatggcc agcaagccag ccacgactat caggtggttc | 540 |
| aaagggaaca cagagctaaa aggcaaatcg gaggtggaag agtggtcaga catgtacact | 600 |
| gtgaccagtc agctgatgct gaaggtgcac aaggaggacg atgggggtccc agtgatctgc | 660 |
| caggtggagc accctgcggt cactggaaac ctgcagaccc agcggtatct agaagtacag | 720 |
| tataagcctc aagtgcacat tcagatgact tatcctctac aaggcttaac ccggaagg | 780 |
| gacgcgcttg agttaacatg tgaagccatc gggaagcccc agcctgtgat ggtaacttgg | 840 |
| gtgagagtcg atgatgaaat gcctcaacac gccgtactgt ctgggcccaa cctgttcatc | 900 |
| aataacctaa acaaaacaga taatggtaca taccgctgtg aagcttcaaa catagtgggg | 960 |
| aaagctcact cggattatat gctgtatgta tacgatcccc ccacaactat ccctcctccc | 1020 |
| acaacaacca ccaccaccac caccaccacc accaccacca tccttaccat catcacagac | 1080 |
| acaacggcga cgacagaacc agcagttcac gattcccgag caggtgaaga aggctcgatc | 1140 |
| agggcagtgg atcatgccgt gatcggtggc gtcgtggcgg tggtggtgtt cgccatgctg | 1200 |
| tgcttgctca tcattctggg gcgctatttt gccagacata aaggtacata cttcactcat | 1260 |
| gaagccaaag gagccgatga cgcagcagac gcagacacag ctataatcaa tgcagaagga | 1320 |
| ggacagaaca actccgaaga aaagaaagag tacttcatct ag | 1362 |

<210> SEQ ID NO 219
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 219

| | |
|---|---|
| ttcagggact tcaggccttt gaag | 24 |

<210> SEQ ID NO 220
<211> LENGTH: 24
<212> TYPE: DNA

```
<213> ORGANISM: Artificial
<220> FEATURE:
<223> OTHER INFORMATION: An artificially synthesized primer sequence

<400> SEQUENCE: 220
caccgatcac ggcatgatcc actg                                          24

<210> SEQ ID NO 221
<211> LENGTH: 119
<212> TYPE: PRT
<213> ORGANISM: Homo sapiens

<400> SEQUENCE: 221

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Thr Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Asn Asn Thr Leu Tyr
65                  70                  75                  80

Leu Gln Met His Ser Leu Arg Ala Glu Asp Thr Ala Leu Tyr Tyr Cys
                85                  90                  95

Ala Arg Gly Leu Tyr Gly Leu Tyr Ala Met Asp Val Trp Gly Gln Gly
            100                 105                 110

Thr Thr Val Thr Val Ser Arg
        115

<210> SEQ ID NO 222
<211> LENGTH: 5
<212> TYPE: PRT
<213> ORGANISM: Homo sapiens

<400> SEQUENCE: 222

Ser Tyr Thr Met Ser
1               5

<210> SEQ ID NO 223
<211> LENGTH: 17
<212> TYPE: PRT
<213> ORGANISM: Homo sapiens

<400> SEQUENCE: 223

Gly Ile Ser Gly Ser Gly Gly Ser Thr Tyr Tyr Ala Asp Ser Val Lys
1               5                   10                  15

Gly

<210> SEQ ID NO 224
<211> LENGTH: 10
<212> TYPE: PRT
<213> ORGANISM: Homo sapiens

<400> SEQUENCE: 224

Gly Leu Tyr Gly Leu Tyr Ala Met Asp Val
1               5                   10

<210> SEQ ID NO 225
<211> LENGTH: 109
<212> TYPE: PRT
<213> ORGANISM: Homo sapiens
```

<400> SEQUENCE: 225

Ser Ser Glu Leu Thr Gln Asp Pro Ala Val Ser Val Ala Ser Gly Gln
1               5                   10                  15

Thr Val Arg Ile Thr Cys Gln Gly Asp Ser Leu Arg His Tyr Tyr Pro
            20                  25                  30

Ser Trp Tyr Gln Gln Lys Pro Arg Gln Ala Pro Val Leu Val Phe Phe
        35                  40                  45

Gly Glu Asn Asn Arg Pro Ser Gly Ile Pro Asp Arg Phe Ser Gly Ser
    50                  55                  60

Ala Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Gly Asn Asp Asp Arg
                85                  90                  95

Trp Leu Phe Gly Gly Gly Thr Lys Val Thr Val Leu Gly
            100                 105

<210> SEQ ID NO 226
<211> LENGTH: 11
<212> TYPE: PRT
<213> ORGANISM: Homo sapiens

<400> SEQUENCE: 226

Gln Gly Asp Ser Leu Arg His Tyr Tyr Pro Ser
1               5                   10

<210> SEQ ID NO 227
<211> LENGTH: 7
<212> TYPE: PRT
<213> ORGANISM: Homo sapiens

<400> SEQUENCE: 227

Gly Glu Asn Asn Arg Pro Ser
1               5

<210> SEQ ID NO 228
<211> LENGTH: 9
<212> TYPE: PRT
<213> ORGANISM: Homo sapiens

<400> SEQUENCE: 228

Ser Ser Arg Asp Gly Asn Asp Asp Arg
1               5

<210> SEQ ID NO 229
<211> LENGTH: 116
<212> TYPE: PRT
<213> ORGANISM: Homo sapiens

<400> SEQUENCE: 229

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
                85                  90                  95

Ala Lys Thr Asn Trp Asn Phe Asp Tyr Trp Gly Gln Gly Thr Leu Val
            100                 105                 110

Thr Val Ser Arg
        115

<210> SEQ ID NO 230
<211> LENGTH: 5
<212> TYPE: PRT
<213> ORGANISM: Homo sapiens

<400> SEQUENCE: 230

Ser Tyr Ala Met Ser
1               5

<210> SEQ ID NO 231
<211> LENGTH: 17
<212> TYPE: PRT
<213> ORGANISM: Homo sapiens

<400> SEQUENCE: 231

Ala Ile Ser Gly Ser Gly Gly Ser Thr Tyr Tyr Ala Asp Ser Val Lys
1               5                   10                  15

Gly

<210> SEQ ID NO 232
<211> LENGTH: 7
<212> TYPE: PRT
<213> ORGANISM: Homo sapiens

<400> SEQUENCE: 232

Thr Asn Trp Asn Phe Asp Tyr
1               5

<210> SEQ ID NO 233
<211> LENGTH: 109
<212> TYPE: PRT
<213> ORGANISM: Homo sapiens

<400> SEQUENCE: 233

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly
            100                 105

<210> SEQ ID NO 234
<211> LENGTH: 11
<212> TYPE: PRT
<213> ORGANISM: Homo sapiens

<400> SEQUENCE: 234

```
Gln Gly Asp Ser Leu Arg Ser Tyr Tyr Ala Ser
1               5                   10
```

<210> SEQ ID NO 235
<211> LENGTH: 7
<212> TYPE: PRT
<213> ORGANISM: Homo sapiens

<400> SEQUENCE: 235

```
Gly Lys Asn Asn Arg Pro Ser
1               5
```

<210> SEQ ID NO 236
<211> LENGTH: 9
<212> TYPE: PRT
<213> ORGANISM: Homo sapiens

<400> SEQUENCE: 236

```
Asn Ser Arg Asp Ser Ser Gly Asn His
1               5
```

<210> SEQ ID NO 237
<211> LENGTH: 116
<212> TYPE: PRT
<213> ORGANISM: Homo sapiens

<400> SEQUENCE: 237

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asn Trp Asn Tyr Asp Tyr Trp Gly Gln Gly Thr Leu Val
            100                 105                 110

Thr Val Ser Arg
        115
```

<210> SEQ ID NO 238
<211> LENGTH: 5
<212> TYPE: PRT
<213> ORGANISM: Homo sapiens

<400> SEQUENCE: 238

```
Gly Tyr Tyr Met His
1               5
```

<210> SEQ ID NO 239
<211> LENGTH: 17
<212> TYPE: PRT
<213> ORGANISM: Homo sapiens

<400> SEQUENCE: 239

```
Trp Ile Asn Pro Asn Ser Gly Gly Thr Asn Tyr Ala Gln Lys Phe Gln
1               5                   10                  15
```

Gly

<210> SEQ ID NO 240
<211> LENGTH: 7
<212> TYPE: PRT
<213> ORGANISM: Homo sapiens

<400> SEQUENCE: 240

Asp Asn Trp Asn Tyr Asp Tyr
1               5

<210> SEQ ID NO 241
<211> LENGTH: 108
<212> TYPE: PRT
<213> ORGANISM: Homo sapiens

<400> SEQUENCE: 241

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Ser Thr Ala Ser Leu Thr Ile Thr Gly Ala Gln Ala Glu
65                  70                  75                  80

Asp Glu Ala Asp Tyr Tyr Cys Asp Ser Arg Asp Ser Ser Gly Asn His
                85                  90                  95

Val Phe Gly Thr Gly Thr Lys Val Thr Val Leu Gly
            100                 105

<210> SEQ ID NO 242
<211> LENGTH: 11
<212> TYPE: PRT
<213> ORGANISM: Homo sapiens

<400> SEQUENCE: 242

Gln Gly Asp Ser Leu Arg Thr Tyr Tyr Ala Ser
1               5                   10

<210> SEQ ID NO 243
<211> LENGTH: 7
<212> TYPE: PRT
<213> ORGANISM: Homo sapiens

<400> SEQUENCE: 243

Gly Lys Asn Asn Arg Pro Ser
1               5

<210> SEQ ID NO 244
<211> LENGTH: 9
<212> TYPE: PRT
<213> ORGANISM: Homo sapiens

<400> SEQUENCE: 244

Asp Ser Arg Asp Ser Ser Gly Asn His
1               5

<210> SEQ ID NO 245
<211> LENGTH: 356
<212> TYPE: DNA
<213> ORGANISM: Homo sapiens

<400> SEQUENCE: 245

```
gaggtgcagc tggtggagtc tgggggaggc ttggtacagc ctggggggtc cctgagactc    60
tcctgtgcag cctctggatt cacctttagg agctatacca tgagctgggt ccgccaggct   120
ccagggaagg ggctggagtg ggtctcaggt attagtggta gtggtggtag cacatactac   180
gcagactccg tgaagggccg gttcaccatc tccagagaca attccaacaa cacgctgtac   240
cttcaaatgc acagcctgag agccgaggac acggccctgt attactgtgc gagaggcttg   300
tatggcttgt acgctatgga cgtctggggc caagggacca cggtcaccgt ctcgag       356
```

<210> SEQ ID NO 246
<211> LENGTH: 15
<212> TYPE: DNA
<213> ORGANISM: Homo sapiens

<400> SEQUENCE: 246

```
agctatacca tgagc                                                     15
```

<210> SEQ ID NO 247
<211> LENGTH: 51
<212> TYPE: DNA
<213> ORGANISM: Homo sapiens

<400> SEQUENCE: 247

```
ggtattagtg gtagtggtgg tagcacatac tacgcagact ccgtgaaggg c             51
```

<210> SEQ ID NO 248
<211> LENGTH: 30
<212> TYPE: DNA
<213> ORGANISM: Homo sapiens

<400> SEQUENCE: 248

```
ggcttgtatg gcttgtacgc tatggacgtc                                     30
```

<210> SEQ ID NO 249
<211> LENGTH: 327
<212> TYPE: DNA
<213> ORGANISM: Homo sapiens

<400> SEQUENCE: 249

```
tcttctgagc tgactcagga ccctgctgtg tctgtggcct cggggcagac agtcaggatc    60
acatgccaag agacagcct  cagacattat tatccaagct ggtaccagca gaagccacga   120
caggcccctg tacttgtctt ctttggtgaa acaaccggc  cctcagggat cccagaccga   180
ttctctggct ccgcctcagg aaacacagct tctttgacca tcgctgggc  acaggcagaa   240
gatgacgctg actattattg ttcttcgcgg gacggcaatg atgaccgctg gctattcggc   300
ggagggacca agtgaccgt  cctgggt                                       327
```

<210> SEQ ID NO 250
<211> LENGTH: 33
<212> TYPE: DNA
<213> ORGANISM: Homo sapiens

<400> SEQUENCE: 250

```
caaggagaca gcctcagaca ttattatcca agc                                 33
```

<210> SEQ ID NO 251
<211> LENGTH: 21
<212> TYPE: DNA
<213> ORGANISM: Homo sapiens
```

<400> SEQUENCE: 251
ggtgaaaaca accggccctc a                                                 21

<210> SEQ ID NO 252
<211> LENGTH: 27
<212> TYPE: DNA
<213> ORGANISM: Homo sapiens

<400> SEQUENCE: 252
tcttcgcggg acggcaatga tgaccgc                                           27

<210> SEQ ID NO 253
<211> LENGTH: 348
<212> TYPE: DNA
<213> ORGANISM: Homo sapiens

<400> SEQUENCE: 253
gaggtgcagc tggtggagtc tgggggaggc ttggtacagc ctggggggtc cctgagactc       60
tcctgtgcag cctctggatt cacctttagc agctatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga acagcctgag agccaaggac acggccgtat attactgtgc gaagacaaac      300
tggaactttg actactgggg ccagggaacc ctggtcaccg tctcgaga                   348

<210> SEQ ID NO 254
<211> LENGTH: 63
<212> TYPE: DNA
<213> ORGANISM: Homo sapiens

<400> SEQUENCE: 254
gaggtgcagc tggtggagtc tgggggaggc ttggtacagc ctgggggag ctatgccatg        60 agc                                                                    63

<210> SEQ ID NO 255
<211> LENGTH: 51
<212> TYPE: DNA
<213> ORGANISM: Homo sapiens

<400> SEQUENCE: 255
gctattagtg gtagtggtgg tagcacatac tacgcagact ccgtgaaggg c                51

<210> SEQ ID NO 256
<211> LENGTH: 21
<212> TYPE: DNA
<213> ORGANISM: Homo sapiens

<400> SEQUENCE: 256
acaaactgga actttgacta c                                                 21

<210> SEQ ID NO 257
<211> LENGTH: 327
<212> TYPE: DNA
<213> ORGANISM: Homo sapiens

<400> SEQUENCE: 257
tcttctgagc tgactcagga ccctgctgtg tctgtggcct tgggacagac agtcaggatc       60
acatgccaag agacagcct cagaagctat tatgcaagct ggtaccagca gaagccagga      120
caggcccctg tacttgtcat ctatggtaaa aacaaccggc cctcagggat cccagaccga      180

```
ttctctggct ccagctcagg aaacacagct tccttgacca tcactggggc tcaggcggaa      240
gatgaggctg actattactg taactcccgg gacagcagtg gtaaccatgt ggtattcggc      300
ggagggacca agctgaccgt cctaggt                                          327
```

<210> SEQ ID NO 258
<211> LENGTH: 33
<212> TYPE: DNA
<213> ORGANISM: Homo sapiens

<400> SEQUENCE: 258

```
caaggagaca gcctcagaag ctattatgca agc                                    33
```

<210> SEQ ID NO 259
<211> LENGTH: 21
<212> TYPE: DNA
<213> ORGANISM: Homo sapiens

<400> SEQUENCE: 259

```
ggtaaaaaca accggccctc a                                                 21
```

<210> SEQ ID NO 260
<211> LENGTH: 27
<212> TYPE: DNA
<213> ORGANISM: Homo sapiens

<400> SEQUENCE: 260

```
aactcccggg acagcagtgg taaccat                                           27
```

<210> SEQ ID NO 261
<211> LENGTH: 348
<212> TYPE: DNA
<213> ORGANISM: Homo sapiens

<400> SEQUENCE: 261

```
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaatccta acagtggtgg cacaaactat      180
gcacagaagt ttcagggcag ggtcaccatg accagggaca cgtccatcag cacagcctac      240
atggagctga gcaggctgag atctgacgac acggccgtgt attactgtgc gagagataac      300
tggaactacg actactgggg ccagggaacc ctggtcaccg tctcgaga                   348
```

<210> SEQ ID NO 262
<211> LENGTH: 15
<212> TYPE: DNA
<213> ORGANISM: Homo sapiens

<400> SEQUENCE: 262

```
ggctactata tgcac                                                        15
```

<210> SEQ ID NO 263
<211> LENGTH: 51
<212> TYPE: DNA
<213> ORGANISM: Homo sapiens

<400> SEQUENCE: 263

```
tggatcaatc ctaacagtgg tggcacaaac tatgcacaga agtttcaggg c                51
```

<210> SEQ ID NO 264
<211> LENGTH: 21

```
<212> TYPE: DNA
<213> ORGANISM: Homo sapiens

<400> SEQUENCE: 264
gataactgga actacgacta c                                              21

<210> SEQ ID NO 265
<211> LENGTH: 324
<212> TYPE: DNA
<213> ORGANISM: Homo sapiens

<400> SEQUENCE: 265
tcttctgagc tgactcagga ccctgctgtg tctgtggcct tgggacagac agtcaggatc    60
acatgccaag agacagcct cagaacctat tatgcaagct ggtaccagca gaagcctgga    120
caggcccctg tacttgtcat ctatggtaaa acaaccggc cctcagggat cccagaccga    180
ttctccggct ccagctcagg aagcacagct tccttgacca tcactggggc tcaggcggaa    240
gatgaggctg actattactg tgactcccgg gacagcagtg gtaaccatgt cttcggaact    300
gggaccaagg tcaccgtcct aggt                                           324

<210> SEQ ID NO 266
<211> LENGTH: 33
<212> TYPE: DNA
<213> ORGANISM: Homo sapiens

<400> SEQUENCE: 266
caaggagaca gcctcagaac ctattatgca agc                                 33

<210> SEQ ID NO 267
<211> LENGTH: 21
<212> TYPE: DNA
<213> ORGANISM: Homo sapiens

<400> SEQUENCE: 267
ggtaaaaaca accggccctc a                                              21

<210> SEQ ID NO 268
<211> LENGTH: 27
<212> TYPE: DNA
<213> ORGANISM: Homo sapiens

<400> SEQUENCE: 268
gactcccggg acagcagtgg taaccat                                        27

<210> SEQ ID NO 269
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 269
ggcccaacct gttcatcaat a                                              21

<210> SEQ ID NO 270
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 270
caccaggctc aacttgttcg tcaatattca agagatattg atgaacaggt tgggcc        56
```

```
<210> SEQ ID NO 271
<211> LENGTH: 52
<212> TYPE: DNA
<213> ORGANISM: Artificial
<220> FEATURE:
<223> OTHER INFORMATION: An artificially synthesized primer sequence

<400> SEQUENCE: 271
ggcccaacct gttcatcaat atctcttgaa tattgacgaa caagttgagc ct          52

<210> SEQ ID NO 272
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 272
tgttctggga aatcaccata                                               20

<210> SEQ ID NO 273
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 273
accgaggaga gggttaggga t                                             21

<210> SEQ ID NO 274
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 274
caccaggctc aacttgttcg tcaatattca agagatattg atgaacaggt tgggcc       56
```